United States Patent
Greene et al.

(10) Patent No.: US 11,446,516 B2
(45) Date of Patent: Sep. 20, 2022

(54) METHODS OF INCREASING RESPONSE TO CANCER RADIATION THERAPY

(71) Applicant: THE TRUSTEES OF THE UNIVERSITY OF PENNSYLVANIA, Philadelphia, PA (US)

(72) Inventors: Mark Greene, Penn Valley, PA (US); Hongtao Zhang, Paoli, PA (US); Hiromichi Tsuchiya, Philadelphia, PA (US); Yasuhiro Nagai, Philadelphia, PA (US); Lian Lam, Philadelphia, PA (US); Aaron Runkle, Philadelphia, PA (US); Jeffrey Drebin, Bryn Mawr, PA (US); Mei Qing Ji, Voorhees, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 17/375,459

(22) Filed: Jul. 14, 2021

(65) Prior Publication Data
US 2022/0040498 A1    Feb. 10, 2022

Related U.S. Application Data

(63) Continuation of application No. 15/019,924, filed on Feb. 9, 2016, now abandoned, which is a (Continued)

(51) Int. Cl.
*A61N 5/10*    (2006.01)

(52) U.S. Cl.
CPC ........ *A61N 5/10* (2013.01); *A61N 2005/1098* (2013.01)

(58) Field of Classification Search
CPC ........ A61N 5/10; A61N 5/1001; A61N 5/103; A61N 5/1048; A61N 5/1077–1079;
(Continued)

(56) References Cited

U.S. PATENT DOCUMENTS 6,399,063 B1    6/2002    Hudziak et al.
6,733,752 B1    5/2004    Greene et al.
(Continued)

FOREIGN PATENT DOCUMENTS

WO    WO 1999/044645 A1    9/1999
WO    WO 2004/105684 A2    12/2004
(Continued)

OTHER PUBLICATIONS

Alberts, D. S. et al. "Randomized phase 3 trial of interferon gamma-1b plus standard carboplatin/paclitaxel versus carboplatin/paclitaxel alone for first-line treatment of advanced ovarian and primary peritoneal carcinomas: results from a prospectively designed analysis of progression-free survival"; Gynecol Oncol., 2008, 109(2), 174-81.
(Continued)

*Primary Examiner* — Carrie R Dorna
(74) *Attorney, Agent, or Firm* — Cooley LLP

(57) ABSTRACT

Disclosed herein are methods of increasing response to radiation therapy in subjects afflicted with cancer. In some embodiments, the method comprises reducing the ability of an immune suppressor cell (e.g., MDSC) to migrate to the microenvironment of the cancer. In some embodiments, the method further comprises suppressing the migration of the immune suppressor cell to a non-malignant cell and/or suppressing the malignant transformation of the non-malignant cells.

3 Claims, 67 Drawing Sheets
Specification includes a Sequence Listing.

Related U.S. Application Data continuation-in-part of application No. PCT/US2014/050442, filed on Aug. 8, 2014.

(60) Provisional application No. 62/220,138, filed on Sep. 17, 2015, provisional application No. 62/115,011, filed on Feb. 11, 2015, provisional application No. 61/864,509, filed on Aug. 9, 2013.

(58) Field of Classification Search
CPC .......... A61N 5/1081–1084; A61N 2005/1098; A61K 31/21; A61K 31/217; A61K 39/39558
See application file for complete search history.

(56) References Cited

U.S. PATENT DOCUMENTS

| | | |
|---|---|---|
| 2010/0172868 A1 | 7/2010 | Morrison et al. |
| 2012/0164066 A1 | 6/2012 | Greene et al. |
| 2014/0050721 A1 | 2/2014 | Moore et al. |
| 2018/0057603 A1 | 3/2018 | Greene et al. |

FOREIGN PATENT DOCUMENTS

| | | | | |
|---|---|---|---|---|
| WO | WO 2009/039409 A1 | 3/2009 | | |
| WO | WO 2012/143523 A1 | 10/2012 | | |
| WO | WO-2015021444 A1 * | 2/2015 | ............. | C07K 14/71 |
| WO | WO 2017/139468 A1 | 8/2017 | | |

OTHER PUBLICATIONS

Balmaña, et al., "BRCA in breast cancer: ESMO Clinical Recommendations." Annals of Oncology, 2009, 20(Supplement 4), iv19-iv20.
Brand, et al., "Prospect for Anti-HER2 Receptor Therapy in Breast Cancer." Anticancer Research, 2006, 26(1B), 463-470.
Cai, et al., "scFv-based "grababody" as a general strategy to improve recruitment of immune effector cells to antibody-targeted tumors." Cancer Research, 2013, 73(8), 2619-2627.
Capelan, M., et al., "Pertuzumab: new hope for patients with HER2-positive breast cancer." Annals of Oncology, 2013, 24(2), 273-282.
Castro, F. et al. "Interferon-Gamma at the Crossroads of Tumor Immune Surveillance or Evasion"; Front Immunol., May 2018, 9(847), 1-19.
Chen, W.Q., et al., "Enhanced anti-tumor effect of an IFN-gamma-EGF fusion protein." Biomedical and Environmental Sciences: BES, 1997, 10(4), 387-395.
Drebin, J. A. et al., "Down-modulation of an oncogene protein product and reversion of the transformed phenotype by monoclonal antibodies", Cell, 1985, 41(3), 697-706.
Drebin, J. A. et al., "Monoclonal antibodies reactive with distinct domains of the neu oncogene-encoded p185 molecule exert synergistic anti-tumor effects in vivo", Oncogene, 1988, 2(3), 273-277.
Ernstoff, M. S. et al. "A randomized phase I/II study of continuous versus intermittent intravenous interferon gamma in patients with metastatic melanoma"; J Clin Oncol., Nov. 1987, 5(11), 1804-10.
European Patent Application No. 14834082.1, Extended European Search Report dated Jun. 13, 2017, 29 pages.
European Patent Application No. 14834082.1, Partial European Search Report dated Feb. 24, 2017, 9 pages.
Finkle, D., et al., "HER2-Targeted Therapy Reduces Incidence and Progression of Midlife Mammary Tumors in Female Murine Mammary Tumor Virus huHER2-Transgenic Mice." Cancer Research, Apr. 2004,10(7), 2499-2511.
Gleave, M. E et al. "Interferon gamma-1b compared with placebo in metastatic renal-cell carcinoma. Canadian Urologic Oncology Group"; N Engl J Med., Apr. 30, 1998, 339(18), 1265-71.
Haga, E., et al. "Therapy of Peritoneally Disseminated Colon Cancer by TAP-Deficient Embryonic Stem Cell-Derived Macrophages in Allogeneic Recipients." The Journal of Immunology, 2014, 193(4), 2024-2033.
Hanahan, D., et al., "Hallmarks of Cancer: The Next Generation," Cell, Mar. 4, 2011, 144, 646-674.
International Application No. PCT/US2014/050442, International Preliminary Report on Patentability dated Feb. 9, 2016, 7 pages.
International Application No. PCT/US2014/050442, International Search Report and Written Opinion dated Nov. 19, 2014, 11 pages.
International Application No. PCT/US2017/017193, International Search Report and Written Opinion dated May 18, 2017, 16 pages.
James, N. D., et al. "A phase II study of the bispecific antibody MDX-H210 (anti-HER2x CD64) with GM-CSF in HER2+ advanced prostate cancer." British Journal of Cancer, 2001, 85(2), 152-156.
Kataja, et al., "Primary breast cancer: ESMO Clinical Recommendations for diagnosis, treatment and follow-up." Annals of Oncology, 2009, Suppl 4, iv10-iv14.
Katsumata, M., et al., "Prevention of breast tumour development in vivo by downregulation of the p185neu receptor." Nature Medicine, 1995, 1(7), 644-648.
Khorana, A. A. et al. "A phase I trial of immunotherapy with intratumoral adenovirus-interferon-gamma (TG1041) in patients with malignant melanoma"; Cancer Gene Ther, 2003, 10(4), 251-9.
Koefoed, et al., "Rational identification of an optimal antibody mixture for targeting the epidermal growth factor receptor." MABS, 2011, 3(6), 584-595.
Kopp, W. C. et al. "Immunomodulatory effects of interferon-gamma in patients with metastatic malignant melanoma"; J Immunother Emphasis Tumor Immunol., Apr. 1993, 13(3), 181-90.
Kopreski, M. S., et al. "Growth inhibition of breast cancer cell lines by combinations of anti-P185HER2 monoclonal antibody and cytokines." Anticancer Research, 1995, 16(1), 433-436, XP002766724, Retrieved from the Internet: URL:://www.ncbi.nlm.nih.gov/pubmed/8615649 [retrieved on Feb. 3, 2017].
Kurai, J., et al., "Antibody-Dependent Cellular Cytotoxicity Mediated by Cetuximab against Lung Cancer Cell Lines." Clinical Cancer Research, 2007, 13(5), 1552-1561.
Leveque, D., et al., "Clinical pharmacology of trastuzumab." Current Clinical Pharmacology, 2008, 3(1), 51-55.
Lewis, L., et al. "The pharmacokinetics of the bispecific antibody MDX-H210 when combined with interferon gamma-1b in a multiple-dose phase I study in patients with advanced cancer." Cancer Chemotherapy and Pharmacology, 2002, 49(5), 375-384.
Liang, K., et al., "Sensitization of breast cancer cells to radiation by trastuzumab." Molecular Cancer Therapeutics, 2003, 2(11), 1113-1120.
Meira, D.D., et al., "Combination of cetuximab with chemoradiation, trastuzumab or MAPK inhibitors: mechanisms of sensitisation of cervical cancer cells." British Journal of Cancer, 2009, 101(5), 782-791.
Milano, F., et al. "S2030 Interferon-Gamma Restores Trastuzumab Mediated CTL Response in Esophageal Adenocarcinoma Through Re-Induction of TAP-2 Expression." Gastroenterology, 2009, 136(5) (Suppl 1), A-316, & Digestive Disease Week/110th Annual Meeting of the American-Gastroenterological-Association, Chicago, IL, USA; May 30-Jun. 4, 2009 ISSN: 0016-5085.
Mortenson, E., et al. "Effective Anti-Neu-Initiated Antitumor Responses Require the Complex Role of CD4+T Cells." Clinical Cancer Research, 2013, 19(6), 1476-1486.
Nagai, Y., et al., "Disabling of the erbB Pathway Followed by IFN-γ Modifies Phenotype and Enhances Genotoxic Eradication of Breast Tumors." Cell Rep., Sep. 2015, 12(12), 2049-2059.
Nelson, et al., "Screening for Breast Cancer: An Update for the U.S. Preventive Services Task Force." Ann. Intern Med., 2009, 151(10), 727-737.
O'Rourke, D. M. et al. "Conversion of a radioresistant phenotype to a more sensitive one by disabling erbB receptor signaling in human cancer cells", Proc Natl Acad Sci USA., Sep. 1, 1998, 95(18), 10842-7.
Pahl, et al., "Macrophages inhibit human osteosarcoma cell growth after activation with the bacterial cell wall derivative liposomal muramyl tripeptide in combination with interferon-γ." Journal of Experimental & Clinical Cancer Research, 2014, 33(1), 27.

(56) References Cited

OTHER PUBLICATIONS

Pollack, B.P., et al., "Epidermal Growth Factor Receptor Inhibition Augments the Expression of MHO Class I and II Genes." Clinical Cancer Research, 2011, 17(13), 4400-4413.

Real, P. J., et al., "Blockade of Epidermal Growth Factor Receptors Chemosensitizes Breast Cancer Cells through Up-Regulation of Bnip3L." Cancer Research, 2005, 65(18), 8151-8157.

Schmitt, "HER2+ breast cancer: How to evaluate?" Advances in Therapy, 2009, 26(Suppl 1), S1-S8.

Stagg, J., et al., "Anti-ErbB-2 mAb therapy requires type I and II interferons and synergizes with anti-PD-1 or anti-CD 137 mAb therapy." Proceedings of the National Academy of Sciences of the United States of America, 2011, 108(17), 7142-7147.

Talpaz, M. et al. "A phase II study alternating alpha-2a-interferon and gamma-interferon therapy in patients with chronic myelogenous leukemia"; Cancer., Nov. 15, 1991, 68(10), 2125-30.

Vahdat, L. T. et al. "Randomized trial of low-dose interleukin-2 vs cyclosporine A and interferon-gamma after high-dose chemotherapy with peripheral blood progenitor support in women with high-risk primary breast cancer"; Bone Marrow Transplant., Aug. 2007, 40(3), 267-72.

Von Hoff, D. D. et al. "Phase II evaluation of recombinant gamma-interferon in patients with advanced pancreatic carcinoma: A Southwest Oncology Group study"; J Biol Response Mod., Dec. 1990, 9(6), 584-7.

Wallace, P., et al. "Bispecific antibody-targeted phagocytosis of HER-2/neu expressing tumor cells by myeloid cells activated in vivo." Journal of Immunological Methods, 2001, 248(1), 167-182.

Wazer, D. E. et al. "Modulation in the radiosensitivity of MCF-7 human breast carcinoma cells by 17B-estradiol and tamoxifen," Br J Radiol., Dec. 1989, 62(744), 1079-83.

Wiesenfeld, M. et al. "Controlled clinical trial of interferon-gamma as postoperative surgical adjuvant therapy for colon cancer"; J Clin Oncol., Sep. 1995, 13(9), 2324-9.

Xiaobing, Z., et al., "Antiproliferative activity of human IFN-= EGF3 fusion protein are related to its EGF receptor competition." Journal of Xi'an Medical University (1999); English Edition, Xi'an Medical University China, 1999, 11(1), 19-22 and 25.

Zaidi, M. R., "The Interferon-Gamma Paradox in Cancer", J Interferon Cytokine Res., 2019, Epub Nov. 9, 2018, 39(1), 30-38.

Zaidi, M. R. et al. "The two faces of interferon-γ in cancer", Clin Cancer Res, Oct. 1, 2011, Epub Jun. 24, 2011, 17(19), 6118-24.

Creagan, E. T. et al. "Phase II study of recombinant interferon-gamma in patients with disseminated malignant melanoma", Cancer Treat Rep., Sep. 1987, 71(9), 843-844.

\* cited by examiner

A431Lx cells

A431Lx cells

A431Lx cells

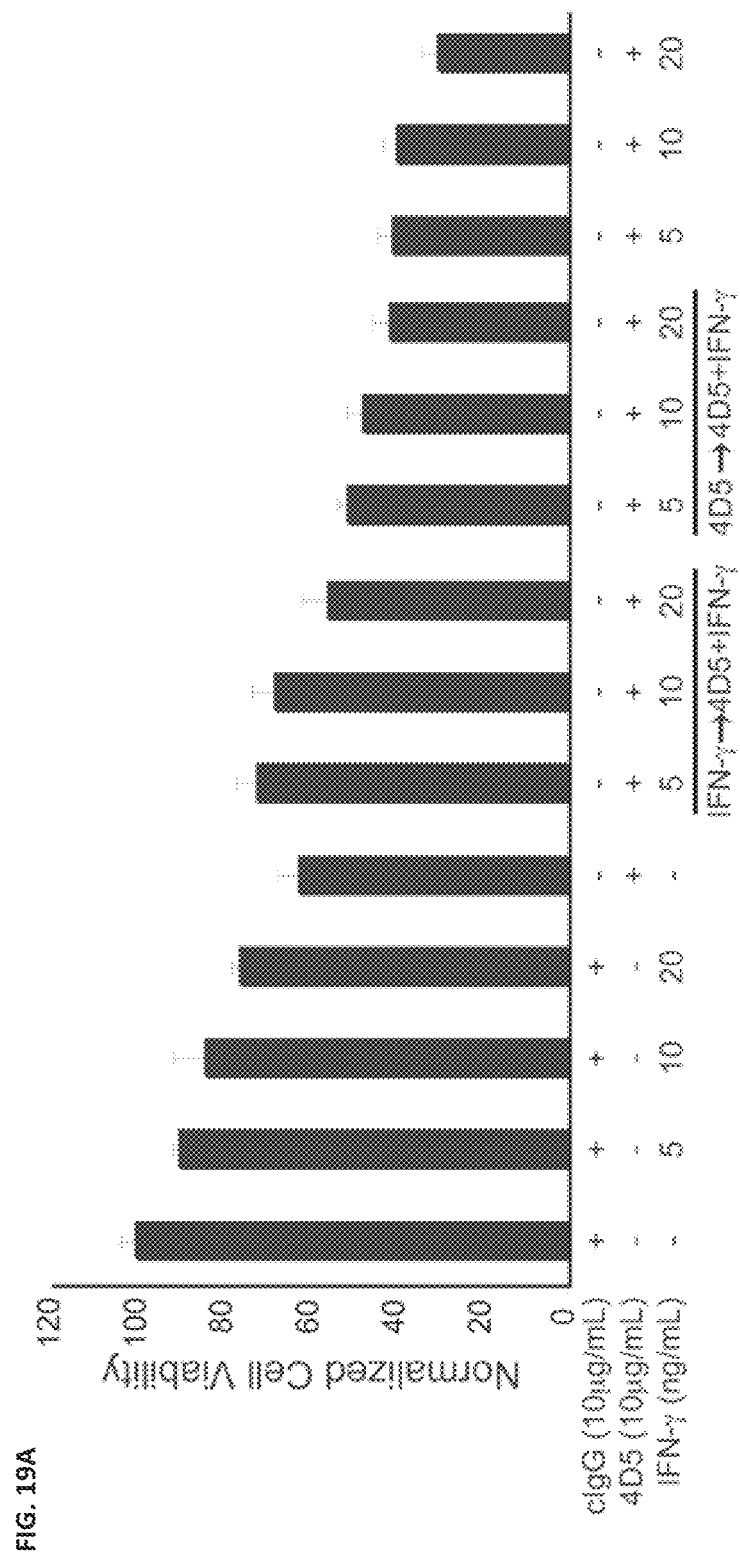

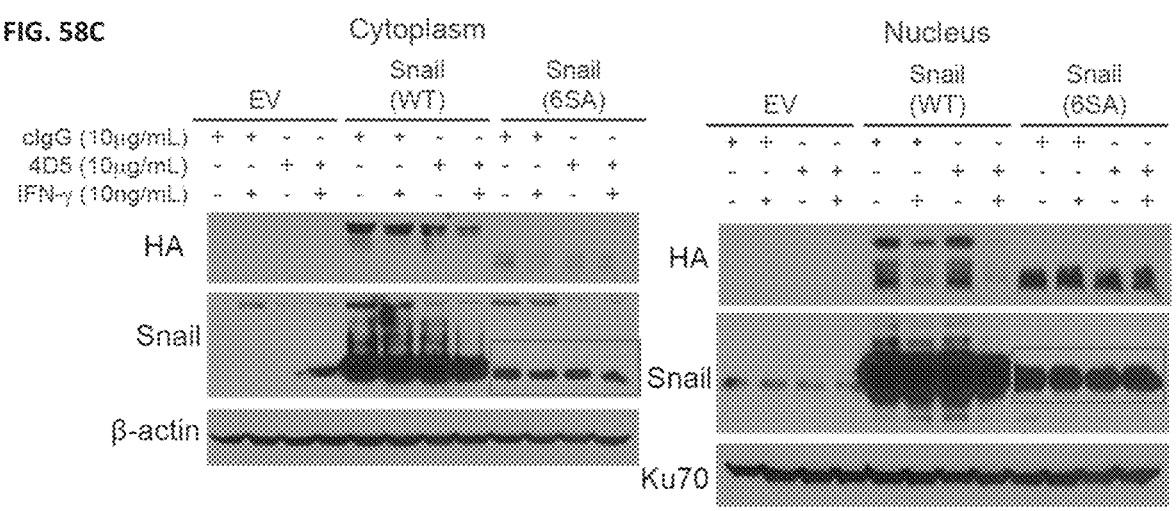

FIG. 60A
PD-L1 short
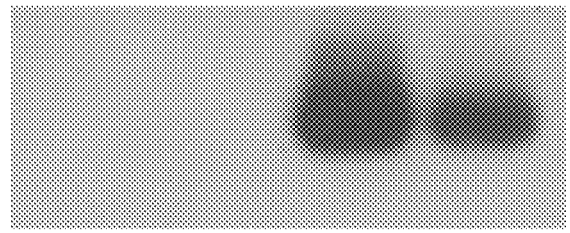
PD-L1 long
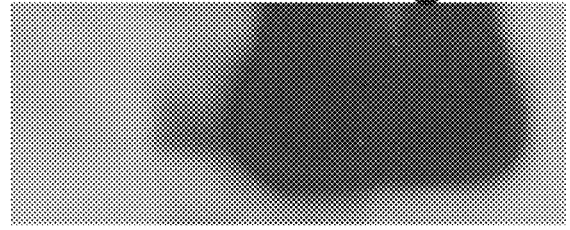
β-actin
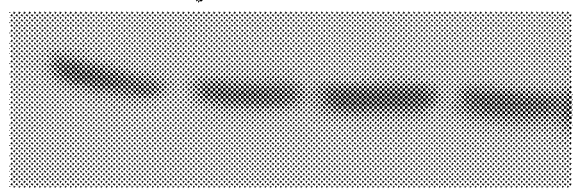
IgG    7.16.4    IFN-γ    7.16.4 + INF-γ

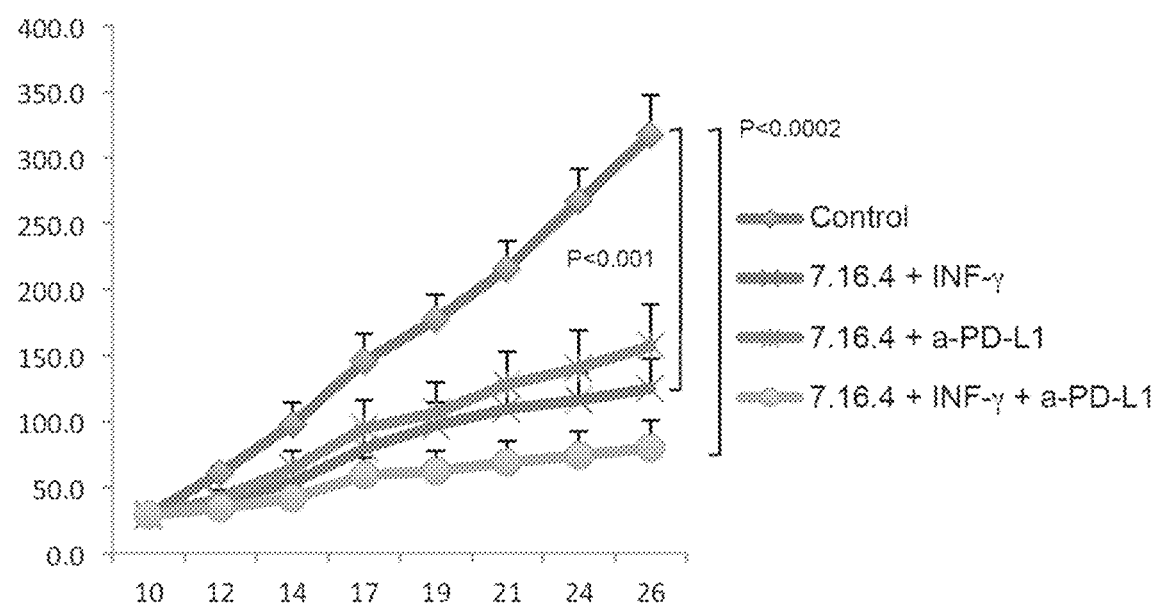

SEQUENCE LISTING

<160> NUMBER OF SEQ ID NOS: 9

<210> SEQ ID NO 1
<211> LENGTH: 324
<212> TYPE: PRT
<213> ORGANISM: Artificial Sequence
<220> FEATURE:
<223> OTHER INFORMATION: 4D5scFvZZ

<400> SEQUENCE: 1

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln His Tyr Thr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Val Asp Asn Lys Phe Asn Lys Glu Gln Gln Asn Ala Phe Tyr
            260                 265                 270

Glu Ile Leu His Leu Pro Asn Leu Asn Glu Glu Gln Arg Asn Ala Phe
        275                 280                 285

Ile Gln Ser Leu Lys Asp Asp Pro Ser Gln Ser Ala Asn Leu Leu Ala
    290                 295                 300

Glu Ala Lys Lys Leu Asn Asp Ala Gln Ala Pro Lys Leu Glu His His
305                 310                 315                 320

His His His His

<210> SEQ ID NO 2
<211> LENGTH: 464
<212> TYPE: PRT
<213> ORGANISM: Artificial Sequence
<220> FEATURE:
<223> OTHER INFORMATION: 4D5scFvZZ-IFN-gamma

<400> SEQUENCE: 2

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser Gly Gly Gly Gly Ser
                245                 250                 255

Val Asp Val Asp Asn Lys Phe Asn Lys Glu Gln Gln Asn Ala Phe Tyr
            260                 265                 270

Glu Ile Leu His Leu Pro Asn Leu Asn Glu Glu Gln Arg Asn Ala Phe
        275                 280                 285

Ile Gln Ser Leu Lys Asp Asp Pro Ser Gln Ser Ala Asn Leu Leu Ala
290                 295                 300

Glu Ala Lys Lys Leu Asn Asp Ala Gln Ala Pro Lys Leu Glu Gly Gly
305                 310                 315                 320

Gly Gly Ser Gln Asp Pro Tyr Val Lys Glu Ala Glu Asn Leu Lys Lys
            325                 330                 335

Tyr Phe Asn Ala Gly His Ser Asp Val Ala Asp Asn Gly Thr Leu Phe
        340                 345                 350

Leu Gly Ile Leu Lys Asn Trp Lys Glu Glu Ser Asp Arg Lys Ile Met
    355                 360                 365

Gln Ser Gln Ile Val Ser Phe Tyr Phe Lys Leu Phe Lys Asn Phe Lys
370                 375                 380

Asp Asp Gln Ser Ile Gln Lys Ser Val Glu Thr Ile Lys Glu Asp Met
385                 390                 395                 400

```
Asn Val Lys Phe Phe Asn Ser Asn Lys Lys Arg Asp Phe Glu
            405                 410                 415

Lys Leu Thr Asn Tyr Ser Val Thr Asp Leu Asn Val Gln Arg Lys Ala
            420                 425                 430

Ile His Glu Leu Ile Gln Val Met Ala Glu Leu Ser Pro Ala Ala Lys
            435                 440                 445

Thr Gly Lys Arg Lys Arg Ser Gln Leu Glu His His His His His His
    450                 455                 460

<210> SEQ ID NO 3
<211> LENGTH: 259
<212> TYPE: PRT
<213> ORGANISM: Artificial Sequence
<220> FEATURE:
<223> OTHER INFORMATION: 4D5scFv

<400> SEQUENCE: 3

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asn
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Gln Gln His Tyr Thr Thr
                85                  90                  95

Pro Pro Thr Phe Gly Gln Gly Thr Lys Val Glu Leu Lys Arg Ala Thr
            100                 105                 110

Pro Ser His Asn Ser His Gln Val Pro Ser Ala Gly Gly Pro Thr Ala
        115                 120                 125

Asn Ser Gly Glu Val Lys Leu Val Glu Ser Gly Gly Gly Leu Val Gln
    130                 135                 140

Pro Gly Gly Ser Leu Arg Leu Ser Cys Ala Thr Ser Gly Phe Asn Ile
145                 150                 155                 160

Lys Asp Thr Tyr Ile His Trp Val Arg Gln Ala Pro Gly Lys Gly Leu
                165                 170                 175

Glu Trp Val Ala Arg Ile Tyr Pro Thr Asn Gly Tyr Thr Arg Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ser Arg Trp Gly Gly Asp Gly Phe Tyr Ala Met Asp Tyr
225                 230                 235                 240

Trp Gly Gln Gly Thr Thr Val Thr Val Ser Ser Leu Glu His His His
                245                 250                 255

His His His

<210> SEQ ID NO 4
<211> LENGTH: 61
<212> TYPE: PRT
<213> ORGANISM: Artificial Sequence
<220> FEATURE:
```

<223> OTHER INFORMATION: ZZ

<400> SEQUENCE: 4

Ser Val Asp Val Asp Asn Lys Phe Asn Lys Glu Gln Gln Asn Ala Phe
1               5                   10                  15
Tyr Glu Ile Leu His Leu Pro Asn Leu Asn Glu Glu Arg Asn Ala
            20                  25                  30
Phe Ile Gln Ser Leu Lys Asp Asp Pro Ser Gln Ser Ala Asn Leu Leu
            35                  40                  45
Ala Glu Ala Lys Lys Leu Asn Asp Ala Gln Ala Pro Lys
        50                  55                  60

<210> SEQ ID NO 5
<211> LENGTH: 133
<212> TYPE: PRT
<213> ORGANISM: Artificial Sequence
<220> FEATURE:
<223> OTHER INFORMATION: IFN-gamma

<400> SEQUENCE: 5

Gln Asp Pro Tyr Val Lys Glu Ala Glu Asn Leu Lys Lys Tyr Phe Asn
1               5                   10                  15
Ala Gly His Ser Asp Val Ala Asp Asn Gly Thr Leu Phe Leu Gly Ile
            20                  25                  30
Leu Lys Asn Trp Lys Glu Glu Ser Asp Arg Lys Ile Met Gln Ser Gln
            35                  40                  45
Ile Val Ser Phe Tyr Phe Lys Leu Phe Lys Asn Phe Lys Asp Asp Gln
        50                  55                  60
Ser Ile Gln Lys Ser Val Glu Thr Ile Lys Glu Asp Met Asn Val Lys
65                  70                  75                  80
Phe Phe Asn Ser Asn Lys Lys Lys Arg Asp Asp Phe Glu Lys Leu Thr
                85                  90                  95
Asn Tyr Ser Val Thr Asp Leu Asn Val Gln Arg Lys Ala Ile His Glu
            100                 105                 110
Leu Ile Gln Val Met Ala Glu Leu Ser Pro Ala Ala Lys Thr Gly Lys
        115                 120                 125
Arg Lys Arg Ser Gln
        130

<210> SEQ ID NO 6
<211> LENGTH: 5
<212> TYPE: PRT
<213> ORGANISM: Artificial Sequence
<220> FEATURE:
<223> OTHER INFORMATION: Glycine-serine oligopeptide linker

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Glycine-serine oligopeptide linker

<400> SEQUENCE: 7

Gly Gly Gly Gly Gly Ser
1               5

```
<210> SEQ ID NO 8
<211> LENGTH: 28
<212> TYPE: DNA
<213> ORGANISM: Artificial Sequence
<220> FEATURE:
<223> OTHER INFORMATION: snail 6SA insert forward primer

<400> SEQUENCE: 8
aaagaagctt atgccgcgct ctttcctc                                          28

<210> SEQ ID NO 9
<211> LENGTH: 32
<212> TYPE: DNA
<213> ORGANISM: Artificial Sequence
<220> FEATURE:
<223> OTHER INFORMATION: snail 6SA insert reverse primer

<400> SEQUENCE: 9
aaagtctaga tcagcgggga catcctgagc ag                                     32
```

METHODS OF INCREASING RESPONSE TO CANCER RADIATION THERAPY

This application is a continuation of U.S. application Ser. No. 15/019,924, filed Feb. 9, 2016, which is (a) a continuation-in-part of PCT International Application No. PCT/US2014/050442, filed on Aug. 8, 2014, claiming benefit of U.S. Provisional Application No. 61/864,509, filed Aug. 9, 2013; (b) claims the benefit of U.S. Provisional Application No. 62/115,011, filed Feb. 11, 2015; and (c) claims the benefit of U.S. Provisional Application No. 62/220,138, filed Sep. 17, 2015, the content of each of the foregoing applications is hereby incorporated by reference in its entirety.

This invention was made with government support under grant numbers R01 CA055306, R01 CA149425, R01 CA089481, T32 CA009140, and P30 CA016520 awarded by the National Institutes of Health. The U.S. Government has certain rights in the invention.

This application incorporates-by-reference nucleotide and/or amino acid sequences which are present in the file named "PENN_002_05US_SeqList_ST25.txt", which is about 12.0 kilobytes in size, and which was created Jul. 13, 2021 in a computer readable format.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF INVENTION

The erbB family of receptors includes erbB1 (EGFR), erbB2 (p185her2/neu), erbB3 and erbB4. Ullrich, et al. (1984) Nature 309, 418-425, which is incorporated herein by reference, describes EGFR. Schechter, A. L., et al. (1984) Nature 312, 513-516, and Yamamoto, T., et al. (1986) Nature 319, 230-234, which are each incorporated herein by reference, describe p185neu/erbB2. Kraus, M. H., et al. (1989) Proc. Natl. Acad. Sci. USA 86, 9193-9197 which is incorporated herein by reference, describes erbB3. Plowman, G. D., (1993) Proc. Natl. Acad. Sci. USA 90, 1746-1750, which is incorporated herein by reference, describes erbB4.

The rat cellular protooncogene c-neu and its human counterpart c-erbB2 encode 185 kDa transmembrane glycoproteins termed p185her2/neu. Tyrosine kinase (tk) activity has been linked to expression of the transforming phenotype of oncogenic p185her2/neu (Bargmann et al., Proc. Natl. Acad. Sci. USA, 1988, 85, 5394; and Stem et al., Mol. Cell. Biol., 1988, 8, 3969, each of which is incorporated herein by reference). Oncogenic neu was initially identified in rat neuroglioblastomas (Schechter et al., Nature, 1984, 312, 513, which is incorporated herein by reference) and was found to be activated by a carcinogen-induced point mutation generating a single amino acid substitution, a Val to Glu substitution at position 664, in the transmembrane region of the transforming protein (Bargmann et al., Cell, 1986, 45, 649, which is incorporated herein by reference). This alteration results in constitutive activity of its intrinsic kinase and in malignant transformation of cells (Bargmann et al., EMBO J., 1988, 7, 2043, which is incorporated herein by reference). The activation of the oncogenic p185her2/neu protein tyrosine kinase appears to be related to a shift in the molecular equilibrium from monomeric to dimeric forms (Weiner et al., Nature, 1989, 339, 230, which is incorporated herein by reference).

Overexpression of c-neu or c-erbB2 to levels 100-fold higher than normal (i.e., $>10^6$ receptors/cell) also results in the transformation of NIH3T3 cells (Chazin et al., Oncogene, 1992, 7, 1859; DiFiore et al., Science, 1987, 237, 178; and DiMarco et al., Mol. Cell. Biol., 1990, 10, 3247, each of Which is incorporated herein by reference). However, NIH3T3 cells or NR6 cells which express cellular p185her2/neu at the level of $10^5$ receptors/cell are not transformed (Hung et al., Proc. Natl. Acad. Sci. USA, 1989, 86, 2545; and Kokai et al., Cell, 1989, 58, 287, each of which is incorporated herein by reference), unless co-expressed with epidermal growth factor receptor (EGFR), a homologous tyrosine kinase (Kokai et al, Cell, 1989, 58, 287, which is incorporated herein by reference). Thus, cellular p185her2/neu and oncogenic p185her2/neu may both result in the transformation of cells.

Cellular p185her2/neu is highly homologous with EGFR (Schechter et al., Nature, 1984, 312, 513; and Yamamoto et al., Nature, 1986, 319, 230, each of which is incorporated herein by reference) but nonetheless is distinct. Numerous studies indicate that EGFR and cellular p185her2/neu are able to interact (Stem et al., Mol. Cell. Biol., 1988, 8, 3969; King et al., EMBO J., 1988, 7, 1647; Kokai et al., Proc. Natl. Acad. Sci. USA, 1988, 85, 5389; and Dougall et al., J. Cell. Biochem., 1993, 53, 61; each of which is incorporated herein by reference). The intermolecular association of EGFR and cellular p185her2/neu appear to up-regulate EGFR function (Wada et al., Cell, 1990, 61, 1339, which is incorporated herein by reference). In addition, heterodimers which form active kinase complexes both in vivo and in vitro can be detected (Qian et al., Proc. Natl. Acad. Sci. USA, 1992, 89, 1330, which is incorporated herein by reference).

Similarly, p185her2/neu interactions with other erbB family members have been reported (Carraway et al., Cell 1994, 78, 5-8; Alroy et al., FEBS Lett. 1997, 410, 83-86; Riese et al., Mol. Cell. Biol. 1995, 15, 5770-5776; Tzahar et al., EMBO J. 1997, 16, 4938-4950; Surden et al., Neuron 1997, 18, 847-855; Pinkas-Kramarski et al., Oncogene 1997, 15, 2803-2815; each of which is incorporated herein by reference). Human p185her2/neu forms heterodimers with either erbB3 or erbB4 under physiologic conditions, primarily in cardiac muscle and the nervous system, particularly in development.

Cellular p185her2/neu proteins are found in adult secretory epithelial cells of the lung, salivary gland, breast, pancreas, ovary, gastrointestinal tract, and skin (Kokai et al., Proc. Natl. Acad. Sci. USA, 1987, 84, 8498; Mori et al., Lab. Invest, 1989, 61, 93; and Press et al., Oncogene, 1990, 5, 953; each of which is incorporated herein by reference). Recent studies have found that the amplification of c-erbB2 occurs with high frequency in a number of human adenocarcinomas such as gastric (Akiyama et al., Science, 1986, 232, 1644, which is incorporated herein by reference), lung (Kern et al., Cancer Res., 1990, 50, 5184, which is incorporated herein by reference) and pancreatic adenocarcinomas (Williams et al., Pathobiol, 1991, 59, 46, which is incorporated herein by reference). It has also been reported that increased c-erbB2 expression in a subset of breast and ovarian carcinomas is linked to a less optimistic clinical prognosis (Slamon et al., Science, 1987, 235, 177; and Slamon et al., Science, 1989, 244, 707, each of which is incorporated herein by reference). Heterodimeric association of EGFR and p185her2/neu has also been detected in human breast cancer cell lines, such as SK-Br-3 (Goldman et al., Biochemistry, 1990, 29, 1 1024, which is incorporated herein by reference), and transfected cells (Spivak-Kroizman et al., J. Biol. Chem, 1992, 267, 8056, which is incorporated herein by reference). Additionally, cases of erbB2 and EGFR coexpression in cancers of the breast and prostate have been reported. In addition, heterodimeric association of p185her2/neu and erbB3 as well as heterodimeric association of p185her2/neu and erbB4 have also been detected in human cancers. Coexpression of erbB2 and erbB3 has been observed in human breast cancers. Coexpression of EGFR, erbB2, and erbB3 has been seen in prostate carcinoma.

Amplification and/or alteration of the EGFr gene is frequently observed in glial tumor progression (Sugawa, et al. (1990) Proc. Natl. Acad. Sci. 87: 8602-8606; Ekstrand, et al. (1992) Proc. Natl. Acad. Sci. 89: 4309-4313), particularly in glioblastoma, the most malignant glial tumor (Libermann, et al. Supra; Wong, et al. Supra; James, et al. (1988) Cancer Res. 48: 5546-5551; Cavenee, W. K. (1992) Cancer 70:1788-93; Nishikawa, et al., (1994) Proc. Natl. Acad. Sci. 91: 7727 7731; Schlegel, et al. (1994) Int J. Cancer 56: 72-77). A significant proportion of these tumors show EGFr amplification with or without gene alteration (Ekstrand, et al. Supra; Libermann, et al. Supra; Wong, et al. (1987) Proc. Natl. Acad. Sci. 84:6899-6903), and this has been correlated with a shorter interval to disease recurrence and poorer survival (Schlegel, et al. Supra).

EGFr amplification can be associated with aberrant EGFr transcripts along with normal EGFr transcripts (Sugawa, et al. Supra). Frequent amplification and subsequent structural alteration suggests the EGFr may be important for the maintenance of the phenotype of malignant glioma. A frequently observed EGFr mutant has been identified in a subset of human glioblastomas and results from an in-frame truncation of 801 bp (corresponding to exons 2-7) in the extracellular domain of the receptor (Sugawa, et al. Supra; Ekstrand, et al. Supra; Malden, et al. (1988) Cancer Res. 48: 2711-2714; Humphrey, et al. (1990) Proc. Natl. Acad. Sci. 87: 4207-4211; Wong, et al. (1992) Proc. Natl. Acad. Sci. 89: 2965-2969), which is thought to result in constitutive kinase activation and may also affect the ligand-binding properties of the molecule (Nishikawa, et al. Supra; Callaghan, et al. (1993) Oncogene 8: 2939-2948).

Observed mutations of EGFr in human epithelial malignancies consist of overexpression with or without amplification and, less commonly, of coding sequence alterations. Oncogenic transformation caused by mutants of EGFr appear to be tissue-specific and have been observed in erythroid leukemia, fibrosarcoma, angiosarcoma, melanoma, as well as glioblastoma (Carter, et al. (1994) Crit Rev Oncogenesis 5:389-428). Overexpression of the normal EGFr may cause oncogenic transformation in certain cases, probably in an EGF-dependent manner (Carter, et al. Supra; Haley, et al. (1989) Oncogene 4: 273-283). Transfection of high amounts of wild-type EGFr into NIH3T3 cells results in ligand-dependent but incomplete transformation (YamaZaki, et al. (1990) Jpn. J. Cancer Res. 81: 773-779). Overexpression may cause altered cell-cycle regulation of the EGFr kinase, and contribute to the transformed state, as has been observed for oncogenic p185neu (Kiyokawa, et al. (1995) Proc. Natl. Acad. Sci. 92:1092-1096).

There is a need for therapeutic compositions useful to treat individuals identified as having erbB2/Her2/neu or EGFR-mediated tumors. There is a need for methods of treating individuals identified as having erbB2/Her2/neu or EGFR-mediated tumors.

SUMMARY OF THE INVENTION

The present invention provides a fusion protein comprising
(a) a first stretch of consecutive amino acids, the sequence of which is the sequence of an anti-p185her2/neu polypeptide;
(b) a second stretch of consecutive amino acids, the sequence of which is the sequence of a polypeptide capable of binding at least one polypeptide other than p185her2/neu; and
(c) a third stretch of consecutive amino acids, the sequence of which comprises the sequence of a biologically active portion of interferon-gamma (IFNγ),
wherein (b) is located at the carboxy-terminal end of (a), and (c) is located at the carboxy-terminal end of (b).

The present invention provides a method of treating a subject afflicted with cancer, which comprises administering to the subject a therapeutically effective amount of a fusion protein of the invention.

The present invention provides a method of sensitizing cancer cells to radiation or a chemotherapeutic agent, which comprises contacting the cancer cells with
i) an anti-p185her2/neu antibody and interferon-gamma (IFNγ); or
ii) a fusion protein of the invention.

The present invention provides a method of sensitizing cells of a cancer in a subject afflicted with the cancer to radiation or a chemotherapeutic agent, which comprises administering to the subject
i) an anti-p185her2/neu antibody and interferon-gamma (IFNγ); or
ii) a fusion protein of the invention.

The present invention provides a method of treating a subject afflicted with cancer, which comprises
a) sensitizing cells of the cancer, and cells that have undergone epithelial to mesenchymal transition (EMT) or are undergoing EMT, to radiation or a chemotherapeutic agent by administering to the subject
i) an anti-p185her2/neu antibody and interferon-gamma (IFNγ); or
ii) a fusion protein of the invention, and
b) thereafter administering radiation or a chemotherapeutic agent to the subject.

The present invention provides a method of treating a subject afflicted with cancer or preventing the development of a tumor in a subject at risk of developing the tumor, which comprises
a) sensitizing a cancer cell to radiation or a chemotherapeutic agent by
i) administering to the subject an anti-p185her2/neu antibody which inhibits p185her2/neu signaling in the cancer cell, wherein said inhibition converts the phenotype of the cancer cell such that the cancer cell is amenable to further phenotypic change by interferon-gamma (IFNγ), and concurrently or subsequently administering IFNγ which induces further phenotypic change in the cancer cell; or
ii) administering to the subject a fusion protein of the invention, wherein the first stretch of consecutive amino acids of the fusion protein inhibits p185her2/neu signaling in a cancer cell, wherein said inhibition converts the phenotype of the cancer cell such that the cancer cell is amenable to further phenotypic change by interferon-gamma (IFNγ), and the third stretch of consecutive amino acids of the fusion protein induces further phenotypic change in the cancer cell; and b) thereafter administering a therapeutically effective amount of radiation or a chemotherapeutic agent to the subject.

The present invention provides a composition for the treatment of a subject afflicted with cancer, comprising
i) a fusion protein of the invention; or
ii) an anti-p185her2/neu antibody and interferon-gamma (IFNγ),
and a pharmaceutically acceptable carrier.

The present invention provides a composition for sensitizing cancer to radiation or a chemotherapeutic agent, comprising
i) a fusion protein of the invention; or
ii) an anti-p185her2/neu antibody and interferon-gamma (IFNγ),
and a pharmaceutically acceptable carrier.

The present invention provides a composition for sensitizing a tumor to radiation or a chemotherapeutic agent, comprising
i) a fusion protein of the invention; or
ii) an anti-p185her2/neu antibody and interferon-gamma (IFNγ),
and a pharmaceutically acceptable carrier.

The present invention provides a fusion protein comprising
(a) a first stretch of consecutive amino acids, the sequence of which is the sequence of an anti-EGFR polypeptide;
(b) a second stretch of consecutive amino acids, the sequence of which is the sequence of a polypeptide capable of binding at least one polypeptide other than EGFR; and
(c) a third stretch of consecutive amino acids, the sequence of which comprises the sequence of a biologically active portion of interferon-gamma (IFNγ),
wherein (b) is located at the carboxy-terminal end of (a), and (c) is located at the carboxy-terminal end of (b).

The present invention provides a method of treating a subject afflicted with cancer, which comprises administering to the subject a therapeutically effective amount of the fusion protein of the invention.

The present invention provides a method of sensitizing cancer cells to radiation or a chemotherapeutic agent, which comprises contacting the cancer cells with
i) an anti-EGFR antibody and interferon-gamma (IFNγ); or
ii) a fusion protein of the invention.

The present invention provides a method of sensitizing cells of a cancer in a subject afflicted with the cancer to radiation or a chemotherapeutic agent, which comprises administering to the subject
i) an anti-EGFR antibody and interferon-gamma (IFNγ); or
ii) a fusion protein of the invention.

The present invention provides a method of treating a subject afflicted with cancer, which comprises
a) sensitizing cells of the cancer, and cells that have undergone epithelial to mesenchymal transition (EMT) or are undergoing EMT, to radiation or a chemotherapeutic agent by administering to the subject
i) an anti-EGFR antibody and interferon-gamma (IFNγ); or
ii) a fusion protein of the invention, and
b) thereafter administering radiation or a chemotherapeutic agent to the subject.

The present invention provides a method of treating a subject afflicted with cancer or preventing the development of a tumor in a subject at risk of developing the tumor, which comprises a) sensitizing a cancer cell to radiation or a chemotherapeutic agent by
i) administering to the subject an anti-EGFR antibody which inhibits EGFR signaling in the cancer cell, wherein said inhibition converts the phenotype of the cancer cell such that the cancer cell is amenable to further phenotypic change by interferon-gamma (IFNγ), and concurrently or subsequently administering IFNγ which induces further phenotypic change in the cancer cell; or
ii) administering to the subject a fusion protein of the invention, wherein the first stretch of consecutive amino acids of the fusion protein inhibits EGFR signaling in a cancer cell, wherein said inhibition converts the phenotype of the cancer cell such that the cancer cell is amenable to further phenotypic change by interferon-gamma (IFNγ), and the third stretch of consecutive amino acids of the fusion protein induces further phenotypic change in the cancer cell; and
b) thereafter administering a therapeutically effective amount of radiation or a chemotherapeutic agent to the subject.

The present invention provides a composition for the treatment of a subject afflicted with cancer, comprising
i) a fusion protein of the invention; or
ii) an anti-EGFR antibody and interferon-gamma (IFNγ),
and a pharmaceutically acceptable carrier.

The present invention provides a composition for sensitizing cancer to radiation or a chemotherapeutic agent, comprising
i) a fusion protein of the invention; or
ii) an anti-EGFR antibody and interferon-gamma (IFNγ),
and a pharmaceutically acceptable carrier.

The present invention provides a composition for sensitizing a tumor to radiation or a chemotherapeutic agent, comprising
i) a fusion protein of the invention; or
ii) an anti-EGFR antibody and interferon-gamma (IFNγ),
and a pharmaceutically acceptable carrier.

The present invention provides a polynucleotide encoding a fusion protein of the invention.

The present invention provides an expression vector comprising a polynucleotide of the invention operably linked to a promoter.

The present invention provides a cell comprising a expression vector of the invention.

The present invention provides a method of inhibiting development into cancer cells of breast cells that overexpress p185her2/neu in a subject in need of such inhibition which comprises administering to said subject
i) a fusion protein of the invention; or
ii) an anti-p185her2/neu antibody and interferon-gamma (IFNγ),
each in a sufficient amount to down regulate the overexpressed p185her2/neu and inhibit the development of said breast cells that overexpress p185her2/neu into breast cancer cells.

The present invention provides a method of inhibiting development into cancer cells of breast cells that overexpress EGFR in a subject in need of such inhibition which comprises administering to said subject
i) a fusion protein of the invention; or
ii) an anti-EGFR antibody and interferon-gamma (IFNγ),
each in a sufficient amount to down regulate the overexpressed p185 and inhibit the development of said breast cells that overexpress p185 into breast cancer cells.

The present invention provides a method of sensitizing cancer cells to radiation or a chemotherapeutic agent, which comprises contacting the cancer cells with i) an erbB inhibitor; and
ii) interferon-gamma (IFNγ).

The present invention also provides a method of sensitizing cells of a cancer in a subject afflicted with the cancer to radiation or a chemotherapeutic agent, which comprises administering to the subject
i) an erbB inhibitor; and
ii) interferon-gamma (IFNγ).

The present invention further provides a method of treating a subject afflicted with cancer, which comprises
a) sensitizing cells of the cancer, and cells that have undergone epithelial to mesenchymal transition (EMT) or are undergoing EMT, to radiation or a chemotherapeutic agent by administering to the subject
i) an erbB inhibitor; and
ii) interferon-gamma (IFNγ), and
b) thereafter administering radiation or a chemotherapeutic agent to the subject.

The present invention also provides a method of treating a subject afflicted with cancer or preventing the development of a tumor in a subject at risk of developing the tumor, which comprises
a) sensitizing a cancer cell to radiation or a chemotherapeutic agent by
i) administering to the subject an erbB inhibitor which inhibits EGFR signaling or p185her2/neu signaling in the cancer cell, wherein said inhibition converts the phenotype of the cancer cell such that the cancer cell is amenable to further phenotypic change by interferon-gamma (IFNγ), and concurrently or subsequently administering IFNγ which induces further phenotypic change in the cancer cell; and
b) thereafter administering a therapeutically effective amount of radiation or a chemotherapeutic agent to the subject.

The present invention provides a method of treating a subject afflicted with a tumor associated with EGFR or p185her2/neu or preventing development of a tumor associated with EGFR or p185her2/neu in a subject, which comprises administering to the subject
i) an erbB inhibitor; and
ii) interferon-gamma (IFNγ).

The present invention provides a method of inhibiting development into cancer cells of breast cells that overexpress p185her2/neu in a subject in need of such inhibition which comprises administering to said subject
i) an erbB inhibitor; and
ii) interferon-gamma (IFNγ),
each in a sufficient amount to down regulate the overexpressed p185her2/neu and inhibit the development of said breast cells that overexpress p185her2/neu into breast cancer cells.

The present invention also provides a method of inhibiting development into cancer cells of breast cells that overexpress EGFR in a subject in need of such inhibition which comprises administering to said subject
i) an erbB inhibitor; and
ii) interferon-gamma (IFNγ),
each in a sufficient amount to down regulate the overexpressed p185 and inhibit the development of said breast cells that overexpress p185 into breast cancer cells.

Aspects of the present invention relate to a composition for the treatment of a subject afflicted with cancer, comprising i) an erbB inhibitor; and ii) interferon-gamma (IFNγ), and a pharmaceutically acceptable carrier.

Aspects of the present invention also relate to a composition for sensitizing cancer to radiation or a chemotherapeutic agent, comprising i) an erbB inhibitor; and ii) interferon-gamma (IFNγ), and a pharmaceutically acceptable carrier.

Aspects of the present invention relate to a composition for preventing the development of a tumor in a subject at risk of developing the tumor, comprising i) an erbB inhibitor; and ii) interferon-gamma (IFNγ), and a pharmaceutically acceptable carrier.

Aspects of the present invention also relate to a composition for sensitizing a tumor to radiation or a chemotherapeutic agent, comprising i) an erbB inhibitor; and ii) interferon-gamma (IFNγ), and a pharmaceutically acceptable carrier.

Aspects of the present invention relate to a combination for the treatment of a subject afflicted with cancer or preventing the development of a tumor in a subject at risk of developing the tumor, comprising i) an erbB inhibitor; and ii) interferon-gamma (IFNγ), and a pharmaceutically acceptable carrier.

BRIEF DESCRIPTION OF THE DRAWINGS

FIG. 2A. Comparison of 4D5scFvZZ (SEQ ID NO: 1) and 4D5scFvZZIFNγ. Tumors were palpable 5 days after inoculation of transformed T6-17 cells. Mice were treated with control (PBS), 4D5 mAb (1 mg/kg, twice; then mg/kg twice, for a total of 4 treatments in 2 weeks), 4D5scFvZZIFNγ (7 mg/kg, 5 times per week), or 4D5scFvZZ (SEQ ID NO: 1) (7 mg/kg, 5 times per week). Tumor growth in the 4D5scFvZZIFNγ group was much suppressed compared with other groups. FIG. 2B. Dose-dependent activity of 4D5scFvZZIFNγ. Mice were treated with control (PBS), 4D5 mAb (1 mg/kg, twice per week), or 4D5scFvZZIFNγ (7 mg/kg, or 1.75 mg/kg, 5 times per week). Tumor growth was dose-dependently suppressed by 4D5scFvZZIFNγ.

1) were provided to mice (3 mg/kg/dose, 5 times per week) started two days after inoculation. Error bars represent the standard error of mean. * & **: The size of tumors was significantly different from the controls (t test, *: p<0.05; **: p<0.01).

Figure 6:
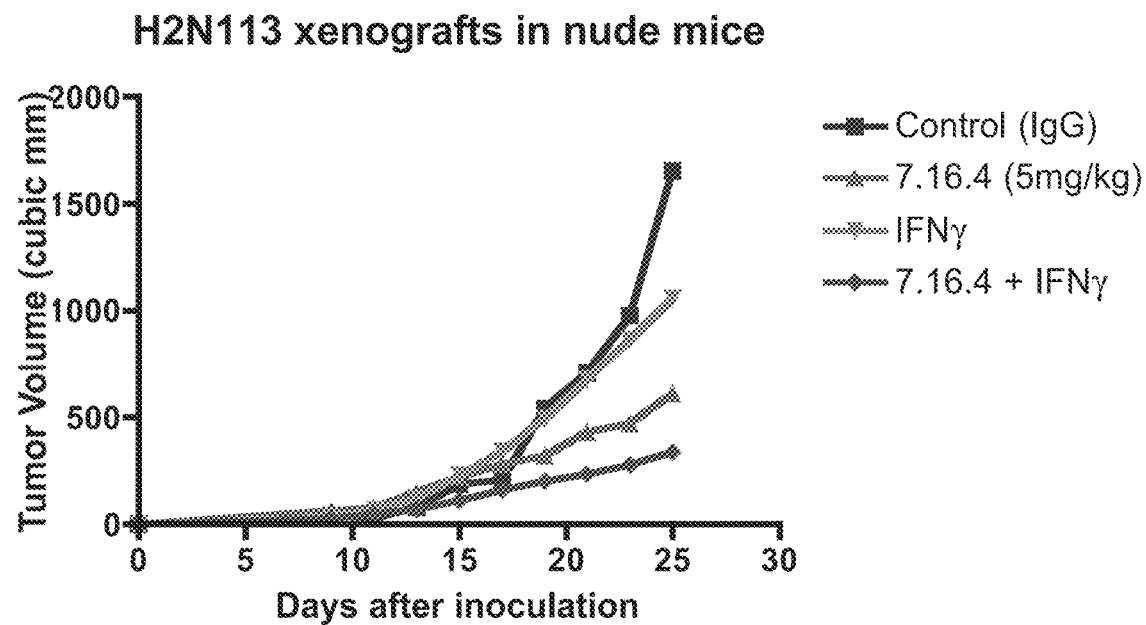

FIG. 6. The enhanced activity of IFNγ and 7.16.4 can be seen in nude mice

Figure 7:
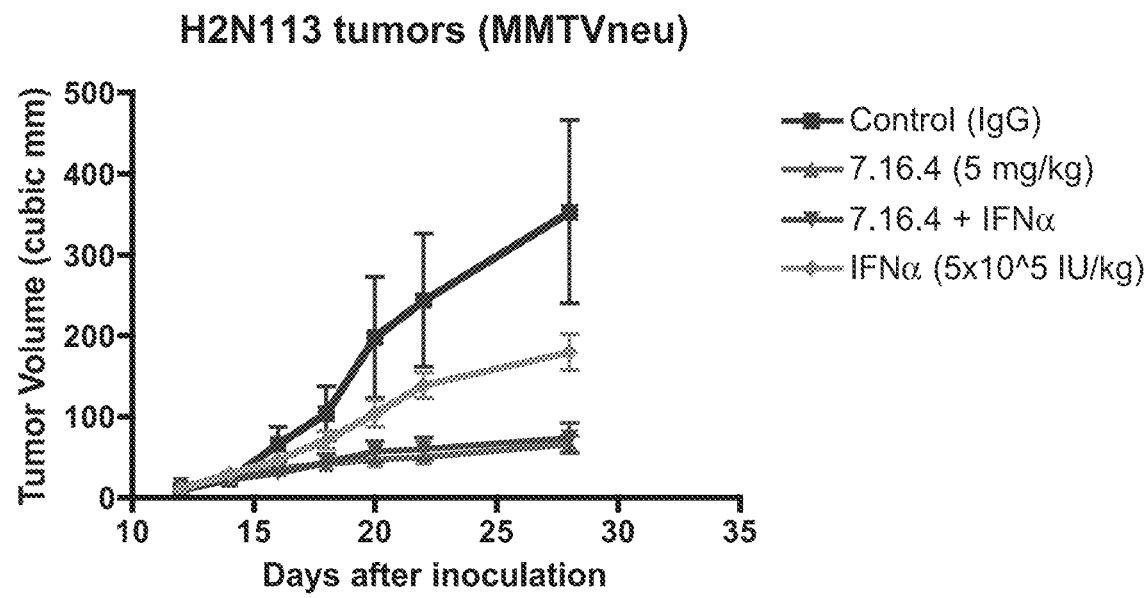

FIG. 7. IFNα appears not to have the same activity as IFNγ to facilitate anti-Her2/neu antibody. IFNα appears to have anti-tumor activity on its own in the in vivo tumor model but it could not enhance mAb 7.16.4 activity to suppress the growth of xenografted tumors.

Figure 8:
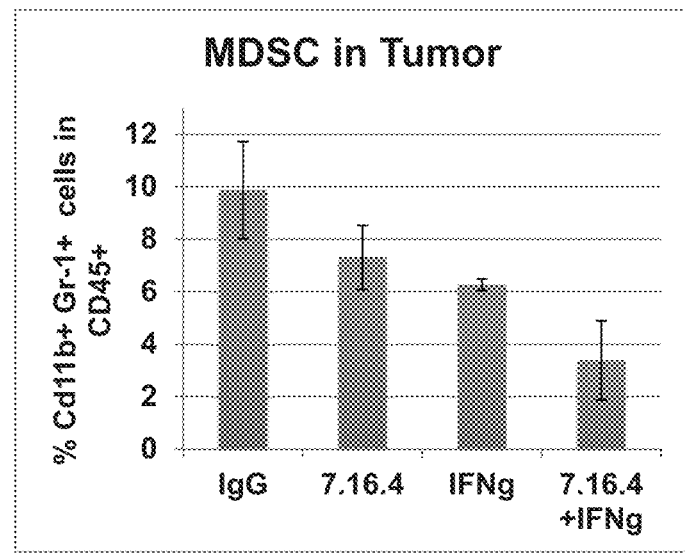

FIG. 8. Effect of co-treatment on MDSC.

Figure 9:
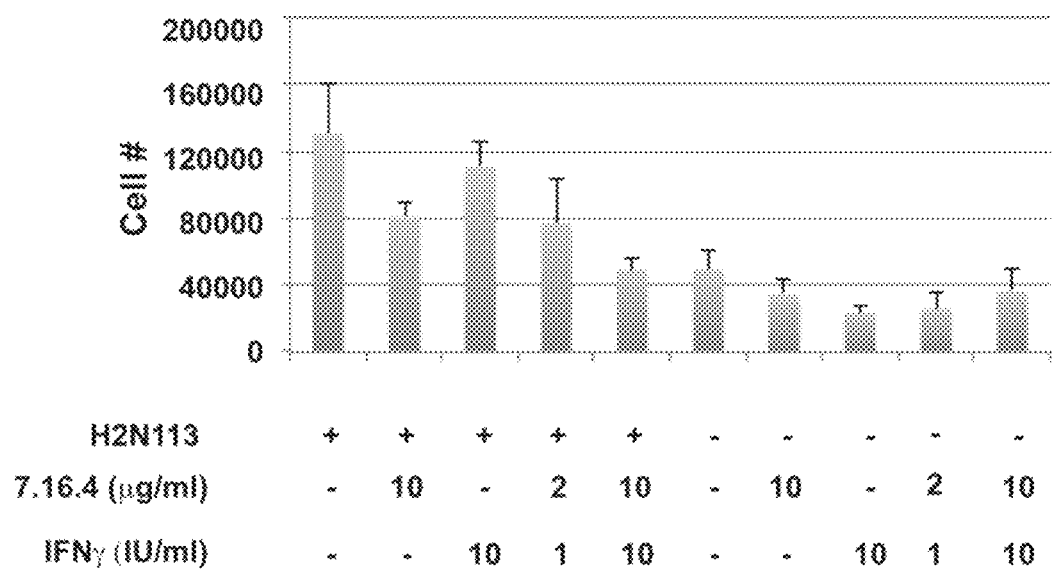

FIG. 9. Total cells migrated to the lower chamber.

Figure 10:
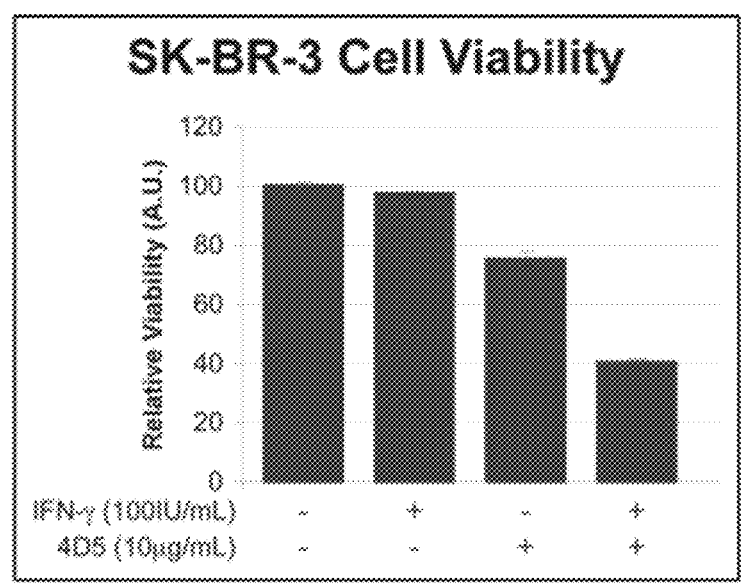

FIG. 10. IFN-γ and 4D5 exhibit enhanced activity on breast cancer cells in vitro. SK-BR-3 cells were treated for eight days with IFN-γ (100 IU/mL), 4D5 (10 μg/mL), or both. On the eighth day, cell viability was measured by MTT assay. Preliminary experiments revealed that combination of IFN-γ and 4D5 for the entire eight days was superior to pre-treatment with 4D5 for four days followed by addition of IFN-γ with 4D5 for the final four days or pre-treatment with IFN-γ followed by addition 4D5 with IFN-γ for the final four days (the latter had no effect).

Figure 11:
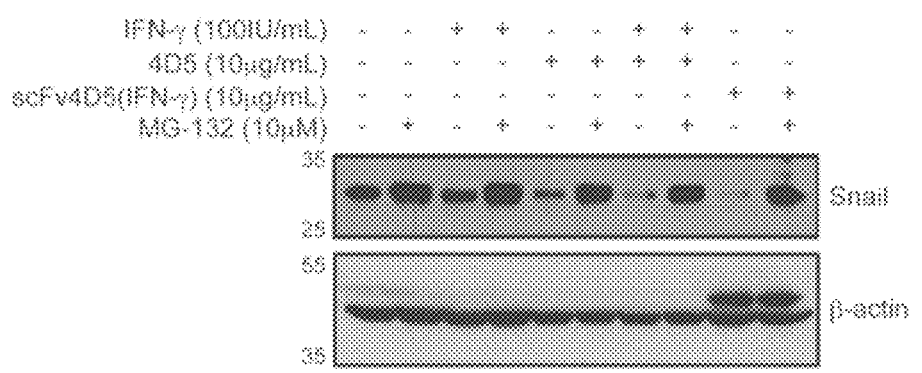

FIG. 11. IFN-γ and 4D5-mediated Snail degradation is mediated through the proteasome. SK-BR-3 cells were treated with IFN-γ (100 IU/mL), 4D5 (10 μg/mL), IFN-γ+ 4D5, or scFv4D5(IFN-γ) (10 μg/mL) for 24 hours in the presence or absence of the proteasome inhibitor, MG-132 (10 μM). After treatment, cells were lysed and Snail content was assayed by Western blot; β-actin was used as a loading control.

Figure 12:
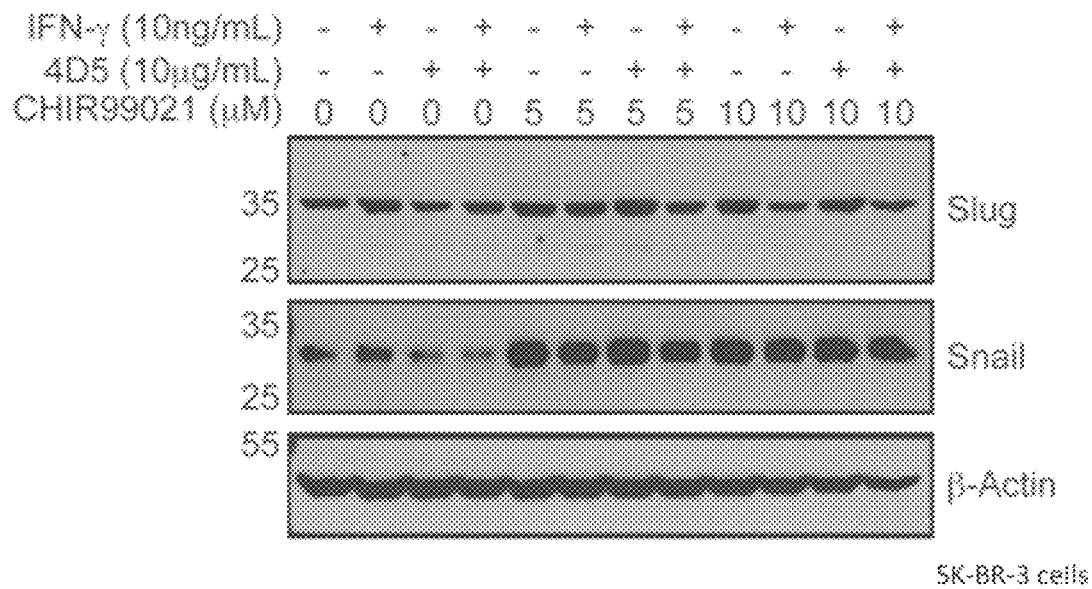

FIG. 12. IFN-γ and 4D5-mediated Snail degradation requires GSK-3β SK-BR-3 cells were treated with IFN-γ (10 ng/mL), 4D5 (10 μg/mL), or both for 24 hours along with the indicated concentration of the GSK-3β inhibitor, CHIR99021. After treatment, cells were lysed and Snail and Slug content was assayed by Western blot; β-actin was used as a loading control.

Figure 13:
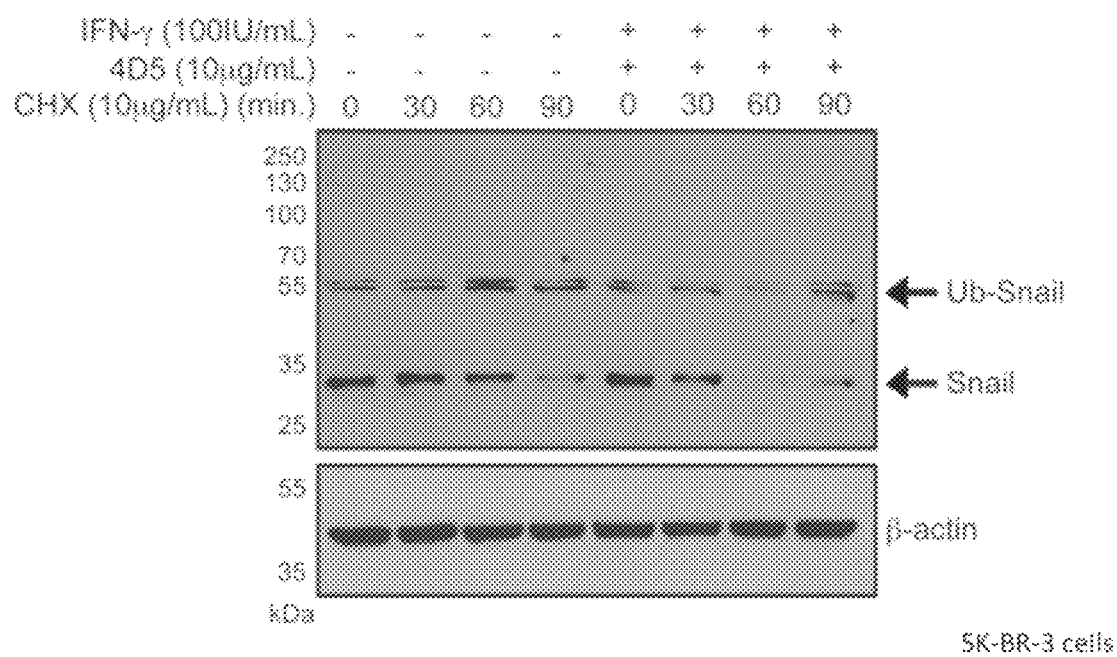

FIG. 13. IFN-γ and 4D5 decreases Snail Half-Life. SK-BR-3 cells were treated as control or IFN-γ (100 IU/mL)+ 4D5 (10 μg/mL) in combination with the translation inhibitor, cycloheximide (CHX, 10 μg/mL) for the indicated times. After treatment, cells were lysed and Snail content was assayed by Western blot; β-actin was used as a loading control. Ub-Snail indicates likely ubiquitinated forms of Snail.

Figure 14:
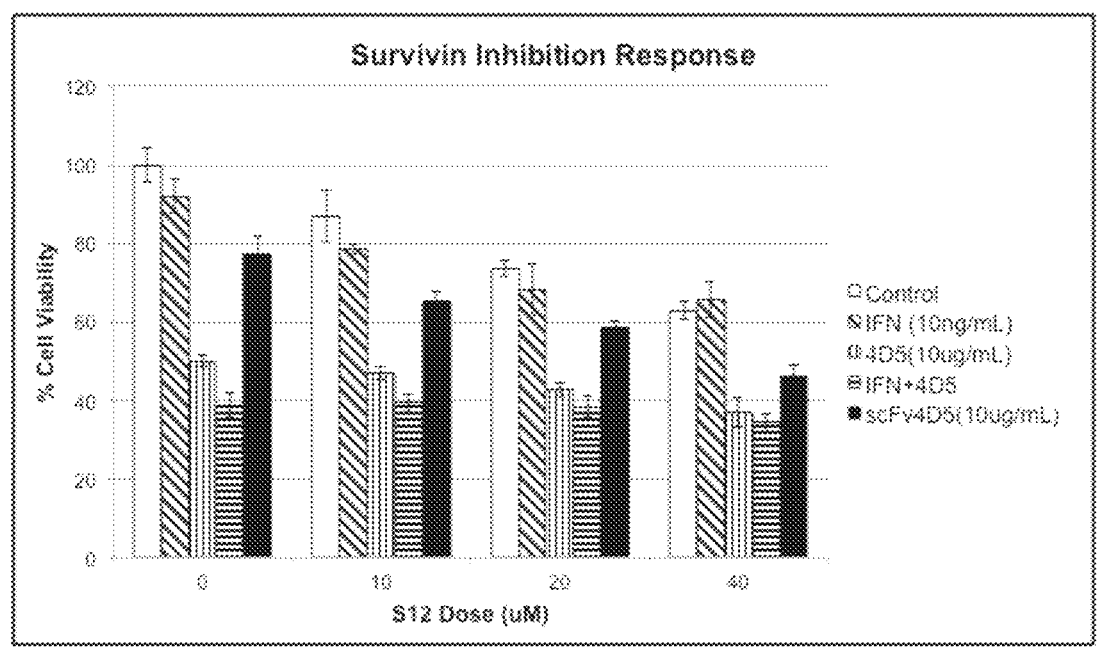

FIG. 14. Survivin Inhibition Response. SK-BR-3 cells were pretreated with IFN-γ (10 ng/mL), 4D5 (10 μg/mL), IFN-γ+4D5, or scFv4D5(IFN-γ) (10 μg/mL) for 24 hours followed by the addition of the Survivin inhibitor, S12 at the indicated doses. Forty-eight hours later, cell viability was measured by MTT assay.

Figure 15:
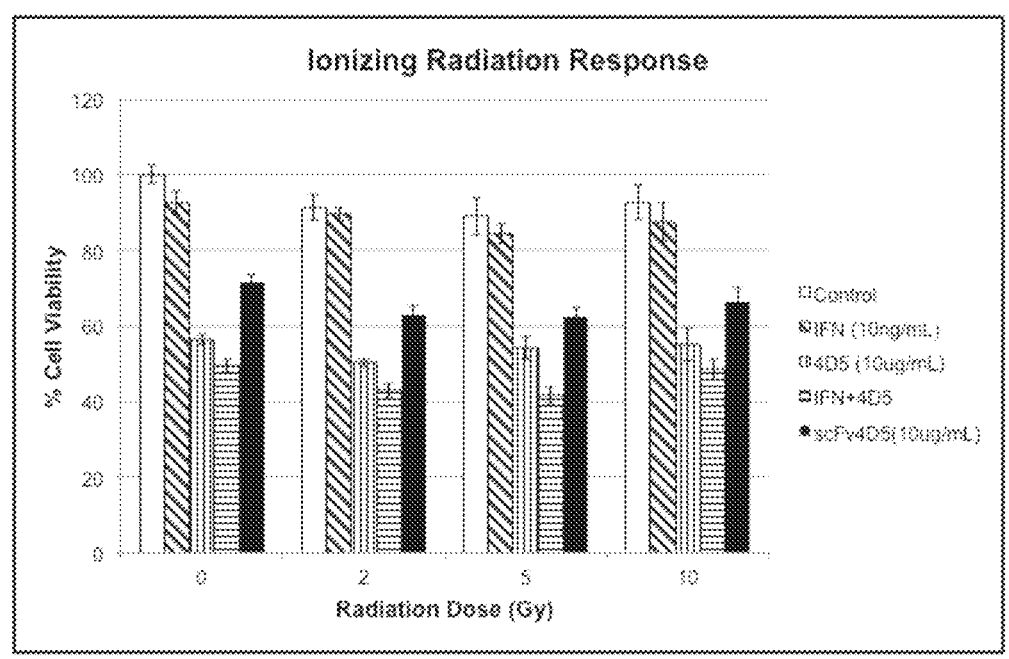

FIG. 15. Ionizing Radiation Response. SK-BR-3 cells were pretreated with IFN-γ (10 ng/mL), 4D5 (10 μg/mL), IFN-γ+4D5, or scFv4D5(IFN-γ) (10 μg/mL) for 24 hours followed by exposure to ionizing radiation at the indicated doses. Forty-eight hours later, cell viability was measured by MTT assay.

Figure 16:
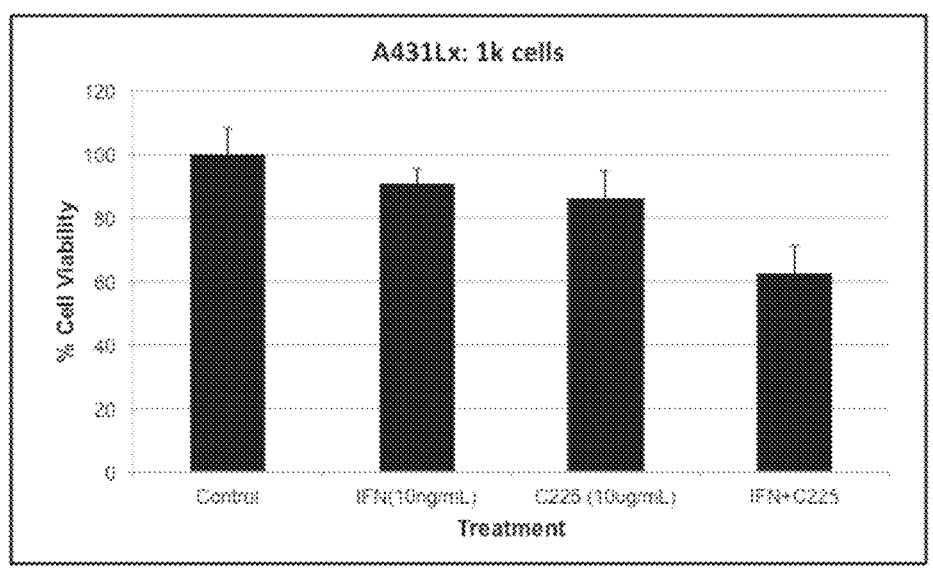

FIG. 16. A431Lx cells were seeded at 1,000 cells/well in a 96-well plate and 24 hours later were treated with IFN-γ (10 ng/mL), C225 (also known as cetuximab) (10 μg/mL), or both. Forty-eight hours later, cell viability was measured by MTT assay.

Figure 17:
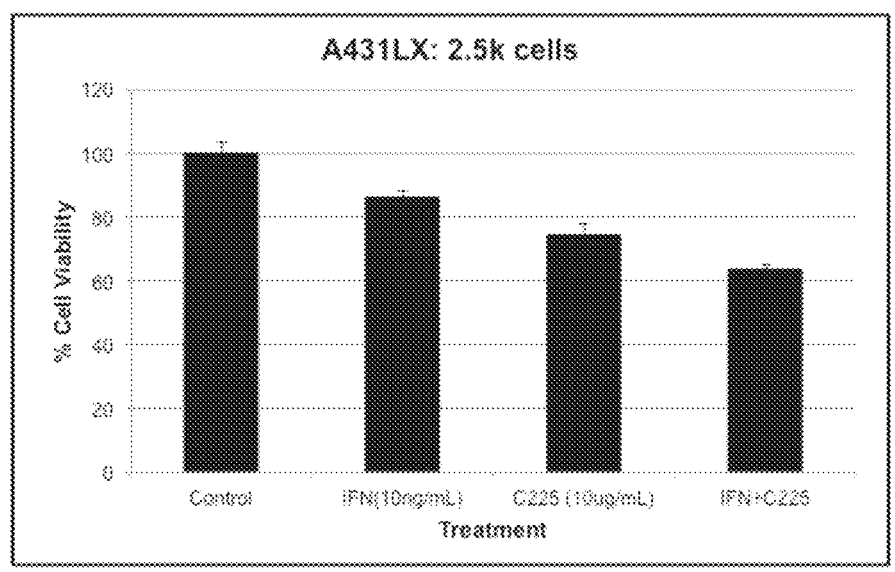

FIG. 17. A431Lx cells were seeded at 2,500 cells/well in a 96-well plate and 24 hours later were treated with IFN-γ (10 ng/mL), C225 (10 μg/mL), or both. Forty-eight hours later, cell viability was measured by MTT assay.

Figure 18:
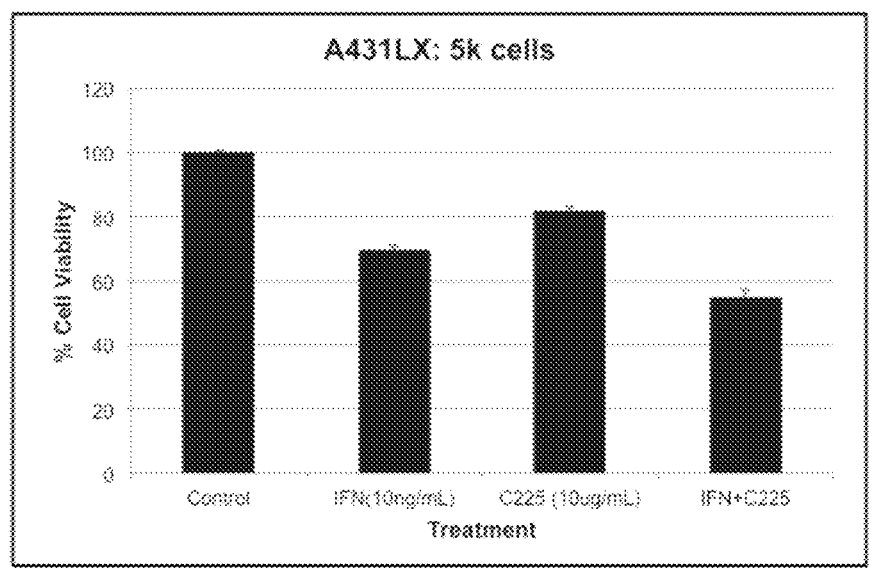

FIG. 18. A431Lx cells were seeded at 5,000 cells/well in a 96-well plate and 24 hours later were treated with IFN-γ (10 ng/mL), C225 (10 μg/mL), or both. Forty-eight hours later, cell viability was measured by MTT assay.

FIG. 19A-FIG. 19D. Anti-erbB2 monoclonal antibody and IFN-γ act directly on HER2-positive breast cancer cells. (FIG. 19A) SK-BR-3 cells were treated with regimens of anti-erbB2 mAb (4D5) and IFN-γ at the indicated concentrations. Treatments described as IFN-γ→4D5+IFN-γ were treated with the indicated dose of IFN-γ for 4 days, then the indicated dose of IFN-γ plus 4D5 for an additional 4 days. Treatments described as 4D5→4D5+IFN-γ were treated with 4D5 for 4 days, then the indicated dose of IFN-γ plus 4D5 for an additional 4 days. All other treatment groups were treated as indicated for 8 days. Following a total of 8 days, an MTT assay was performed. Data were normalized to the cIgG group. Bar graphs represent the mean±S.D. of a typical experiment (n=5). (FIG. 19B) SK-BR-3 cells were treated as indicated and MTT assays were performed every second day. Data were normalized to the cIgG group on Day 0. Data points represent the mean±S.D. of a typical experiment (n=6). (FIG. 19C) SK-BR-3 cells were seeded in a 0.2% agar solution containing the indicated treatments, which was layered over a 0.8% agar solution. After 14 days in culture, viable foci were visualized following incubation with MTT solution. Scale bar is 250 μm. (FIG. 19D) Foci from panel C were quantified using NIH-endorsed software (ImageJ). Bar graphs represent the mean±S.D. of a typical experiment (n=3 or 4; n.s., not significant; *, p<0.05; , p<0.01; *; p<0.001).

FIG. 20A-FIG. 20D. Disabling HER2 kinase activity principally inactivates Akt signaling. (FIG. 20A) SK-BR-3 cells were treated with vehicle (0.001% DMSO), lapatinib, cIgG, 4D5, or C225 as indicated for 24 hours. (FIG. 20B) After three days in culture, MDAMB-453 and SK-BR-3 cells were treated with vehicle (0.001%) or indicated doses of lapatinib for 24 hours. (FIG. 20C) SK-BR-3 cells were treated with vehicle (0.05% DMSO) or the PI-3K inhibitor LY294002 at the indicated dose for 24 hours. (FIG. 20D) SK-BR-3 cells were treated with vehicle (0.01% DMSO) or the indicated dose of the Akt 1 and 2 inhibitor for 24 hours. In all instances, equal amounts of lysate were separated by SDS-PAGE, transferred, and immunoblotted with the indicated antibodies. β-actin is used as a loading control. Shown are representative Western blots of typical experiments.

FIG. 21A-FIG. 21D. Inclusion of IFN-γ potentiates the erbB2 disabling-caused snail degradation. (FIG. 21A) SK-BR-3 cells were treated for two days with cIgG, 4D5, or IFN-γ as indicated. (FIG. 21B) SK-BR-3 cells were treated for one day with cIgG, 4D5, or IFN-γ as indicated. The following day, nuclear and cytoplasmic fractions were prepared from these cells. (FIG. 21C) SK-BR-3 cells were treated for two days with cIgG, 4D5, C225, or IFN-γ as indicated. (FIG. 21D) SK-BR-3 cells were treated for one day with vehicle (0.001% DMSO), three doses of lapatinib, or IFN-γ (two doses) as indicated. In all instances, equal amounts of lysate were separated by SDS-PAGE, transferred, and immunoblotted with the indicated antibodies. β-actin was used as a loading control. In panel B, Ku70 and phosphoinositide-dependent kinase-1 (PDK1) demonstrate enrichment for nuclear and cytoplasmic fractions, respectively. Shown are representative Western blots of typical experiments.

Figure 22A:
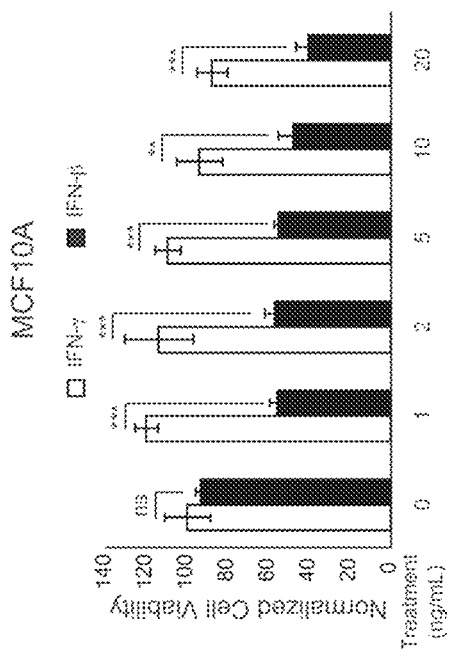
Figure 22C:
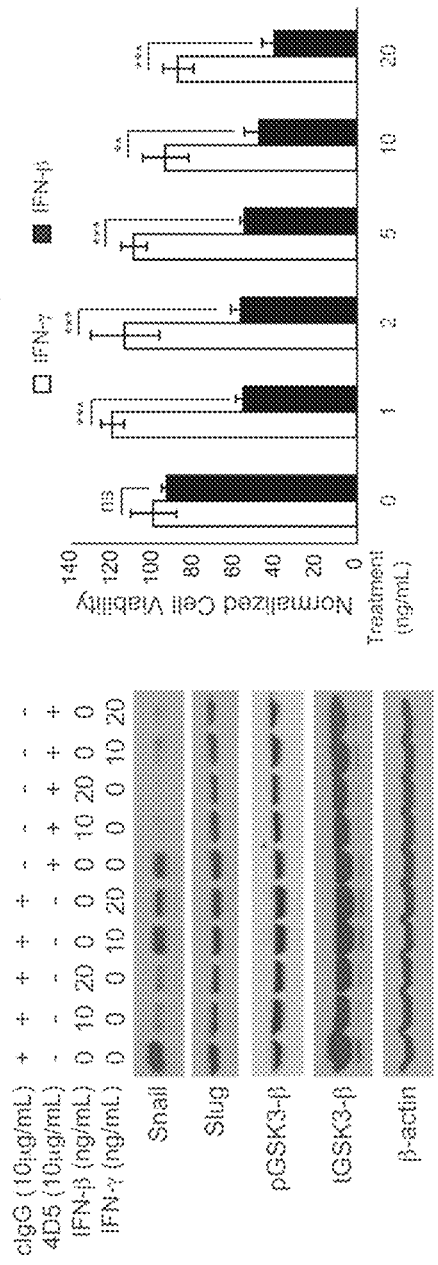
Figure 22B:
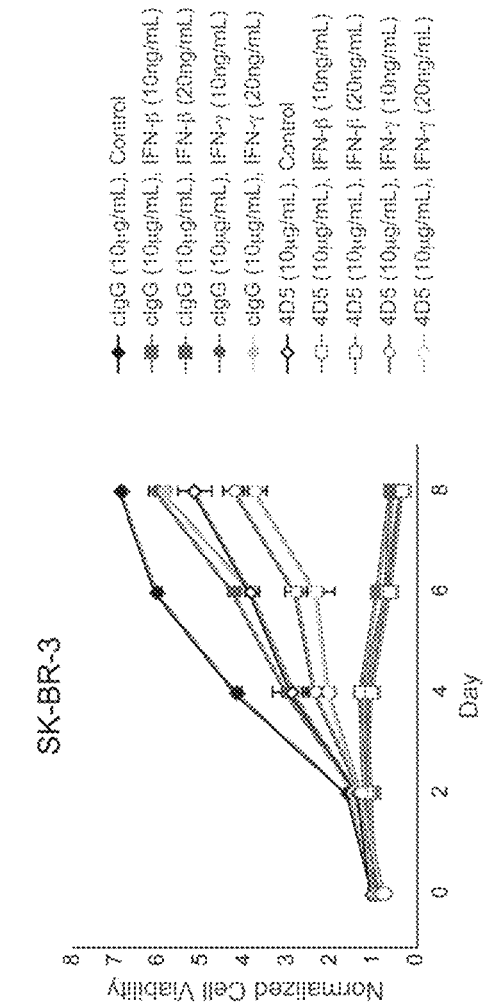

FIG. 22A-FIG. 22C. IFN-γ, but not IFN-β, requires the inclusion of anti-erbB2 mAb. (FIG. 22A) SK-BR-3 cells were treated for one day with cIgG, 4D5, IFN-β, or IFN-γ as indicated. Equal amounts of lysate were separated by SDS-PAGE, transferred, and immunoblotted with the indicated antibodies. β-actin is used as a loading control. Shown is a representative Western blot of a typical experiment. (FIG. 22B) SK-BR-3 cells were treated as indicated and MTT assays were performed every second day. Data were normalized to the cIgG group on Day 0. Data points represent the mean±S.D. of a typical experiment (n=6). (FIG. 22C) MCF10A cells were treated as indicated for 8 days. Vehicle control for IFN-γ experiments was performed by addition of media whereas vehicle control for IFN-β experiments was a vehicle (50 mM NaOAc, pH 5.5 containing 0.1% BSA). Following treatment, an MTT assay was used to assess viability. Data were normalized to IFN-γ control values. Bar graphs represent the mean±S.D. of a typical experiment (n=5) (n.s., not significant; , $p<0.01$; *; $p<0.001$).

Figure 23B:
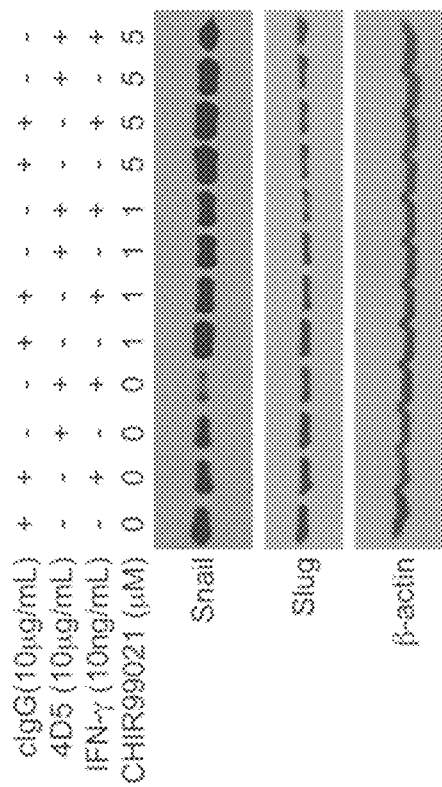
Figure 23A:
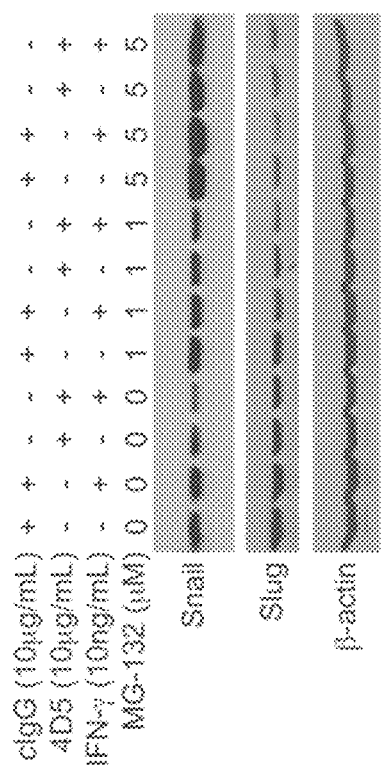
Figure 23C:
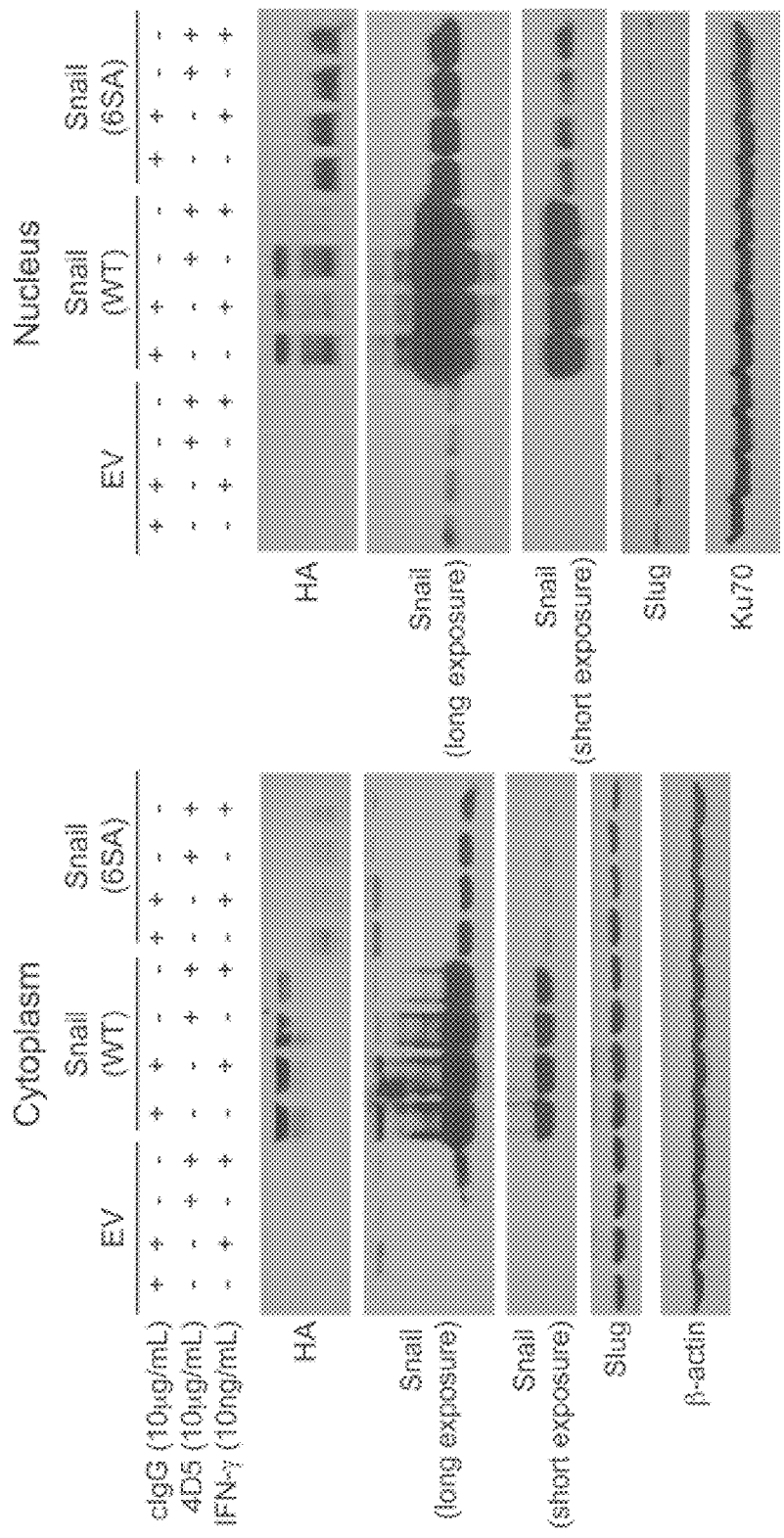

FIG. 23A-FIG. 23C. Anti-erbB2 and IFN-γ degrade snail through the GSK3-β/proteasome pathway. SK-BR-3 cells were treated with cIgG, 4D5, and IFN-γ as indicated for two days. (FIG. 23A) During the final 8 hours of treatment, vehicle (0.025% ethanol) or the indicated doses of the proteasome inhibitor MG-132 were added. (FIG. 23B) During the final 8 hours of treatment, vehicle (0.01% DMSO) or the indicated doses of the GSK3-β inhibitor CHIR99021 were added. (FIG. 23C) SK-BR-3 cells were transfected with either empty vector (EV), wild-type (WT) snail, or snail with serines 97, 101, 108, 112, 116, and 120 mutated to alanines (6SA). The day following transfection, cytoplasmic and nuclear fractions were prepared from these cells. In all instances, equal amounts of lysate were separated by SDS-PAGE, transferred, and immunoblotted with the indicated antibodies. β-actin and Ku70 (nuclear fraction) were used as loading controls. Shown are representative Western blots of typical experiments.

Figure 24:
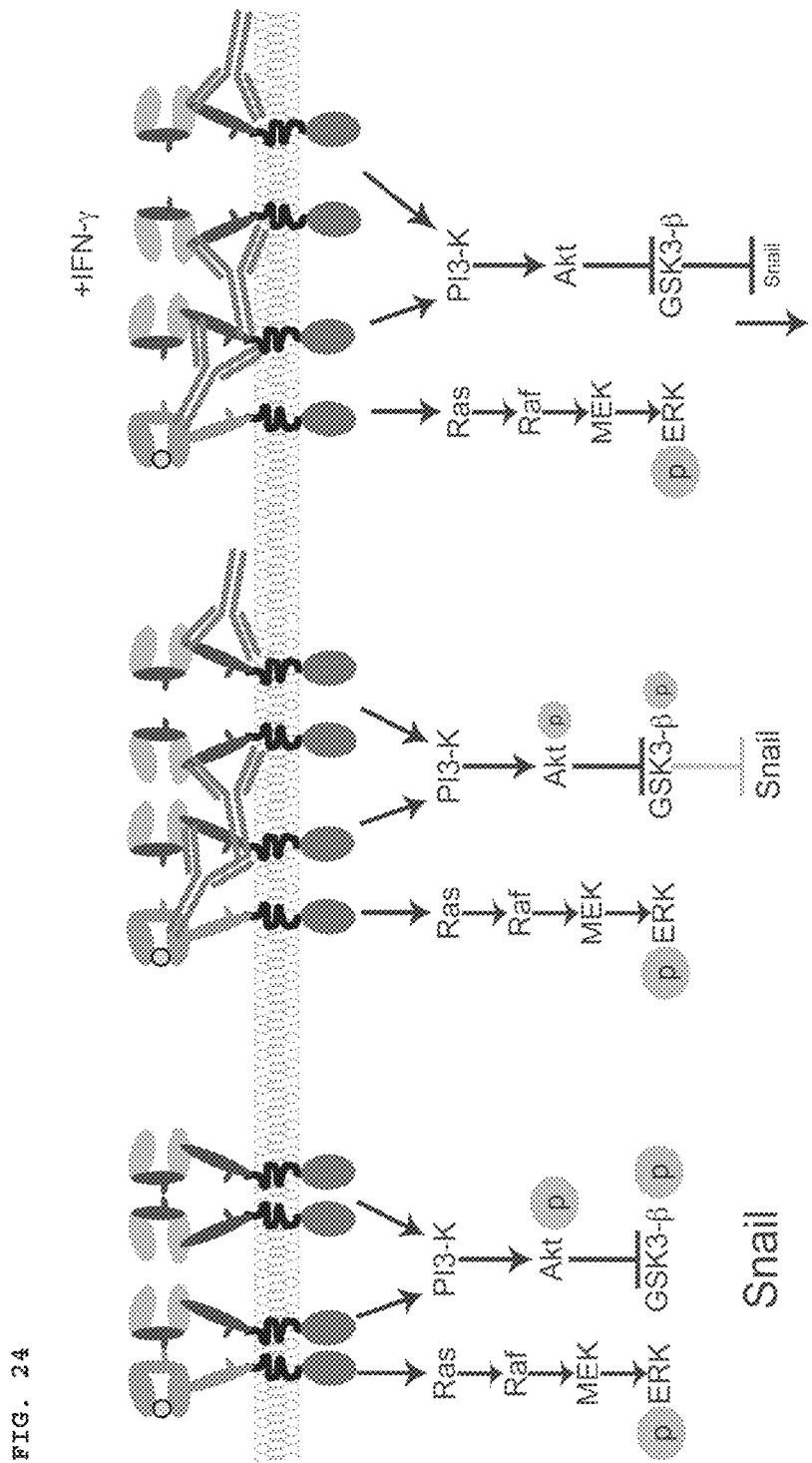

FIG. 24. Graphical Abstract. In transformed cells, EGFR (purple and gray) and erbB2 (light and dark blue) can exist as heterodimers or homodimers. These receptors activate the Ras/Raf/MEK/Erk and PI-3K/Akt pathways. Upon treatment with anti-erbB2 mAb, the Akt pathway becomes moderately inactivated. Upon addition of IFN-γ to the mAb-disabled cells, the Akt pathway is further inactivated and snail is degraded through activated (nonphosphorylated GSK3-β).

Figure 25:
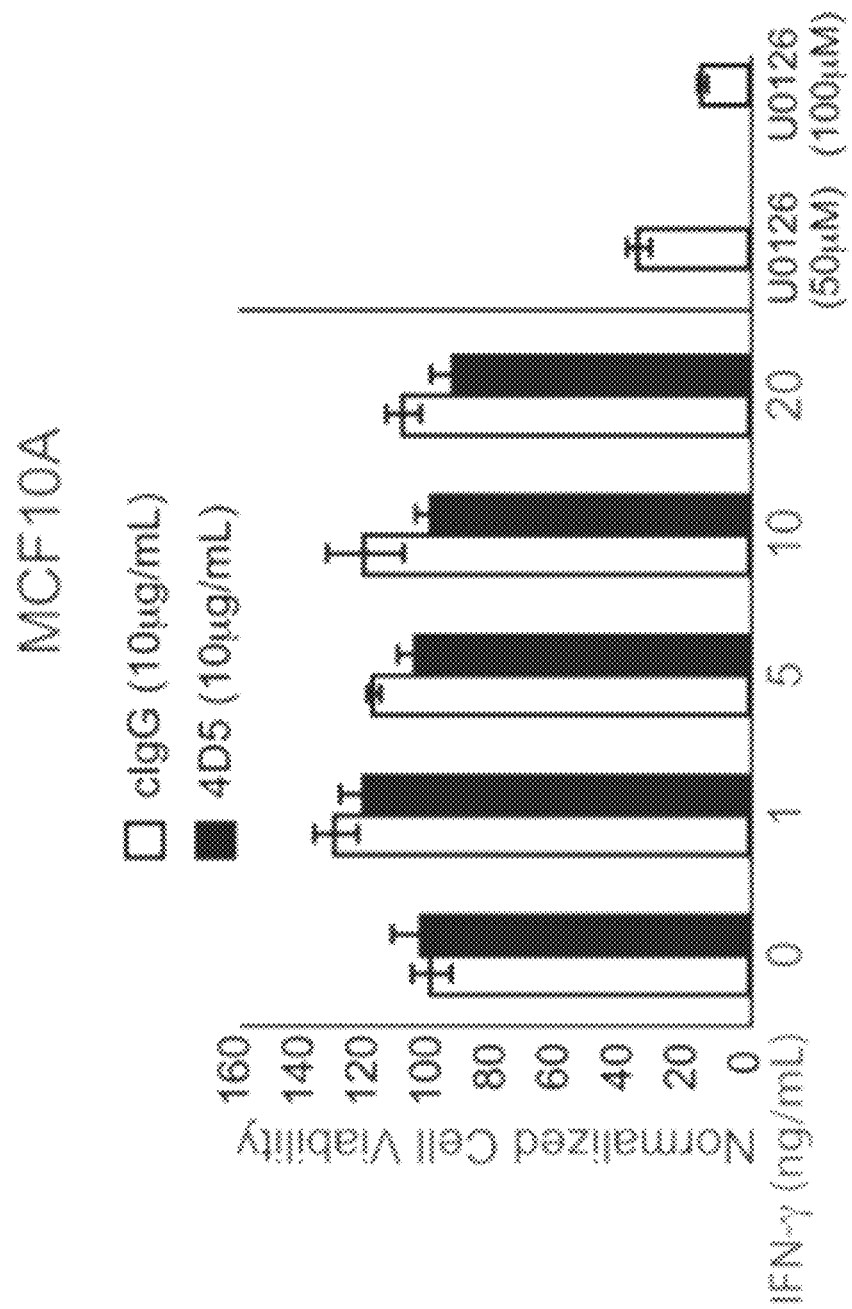

FIG. 25. MCF10A cells are apathetic to anti-erbB2 mAb and IFN-γ treatments. MCF10A cells were treated as indicated for 8 days. After 8 days, an MTT assay was performed. Data were normalized to the cIgG group. Bar graphs represent the mean±S.D. of a typical experiment (n=6). MCF10A cells were treated with the MEK1/2 inhibitor U0126 as a kill control.

Figure 26:
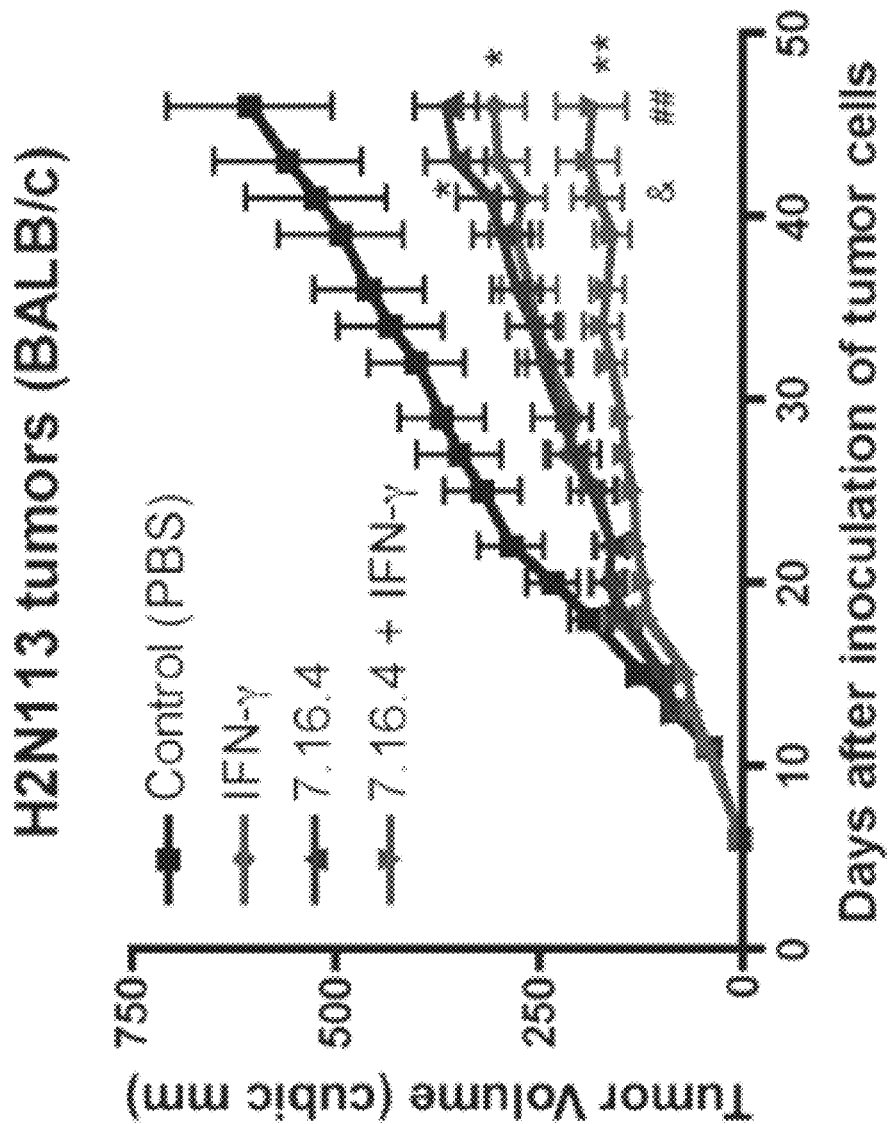

FIG. 26. Surprising combined effects of anti-neu/p185 mAb therapy combined with IFN-γ in vivo. H2N113 tumor cells were injected subcutaneously into both sides of the back of BALB/c mice. After tumors reached an average size of 30-40 mm$^3$, mice were treated with control (PBS), IFN-γ ($5\times10^5$IU/kg), 7.16.4 (1.5 mg/kg), or IFN-γ+7.16.4. Data represent mean+SEM (*$P<0.05$, **$P<0.01$, compared with control; #$P<0.05$, ##$P<0.01$, compared with the 7.16.4 group; & $P<0.05$, && $P<0.01$, compared with the IFN-γ group).

Figure 27:
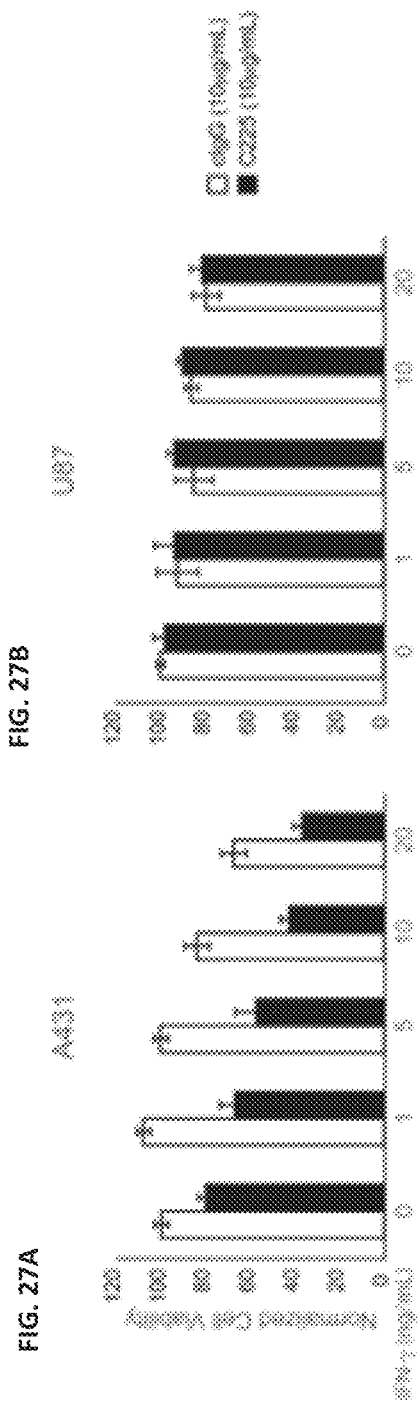

FIG. 27A-FIG. 27B. Dose-response effects of IFN-γ in the presence and absence of mAb. A431 (FIG. 27A) and U87 (FIG. 27B) cells were treated as indicated for 8 days. After 8 days, an MTT assay was performed. Data were normalized to the cIgG group. Bar graphs represent the mean±S.D. of a typical experiment (n=6).

Figure 28:
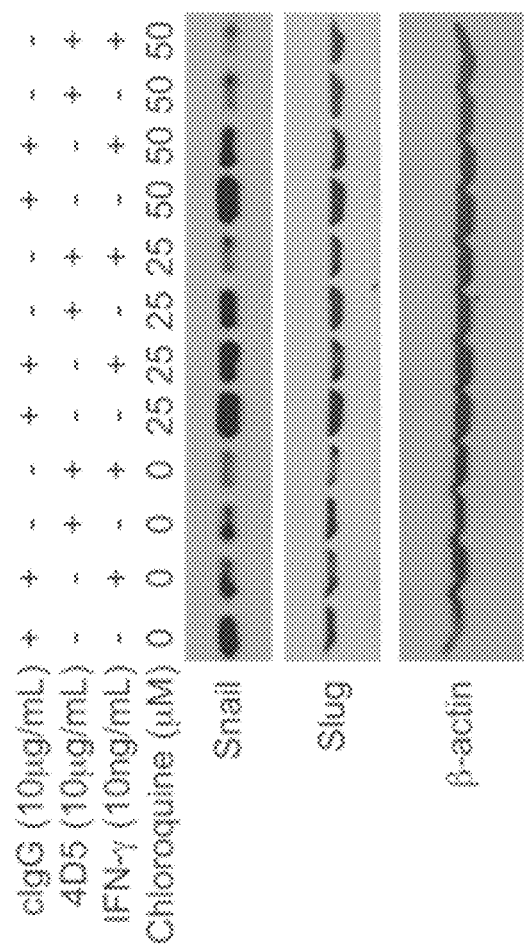

FIG. 28. Anti-erbB2 and IFN-γ degrade snail independently of the lysosome. SK-BR-3 cells were treated with cIgG, 4D5, and IFN-γ as indicated for two days. During the final 8 hours of treatment, vehicle (ddH$_2$O) or the indicated doses of the lysosome inhibitor Chloroquine were added. Equal amounts of lysate were separated by SDS-PAGE, transferred, and immunoblotted with the indicated antibodies. β-actin was used as a loading control. Shown are representative Western blots of a typical experiment.

Figure 29:
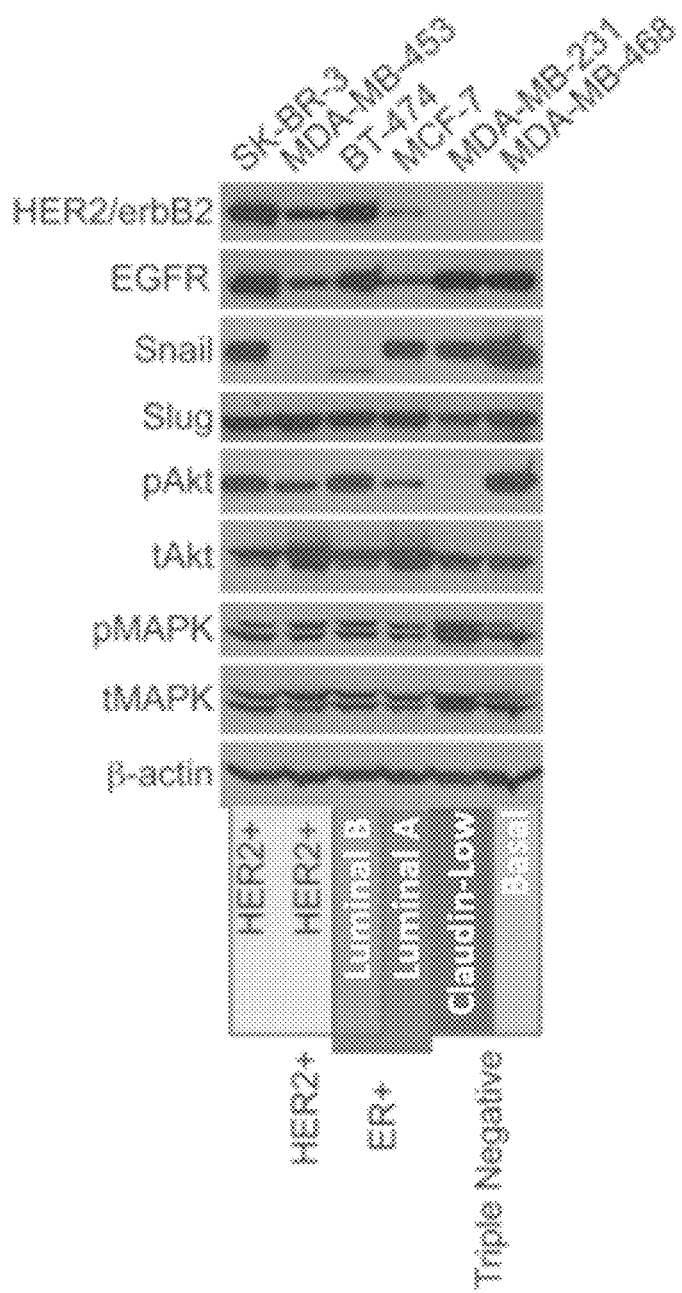

FIG. 29. Analysis of cell lines encompassing each subtype of breast cancer. Cell lines that model each classification of breast cancer were harvested following three days in culture. Equal amounts of lysate were separated by SDS-PAGE, transferred, and immunoblotted with the indicated antibodies. β-actin was used as a loading control. Shown are representative Western blots of a typical experiment.

Figure 30A:
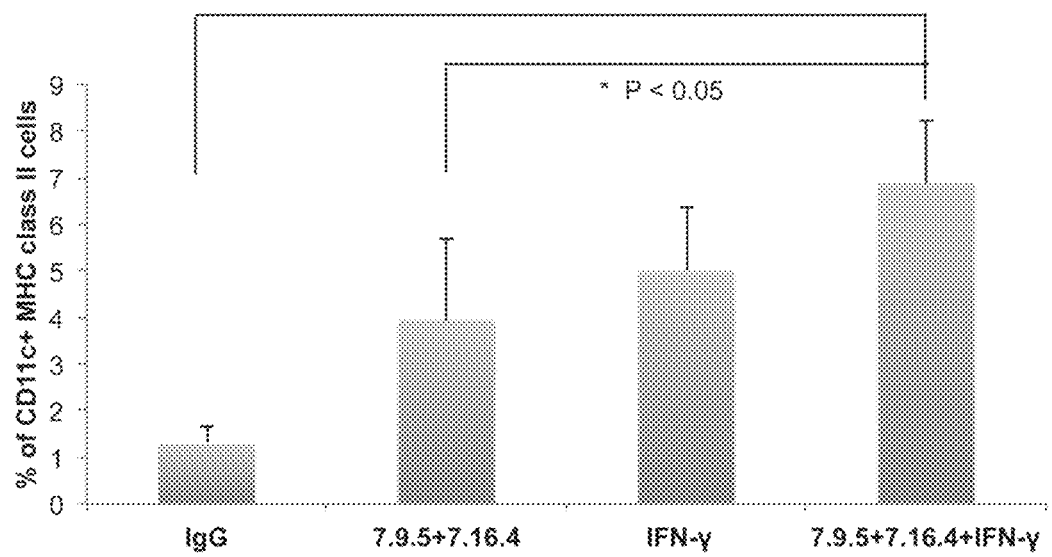
Figure 30B:
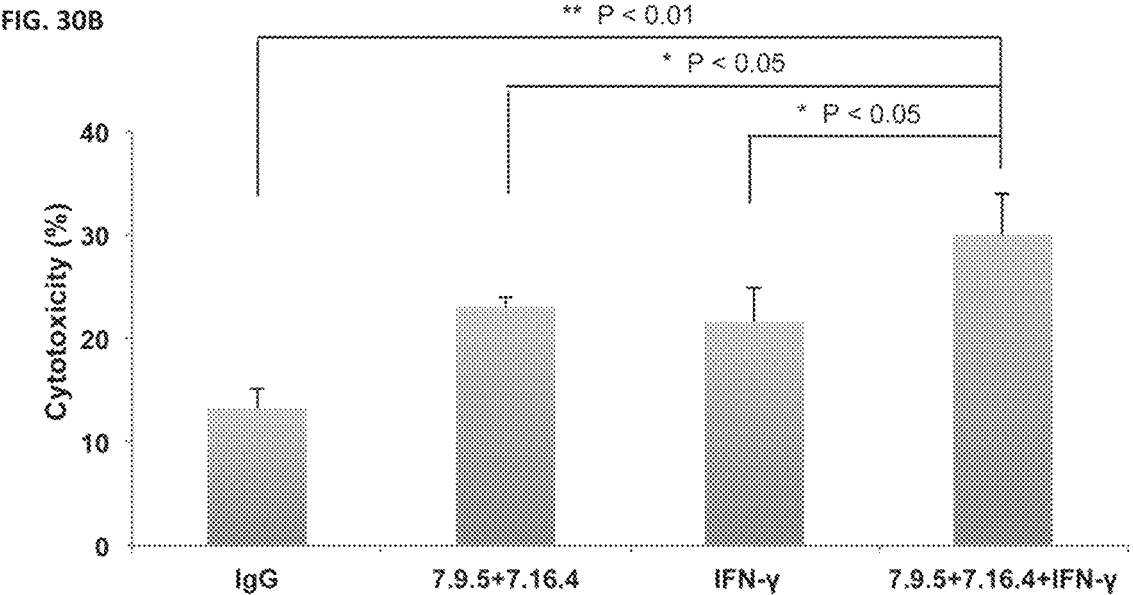

FIG. 30A-FIG. 30B. CD8+DC populations and cytotoxicity of CD8+ T cells from spleen. FIG. 30A. Cells were gated on CD11c+ MHC Class II+ cells without MDSC (CD11$^{high}$ and Gr-1$^{high}$ cells). CD8+ DEC205+ cell populations were shown as a percentage of CD11c+ MHC class II+ cells. FIG. 30B: CD8+ T cells were collected from mouse spleens treated with control IgG, 7.16.4+7.9.5, IFN-γ, and 7.16.4+7.9.5+IFN-γ. Cytotoxicity assays of the collected T cells were performed as described. Statistical significance was calculated by the Student's t test.

Figure 31:
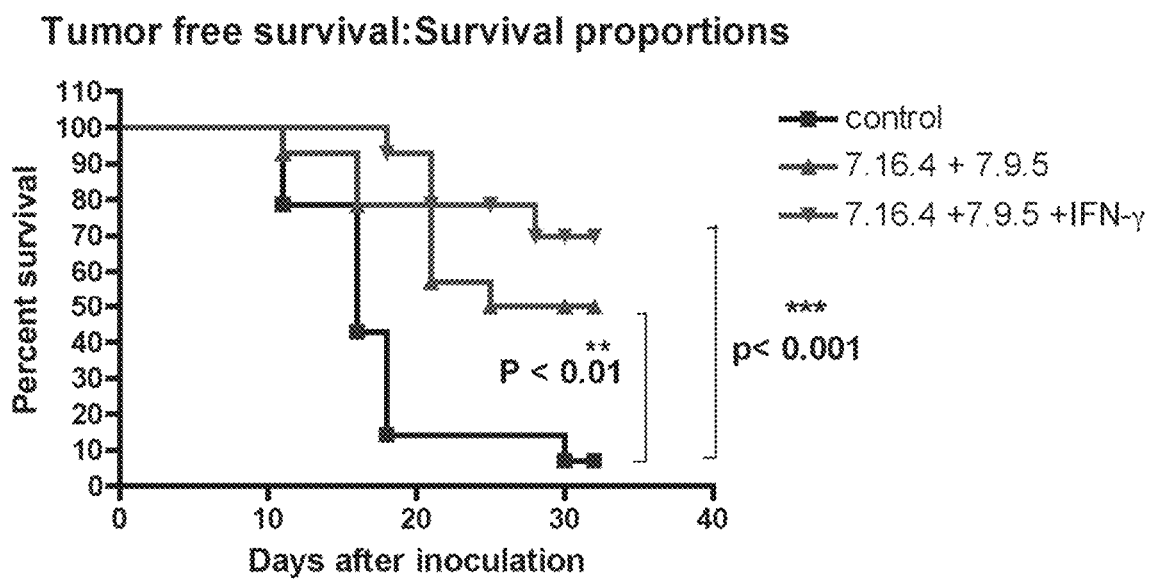

FIG. 31. IFN-γ improves two-antibody effect on the prevention of tumor development. H2N113 tumor cells ($0.25\times10^6$) were injected s.c. into MMTVneu mice at both flanks on day 0. Treatment for mice started at day 1. The doses for each agent included in the treatment were: 3.75 μg/mouse for 7.16.4, 12.5 μg/mouse for 7.9.5, and $1\times10^4$ IU/mouse for IFN-γ. Treatments were performed following a twice per week for antibodies and three times per week for αγ. t test indicated the tumor free survival of the "7.16.4+7.9.5+IFN-γ group" is very significantly different from the control group ($P<0.001$).

Figure 32A:
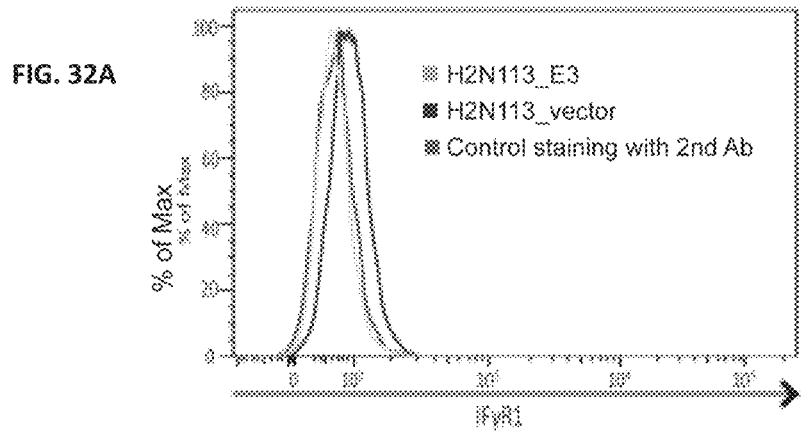
Figure 32B:
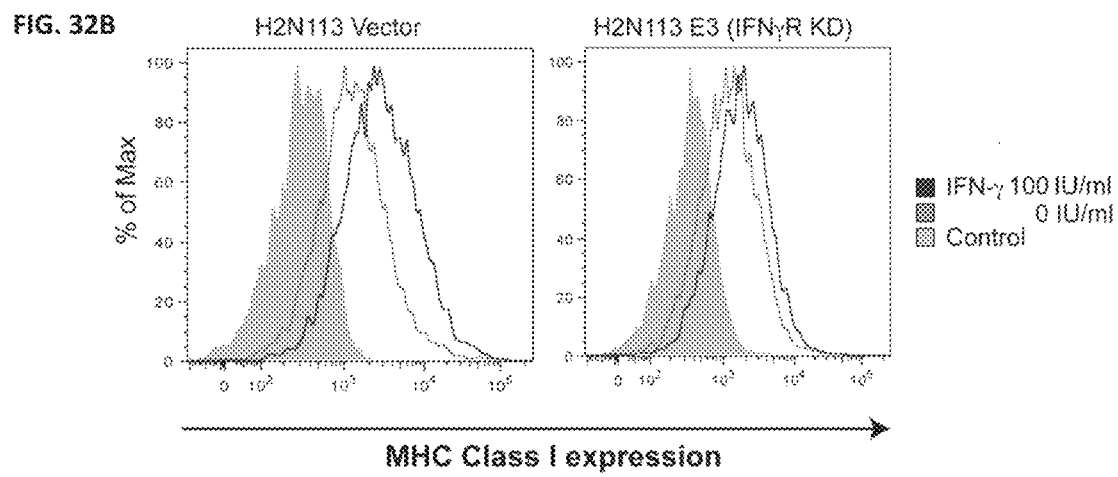
Figure 32C:
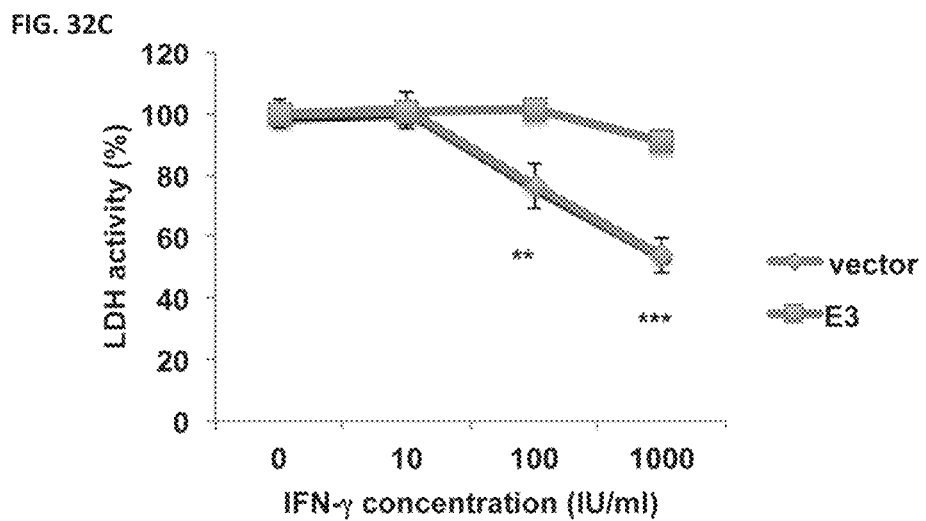

FIG. 32A-FIG. 32C. Establishment of IFNγR KD cells. FIG. 32A: Expression level of IFNγR1 in H2N113 transfected with empty vector and shRNA (E3). FIG. 32B: Cells were stimulated with indicated concentration of IFN-γ for 16 h and MHC class I expression was assessed by flow cytometry with the anti-H2Dd antibody. FIG. 32C: Cells were treated with indicated concentration of IFN-γ for 5 days before relative cell numbers were determined by the LDH activity of cell lysates.$P<0.01$, *$P<0.005$ FIG. 33. Combination activity of anti-erbB2/neu antibody and IFN-γ is dependent on the IFN-γ receptor in the tumor cells. IFN-γ receptor was knocked down by shRNA in H2N113. H2N113 cells were infected with empty or shRNA-containing lentivirus and selected with 1 μg/ml puromycin. IFγR1 knockdown was confirmed by FACS analysis using anti-IFγR1 antibody and by analyzing their expression of MHC class I following stimulation with IFN-γ and proliferation (FIG. 32A-FIG. 32C). The resulting tumor cells ($1\times10^6$) were injected subcutaneously into MMTV-neu mice and treated similarly as in FIG. 1. Once tumors reached an average size of 30-40 mm$^3$ (10-12 days after tumor inoculation), mice were treated with PBS, IFN-γ ($5\times10^5$ IU/kg, three times per week), 7.16.4 (1.5 mg/kg, twice per week), or the combination of IFN-γ and 7.16.4. Data represent mean+SEM. t test was performed to compare the difference in the tumor size of different treatment groups. *$P<0.05$, **$P<0.01$, compared with control; #$P<0.05$, ##$P<0.01$, compared with the 7.16.4 group; &$P<0.05$, &&$P<0.01$, compared with the IFN-γ group.

Figure 34:
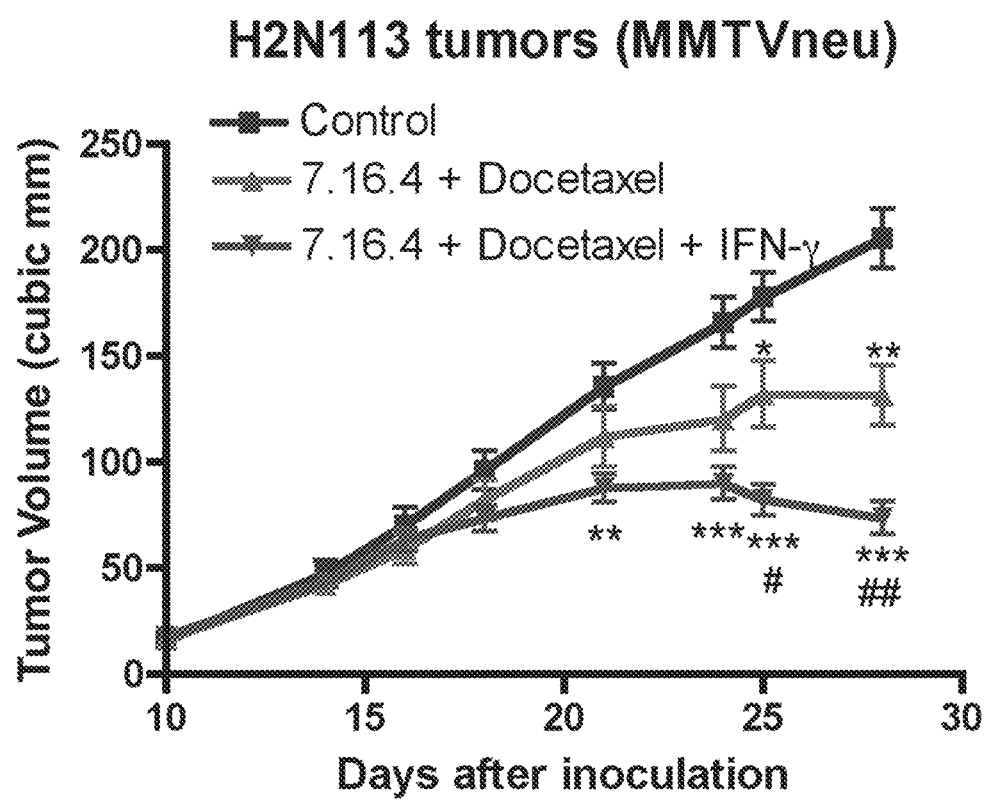

FIG. 34. IFN-γ further enhances the activity of anti-erbB2/neu antibody and chemotherapy. H2N113 tumor cells (1×10$^6$) were injected subcutaneously into both side of the back of 6-10 weeks old MMTV-neu mice. Once tumors reached an average size of 30-40 mm$^3$ (10-12 days after tumor inoculation), mice were treated with control, 7.16.4 (1.5 mg/kg, twice per week)+docetaxel (5.5 mg/kg, twice per week), or 7.16.4+docetaxel+IFN-γ (5×10$^5$ IU/kg, three times per week). Data represent mean+SEM. t test was performed to compare the difference in the tumor size of different treatment groups. *P<0.05, P<0.01, *P<0.001, compared with control; #P<0.05, ##P<0.01, compared with the 7.16.4+docetaxel group.

Figure 35:
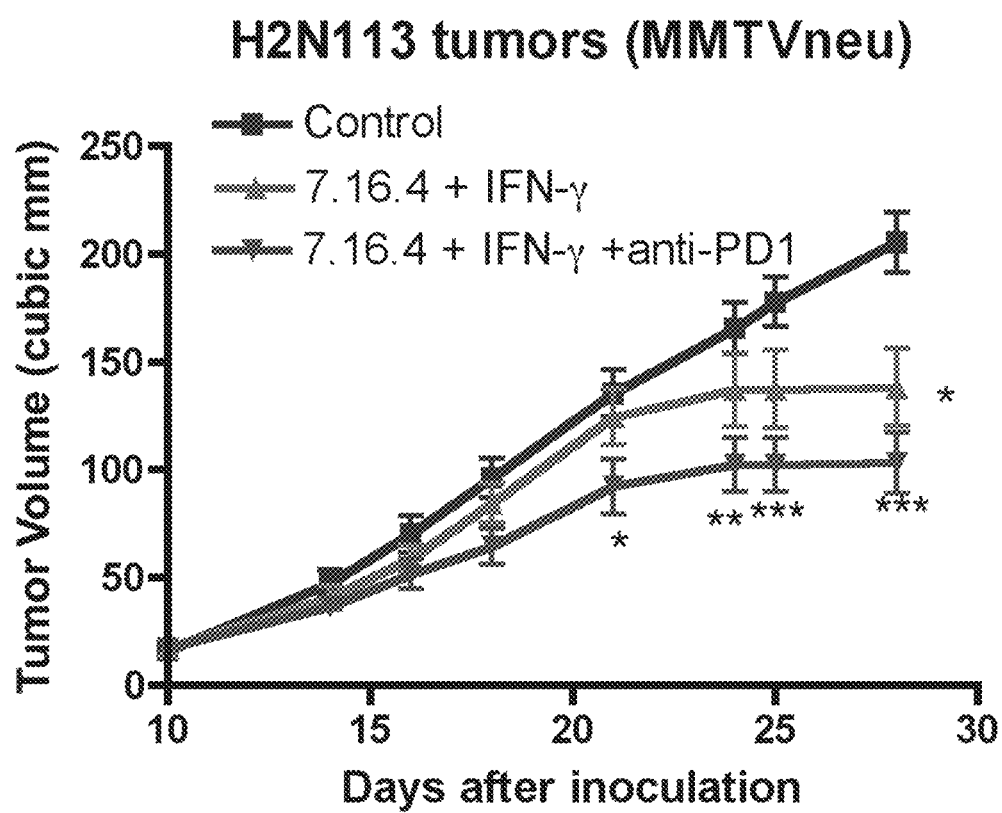

FIG. 35. Effect of anti-PD1 antibody on IFN-γ and anti-erbB2/neu antibody. H2N113 tumor cells (1×10$^6$) were injected subcutaneously into both side of the back of 6-10 weeks old MMTV-neu mice. Once tumors reached an average size of 30-40 mm$^3$ (10-12 days after tumor inoculation), mice were treated with control, 7.16.4 (1.5 mg/kg, twice per week)+IFN-γ (5×10$^5$ IU/kg, three times per week), or 7.16.4+IFN-γ+anti-PD1 antibody (5 mg/kg, twice per week). Data represent mean+SEM. t test was performed to compare the difference in the tumor size of different treatment groups. *P<0.05, P<0.01, *P<0.001, compared with control.

Figure 36:
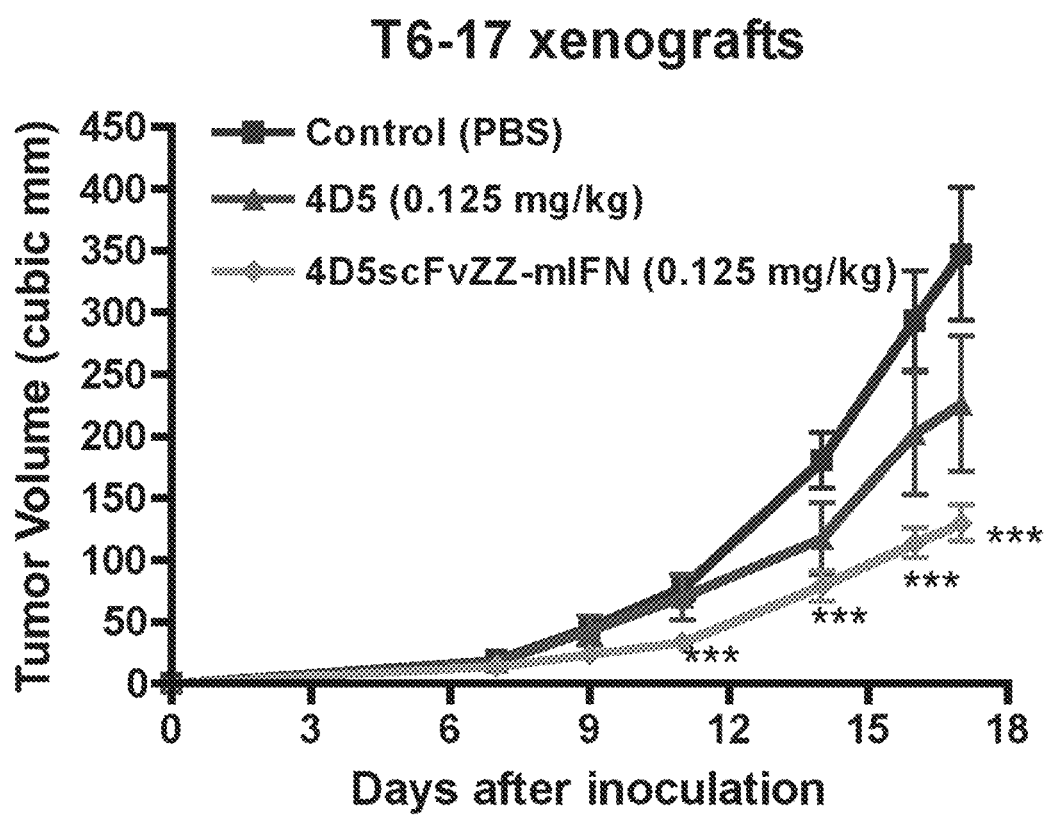

FIG. 36. In vivo activity of 4D5scFvZZ-mIFN-γ. T6-17 tumor cells (5×10$^5$) were injected subcutaneously into both side of the back of 6-10 weeks nude mice. The next day, mice were treated with control, 4D5 (0.125 mg/kg) or 4D5scFvZZ-mIFN-γ (0.125 mg/kg), five times per week. Data represent mean+SEM. t test was performed to compare the difference in the tumor size of different treatment groups. *P<0.05, P<0.01, *P<0.001, compared with control.

Figure 37A:
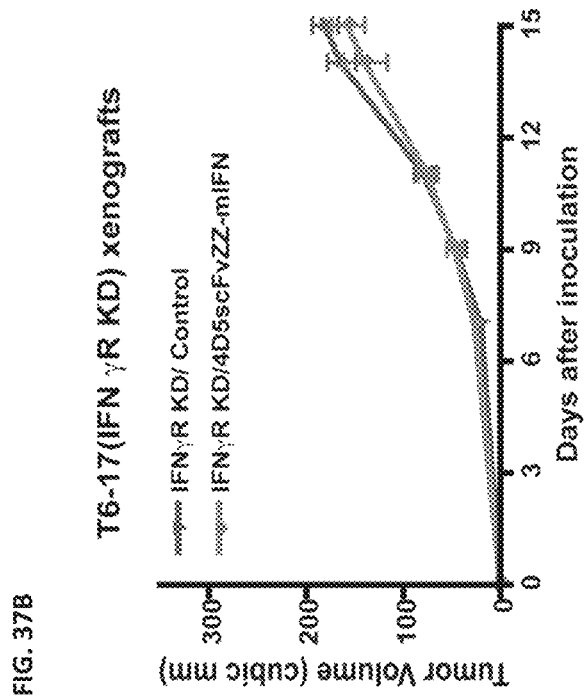
Figure 37B:
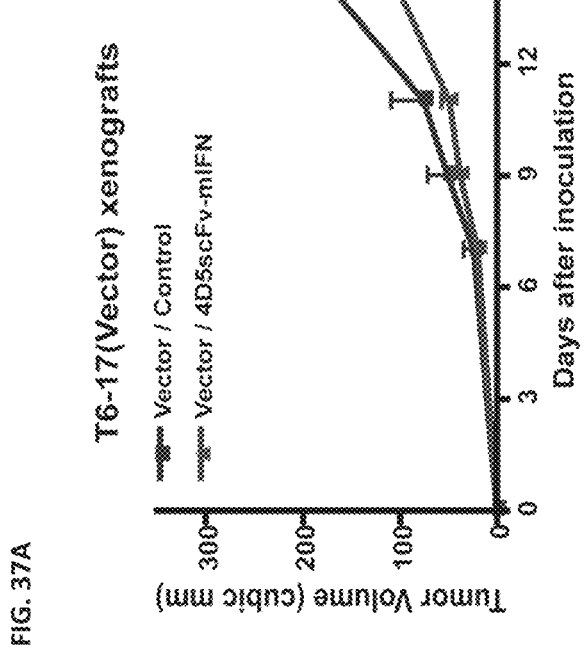

FIG. 37A-FIG. 37B. In vivo activity of 4D5scFvZZ-mIFN-γ is dependent on IFN-γ receptor. T6-17(Vector; as shown in FIG. 37A) or T6-17(IFN-γR KD; as shown in FIG. 37B) tumor cells (5×10$^5$) were injected subcutaneously into the back of 6-10 weeks nude mice. The next day, mice were treated with control, 4D5 (0.125 mg/kg) or 4D5scFvZZ-mIFN-γ (0.125 mg/kg), five times per week. Data represent mean+SEM.

Figure 38A:
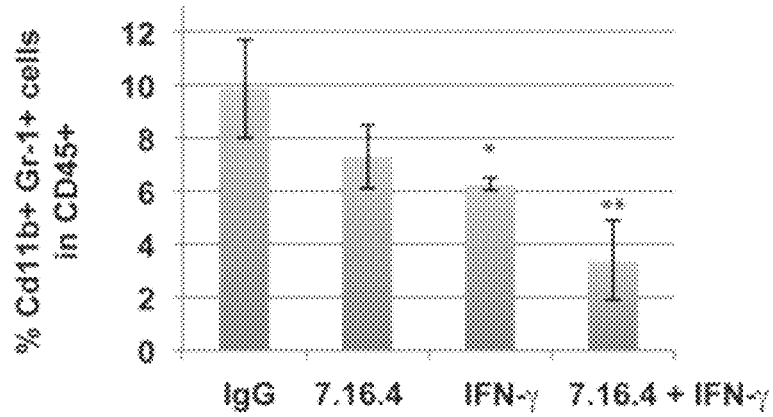
Figure 38B:
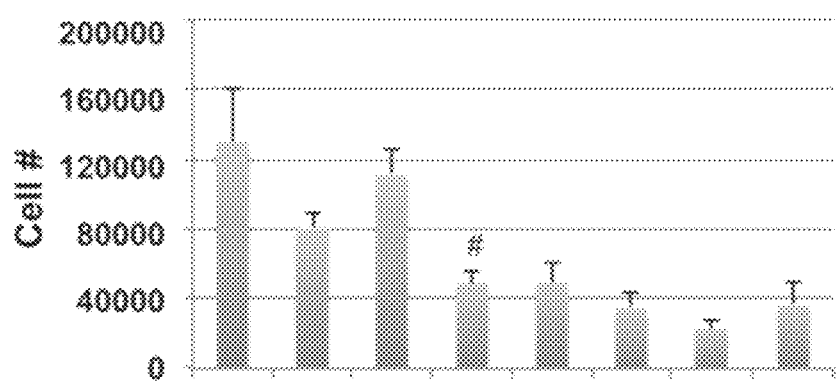

FIG. 38A-FIG. 38B. Effect of co-treatment on MDSC cells. FIG. 38A. H2N113 tumors from each group of mice treated as indicated were obtained after treatment for FIG. 1 was finished. Tumor tissue was minced and digested with collagenase P for 1 hr, followed by incubation with dispase and DNase for 5 minutes. Tumor-infiltrated MDSC cells were isolated and compared using CD11b, Gr-1 and CD45 antibody by FACS. *P<0.05, *P<0.01, as compared with the IgG treated group. FIG. 38B. In vitro migration assay. H2N113 cells were seeded on 12-well plate and cultured until sub-confluent. Cells were then treated as indicated and conditioned media were collected at day 3 of culture. Migration of MDSC was measured by the Transwell system (pore size: 4 μm). MDSCs were isolated from spleens of tumor-bearing mice using MACS MDSC isolation kit, then seeded in the apical chamber. Condition media was then placed in the basolateral chamber and incubated for 3 hr. The cells that migrated to bottom chamber were collected and analyzed by flow cytometry. Fresh medium containing treatment reagents were used as controls. #. P<0.05 (compared with either 7.16.4 or IFN-γ treated group.

Figure 39:
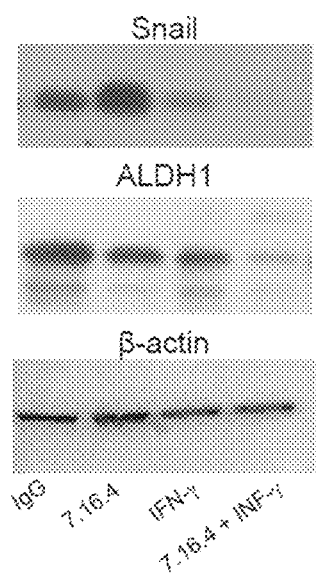

FIG. 39. In vivo co-treatment significantly reduced the expression of ALDH1 in the tumor. Tumors from each group of mice treated as indicated were obtained after treatment for FIG. 1 was finished. Tumor tissue was lysed with modified RIPA buffer containing proteinase inhibitor cocktail. Each lysate was adjusted to 10 μg/lane and examined for Snail and ALDH1 expression by Western blot. β-actin was used as the loading control. Shown are representative Western blots of typical experiments.

Figure 40:
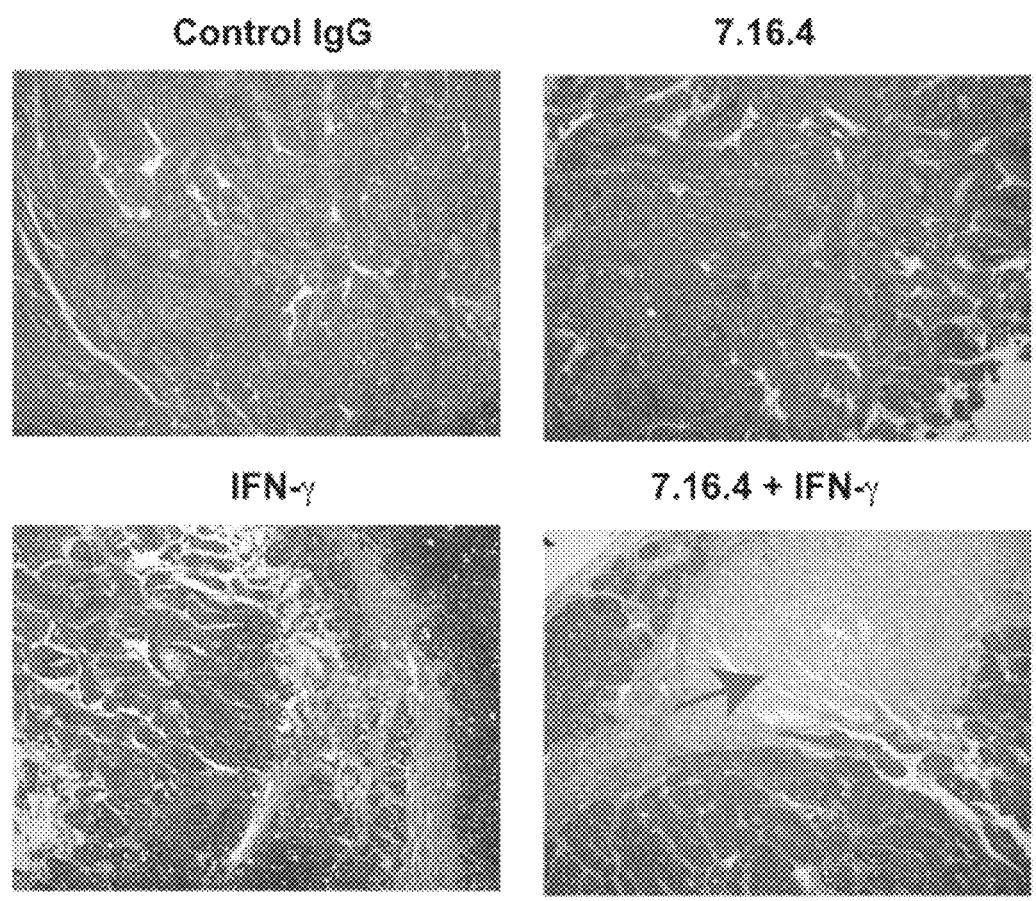

FIG. 40. H&E staining of tumors. Tumors were resected at the day after final treatment and fixed with 10% buffered formalin, and subjected to H&E staining. Tumors from mice treated with 7.16.4 and IFN-γ shows higher necrosis. Arrows show necrotic area.

Figure 41A:
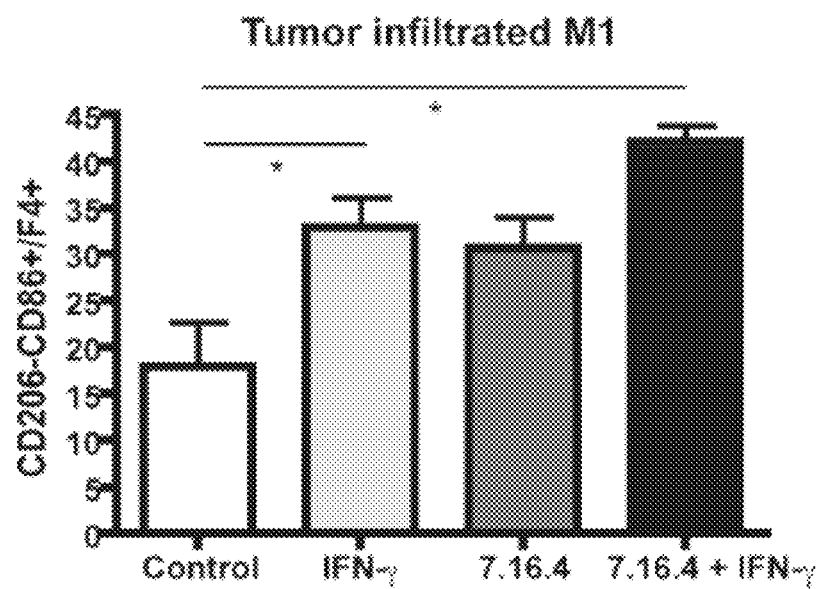
Figure 41B:
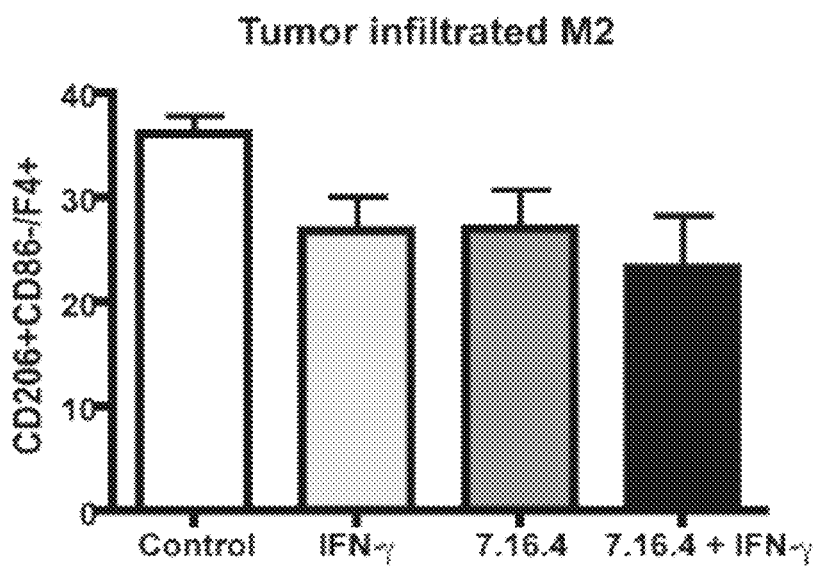
Figure 41C:
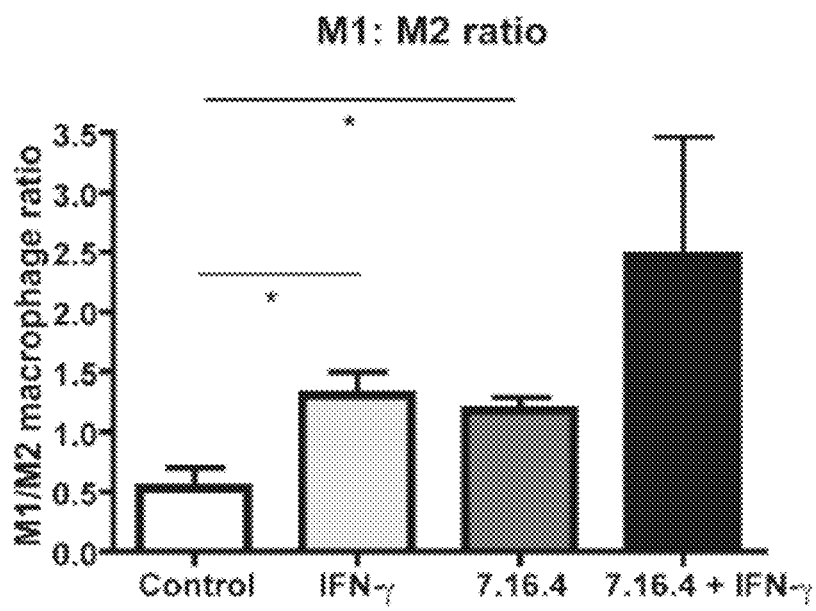

FIG. 41A-FIG. 41C. In vivo co-treatment led to increased M1 macrophage and reduced M2 macrophages in the tumors. Tumors from mice treated as indicated were obtained after treatment for FIG. 33 was finished. Tumor infiltrated macrophages were examined by FACS. Accumulation of M1 macrophages is shown in FIG. 41A; accumulation of M2 macrophages is shown in FIG. 41B; and the ratio of M1 macrophages to M2 macrophages in each of the treatment conditions is shown in FIG. 41C. *P<0.05.

Figure 42:
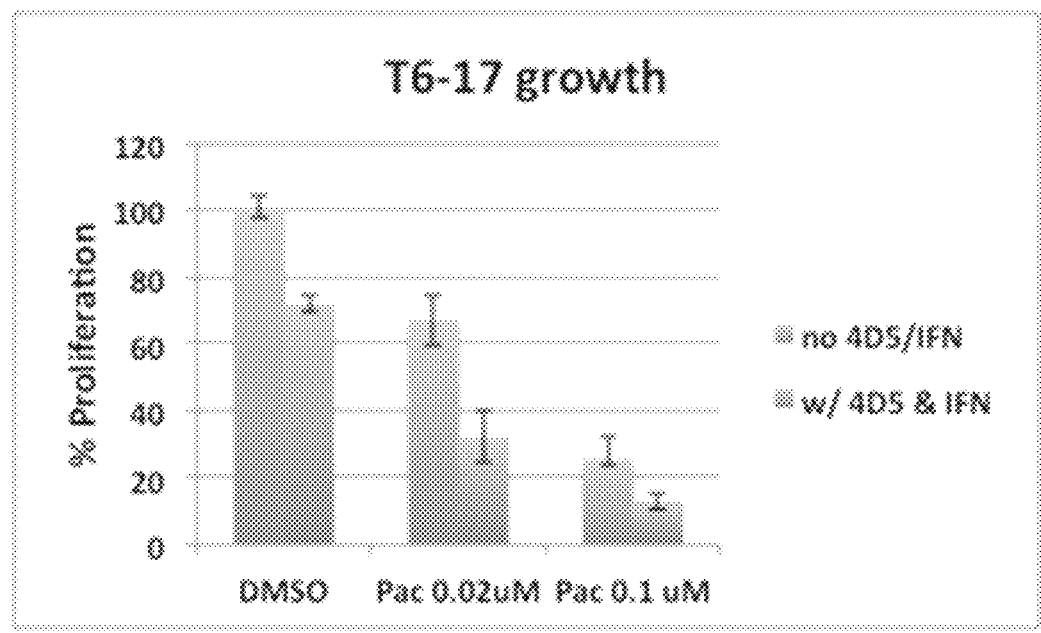

FIG. 42. Treatment with mAb 4D5 (Herceptin) that targets the erbB2 ectodomain, followed by IFN-γ, limits tumor growth. Interestingly, when the treatment is coupled with paclitaxel, greater tumor death was noted. In this growth assay we see doubling of the paclitaxel effectiveness when coupled with mAb and IFN-γ therapy using a standard MTT assay. Effective inhibition is seen with a much lower dose of paclitaxel. This preliminary study clearly indicates it is possible to reduce the genotoxic drug amount when coupled with targeted mAb therapy followed by IFN-γ.

FIG. 43A-FIG. 43D. Effects of mAb therapy combined with IFN-γ in vitro. Different cell types (MDA-MB-453 in FIG. 43A; BT-474 in FIG. 43B; MDA-MB-231 in FIG. 43C; and A431 in FIG. 43D) were treated as indicated and MTT assays were performed every second day. Data were normalized to the cIgG group on Day 0. Data points represent the mean±S.D. of a typical experiment (n=6).

Figure 44:
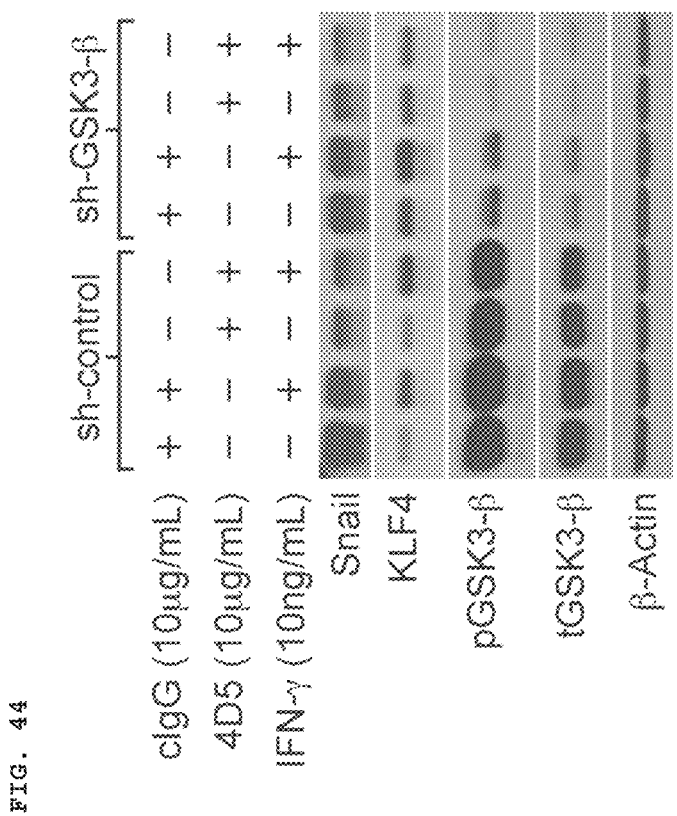

FIG. 44. Snail and KLF4 expressions in GSK3-13 knock down SK-BR-3. SK-BR-3 cells were stably transfected with either control or GSK3-β silencing short hairpin RNAs. Cells were treated for two days with cIgG, 4D5 or IFN-γ as indicated. In each instance, cIgG concentration was 10 μg/ml, 4D5 concentration was 10 μg/ml, and IFN-γ concentration was 10 ng/ml. In all instances, equal amounts of lysate were separated by SDS-PAGE, transferred, and immunoblotted with the indicated antibodies. β-Actin was used as a loading control. Shown are representative Western blots of typical experiments.

Figure 45A:
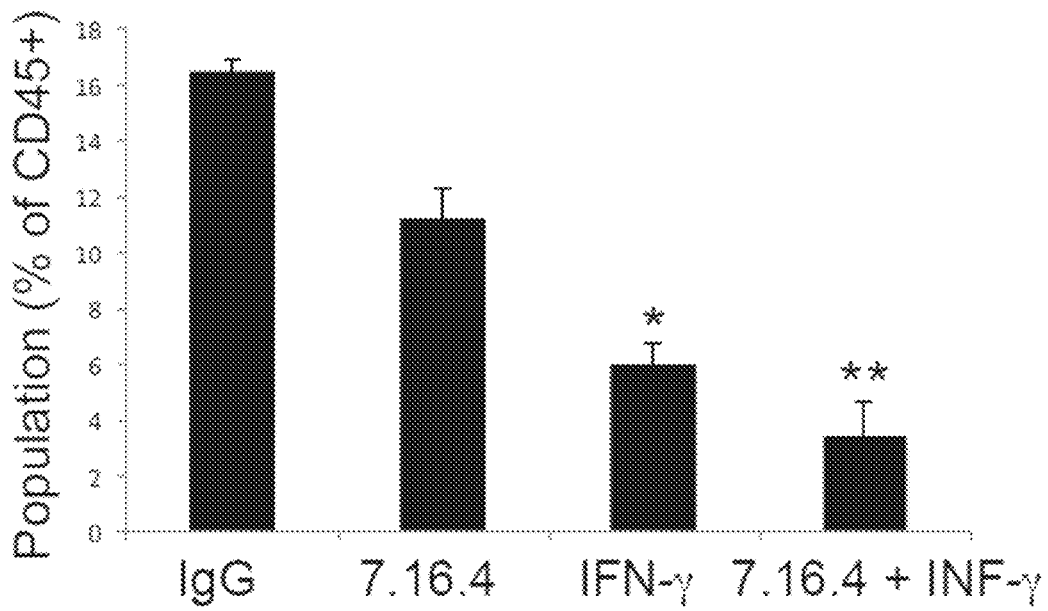
Figure 45B:
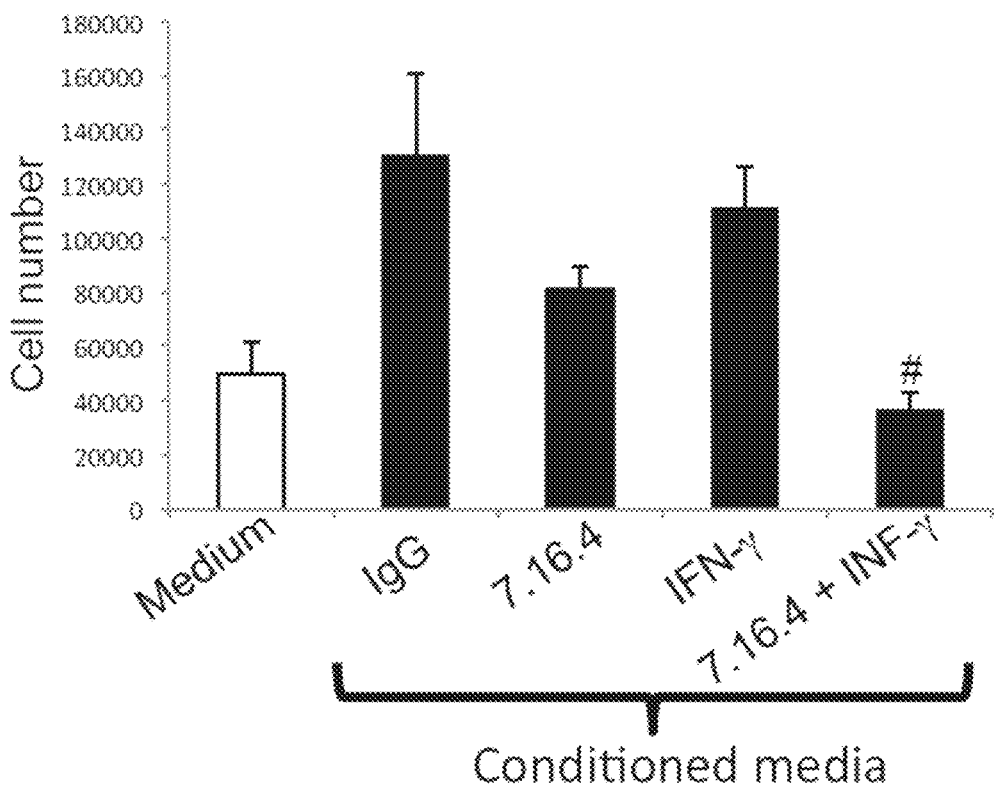

FIG. 45A-FIG. 45B. FIG. 45A. H2N113 tumors from each group of mice treated as indicated were obtained after treatment for FIG. 8A was finished. Tumor-infiltrated MDSC cells were isolated and compared using CD11b, Gr-1 and CD45 antibody by FACS. *P<0.05, **P<0.01, as compared with the IgG treated group. FIG. 45B. In vitro migration assay. H2N113 cells were seeded on 12-well plate and cultured until sub-confluent. Cells were then treated with control IgG (10 μg/ml), 7.16.4 (10 μg/ml), INF-γ (10 IU/ml), and 7.16.4 and INF-γ. and conditioned media were collected at day 3 of culture. Migration of MDSC was measured by the Transwell system (pore size: 4 μm). MDSCs were isolated from spleens of tumor-bearing mice, then seeded in the apical chamber. Condition media was then placed in the basolateral chamber and incubated for 3 hr. The cells that migrated to bottom chamber were collected and analyzed by FACS. Fresh medium was used as controls (medium). #. P<0.05 (compared with either 7.16.4 or IFN-γ treated group.

Figure 46:
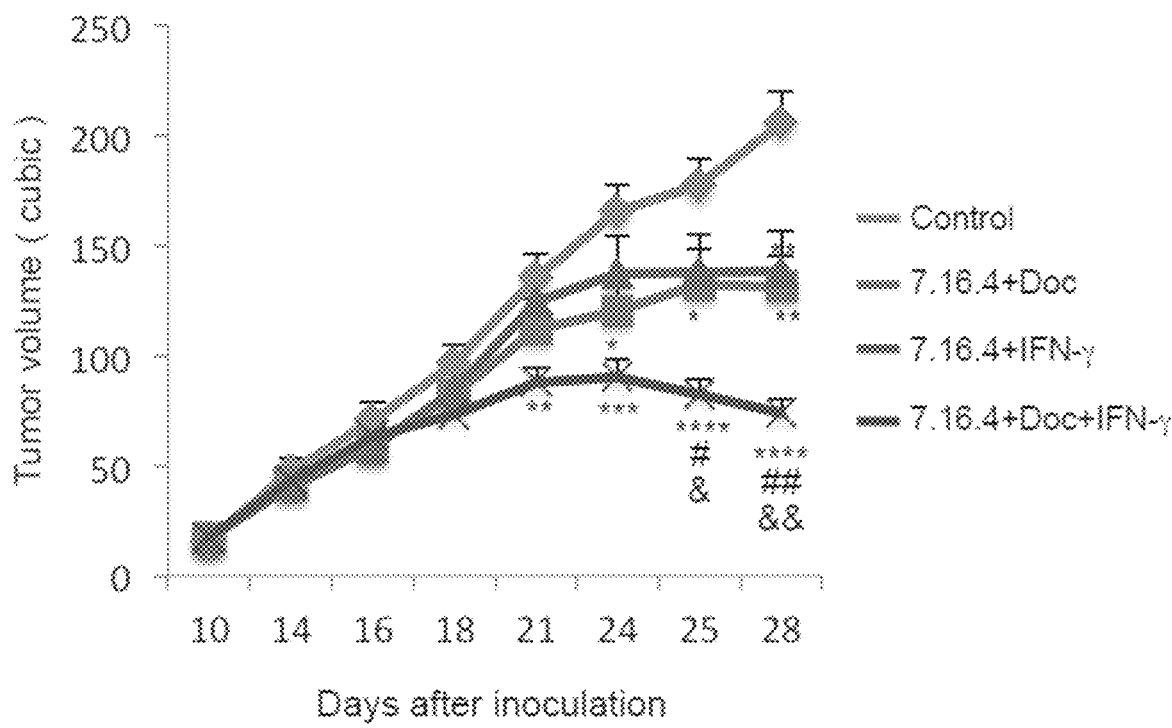

FIG. 46. H2N113 tumor cells (1×106) were injected subcutaneously into MMTV-neu mice similarly as in A. Mice were treated with control PBS, 7.16.4 (1.5 mg/kg, twice per week) and docetaxel (5.5 mg/kg, twice per week), 7.16.4 and IFN-γ (5×105 IU/kg, three times per week), or the combination of IFN-γ, 7.16.4 and docetaxel. Data represent mean+SEM. A student t-test was performed to compare the difference in the tumor size of different treatment groups. *P<0.05, P<0.01, *P<0.001, ****P<0.0001 compared with control; #P<0.05, ##P<0.01, compared with the 7.16.4 and docetaxel group; & P<0.05, && P<0.01, compared with the 7.16.4 and IFN-γ group.

Figure 47:
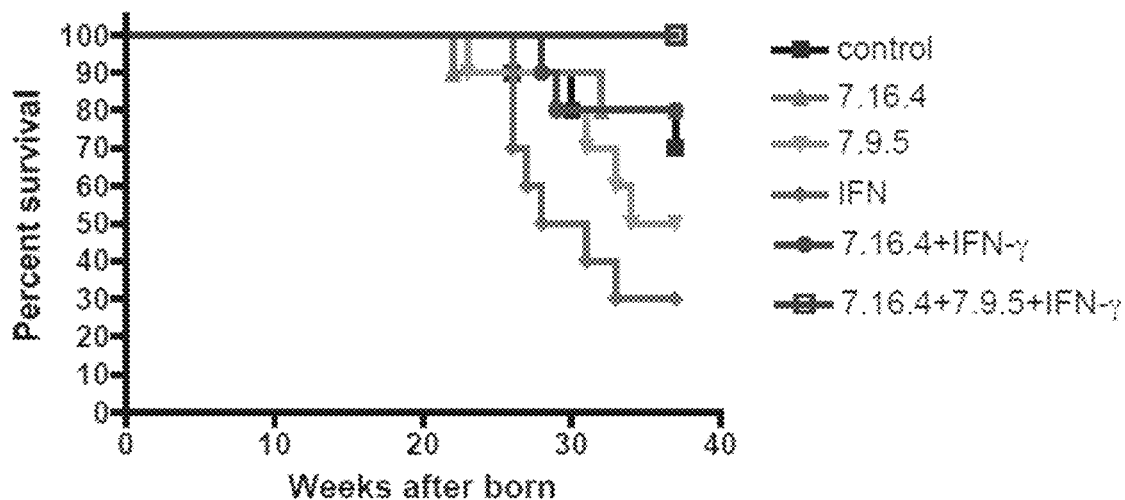

FIG. 47. Tumor free survival: Survival proportions. Treatments were Started at 6 weeks of age. Antibody treatment: I.P. injection at 10 ug/mouse, twice/week. IFN-γ treatment: 1,000 IU/mouse, twice/week.

Mice are genetically programmed to develop breast cancers in a stochastic manner. The actual development of tumors from tissue activated by the neu gene is used. An MMTV neu promotor is used. This model is described in U.S. Pat. No. 6,733,752, issued May 11, 2004, the entire content of which is hereby incorporated herein by reference.

Figure 48:
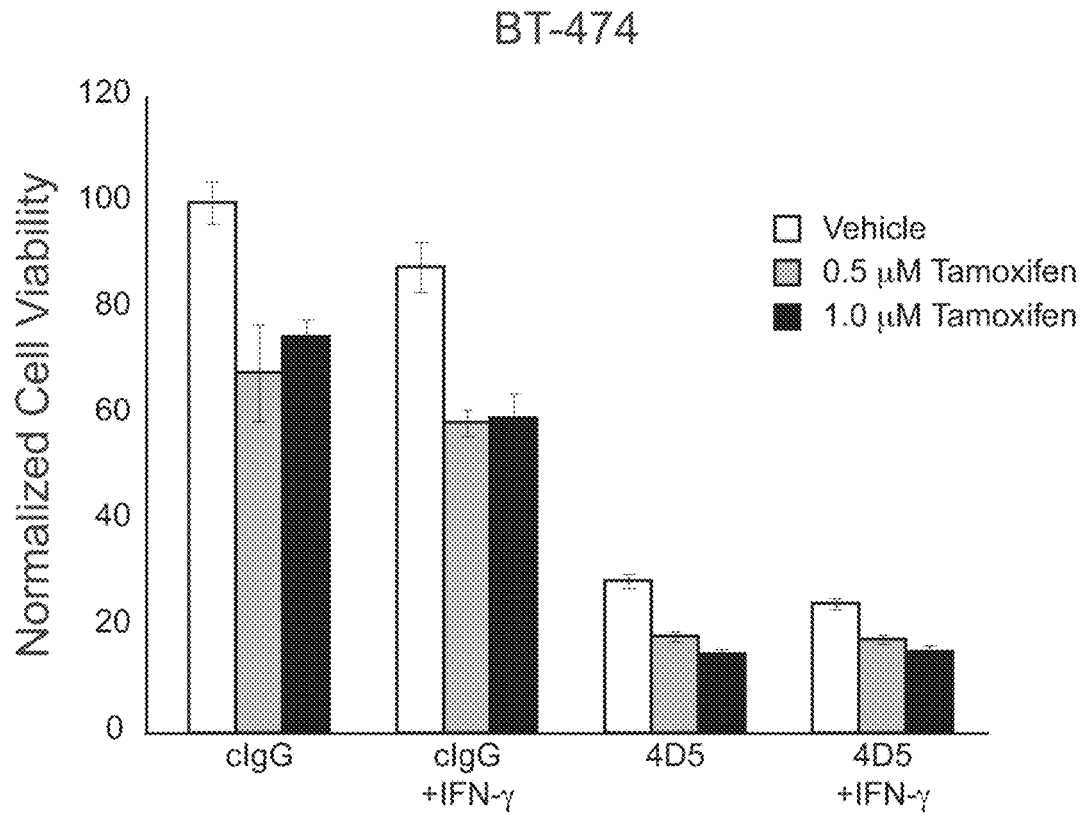

FIG. 48. Inclusion of tamoxifen does not permit IFN-γ to accentuate anti-erbB2 mAb. BT-474 cells were treated as indicated for 8 days. After 8 days, an MTT assay was performed. Data were normalized to the cIgG group. Bar graphs represent the mean±S.D. of a typical experiment (n=6).

Figure 49:
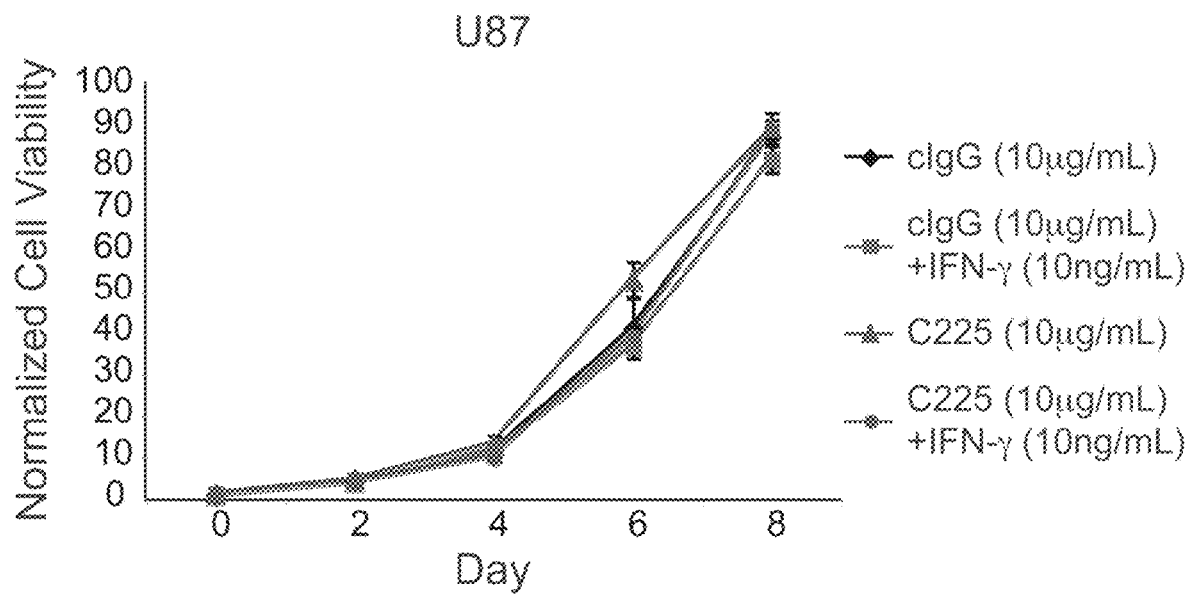

FIG. 49. U87 cells were not affected by the treatment. U87 cells were treated as indicated and MTT assays were performed every second day. Data were normalized to the cIgG group on Day 0. Data points represent the mean±S.D. of a typical experiment (n=6).

Figure 50:
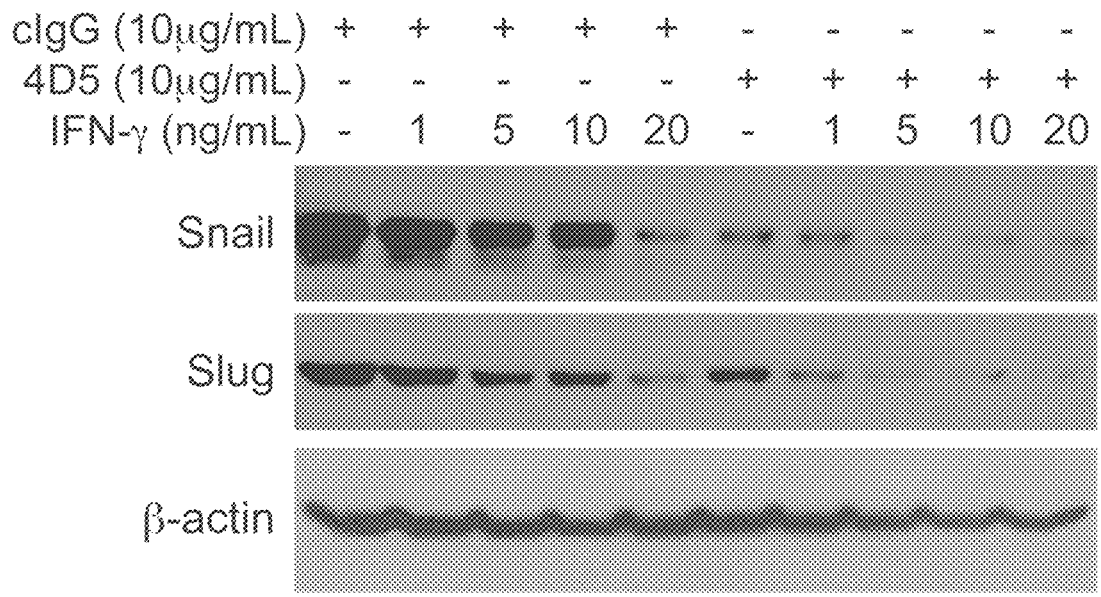

FIG. 50. Inclusion of IFN-γ potentiates the erbB2 disabling-caused snail and slug degradation. SK-BR-3 cells were treated for three days with cIgG, 4D5, or IFN-γ as indicated. Equal amount of lysate were separated by SDS-PAGE, transferred, and immunoblotted with the indicated antibodies. β-actin was used as a loading control. Shown are representative Western blots of a typical experiment.

Figure 51:
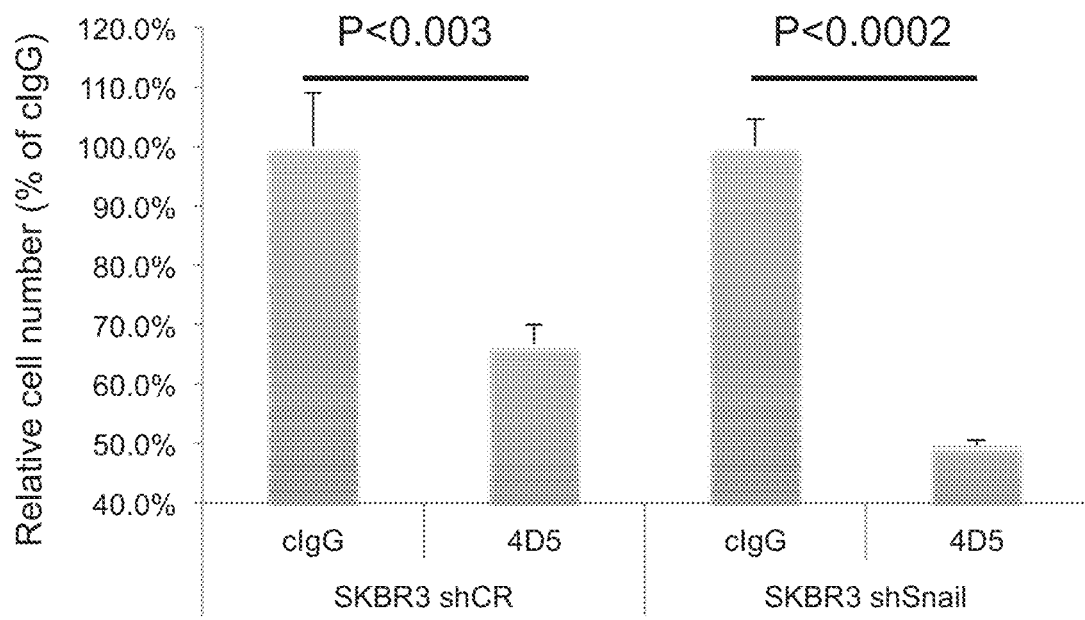

FIG. 51. Knock down of Snail enhances the effect of 4D5 on SK-BR-3 proliferation. SK-BR-3 cells were treated with or without 4D5 mAb (5 μg/ml). After 6 days, MTT assays were performed. Data points represent the mean±S.D.

Figure 52:
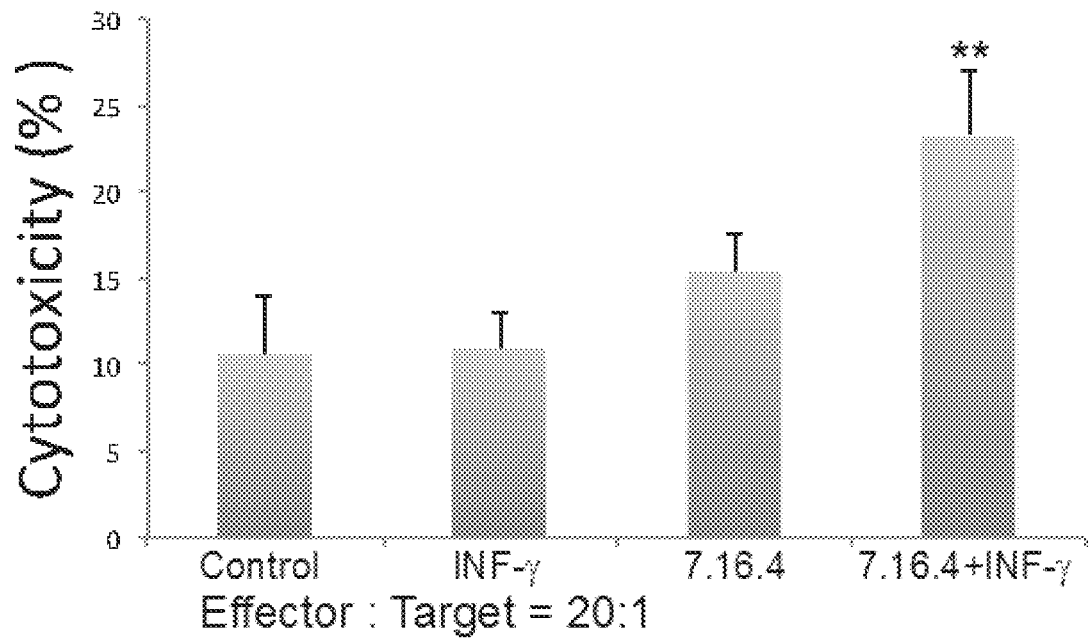

FIG. 52. Tumor-specific cytotoxicity of CD8+ T cells in mouse spleens. CD8+ T cells were collected from the spleens of mice treated with control IgG (IgG), 7.16.4, IFN-γ, and 7.16.4 and IFN-γ, then subjected to cytotoxicity assay. Statistical analysis was performed using a Student's t-test. **P<0.02 compared to control.

Figure 53:
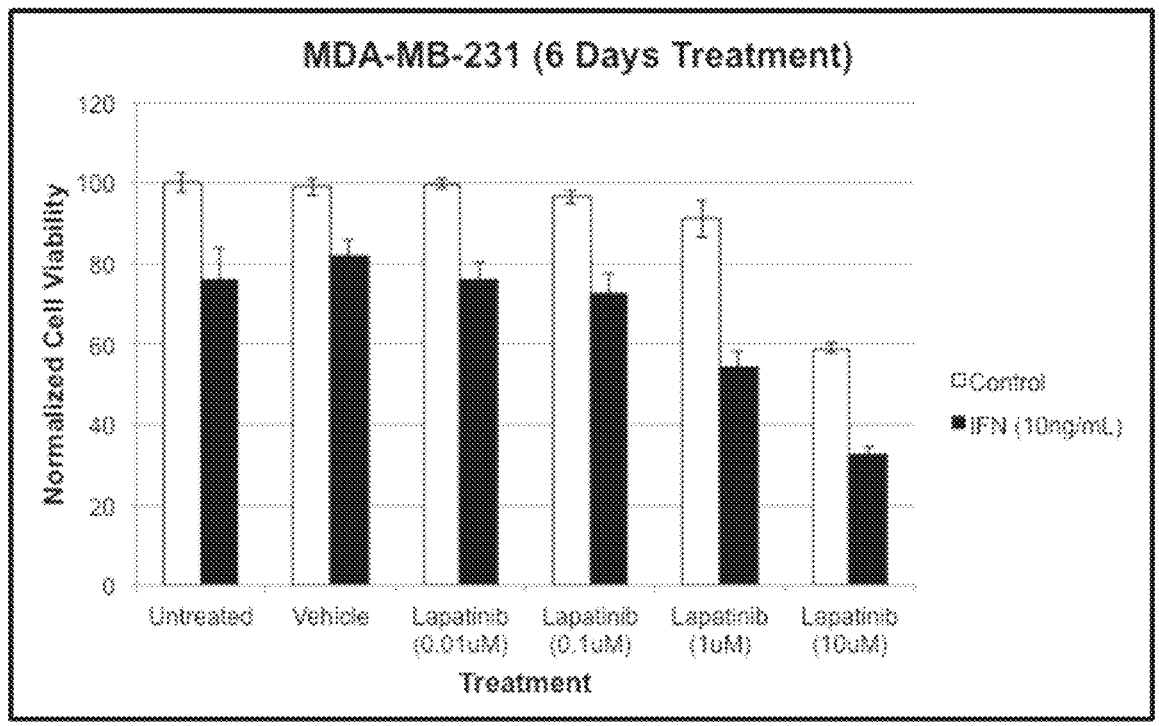

FIG. 53. MDA-MB-231 cells (Triple negative breast cancer cell line) were treated with Lapatinib and INF-γ as indicated concentrations. After 6 days, MTT assays were performed. Data points represent the mean±SD.

Figure 54A:
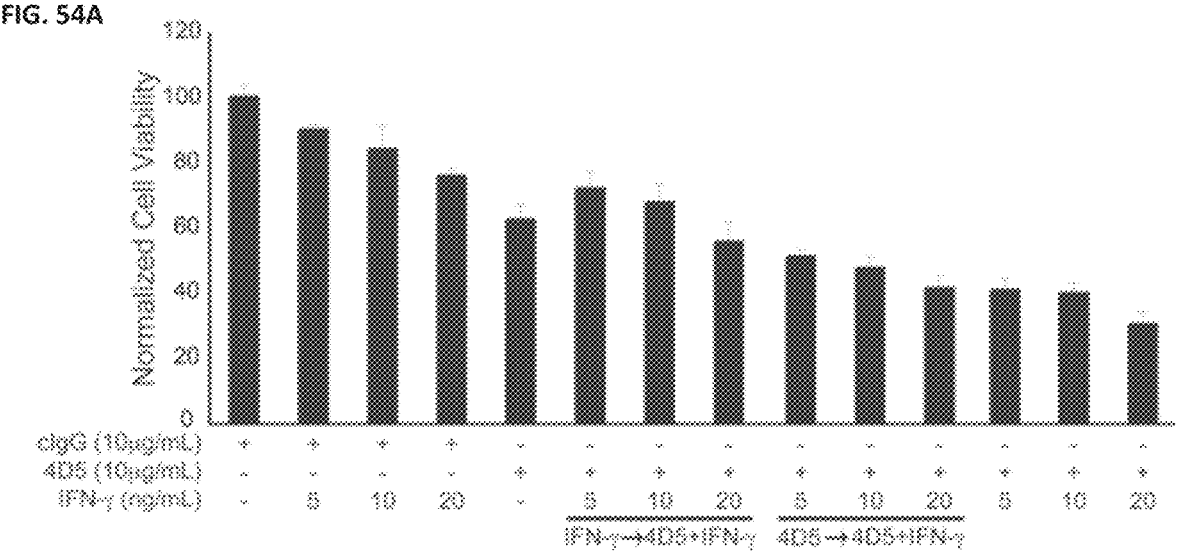
Figure 54B:
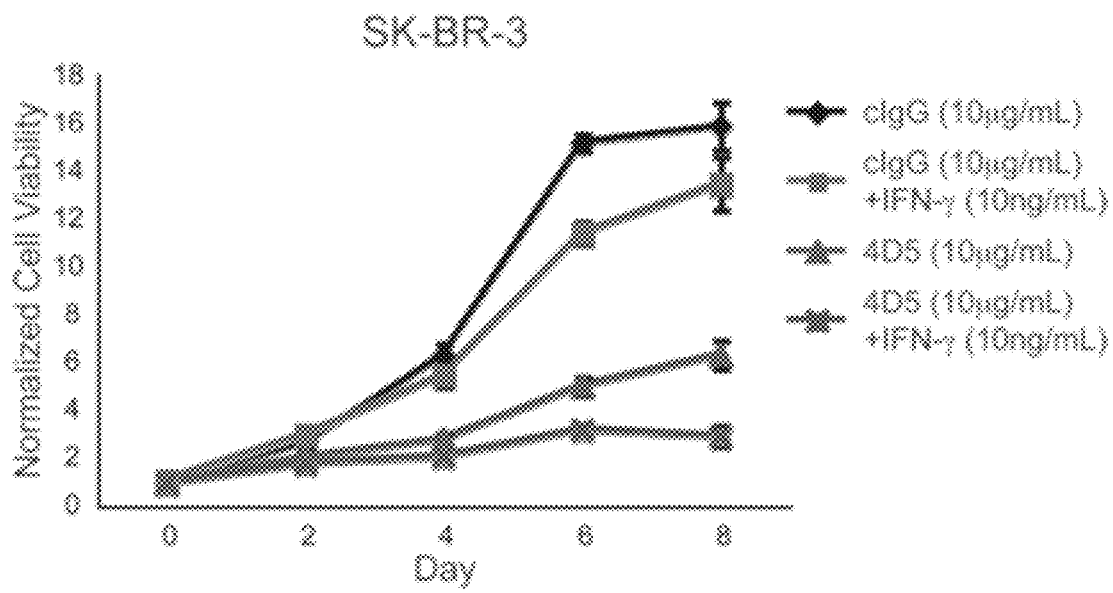
Figure 54C:
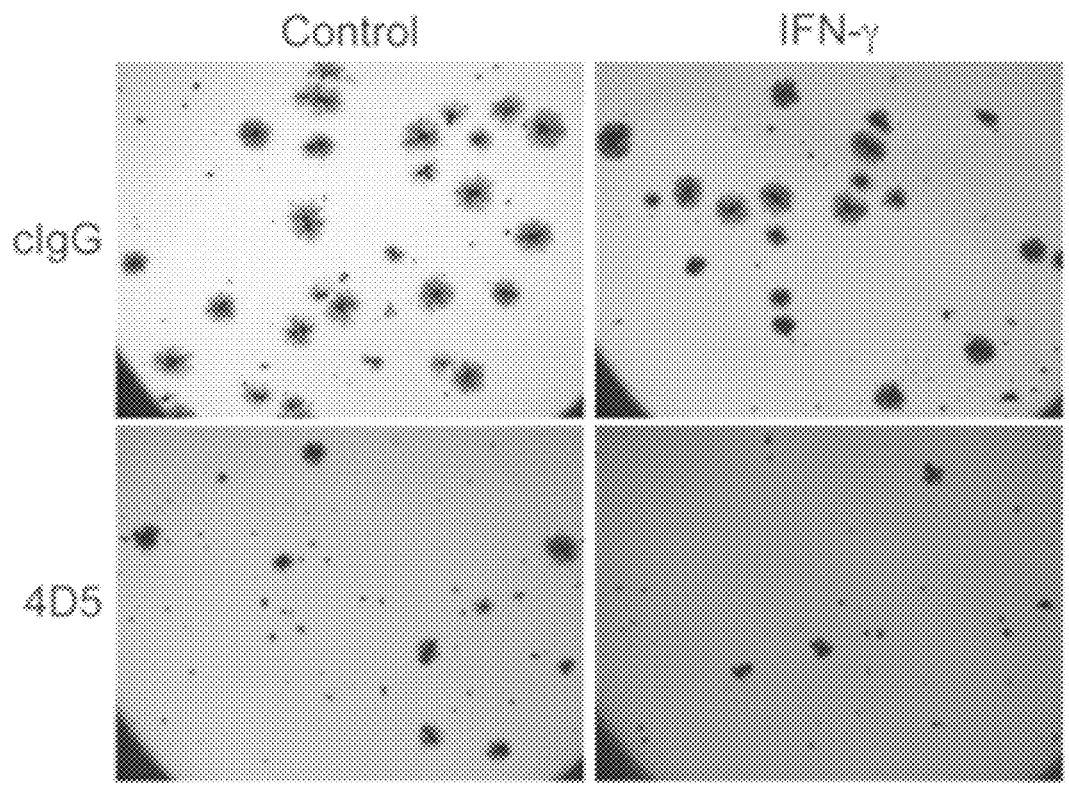
Figure 54D:
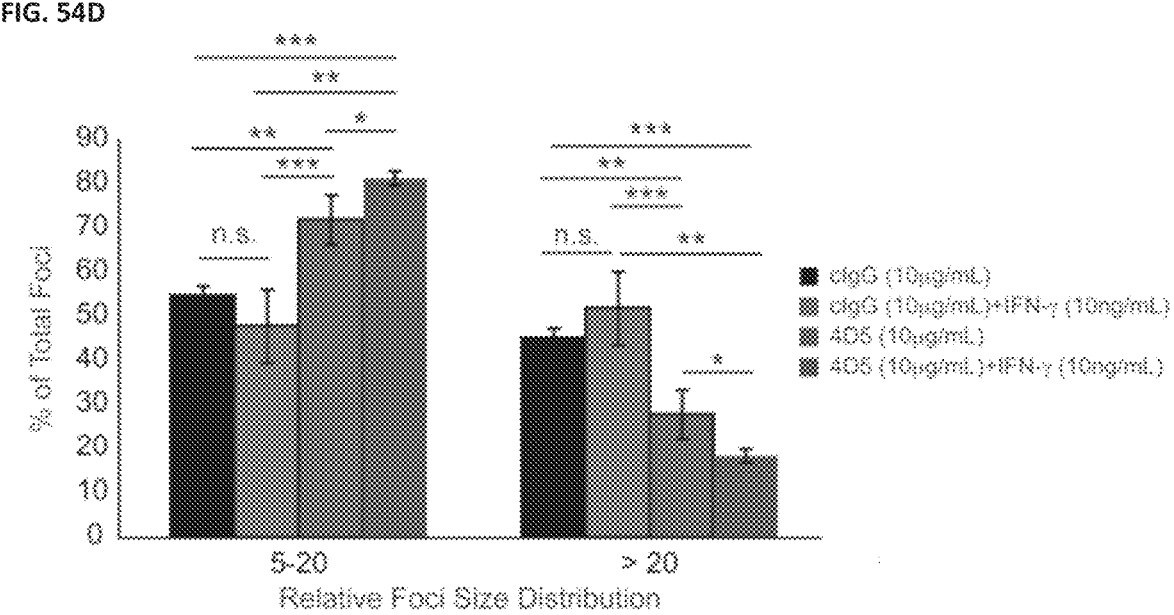

FIG. 54A-FIG. 54D. Anti-erbB2 monoclonal antibody and IFN-γ act directly on HER2-positive breast cancer cells. FIG. 54A—SK-BR-3 cells were treated with regimens of anti-erbB2 mAb (4D5) and IFN-γ at the indicated concentrations. Protocols described as IFN-γ→4D5+IFN-γ were treated with the indicated dose of IFN-γ for 4 days, then the indicated dose of IFN-γ plus 4D5 for an additional 4 days. Protocols described as 4D5→4D5+IFN-γ were treated with 4D5 for 4 days, then the indicated dose of IFN-γ plus 4D5 for an additional 4 days. All other treatment groups were treated as indicated for 8 days. Following a total of 8 days, an MTT assay was performed. Data were normalized to the cIgG group. Bar graphs represent the mean±S.D. of a typical experiment (n=5). FIG. 54B SK-BR-3 cells were treated as indicated and MTT assays were performed every second day. Data were normalized to the cIgG group on Day 0. Data points represent the mean±S.D. of a typical experiment (n=6). FIG. 54C—SK-BR-3 cells were seeded in a 0.2% agar solution containing the indicated treatments, which was layered over a 0.8% agar solution. After 14 days in culture, viable foci were visualized following incubation with MTT solution. FIG. 54D—Foci from panel C were quantified using NIHendorsed software (ImageJ). Bar graphs represent the mean±S.D. of a typical experiment (n=3 or 4; n.s., not significant; *, p<0.05; , p<0.01; *; p<0.001).

FIG. 55A-FIG. 55D. Effects of mAb therapy combined with IFN-γ in vitro. Different cell types (A431 in FIG. 55A; MDA-MB-453 in FIG. 55B; MDA-MB-231 in FIG. 55C; and BT-474 in FIG. 55D) were treated as indicated and MTT assays were performed every second day. Data were normalized to the cIgG group on Day 0. Data points represent the mean±S.D. of a typical experiment (n=6).

Figure 56A:
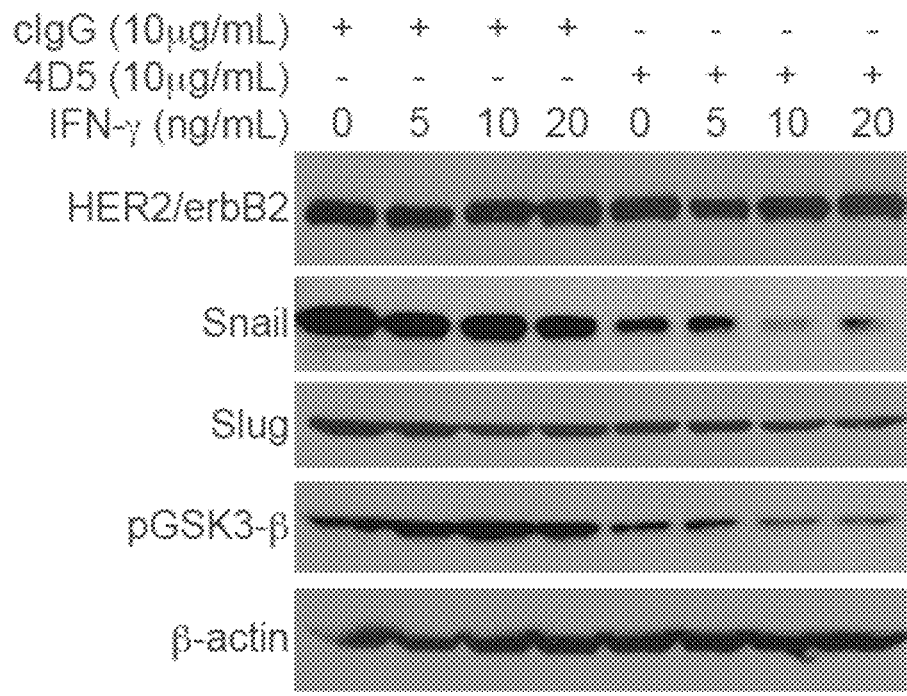
Figure 56B:
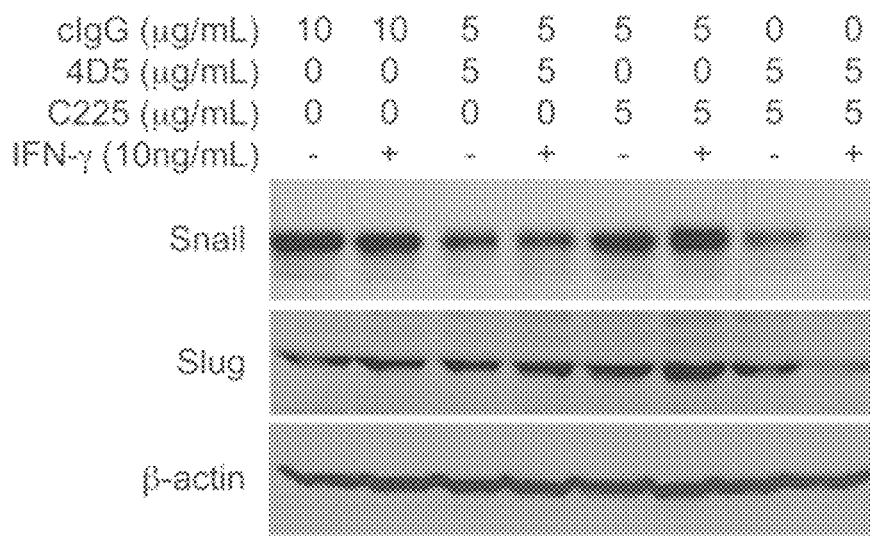
Figure 56C:
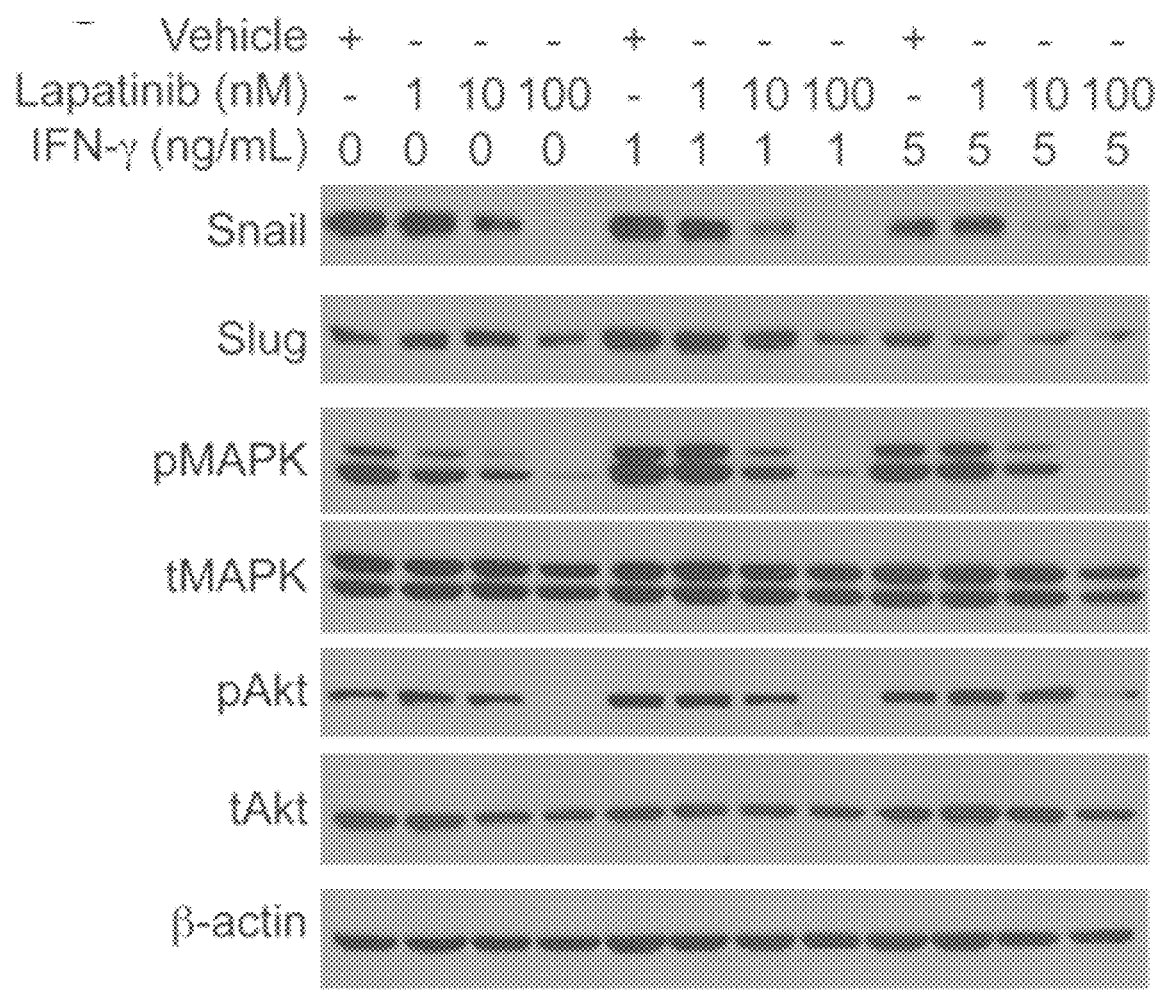

FIG. 56A-FIG. 56C. Inclusion of IFN-γ potentiates the erbB2 disabling-caused Snail degradation. FIG. 56A—SK-BR-3 cells were treated for 48 hours with cIgG, 4D5, or IFN-γ as indicated and subjected to western blotting. FIG. 56B—SK-BR-3 cells were treated for two days with cIgG, 4D5, C225, or IFN-γ as indicated, and the expression of Snail and Slug were detected by western blotting. FIG. 56C—SK-BR-3 cells were treated for 24 hours with vehicle (0.001% DMSO), three doses of lapatinib, or IFN-γ (two doses) as indicated. In all instances, equal amounts of lysate were separated by SDS-PAGE, transferred, and immunoblotted with the indicated antibodies. β-actin is used as a loading control.

Figure 57A:
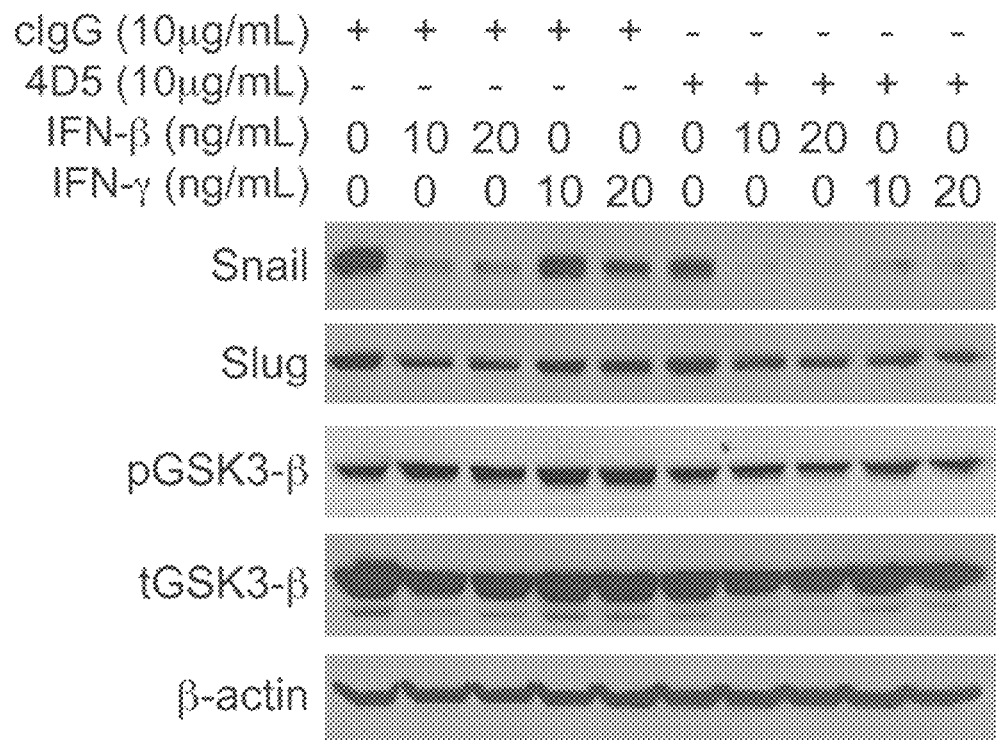
Figure 57B:
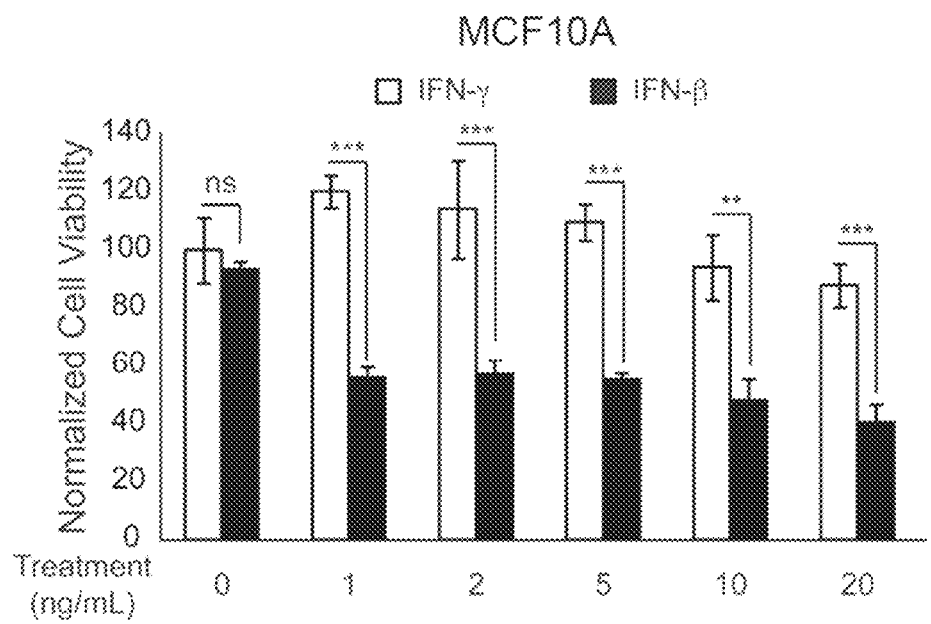
Figure 57C:
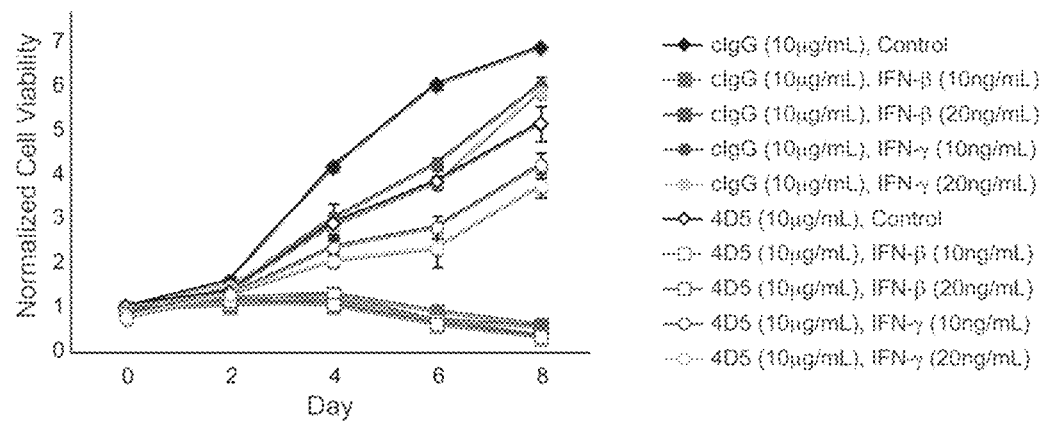

FIG. 57A-FIG. 57C. IFN-γ, but not IFN-β, requires the inclusion of anti-erbB2 mAb. FIG. 57A—SK-BR-3 cells were treated for one day with cIgG, 4D5, IFN-β, or IFN-γ as indicated. Equal amounts of lysate were separated by SDS-PAGE, transferred, and immunoblotted with the indicated antibodies. β-actin is used as a loading control. Shown is a representative Western blot of a typical experiment. FIG. 57B—MCF10A cells were treated as indicated for 8 days. Vehicle control for IFN-γ experiments was performed by addition of media whereas vehicle control for IFN-β experiments was a vehicle (50 mM NaOAc, pH 5.5 containing 0.1% BSA). Following treatment, an MTT assay was used to assess viability. Data were normalized to IFN-γ control values. Bar graphs represent the mean±S.D. of a typical experiment (n=5) (n.s., not significant; , p<0.01; *; p<0.001). FIG. 57C SKBR-3 cells were treated as indicated and MTT assays were performed every second day. Data were normalized to the cIgG group on Day 0. Data points represent the mean±S.D. of a typical experiment (n=6).

Figure 58A:
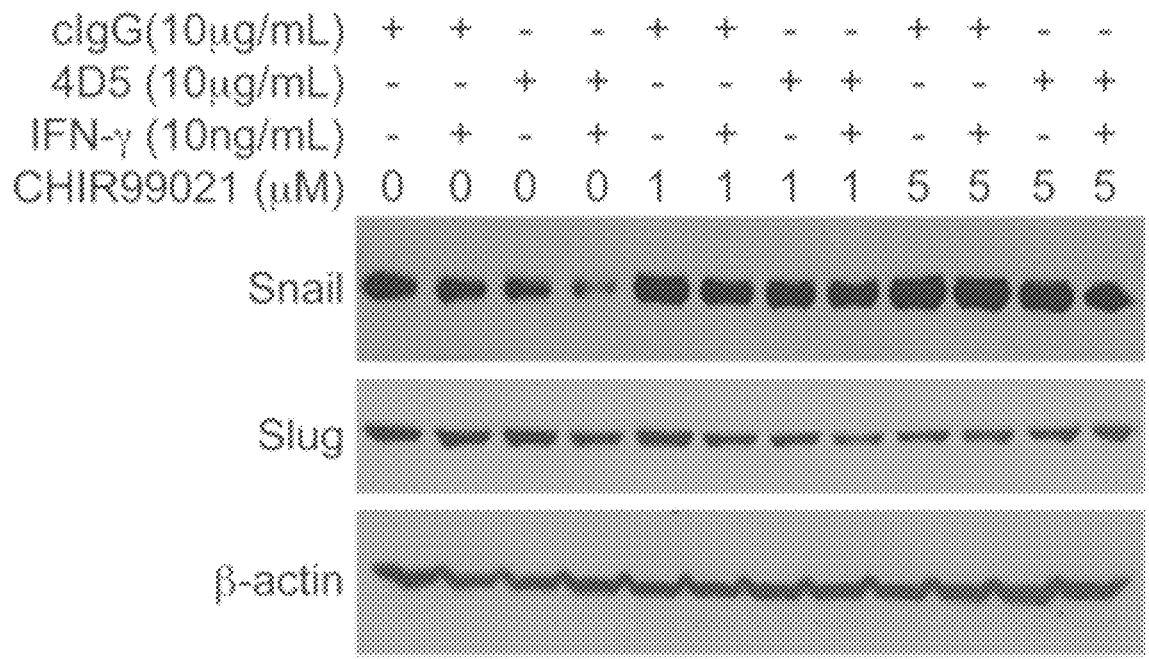
Figure 58B:
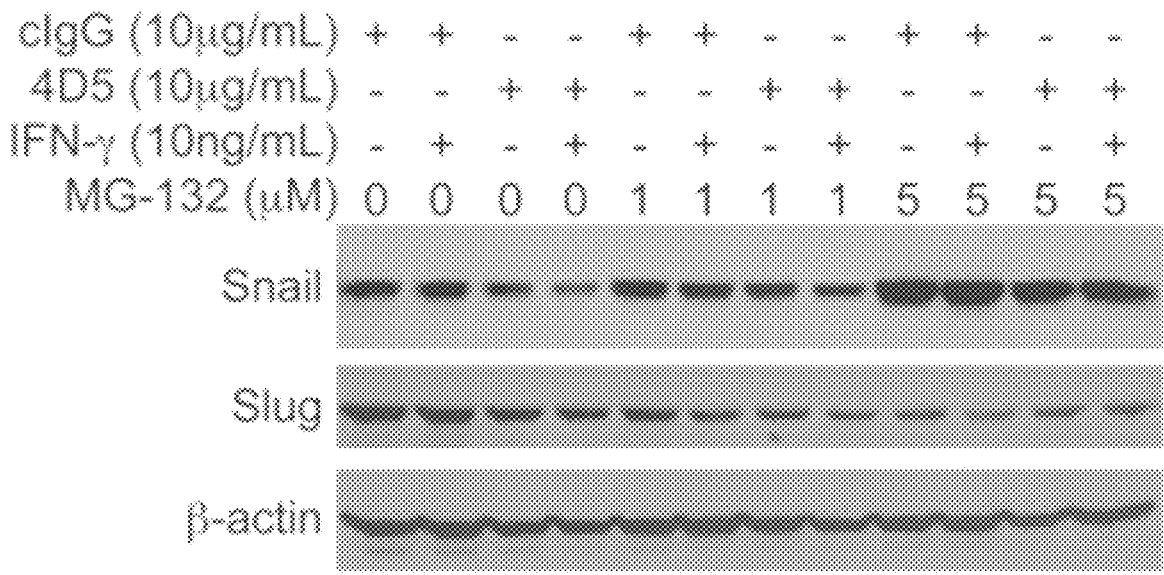

FIG. 58A-FIG. 58C. Anti-erbB2 and IFN-γ degrade Snail through the GSK3-8/proteasome pathway. SK-BR-3 cells were treated with cIgG, 4D5, and IFN-γ as indicated for two days. FIG. 58A—During the final 8 hours of treatment, vehicle (0.01% DMSO) or the indicated doses of the GSK3-β inhibitor CHIR99021 were added. FIG. 58B—During the final 8 hours of treatment, vehicle (0.025% ethanol) or the indicated doses of the proteasome inhibitor MG-132 were added. FIG. 58C—SK-BR-3 cells were transfected with either empty vector (EV), wild-type (WT) Snail, or Snail with serines 97, 101, 108, 112, 116, and 120 mutated to alanines (6SA). The day following transfection, cytoplasmic and nuclear fractions were prepared from these cells. In all instances, equal amounts of lysate were separated by SDS-PAGE, transferred, and immunoblotted with the indicated antibodies. β-actin and Ku70 (nuclear fraction) were used as loading controls. Shown are representative Western blots of typical experiments.

Figure 59A:
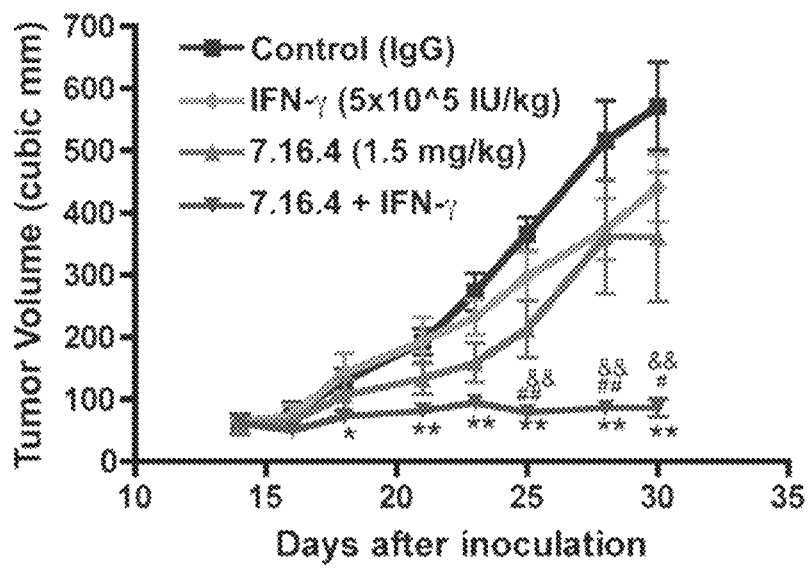
Figure 59B:
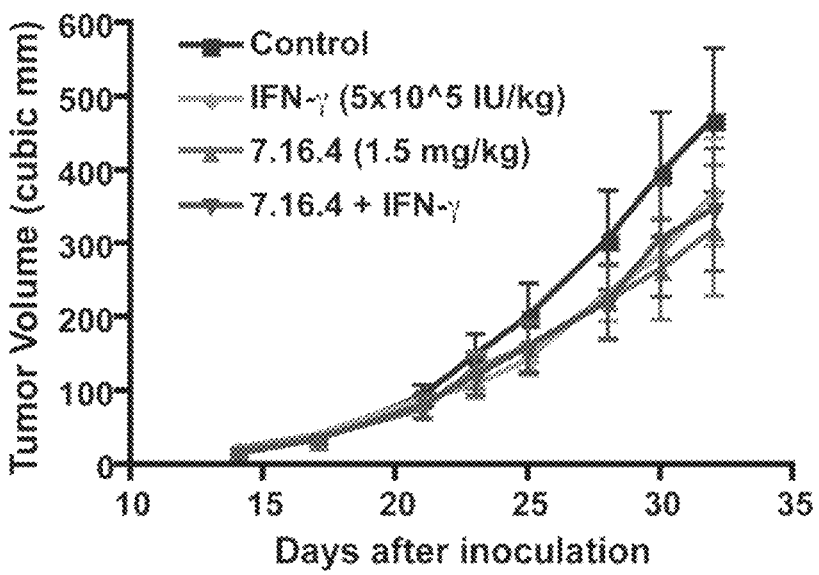
Figure 59C:
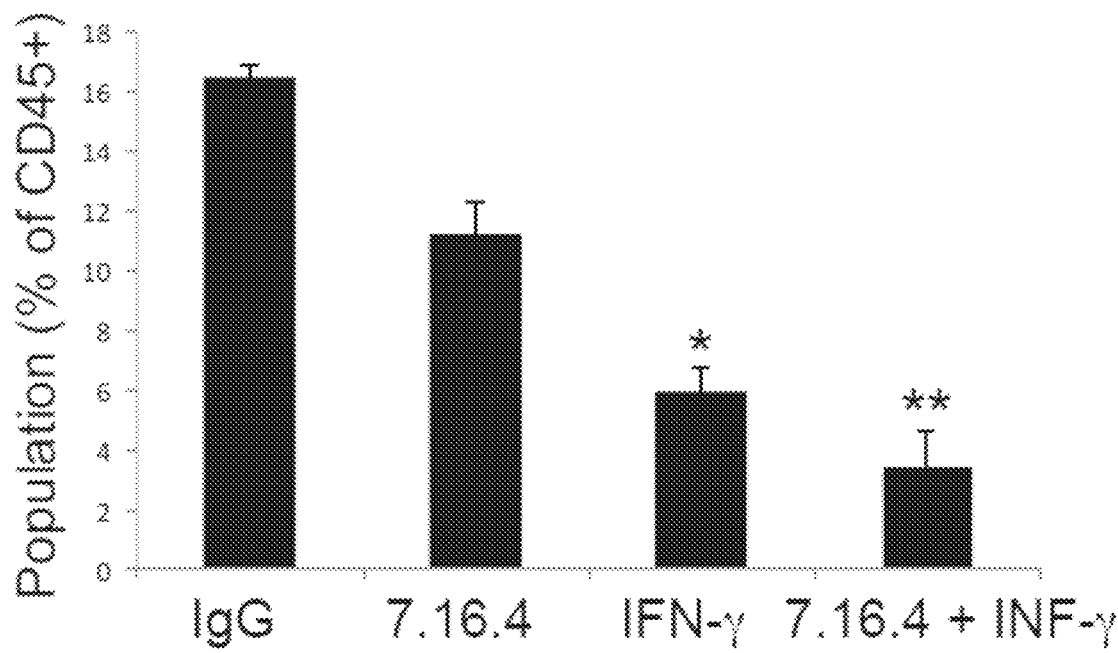
Figure 59D:
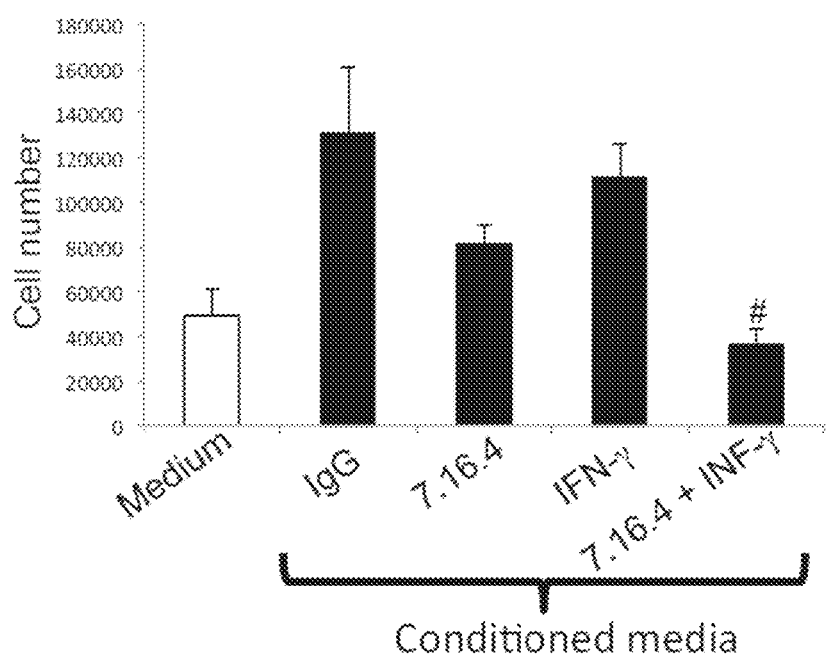
Figure 59E:
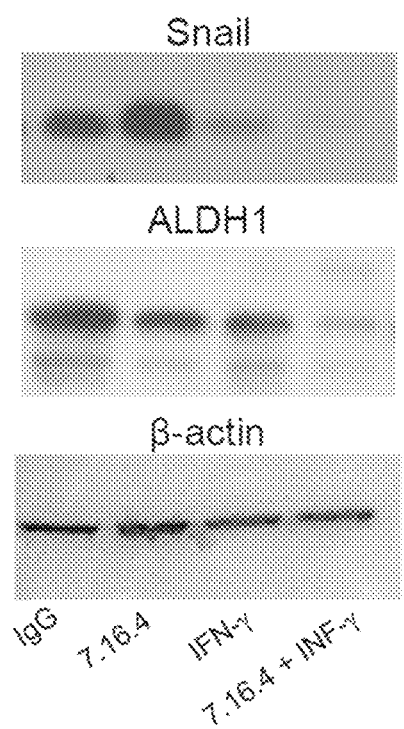
Figure 59F:
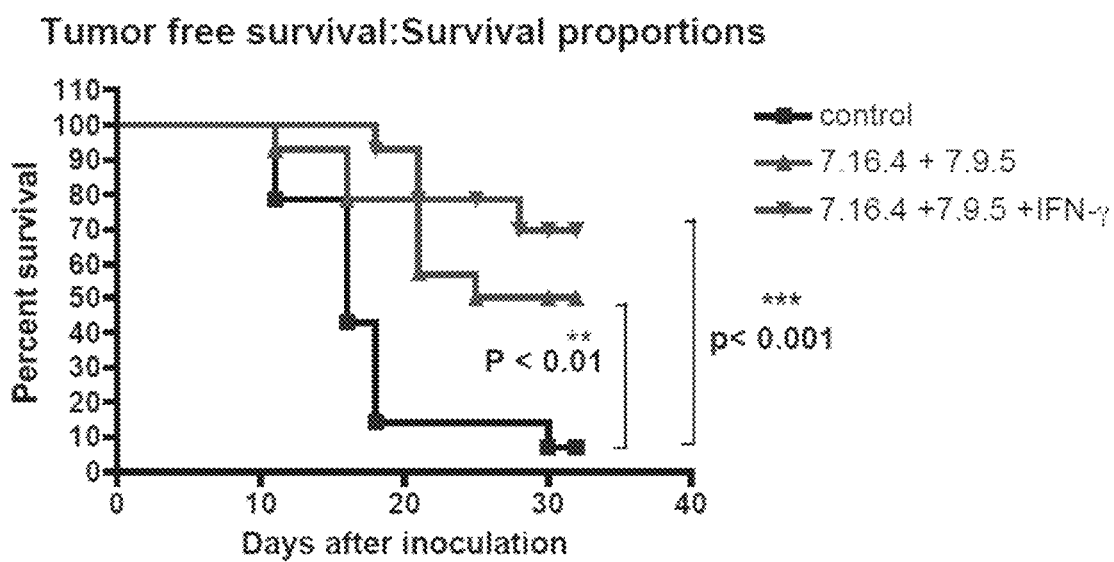
Figure 59G:
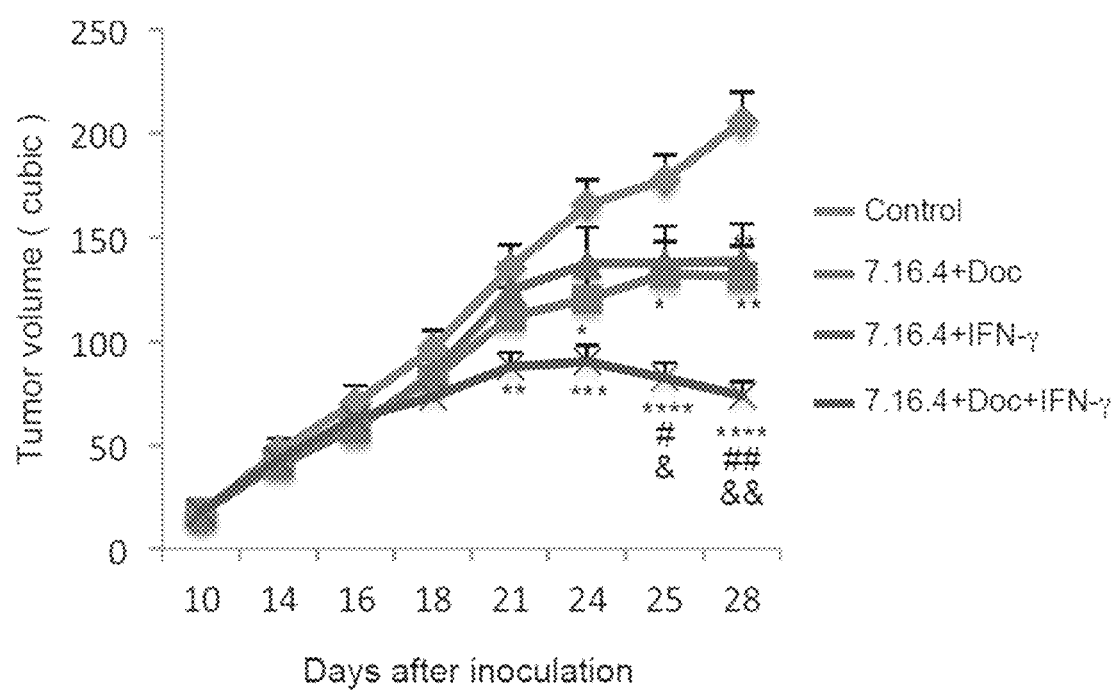

FIG. 59A-FIG. 59G. Synergistic activity of anti-erbB2/neu antibody and IFN-γ. FIG. 59A—Implanted H2N113 tumors were treated with control IgG, IFN-γ (three times per week), 7.16.4 (twice per week), or the combination of IFN-γ and 7.16.4. FIG. 59B—IFN-γ receptor was knocked down by shRNA in H2N113. The resulting tumor cells (1×106) were injected subcutaneously into MMTV-neu mice and treated similarly as in A. Data represent mean+SEM. A student's t-test was performed to compare the difference in the tumor size of different treatment groups. *P<0.05, **P<0.01, compared with control; #P<0.05, ##P<0.01, compared with the 7.16.4 group; & P<0.05, && P<0.01, compared with the IFN-γ group. FIG. 59C—H2N113 tumors from each group of mice treated as indicated were obtained after treatment for FIG. 59A was finished. Tumor-infiltrated MDSC cells were isolated and compared using CD11b, Gr-1 and CD45 antibody by FACS. *P<0.05, **P<0.01, as compared with the IgG treated group. FIG. 59D—In vitro migration assay. H2N113 cells were seeded on 12-well plate and cultured until sub-confluent. Cells were then treated with control IgG (10 μg/ml), 7.16.4 (10 μg/ml), INF-γ (10 IU/ml), and 7.16.4 and INF-γ. and conditioned media were collected at day 3 of culture. Migration of MDSC was measured by the Transwell system (pore size: 4 μm). MDSCs were isolated from spleens of tumor-bearing mice, then seeded in the apical chamber. Conditioned media were then placed in the basolateral chamber and incubated for 3 hr. The cells that migrated to the bottom chamber were collected and counted. Fresh medium was used as control (medium). #. P<0.05 (compared with either 7.16.4 or IFN-γ treated group). FIG. 59E—In vivo cotreatment significantly reduced the expression of ALDH1 in the tumor. Tumors from each group of mice treated as indicated were obtained after treatment for FIG. 59A was finished. Each lysate was adjusted to 10 μg/lane and examined for Snail and ALDH1 expression by Western blot. β-actin was used as the loading control. Shown are representative Western blots of typical experiments. FIG. 59F—H2N113 tumor cells (0.25×106) were injected subcutaneously into both side of the back of 6-10 weeks old MMTV-neu mice at day 0. Mice were treated with control PBS, 7.9.5 and 7.16.4 (0.625 mg/kg each), or the combination of IFN-γ, 7.9.5 and 7.16.4 twice per week from day 1. FIG. 59G—H2N113 tumor cells (1×106) were injected subcutaneously into MMTV-neu mice similarly as in A. Mice were treated with control PBS, 7.16.4 (1.5 mg/kg, twice per week) and docetaxel (5.5 mg/kg, twice per week), 7.16.4 and IFN-γ (5×105 IU/kg, three times per week), or the combination of IFN-γ, 7.16.4 and docetaxel. Data represent mean+SEM. A student t-test was performed to compare the difference in the tumor size of different treatment groups. *P<0.05, P<0.01, *P<0.001, ****P<0.0001 compared with control; #P<0.05, ##P<0.01, compared with the 7.16.4 and docetaxel group; & P<0.05, && P<0.01, compared with the 7.16.4 and IFN-γ group.

Figure 60B:
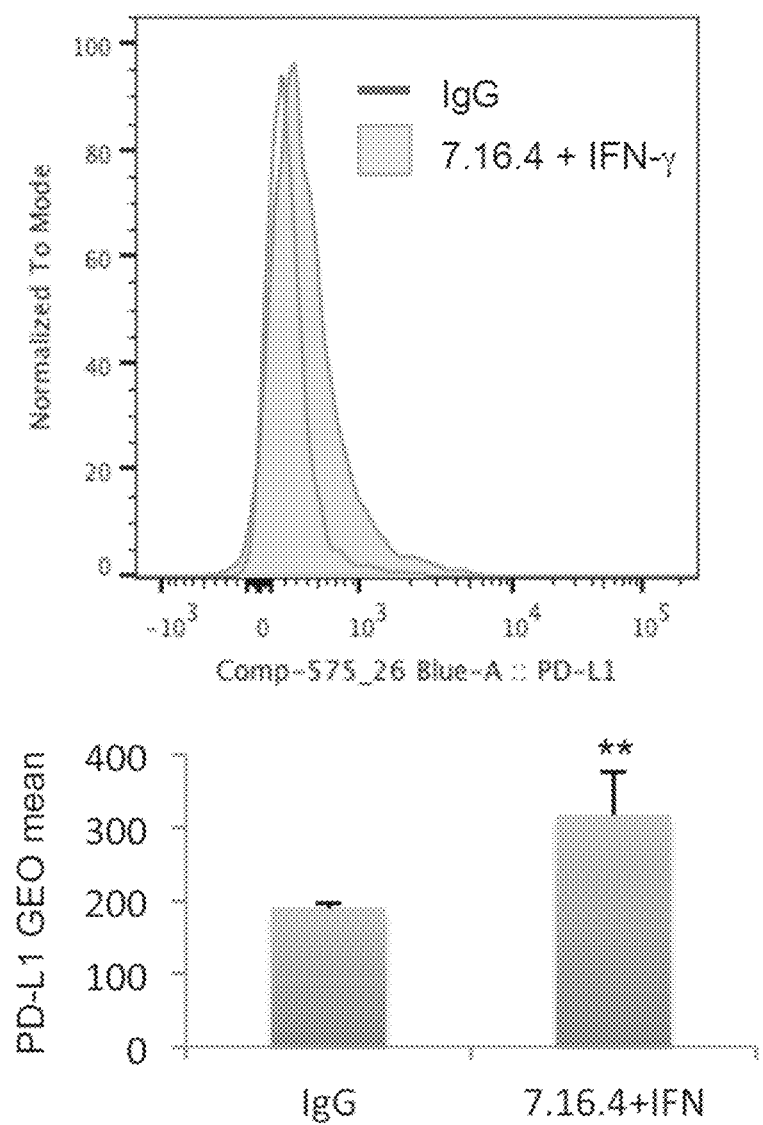

FIG. 60A-FIG. 60C. PD-L1 expression is increased in tumors treated with IFN-γ. FIG. 60A—Western blotting was performed with anti-PD-L1 antibody with the tumors from each indicated group of mice after treatment in the same way as FIG. 59A. FIG. 60B—FACS analysis of PD-L1 expression in tumor cells from control IgG and 7.16.4+IFN-γ treated mice. Tumor cells are gated as CD45-large size cells which we confirmed most of them are tumor cells by 7.16.4 antibody. **P<0.02. FIG. 60C—Administration of anti-PD-L1 antibody with the ordered therapy. Mice were treated with control PBS, 7.16.4 (1.5 mg/kg, three times per week) and anti-PDL1 (5 mg/kg, twice per week), 7.16.4 and IFN-γ (5×105 IU/kg, three times per week), or the combination of IFN-γ, 7.16.4 and anti-PD-L1. Data represent mean+SEM.

DETAILED DESCRIPTION OF THE INVENTION

The present invention provides a fusion protein comprising
(a) a first stretch of consecutive amino acids, the sequence of which is the sequence of an anti-p185her2/neu polypeptide;
(b) a second stretch of consecutive amino acids, the sequence of which is the sequence of a polypeptide capable of binding at least one polypeptide other than p185her2/neu; and
(c) a third stretch of consecutive amino acids, the sequence of which comprises the sequence of a biologically active portion of interferon-gamma (IFNγ),
wherein (b) is located at the carboxy-terminal end of (a), and (c) is located at the carboxy-terminal end of (b).

In some embodiments, the fusion protein further comprises an oligopeptide linker between (a) and (b).

In some embodiments, the fusion protein further comprises an oligopeptide linker between (b) and (c).

In some embodiments, the fusion protein further comprises a second oligopeptide linker between (b) and (c).

In some embodiments, the amino acid sequence of the oligopeptide linker is identical to the amino acid sequence of the second oligopeptide linker.

In some embodiments, the amino acid sequence of the oligopeptide linker is different from the amino acid sequence of the second oligopeptide linker.

In some embodiments,
i) the oligopeptide is a polyglycine oligopeptide linker or a glycine-serine oligopeptide linker; and
ii) the second oligopeptide is independently a polyglycine oligopeptide linker or a glycine-serine oligopeptide linker.

In some embodiments, the amino acid sequence of the polyglycine oligopeptide linker comprises at least two, three, four, five, six, seven, eight, nine, or ten, consecutive glycine residues.

In some embodiments, the amino acid sequence of the glycine-serine oligopeptide linker comprises at least two, three, four, five, six, seven, eight, nine, or ten, consecutive glycine residues.

In some embodiments, the C-terminal residue of the glycine-serine oligopeptide linker is a serine residue.

In some embodiments, (a) is directly contiguous with (b).
In some embodiments, (b) is directly contiguous with (c).
In some embodiments, the anti-p185her2/neu polypeptide is a chain of an antibody or a portion thereof.

In some embodiments, the antibody chain is a single chain variable fragment (scFv).

In some embodiments, the antibody chain is a monoclonal antibody chain.

In some embodiments, the monoclonal antibody chain is a human monoclonal antibody chain, a humanized monoclonal antibody chain, or a chimeric antibody chain.

In some embodiments, the monoclonal antibody chain is a chimeric antibody chain, and wherein a portion of the chimeric antibody chain is derived from a human antibody chain.

In some embodiments, the antibody is an anti-p185her2/neu antibody.

In some embodiments, the anti-p185her2/neu antibody is 4D5.

In some embodiments, the anti-p185her2/neu antibody is pertuzumab.

In some embodiments, the anti-p185her2/neu antibody is a trastuzumab.

In some embodiments, the anti-p185her2/neu antibody binds at least a portion of the same epitope as trastuzumab.

In some embodiments, the anti-p185her2/neu antibody is 7.16.4.

In some embodiments, the anti-p185her2/neu antibody is 7.9.5.

In some embodiments, the polypeptide that is capable of binding a polypeptide other than p185her2/neu is capable of binding at least one antibody.

In some embodiments, the polypeptide that is capable of binding a polypeptide other than p185her2/neu is capable of binding at least one antibody Fc-region.

In some embodiments, the polypeptide that is capable of binding a polypeptide other than p185her2/neu is derived from a portion of Protein A or Protein G that is capable of binding at least one antibody Fc-region.

In some embodiments, the least one antibody is endogenously expressed in a mammal.

In some embodiments, the sequence of the third stretch of consecutive amino acids is identical to the sequence of IFNγ (SEQ ID NO: 5).

In some embodiments, the sequence of the fusion protein has been modified to reduce immunogenicity in a human.

In some embodiments, (a), (b), or (c) has been humanized.

In some embodiments, each of (a), (b), and (c) has been humanized.

In some embodiments, the sequence of each of (a), (b), and (c) is found in an endogenous human polypeptide.

In some embodiments, the fusion protein is 4D5scFvZZ-IFNγ, or a humanized derivative thereof.

The present invention provides a method of treating a subject afflicted with cancer, which comprises administering to the subject a therapeutically effective amount of a fusion protein of the invention.

In some embodiments, the method further comprises administering an antibody to the subject.

In some embodiments, the antibody is an anti-p185her2/neu antibody.

In some embodiments, the antibody is an anti-EGFR antibody.

In some embodiments, the anti-EGFR antibody is cetuximab.

In some embodiments, the antibody is an anti-PD1 or an anti-PD-L1 antibody.

In some embodiments, the antibody is a monoclonal antibody.

In some embodiments, the method further comprises administering a chemotherapeutic agent to the subject.

In some embodiments, the chemotherapeutic agent is administered to the subject in an amount that is less than the amount that would be effective to treat the subject if the chemotherapeutic agent was administered without the fusion protein.

In some embodiments, the method further comprises comprising administering a radiation to the subject.

In some embodiments, the radiation is administered to the subject in an amount that is less than the amount that would be effective to treat the subject if the radiation was administered without the fusion protein.

The present invention provides a method of sensitizing cancer cells to radiation or a chemotherapeutic agent, which comprises contacting the cancer cells with i) an anti-p185her2/neu antibody and interferon-gamma (IFNγ); or ii) a fusion protein of the invention.

The present invention provides a method of sensitizing cells of a cancer in a subject afflicted with the cancer to radiation or a chemotherapeutic agent, which comprises administering to the subject i) an anti-p185her2/neu antibody and interferon-gamma (IFNγ); or ii) a fusion protein of the invention.

The present invention provides a method of treating a subject afflicted with cancer, which comprises a) sensitizing cells of the cancer, and cells that have undergone epithelial to mesenchymal transition (EMT) or are undergoing EMT, to radiation or a chemotherapeutic agent by administering to the subject i) an anti-p185her2/neu antibody and interferon-gamma (IFNγ); or ii) a fusion protein of the invention, and b) thereafter administering radiation or a chemotherapeutic agent to the subject.

The present invention provides a method of treating a subject afflicted with cancer, which comprises a) sensitizing the cancer to radiation or a chemotherapeutic agent by administering to the subject i) an anti-p185her2/neu antibody which inhibits p185her2/neu signaling in a cancer cell, wherein said inhibition induces a cytostatic phenotype in the cancer cell, and interferon-gamma (IFNγ) which induces a phenotype in the cancer cell or in a non-malignant cell in the subject; or ii) a fusion protein of the invention, wherein the first stretch of consecutive amino acids of the fusion protein inhibits p185her2/neu signaling in a cancer cell, said inhibition having a cytostatic effect on the cancer cell; and b) thereafter administering a therapeutically effective amount of radiation or a chemotherapeutic agent to the subject.

The present invention provides a method of treating a subject afflicted with cancer, which comprises a) sensitizing the cancer to radiation or a chemotherapeutic agent by administering to the subject i) an anti-p185her2/neu antibody which inhibits p185her2/neu signaling in a cancer cell, wherein said inhibition induces a phenotype in the cancer cell, and interferon-gamma (IFNγ) which induces a further phenotype in the cancer cell or in a non-malignant cell in the subject; or ii) a fusion protein of the invention, wherein the first stretch of consecutive amino acids of the fusion protein inhibits p185her2/neu signaling in a cancer cell, wherein said inhibition induces a cytostatic phenotype in the cancer cell and the third stretch of consecutive amino acids of the fusion protein induces a phenotype in the cancer cell or in a non-malignant cell in the subject; and b) thereafter administering a therapeutically effective amount of radiation or a chemotherapeutic agent to the subject.

In some embodiments, the effective amount of the radiation or the chemotherapeutic agent is less than the amount that would be effective to treat the subject if the radiation or chemotherapeutic agent was administered without the anti-p185her2/neu antibody or the fusion protein.

In some embodiments, the effective amount of the radiation or the chemotherapeutic agent is less than the amount that would be effective to treat the subject if the radiation or chemotherapeutic agent was administered without the anti-p185her2/neu antibody and IFNγ or the fusion protein and IFNγ.

In some embodiments, the anti-p185her2/neu antibody or the fusion protein is administered to the subject in an amount that is less than the amount that would be effective to treat the subject if the anti-p185her2/neu antibody or the fusion protein was administered without IFNγ.

In some embodiments, the anti-p185her2/neu antibody inhibits formation of p185her2/neu-containing ErbB protein dimers that produce elevated tyrosine kinase activity in the cancer cell, thereby inhibiting p185her2/neu signaling in the cancer cell.

In some embodiments, the IFNγ induces the phenotype of class I major histocompatibility complex (MHC) antigen expression in the cancer cell.

In some embodiments, the IFNγ induces the phenotype of a reduced ability to attract an immune suppressor cell to migrate into the microenvironment of the cancer cell or the non-malignant cell.

In some embodiments, the immune suppressor cell is a myeloid-derived suppressor cell (MDSC).

In some embodiments, the IFNγ induces the phenotype of class I MHC antigen expression in the non-malignant cell.

In some embodiments, the IFNγ inhibits the malignant transformation of the non-malignant cell or increases the differentiation of the non-malignant cell.

In some embodiments, the IFNγ induces a cytostatic phenotype in the non-malignant cell.

In some embodiments, the IFNγ induces the phenotype of accelerated and/or maintained degradation of Snail or Slug in the non-malignant cell.

In some embodiments, the IFNγ induces the phenotype of increased sensitivity to radiation or a chemotherapeutic agent.

In some embodiments, the IFNγ induces the phenotype of a reduced ability to evade the immune system of the subject.

In some embodiments, the first stretch of consecutive amino acids of the fusion protein inhibits formation of p185her2/neu-containing ErbB protein dimers that produce elevated tyrosine kinase activity in the cancer cell, thereby inhibiting p185her2/neu signaling in the cancer cell.

In some embodiments, the third stretch of consecutive amino acids of the fusion protein induces the phenotype of class I major histocompatibility complex (MHC) antigen expression in the cancer cell.

In some embodiments, the third stretch of consecutive amino acids of the fusion protein induces the phenotype of a reduced ability to attract an immune suppressor cell to migrate into the microenvironment of the cancer cell or the non-malignant cell.

In some embodiments, the immune suppressor cell is a myeloid-derived suppressor cell (MDSC).

In some embodiments, the third stretch of consecutive amino acids of the fusion protein induces the phenotype of class I MHC antigen expression in the non-malignant cell.

In some embodiments, the third stretch of consecutive amino acids of the fusion protein inhibits the malignant transformation of the non-malignant cell or increases the differentiation of the non-malignant cell.

In some embodiments, the third stretch of consecutive amino acids of the fusion protein induces a cytostatic phenotype in the non-malignant cell.

In some embodiments, the third stretch of consecutive amino acids of the fusion protein induces the phenotype of accelerated and/or maintained degradation of Snail or Slug in the non-malignant cell.

In some embodiments, the third stretch of consecutive amino acids of the fusion protein induces the phenotype of increased sensitivity to radiation or a chemotherapeutic agent.

In some embodiments, the third stretch of consecutive amino acids of the fusion protein induces the phenotype of a reduced ability to evade the immune system of the subject.

In some embodiments, the non-malignant cell is a stem cell-like cell, a dedifferentiated cell, and/or a cell that has undergone or is undergoing an epithelial to mesenchymal transition (EMT).

In some embodiments, the non-malignant cell is in a tumor with the cancer cell or is in the microenvironment of the cancer cell.

The present invention provides a method of treating a subject afflicted with cancer or preventing the development of a tumor in a subject at risk of developing the tumor, which comprises a) sensitizing a cancer cell to radiation or a chemotherapeutic agent by i) administering to the subject an anti-p185her2/neu antibody which inhibits p185her2/neu signaling in the cancer cell, wherein said inhibition converts the phenotype of the cancer cell such that the cancer cell is amenable to further phenotypic change by interferon-gamma (IFNγ), and concurrently or subsequently administering IFNγ which induces further phenotypic change in the cancer cell; or ii) administering to the subject a fusion protein of the invention, wherein the first stretch of consecutive amino acids of the fusion protein inhibits p185her2/neu signaling in a cancer cell, wherein said inhibition converts the phenotype of the cancer cell such that the cancer cell is amenable to further phenotypic change by interferon-gamma (IFNγ), and the third stretch of consecutive amino acids of the fusion protein induces further phenotypic change in the cancer cell; and b) thereafter administering a therapeutically effective amount of radiation or a chemotherapeutic agent to the subject.

In some embodiments, the anti-p185her2/neu antibody inhibits formation of p185her2/neu-containing ErbB protein dimers that produce elevated tyrosine kinase activity in the cancer cell, thereby inhibiting p185her2/neu signaling in the cancer cell.

In some embodiments, the anti-p185her2/neu antibody converts the phenotype of the cancer cell to
i) a cytostatic phenotype;
ii) a less malignant phenotype;
iii) a stem cell-like phenotype;
iv) a less dedifferentiated phenotype;
v) a more epithelial phenotype; or
vi) a less mesenchymal phenotype.

In some embodiments, the anti-p185her2/neu antibody or the IFNγ induces the phenotype of a reduced ability to attract an immune suppressor cell to migrate into the microenvironment of the cancer cell.

In some embodiments, the immune suppressor cell is a myeloid-derived suppressor cell (MDSC).

In some embodiments, the anti-p185her2/neu antibody or the IFNγ induces the phenotype of class I major histocompatibility complex (MHC) antigen expression in the cancer cell.

In some embodiments, the anti-p185her2/neu antibody or the IFNγ induces the phenotype of accelerated or maintained degradation of Snail or Slug in the cancer cell.

In some embodiments, the anti-p185her2/neu antibody or the IFNγ induces the phenotype of
a) a reduced level of p185her2/neu protein on the surface of the cancer cell;
b) increased KLF4 expression in the cancer cell;
c) reduced expression of ALDH1 in the cancer cell;
d) increased effector T cell activity against the cancer cell; or
e) increased accumulation of cytolytic anti-tumor M1 macrophages in the microenvironment of the cancer cell, wherein the cancer cell is in a tumor.

In some embodiments, the IFNγ induces a cytostatic phenotype in the cancer cell.

In some embodiments, the IFNγ increases the differentiation of the cancer cell.

In some embodiments, the IFNγ induces the further phenotypic change of increased sensitivity to radiation or a chemotherapeutic agent.

In some embodiments, the IFNγ induces the further phenotypic change of a reduced ability to evade the immune system of the subject.

In some embodiments, the first stretch of consecutive amino acids of the fusion protein inhibits formation of p185her2/neu-containing ErbB protein dimers that produce elevated tyrosine kinase activity in the cancer cell, thereby inhibiting p185her2/neu signaling in the cancer cell.

In some embodiments, the anti-p185her2/neu antibody converts the phenotype of the cancer cell to
i) a cytostatic phenotype;
ii) a less malignant phenotype;
iii) a stem cell-like phenotype;
iv) a less dedifferentiated phenotype;
v) a more epithelial phenotype; or
vi) a less mesenchymal phenotype.

In some embodiments, the anti-p185her2/neu antibody or the third stretch of consecutive amino acids of the fusion protein induces the phenotype of a reduced ability to attract an immune suppressor cell to migrate into the microenvironment of the cancer cell.

In some embodiments, the immune suppressor cell is a myeloid-derived suppressor cell (MDSC).

In some embodiments, the anti-p185her2/neu antibody or the third stretch of consecutive amino acids of the fusion protein induces the phenotype of class I major histocompatibility complex (MHC) antigen expression in the cancer cell.

In some embodiments, the anti-p185her2/neu antibody or the third stretch of consecutive amino acids of the fusion protein induces the phenotype of accelerated or maintained degradation of Snail or Slug in the cancer cell.

In some embodiments, the anti-p185her2/neu antibody or the third stretch of consecutive amino acids of the fusion protein induces the phenotype of
a) a reduced level of p185her2/neu protein on the surface of the cancer cell;
b) increased KLF4 expression in the cancer cell;
c) reduced expression of ALDH1 in the cancer cell;
d) increased effector T cell activity against the cancer cell; or
e) increased accumulation of cytolytic anti-tumor M1 macrophages in the microenvironment of the cancer cell, wherein the cancer cell is in a tumor.

In some embodiments, the combination of the anti-p185her2/neu antibody and IFNγ alters the stem cell-ness of the cancer cell. In an embodiment the combination reduces the stem cell-ness of the cancer cell. In some embodiments, reducing the stem cell-ness of the cancer comprises increasing differentiation of the cancer cell.

In some embodiments, the third stretch of consecutive amino acids of the fusion protein induces a cytostatic phenotype in the cancer cell.

In some embodiments, the third stretch of consecutive amino acids of the fusion protein increases the differentiation of the cancer cell.

In some embodiments, the third stretch of consecutive amino acids of the fusion protein induces the further phenotypic change of increased sensitivity to radiation or a chemotherapeutic agent.

In some embodiments, the third stretch of consecutive amino acids of the fusion protein induces the further phenotypic change of a reduced ability to evade the immune system of the subject.

In some embodiments, the phenotype of the cancer cell is converted to the phenotype of a non- or less-malignant cell that is a stem cell-like cell, a dedifferentiated cell, and/or a cell that has undergone or is undergoing an epithelial to mesenchymal transition (EMT).

The present invention provides a method of treating a subject afflicted with a tumor associated with p185her2/neu or preventing development of a tumor associated with p185her2/neu in a subject, which comprises administering to the subject
i) an anti-p185her2/neu antibody and interferon-gamma (IFNγ); or
ii) a fusion protein of the invention.

The present invention provides a method of treating a subject afflicted with a tumor associated with p185her2/neu or preventing development of a tumor associated with p185her2/neu in a subject, which comprises administering to the subject a composition including
i) an anti-p185her2/neu antibody and interferon-gamma (IFNγ); or
ii) a fusion protein of the invention,
and a pharmaceutically acceptable carrier.

The present invention provides a method of inhibiting development into cancer cells of breast cells that overexpress p185her2/neu in a subject in need of such inhibition which comprises administering to said subject
i) a fusion protein of the invention; or
ii) an anti-p185her2/neu antibody and interferon-gamma (IFNγ),
each in a sufficient amount to down regulate the overexpressed p185her2/neu and inhibit the development of said breast cells that overexpress p185her2/neu into breast cancer cells.

In some embodiments, the anti-p185her2/neu antibody is administered to the subject before the IFNγ.

In some embodiments, the anti-p185her2/neu antibody is administered to the subject at least 0.5, 1, 1.5, 2, 2.5, 3, 3.5, 4. 4.5, or 5 days before IFNγ is administered to the subject.

In some embodiments,
i) the anti-p185her2/neu antibody and the IFNγ; or
ii) the fusion protein of the invention,
is administered to the subject before the radiation or the chemotherapeutic agent.

In some embodiments,
i) the anti-p185her2/neu antibody and the IFNγ; or
ii) the fusion protein of the invention,
is administered to the subject at least 0.1, 0.5, 1, 1.5, 2, 2.5, 3, 3.5, 4. 4.5, or 5 days before the radiation or the chemotherapeutic agent is administered to the subject.

In some embodiments, the method comprises administering a chemotherapeutic agent to the subject.

In some embodiments, the chemotherapeutic agent is administered to the subject in an amount that is less than the amount that would be effective to treat the subject if the chemotherapeutic agent was administered without the anti-p185her2/neu antibody and the IFNγ or the fusion protein and the IFNγ.

In some embodiments, the chemotherapeutic agent is a cytotoxic agent.

In some embodiments, the cytotoxic agent is a taxane or a platinum-based chemotherapeutic agent.

In some embodiments, the method comprises administering radiation to the subject.

In some embodiments, the radiation is administered to the subject in an amount that is less than the amount that would be effective to treat the subject if the radiation was administered without the anti-p185her2/neu antibody and the IFNγ or the fusion protein and the IFNγ.

In some embodiments, the radiation is ionizing radiation.

In some embodiments, the ionizing radiation is gamma radiation.

In some embodiments, the cancer is associated with p185her2/neu.

In some embodiments, cells of the cancer have more p185her2/neu activity than cells from normal tissue of the same type.

In some embodiments, cells of the cancer express p185her2/neu at a higher level than cells from normal tissue of the same type.

In some embodiments, the cancer is in the form of, or comprises at least one tumor.

In some embodiments, administering to the subject
i) an anti-p185her2/neu antibody and interferon-gamma (IFNγ); or
ii) a fusion protein of the invention,
is effective to reduce cancer cell proliferation in the tumor and the migration of immune suppressor cells into the tumor.

In some embodiments, the cancer is an adenocarcinoma.

In some embodiments, the cancer is glioblastoma, prostate cancer, lung cancer, pancreatic cancer, ovarian cancer, breast cancer, colon cancer, or stomach cancer.

In some embodiments, the cancer is breast cancer, and the breast cancer is ductal carcinoma in situ (DCIS).

In some embodiments, the cancer is breast cancer and the breast cancer is
a) estrogen receptor positive;
b) estrogen receptor negative;
c) Her2 positive;
d) Her2 negative;
e) progesterone receptor positive;
f) progesterone receptor negative; or
g) any combination of a) through f).

In some embodiments, treating the subject comprises preventing or reducing tumor growth in the subject.

In some embodiments, treating the subject comprises completely arresting cancer cell growth in the subject.

In some embodiments, treating the subject comprises increased lysis of cancer cells in the subject.

In some embodiments, the subject is treated such that an increase in the volume of the at least one tumor cannot be detected for a period of at least 30 days during or after treatment.

In some embodiments, the subject is a mammalian subject.

In some embodiments, the mammalian subject is a human subject.

In some embodiments, the anti-p185her2/neu antibody is administered twice per week, and the IFNγ is administered three times per week.

In some embodiments, the anti-p185her2/neu antibody is a monoclonal antibody.

In some embodiments, the anti-p185her2/neu antibody is 4D5, pertuzumab, trastuzumab, or 7.16.4.

In some embodiments, the anti-p185her2/neu antibody binds at least a portion of the same epitope as trastuzumab.

In some embodiments, the method further comprises administering a second antibody to the subject.

In some embodiments, the second antibody is an anti-p185her2/neu antibody.

In some embodiments, two anti-p185her2/neu antibodies are administered to the subject, and each anti-p185her2/neu antibody targets a different epitope of p185her2/neu.

In some embodiments, the second antibody is an anti-EGFR antibody.

In some embodiments, the anti-EGFR antibody is cetuximab.

In some embodiments, the second antibody is an anti-PD1 antibody.

In some embodiments, the second antibody is an anti-PD1 antibody or an anti-PD-L1 antibody.

In some embodiments, each of the antibodies is administered to the subject before IFNγ is administered to the subject.

In some embodiments, each of the antibodies is administered to the subject at least 0.5, 1, 1.5, 2, 2.5, 3, 3.5, 4. 4.5, or 5 days before IFNγ is administered to the subject.

In some embodiments, IFNγ is administered to the subject concomitantly with the antibodies, or within 24 hours after the antibodies are administered to the subject.

In some embodiments, the second antibody is administered to the subject after IFNγ is administered to the subject.

In some embodiments, the second antibody is administered to the subject at least 0.5, 1, 1.5, 2, 2.5, 3, 3.5, 4. 4.5, or 5 days after IFNγ is administered to the subject.

In some embodiments, the second antibody is a monoclonal antibodies.

In some embodiments, the anti-PD1 antibody or anti-PD-L1 antibody is administered after the anti-p185her2/neu antibody and IFNγ.

In some embodiments, the anti-p185her2/neu antibody or the fusion protein is administered to the subject in an amount that is less than the amount that would be effective to treat the subject if the anti-p185her2/neu antibody or the fusion protein was administered without IFNγ.

The present invention provides a composition for the treatment of a subject afflicted with cancer, comprising
i) a fusion protein of the invention; or
ii) an anti-p185her2/neu antibody and interferon-gamma (IFNγ),
and a pharmaceutically acceptable carrier.

The present invention provides a composition for sensitizing cancer to radiation or a chemotherapeutic agent, comprising
i) a fusion protein of the invention; or
ii) an anti-p185her2/neu antibody and interferon-gamma (IFNγ),
and a pharmaceutically acceptable carrier.

The present invention provides a composition for sensitizing a tumor to radiation or a chemotherapeutic agent, comprising
i) a fusion protein of the invention; or
ii) an anti-p185her2/neu antibody and interferon-gamma (IFNγ),
and a pharmaceutically acceptable carrier.

The present invention provides a composition for preventing the development of a tumor in a subject at risk of developing the tumor, comprising
i) the fusion protein of the invention; or
ii) an anti-p185her2/neu antibody and interferon-gamma (IFNγ),
and a pharmaceutically acceptable carrier.

The present invention provides a combination for the treatment of a subject afflicted with cancer or preventing the development of a tumor in a subject at risk of developing the tumor, comprising
i) the fusion protein of the invention or ii) an anti-p185her2/neu antibody and interferon-gamma (IFNγ), and
ii) a second antibody,
and a pharmaceutically acceptable carrier.

The present invention provides a polynucleotide encoding the fusion protein of the invention.

The present invention provides an expression vector comprising a polynucleotide of the invention operably linked to a promoter.

The present invention provides a cell comprising a expression vector of the invention.

The present invention provides a fusion protein comprising
(a) a first stretch of consecutive amino acids, the sequence of which is the sequence of an anti-EGFR polypeptide;
(b) a second stretch of consecutive amino acids, the sequence of which is the sequence of a polypeptide capable of binding at least one polypeptide other than EGFR; and
(c) a third stretch of consecutive amino acids, the sequence of which comprises the sequence of a biologically active portion of interferon-gamma (IFNγ),
wherein (b) is located at the carboxy-terminal end of (a), and (c) is located at the carboxy-terminal end of (b).

In some embodiments, the fusion protein further comprises an oligopeptide linker between (a) and (b).

In some embodiments, the fusion protein further comprises an oligopeptide linker between (b) and (c).

In some embodiments, the fusion protein further comprises a second oligopeptide linker between (b) and (c).

In some embodiments, the amino acid sequence of the oligopeptide linker is identical to the amino acid sequence of the second oligopeptide linker.

In some embodiments, the amino acid sequence of the oligopeptide linker is different from the amino acid sequence of the second oligopeptide linker.

In some embodiments,
i) the oligopeptide is a polyglycine oligopeptide linker or a glycine-serine oligopeptide linker; and
ii) the second oligopeptide is independently a polyglycine oligopeptide linker or a glycine-serine oligopeptide linker.

In some embodiments, the amino acid sequence of the polyglycine oligopeptide linker comprises at least two, three, four, five, six, seven, eight, nine, or ten, consecutive glycine residues.

In some embodiments, the amino acid sequence of the glycine-serine oligopeptide linker comprises at least two, three, four, five, six, seven, eight, nine, or ten, consecutive glycine residues.

In some embodiments, the C-terminal residue of the glycine-serine oligopeptide linker is a serine residue.

In some embodiments, (a) is directly contiguous with (b).
In some embodiments, (b) is directly contiguous with (c).
In some embodiments, the anti-EGFR polypeptide is a chain of an antibody or a portion thereof.
In some embodiments, the antibody chain is a single chain variable fragment (scFv).

In some embodiments, the antibody chain is a monoclonal antibody chain.

In some embodiments, the monoclonal antibody chain is a human monoclonal antibody chain, a humanized monoclonal antibody chain, or a chimeric antibody chain.

In some embodiments, the monoclonal antibody chain is a chimeric antibody chain, and wherein a portion of the chimeric antibody chain is derived from a human antibody chain.

In some embodiments, the antibody is an anti-EGFR antibody.

In some embodiments, the anti-EGFR antibody is a monoclonal antibody.

In some embodiments, the anti-EGFR monoclonal antibody is a human monoclonal antibody.

In some embodiments, the anti-EGFR monoclonal antibody is a humanized monoclonal antibody.

In some embodiments, the anti-EGFR antibody binds at least a portion of the same epitope as cetuximab.

In some embodiments, the anti-EGFR antibody is cetuximab.

In some embodiments, the polypeptide that is capable of binding a polypeptide other than EGFR is capable of binding at least one antibody.

In some embodiments, the polypeptide that is capable of binding a polypeptide other than EGFR is capable of binding at least one antibody Fc-region.

In some embodiments, the polypeptide that is capable of binding a polypeptide other than EGFR is derived from a portion of Protein A or Protein G that is capable of binding at least one antibody Fc-region.

In some embodiments, the least one antibody is endogenously expressed in a mammal.

In some embodiments, the sequence of the third stretch of consecutive amino acids is identical to the sequence of IFNγ.

In some embodiments, the sequence of the fusion protein has been modified to reduce immunogenicity in a human.

In some embodiments, (a), (b), or (c) has been humanized.
In some embodiments, each of (a), (b), and (c) has been humanized.

In some embodiments, the sequence of each of (a), (b), and (c) is found in an endogenous human polypeptide.

In some embodiments, the fusion protein is 4D5scFvZZ-IFNγ, or a humanized derivative thereof.

The present invention provides a method of treating a subject afflicted with cancer, which comprises administering to the subject a therapeutically effective amount of the fusion protein of the invention.

In some embodiments, the method further comprises administering an antibody to the subject.

In some embodiments, the antibody is an anti-p185her2/neu antibody.

In some embodiments, the antibody is an anti-EGFR antibody.

In some embodiments, the anti-EGFR antibody is cetuximab.

In some embodiments, the antibody is an anti-PD1 or an anti-PD-L1 antibody.

In some embodiments, the antibody is a monoclonal antibody.

In some embodiments, the method further comprises administering a chemotherapeutic agent to the subject.

In some embodiments, the chemotherapeutic agent is administered to the subject in an amount that is less than the amount that would be effective to treat the subject if the chemotherapeutic agent was administered without the fusion protein.

In some embodiments, the method further comprises administering a radiation to the subject.

In some embodiments, the radiation is administered to the subject in an amount that is less than the amount that would be effective to treat the subject if the radiation was administered without the fusion protein.

The present invention provides a method of sensitizing cancer cells to radiation or a chemotherapeutic agent, which comprises contacting the cancer cells with
i) an anti-EGFR antibody and interferon-gamma (IFNγ); or
ii) a fusion protein of the invention.

The present invention provides a method of sensitizing cells of a cancer in a subject afflicted with the cancer to radiation or a chemotherapeutic agent, which comprises administering to the subject
i) an anti-EGFR antibody and interferon-gamma (IFNγ); or
ii) a fusion protein of the invention.

The present invention provides a method of treating a subject afflicted with cancer, which comprises
a) sensitizing cells of the cancer, and cells that have undergone epithelial to mesenchymal transition (EMT) or are undergoing EMT, to radiation or a chemotherapeutic agent by administering to the subject
i) an anti-EGFR antibody and interferon-gamma (IFNγ); or
ii) a fusion protein of the invention, and
b) thereafter administering radiation or a chemotherapeutic agent to the subject.

The present invention provides a method of treating a subject afflicted with cancer, which comprises
a) sensitizing the cancer to radiation or a chemotherapeutic agent by administering to the subject
i) an anti-EGFR antibody which inhibits EGFR signaling in a cancer cell, wherein said inhibition induces a phenotype in the cancer cell, and interferon-gamma (IFNγ) which induces a further phenotype in the cancer cell or in a non-malignant cell in the subject; or
ii) a fusion protein of the invention, wherein the first stretch of consecutive amino acids of the fusion protein inhibits EGFR signaling in a cancer cell, wherein said inhibition induces a cytostatic phenotype in the cancer cell and the third stretch of consecutive amino acids of the fusion protein induces a phenotype in the cancer cell or in a non-malignant cell in the subject; and b) thereafter administering a therapeutically effective amount of radiation or a chemotherapeutic agent to the subject.

In some embodiments, the effective amount of the radiation or the chemotherapeutic agent is less than the amount that would be effective to treat the subject if the radiation or chemotherapeutic agent was administered without the anti-EGFR antibody or the fusion protein.

In some embodiments, the effective amount of the radiation or the chemotherapeutic agent is less than the amount that would be effective to treat the subject if the radiation or chemotherapeutic agent was administered without the anti-EGFR antibody and IFNγ or the fusion protein and IFNγ.

In some embodiments, the anti-EGFR antibody or the fusion protein is administered to the subject in an amount that is less than the amount that would be effective to treat the subject if the anti-EGFR antibody or the fusion protein was administered without IFNγ.

In some embodiments, the anti-EGFR antibody inhibits formation of EGFR-containing ErbB protein dimers that produce elevated tyrosine kinase activity in the cancer cell, thereby inhibiting EGFR signaling in the cancer cell.

In some embodiments, the IFNγ induces the phenotype of class I major histocompatibility complex (MHC) antigen expression in the cancer cell.

In some embodiments, the IFNγ induces the phenotype of a reduced ability to attract an immune suppressor cell to migrate into the microenvironment of the cancer cell or the non-malignant cell.

In some embodiments, the immune suppressor cell is a myeloid-derived suppressor cell (MDSC).

In some embodiments, the IFNγ induces the phenotype of class I MHC antigen expression in the non-malignant cell.

In some embodiments, the IFNγ inhibits the malignant transformation of the non-malignant cell or increases the differentiation of the non-malignant cell.

In some embodiments, the IFNγ induces a cytostatic phenotype in the non-malignant cell.

In some embodiments, the IFNγ induces the phenotype of accelerated and/or maintained degradation of Snail or Slug in the non-malignant cell.

In some embodiments, the IFNγ induces the phenotype of increased sensitivity to radiation or a chemotherapeutic agent.

In some embodiments, the IFNγ induces the phenotype of a reduced ability to evade the immune system of the subject.

In some embodiments, the first stretch of consecutive amino acids of the fusion protein inhibits formation of EGFR-containing ErbB protein dimers that produce elevated tyrosine kinase activity in the cancer cell, thereby inhibiting EGFR signaling in the cancer cell.

In some embodiments, the third stretch of consecutive amino acids of the fusion protein induces the phenotype of class I major histocompatibility complex (MHC) antigen expression in the cancer cell.

In some embodiments, the third stretch of consecutive amino acids of the fusion protein induces the phenotype of a reduced ability to attract an immune suppressor cell to migrate into the microenvironment of the cancer cell or the non-malignant cell.

In some embodiments, the immune suppressor cell is a myeloid-derived suppressor cell (MDSC).

In some embodiments, the third stretch of consecutive amino acids of the fusion protein induces the phenotype of class I MHC antigen expression in the non-malignant cell.

In some embodiments, the third stretch of consecutive amino acids of the fusion protein inhibits the malignant transformation of the non-malignant cell or increases the differentiation of the non-malignant cell.

In some embodiments, the third stretch of consecutive amino acids of the fusion protein induces a cytostatic phenotype in the non-malignant cell.

In some embodiments, the third stretch of consecutive amino acids of the fusion protein induces the phenotype of accelerated and/or maintained degradation of Snail or Slug in the non-malignant cell.

In some embodiments, the third stretch of consecutive amino acids of the fusion protein induces the phenotype of increased sensitivity to radiation or a chemotherapeutic agent.

In some embodiments, the third stretch of consecutive amino acids of the fusion protein induces the phenotype of a reduced ability to evade the immune system of the subject.

In some embodiments, the non-malignant cell is a stem cell-like cell, a dedifferentiated cell, and/or a cell that has undergone or is undergoing an epithelial to mesenchymal transition (EMT).

In some embodiments, the non-malignant cell is in a tumor with the cancer cell or is in the microenvironment of the cancer cell.

The present invention provides a method of treating a subject afflicted with cancer or preventing the development of a tumor in a subject at risk of developing the tumor, which comprises
a) sensitizing a cancer cell to radiation or a chemotherapeutic agent by
i) administering to the subject an anti-EGFR antibody which inhibits EGFR signaling in the cancer cell, wherein said inhibition converts the phenotype of the cancer cell such that the cancer cell is amenable to further phenotypic change by interferon-gamma (IFNγ), and concurrently or subsequently administering IFNγ which induces further phenotypic change in the cancer cell; or
ii) administering to the subject a fusion protein of the invention, wherein the first stretch of consecutive amino acids of the fusion protein inhibits EGFR signaling in a cancer cell, wherein said inhibition converts the phenotype of the cancer cell such that the cancer cell is amenable to further phenotypic change by interferon-gamma (IFNγ), and the third stretch of consecutive amino acids of the fusion protein induces further phenotypic change in the cancer cell; and
b) thereafter administering a therapeutically effective amount of radiation or a chemotherapeutic agent to the subject.

In some embodiments, the anti-EGFR antibody inhibits formation of EGFR-containing ErbB protein dimers that produce elevated tyrosine kinase activity in the cancer cell, thereby inhibiting EGFR signaling in the cancer cell.

In some embodiments, the anti-EGFR antibody converts the phenotype of the cancer cell to
i) a cytostatic phenotype;
ii) a less malignant phenotype;
iii) a stem cell-like phenotype;
iv) a less dedifferentiated phenotype;
v) a more epithelial phenotype; or
vi) a less mesenchymal phenotype.

In some embodiments, the anti-EGFR antibody or the IFNγ induces the phenotype of a reduced ability to attract an immune suppressor cell to migrate into the microenvironment of the cancer cell.

In some embodiments, the immune suppressor cell is a myeloid-derived suppressor cell (MDSC).

In some embodiments, the anti-EGFR antibody or the IFNγ induces the phenotype of class I major histocompatibility complex (MHC) antigen expression in the cancer cell.

In some embodiments, the anti-EGFR antibody or the IFNγ induces the phenotype of accelerated or maintained degradation of Snail or Slug in the cancer cell.

In some embodiments, the anti-EGFR antibody or the IFNγ induces the phenotype of
a) a reduced level of p185her2/neu protein on the surface of the cancer cell;
b) increased KLF4 expression in the cancer cell;
c) reduced expression of ALDH1 in the cancer cell;
d) increased effector T cell activity against the cancer cell; or
e) increased accumulation of cytolytic anti-tumor M1 macrophages in the microenvironment of the cancer cell, wherein the cancer cell is in a tumor.

In some embodiments, the IFNγ induces a cytostatic phenotype in the cancer cell.

In some embodiments, the IFNγ increases the differentiation of the cancer cell.

In some embodiments, the IFNγ induces the further phenotypic change of increased sensitivity to radiation or a chemotherapeutic agent.

In some embodiments, the IFNγ induces the further phenotypic change of a reduced ability to evade the immune system of the subject.

In some embodiments, the first stretch of consecutive amino acids of the fusion protein inhibits formation of EGFR-containing ErbB protein dimers that produce elevated tyrosine kinase activity in the cancer cell, thereby inhibiting EGFR signaling in the cancer cell.

In some embodiments, the anti-EGFR antibody converts the phenotype of the cancer cell to
i) a cytostatic phenotype;
ii) a less malignant phenotype;
iii) a stem cell-like phenotype;
iv) a less dedifferentiated phenotype;
v) a more epithelial phenotype; or
vi) a less mesenchymal phenotype.

In some embodiments, the anti-EGFR antibody or the third stretch of consecutive amino acids of the fusion protein induces the phenotype of a reduced ability to attract an immune suppressor cell to migrate into the microenvironment of the cancer cell.

In some embodiments, the immune suppressor cell is a myeloid-derived suppressor cell (MDSC).

In some embodiments, the anti-EGFR antibody or the third stretch of consecutive amino acids of the fusion protein induces the phenotype of class I major histocompatibility complex (MHC) antigen expression in the cancer cell.

In some embodiments, the anti-EGFR antibody or the third stretch of consecutive amino acids of the fusion protein induces the phenotype of accelerated or maintained degradation of Snail or Slug in the cancer cell.

In some embodiments, the anti-EGFR antibody or the third stretch of consecutive amino acids of the fusion protein induces the phenotype of
a) a reduced level of p185her2/neu protein on the surface of the cancer cell;
b) increased KLF4 expression in the cancer cell;
c) reduced expression of ALDH1 in the cancer cell;
d) increased effector T cell activity against the cancer cell; or
e) increased accumulation of cytolytic anti-tumor M1 macrophages in the microenvironment of the cancer cell, wherein the cancer cell is in a tumor.

In some embodiments, the combination of the anti-EGFR antibody and IFNγ alters the stem cell-ness of the cancer cell. In an embodiment the combination reduces the stem cell-ness of the cancer cell. In some embodiments, reducing the stem cell-ness of the cancer comprises increasing differentiation of the cancer cell.

In some embodiments, the third stretch of consecutive amino acids of the fusion protein induces a cytostatic phenotype in the cancer cell.

In some embodiments, the third stretch of consecutive amino acids of the fusion protein increases the differentiation of the cancer cell.

In some embodiments, the third stretch of consecutive amino acids of the fusion protein induces the further phenotypic change of increased sensitivity to radiation or a chemotherapeutic agent.

In some embodiments, the third stretch of consecutive amino acids of the fusion protein induces the further phenotypic change of a reduced ability to evade the immune system of the subject.

In some embodiments, the phenotype of the cancer cell is converted to the phenotype of a non- or less-malignant cell that is a stem cell-like cell, a dedifferentiated cell, and/or a cell that has undergone or is undergoing an epithelial to mesenchymal transition (EMT).

The present invention provides a method of treating a subject afflicted with a tumor associated with EGFR or preventing development of a tumor associated with EGFR in a subject, which comprises administering to the subject
i) an anti-EGFR antibody and interferon-gamma (IFNγ); or
ii) a fusion protein of the invention.

The present invention also provides a method of treating a subject afflicted with a tumor associated with EGFR or preventing development of a tumor associated with EGFR in a subject, which comprises administering to the subject a composition including
i) an anti-EGFR antibody and interferon-gamma (IFNγ); or
ii) a fusion protein of the invention,
and a pharmaceutically acceptable carrier.

The present invention provides a method of inhibiting development into cancer cells of breast cells that overexpress EGFR in a subject in need of such inhibition which comprises administering to said subject
i) a fusion protein of the invention; or
ii) an anti-EGFR antibody and interferon-gamma (IFNγ),
each in a sufficient amount to down regulate the overexpressed p185 and inhibit the development of said breast cells that overexpress p185 into breast cancer cells.

In some embodiments, the anti-EGFR antibody is administered to the subject before the IFNγ.

In some embodiments, the anti-EGFR antibody is administered to the subject at least 0.5, 1, 1.5, 2, 2.5, 3, 3.5, 4. 4.5, or 5 days before IFNγ is administered to the subject.

In some embodiments,
i) the anti-EGFR antibody and the IFNγ; or
ii) the fusion protein of the invention,
is administered to the subject before the radiation or the chemotherapeutic agent.

In some embodiments,
i) the anti-EGFR antibody and the IFNγ; or
ii) the fusion protein of the invention,
is administered to the subject at least 0.1, 0.5, 1, 1.5, 2, 2.5, 3, 3.5, 4. 4.5, or 5 days before the radiation or the chemotherapeutic agent is administered to the subject.

In some embodiments, the method further comprises administering a chemotherapeutic agent to the subject.

In some embodiments, the chemotherapeutic agent is administered to the subject in an amount that is less than the amount that would be effective to treat the subject if the chemotherapeutic agent was administered without the anti-EGFR antibody and the IFNγ or the fusion protein and the IFNγ.

In some embodiments, the chemotherapeutic agent is a cytotoxic agent.

In some embodiments, the cytotoxic agent is a taxane or a platinum-based chemotherapeutic agent.

In some embodiments, the method further comprises administering radiation to the subject.

In some embodiments, the radiation is administered to the subject in an amount that is less than the amount that would be effective to treat the subject if the radiation was administered without the anti-p185her2/neu antibody and the IFNγ or the fusion protein and the IFNγ.

In some embodiments, the radiation is ionizing radiation.

In some embodiments, the ionizing radiation is gamma radiation.

In some embodiments, the cancer is associated with EGFR.

In some embodiments, cells of the cancer have more EGFR activity than cells from normal tissue of the same type.

In some embodiments, cells of the cancer express EGFR at a higher level than cells from normal tissue of the same type.

In some embodiments, the cancer is in the form of, or comprises at least one tumor.

In some embodiments, administering to the subject
i) an anti-EGFR antibody and interferon-gamma (IFNγ); or
ii) a fusion protein of the invention,
is effective to reduce cancer cell proliferation in the tumor and the migration of immune suppressor cells into the tumor.

In some embodiments, the cancer is an adenocarcinoma.

In some embodiments, the cancer is glioblastoma, prostate cancer, lung cancer, pancreatic cancer, ovarian cancer, breast cancer, colon cancer, or stomach cancer.

In some embodiments, the cancer is breast cancer, and the beast cancer is DCIS.

In some embodiments, the cancer is breast cancer and the breast cancer is
a) estrogen receptor positive;
b) estrogen receptor negative;
c) Her2 positive;
d) Her2 negative;
e) progesterone receptor positive;
f) progesterone receptor negative; or
g) any combination of a) through f).

In some embodiments, treating the subject comprises preventing or reducing tumor growth.

In some embodiments, the subject is treated such that an increase in the volume of the at least one tumor cannot be detected for a period of at least 30 days during or after treatment.

In some embodiments, treating the subject comprises completely arresting cancer cell growth in the subject.

In some embodiments, treating the subject comprises increased lysis of cancer cells in the subject.

In some embodiments, the subject is a mammalian subject.

In some embodiments, the mammalian subject is a human subject.

In some embodiments, the anti-EGFR antibody is administered twice per week, and the IFNγ is administered three times per week.

In some embodiments, the anti-EGFR antibody is a monoclonal antibody.

In some embodiments, the anti-EGFR antibody is cetuximab.

In some embodiments, the anti-EGFR antibody binds at least a portion of the same epitope as cetuximab.

In some embodiments, the method further comprises administering a second antibody to the subject.

In some embodiments, the second antibody is an anti-EGFR antibody.

In some embodiments, the second antibody is an anti-PD1 antibody or an anti-PD-L1 antibody.

In some embodiments, the second antibody is an anti-p185her2/neu antibody.

In some embodiments, the anti-p185her2/neu antibody is trastuzumab.

In some embodiments, each of the antibodies is administered to the subject before IFNγ is administered to the subject.

In some embodiments, each of the antibodies is administered to the subject at least 0.5, 1, 1.5, 2, 2.5, 3, 3.5, 4. 4.5, or 5 days before IFNγ is administered to the subject.

In some embodiments, IFNγ is administered to the subject concomitantly with the antibodies, or within 24 hours after the antibodies are administered to the subject.

In some embodiments, the second antibody is administered to the subject after IFNγ is administered to the subject.

In some embodiments, the second antibody is administered to the subject at least 0.5, 1, 1.5, 2, 2.5, 3, 3.5, 4. 4.5, or 5 days after IFNγ is administered to the subject.

In some embodiments, the second antibody is a monoclonal antibodies.

In some embodiments, the anti-PD1 antibody or anti-PD-L1 antibody is administered after the anti-EGFR antibody and IFNγ.

In some embodiments, the anti-EGFR antibody or the fusion protein is administered to the subject in an amount that is less than the amount that would be effective to treat the subject if the anti-EGFR antibody or the fusion protein was administered without IFNγ.

The present invention provides a composition for the treatment of a subject afflicted with cancer, comprising
i) a fusion protein of the invention; or
ii) an anti-EGFR antibody and interferon-gamma (IFNγ),
and a pharmaceutically acceptable carrier.

The present invention provides a composition for sensitizing cancer to radiation or a chemotherapeutic agent, comprising
i) a fusion protein of the invention; or
ii) an anti-EGFR antibody and interferon-gamma (IFNγ),
and a pharmaceutically acceptable carrier.

The present invention provides a composition for sensitizing a tumor to radiation or a chemotherapeutic agent, comprising
i) a fusion protein of the invention; or
ii) an anti-EGFR antibody and interferon-gamma (IFNγ),
and a pharmaceutically acceptable carrier.

The present invention provides a composition for preventing the development of a tumor in a subject at risk of developing the tumor, comprising
i) the fusion protein of the invention; or
ii) an anti-p185her2/neu antibody and interferon-gamma (IFNγ),
and a pharmaceutically acceptable carrier.

The present invention provides a combination for the treatment of a subject afflicted with cancer or preventing the development of a tumor in a subject at risk of developing the tumor, comprising
i) the fusion protein of the invention or ii) an anti-p185her2/neu antibody and interferon-gamma (IFNγ), and
ii) a second antibody,
and a pharmaceutically acceptable carrier.

The present invention provides a polynucleotide encoding a fusion protein of the invention.

The present invention provides an expression vector comprising a polynucleotide of the invention operably linked to a promoter.

The present invention provides a cell comprising a expression vector of the invention.

In some embodiments, the method further comprises administering to the subject an EGFr inhibitor.

In some embodiments, the EGFRr inhibitor inhibits the kinase activity of p185her2/neu or EGFR.

In some embodiments, the EGFRr inhibitor is C318, gefitinib, erlotinib, lapatinib, or vandetanib, or a pharmaceutically acceptable salt or ester thereof.

In some embodiments, the EGFRr inhibitor is an organic compound having a molecular weight less than 1000 Daltons.

In some embodiments of the invention relating to an anti-p185her2/neu polypeptide (AHNP), the AHNP has the amino acid sequence set forth in SEQ ID NO: 3.

The present invention provides a method of treating a subject afflicted with a tumor or preventing development of a tumor in a subject, which comprises administering to the subject
i) at least one antibody; and
ii) interferon-gamma (IFNγ).

In some embodiments, the at least one antibody is a monoclonal antibody.

In some embodiments, the at least one antibody is one, two, three, four, five or more antibodies, comprising at least one an anti-p185her2/neu antibody, at least one anti-EGFR antibody, at least one anti-PD1 antibody, or at least one anti-PD-L1 antibody.

In some embodiments, the at least one antibody is administered before IFNγ.

The present invention provides a fusion protein comprising
(i) a first stretch of consecutive amino acids, the sequence of which is the sequence of an anti-p185her2/neu polypeptide or an anti-EGFR polypeptide; and
(ii) a second stretch of consecutive amino acids, the sequence of which comprises the sequence of a biologically active portion of interferon-gamma (IFNγ),
wherein (ii) is located at the carboxy-terminal end of (i).

In some embodiments, the fusion protein further comprises an oligopeptide linker between (i) and (ii).

In some embodiments, a linker within a fusion protein of the invention comprises a labile cleavage site.

In some embodiments, the anti-p185her2/neu polypeptide or the anti-EGFR polypeptide is a chain of an antibody or a portion thereof.

In some embodiments, the antibody chain is a single chain variable fragment (scFv).

In some embodiments, the antibody chain is a monoclonal antibody chain.

In some embodiments, the monoclonal antibody chain is a human monoclonal antibody chain, a humanized monoclonal antibody chain, or a chimeric antibody chain.

In some embodiments, wherein the monoclonal antibody chain is a chimeric antibody chain, and wherein a portion of the chimeric antibody chain is derived from a human antibody chain.

In some embodiments, the antibody is an anti-p185her2/neu antibody or an anti-EGFR antibody.

In some embodiments, the fusion protein further comprises (iii) a third stretch of consecutive amino acids, the sequence of which comprises the sequence of a biologically active portion of interferon-gamma (IFNγ). In some embodiments, (iii) is located at the carboxy-terminal end of (ii)

In some embodiments, the fusion protein further comprises an oligopeptide linker between (ii) and (iii).

In some embodiments, the fusion protein further comprises the linker comprises a labile cleavage site.

In some embodiments, the fusion protein further comprises the sequence of the second or the third stretch of consecutive amino acids is identical to the sequence of IFNγ.

In some embodiments, the fusion protein comprises an IFNγ dimer.

In some embodiments, a biologically active portion of IFNγ is a portion of IFNγ that is biologically active. In some embodiments, a biologically active portion of IFNγ is full-length IFNγ.

The present invention provides a method of sensitizing cancer cells to radiation or a chemotherapeutic agent, which comprises contacting the cancer cells with
i) an erbB inhibitor; and
ii) interferon-gamma (IFNγ).

The present invention also provides a method of sensitizing cells of a cancer in a subject afflicted with the cancer to radiation or a chemotherapeutic agent, which comprises administering to the subject
i) an erbB inhibitor; and
ii) interferon-gamma (IFNγ).

The present invention further provides a method of treating a subject afflicted with cancer, which comprises
a) sensitizing cells of the cancer, and cells that have undergone epithelial to mesenchymal transition (EMT) or are undergoing EMT, to radiation or a chemotherapeutic agent by administering to the subject
i) an erbB inhibitor; and
ii) interferon-gamma (IFNγ), and
b) thereafter administering radiation or a chemotherapeutic agent to the subject.

The present invention also provides a method of treating a subject afflicted with cancer or preventing the development of a tumor in a subject at risk of developing the tumor, which comprises
a) sensitizing a cancer cell to radiation or a chemotherapeutic agent by
i) administering to the subject an erbB inhibitor which inhibits EGFR signaling or p185her2/neu signaling in the cancer cell, wherein said inhibition converts the phenotype of the cancer cell such that the cancer cell is amenable to further phenotypic change by interferon-gamma (IFNγ), and concurrently or subsequently administering IFNγ which induces further phenotypic change in the cancer cell; and
b) thereafter administering a therapeutically effective amount of radiation or a chemotherapeutic agent to the subject.

In some embodiments, the effective amount of the radiation or the chemotherapeutic agent is less than the amount that would be effective to treat the subject if the radiation or chemotherapeutic agent was administered without the erbB inhibitor and IFNγ.

In some embodiments, the erbB inhibitor is administered to the subject in an amount that is less than the amount that would be effective to treat the subject if the erbB inhibitor was administered without IFNγ.

In some embodiments, the erbB inhibitor converts the phenotype of the cancer cell to
i) a cytostatic phenotype;
ii) a less malignant phenotype;
iii) a stem cell-like phenotype;
iv) a less dedifferentiated phenotype;
v) a more epithelial phenotype; or
vi) a less mesenchymal phenotype.

In some embodiments, the erbB inhibitor or the IFNγ induces the phenotype of a reduced ability to attract an immune suppressor cell to migrate into the microenvironment of the cancer cell.

In some embodiments, the immune suppressor cell is a myeloid-derived suppressor cell (MDSC).

In some embodiments, the erbB inhibitor or the IFNγ induces the phenotype of increased class I major histocompatibility complex (MHC) antigen expression in the cancer cell.

In some embodiments, the erbB inhibitor or the IFNγ induces the phenotype of accelerated or maintained degradation of Snail or Slug in the cancer cell.

In some embodiments, the erbB inhibitor or the IFNγ induces the phenotype of
a) a reduced level of p185her2/neu protein on the surface of the cancer cell;
b) increased KLF4 expression in the cancer cell;
c) reduced expression of ALDH1 in the cancer cell;
d) increased effector T cell activity against the cancer cell; or
e) increased accumulation of cytolytic anti-tumor M1 macrophages in the microenvironment of the cancer cell, wherein the cancer cell is in a tumor.

In some embodiments, the IFNγ induces a cytostatic phenotype in the cancer cell.

In some embodiments, the IFNγ increases the differentiation of the cancer cell.

In some embodiments, the IFNγ induces the further phenotypic change of increased sensitivity to radiation or a chemotherapeutic agent.

In some embodiments, the IFNγ induces the further phenotypic change of a reduced ability of the cancer to evade the immune system of the subject.

In some embodiments, the phenotype of the cancer cell is converted to the phenotype of a non- or less-malignant cell that is a stem cell-like cell, a dedifferentiated cell, or a cell that has undergone or is undergoing an epithelial to mesenchymal transition (EMT).

The present invention provides a method of treating a subject afflicted with a tumor associated with EGFR or p185her2/neu or preventing development of a tumor associated with EGFR or p185her2/neu in a subject, which comprises administering to the subject
i) an erbB inhibitor; and
ii) interferon-gamma (IFNγ).

In some embodiments, the erbB inhibitor is administered to the subject before the IFNγ.

In some embodiments, the erbB inhibitor is administered to the subject at least 0.5, 1, 1.5, 2, 2.5, 3, 3.5, 4, 4.5, or 5 days before IFNγ is administered to the subject.

In some embodiments, the erbB inhibitor and the IFNγ are administered to the subject before the radiation or the chemotherapeutic agent.

In some embodiments, the erbB inhibitor and the IFNγ are administered to the subject at least 0.1, 0.5, 1, 1.5, 2, 2.5, 3, 3.5, 4, 4.5, or 5 days before the radiation or the chemotherapeutic agent is administered to the subject.

In some embodiments, the method comprises administering a chemotherapeutic agent to the subject.

In some embodiments, the chemotherapeutic agent is administered to the subject in an amount that is less than the amount that would be effective to treat the subject if the chemotherapeutic agent was administered without the erbB inhibitor and the IFNγ.

In some embodiments, the chemotherapeutic agent is a cytotoxic agent.

In some embodiments, the cytotoxic agent is a taxane or a platinum-based chemotherapeutic agent.

In some embodiments, the method comprises administering radiation to the subject.

In some embodiments, the radiation is administered to the subject in an amount that is less than the amount that would be effective to treat the subject if the radiation was administered without the erbB inhibitor and the IFNγ.

In some embodiments, the radiation is ionizing radiation.

In some embodiments, the ionizing radiation is gamma radiation.

In some embodiments, the cancer is associated with p185her2/neu.

In some embodiments, cells of the cancer have more p185her2/neu activity than cells from normal tissue of the same type.

In some embodiments, cells of the cancer express p185her2/neu at a higher level than cells from normal tissue of the same type.

In some embodiments, the cancer is in the form of, or comprises at least one tumor.

In some embodiments, administering to the subject the erbB inhibitor and the IFNγ is effective to reduce cancer cell proliferation in the tumor or the migration of immune suppressor cells into the tumor.

In some embodiments, the cancer is an adenocarcinoma.

In some embodiments, the cancer is glioblastoma, prostate cancer, lung cancer, pancreatic cancer, ovarian cancer, breast cancer, colon cancer, or stomach cancer.

In some embodiments, the cancer is breast cancer, and the breast cancer is ductal carcinoma in situ (DCIS).

In some embodiments, the cancer is breast cancer and the breast cancer is
a) estrogen receptor positive;
b) estrogen receptor negative;
c) Her2 positive;
d) Her2 negative;
e) progesterone receptor positive;
f) progesterone receptor negative; or
g) any combination of a) through f).

In some embodiments, treating the subject comprises preventing or reducing tumor growth in the subject.

In some embodiments, treating the subject comprises completely arresting cancer cell growth in the subject.

In some embodiments, treating the subject comprises increased lysis of cancer cells in the subject.

In some embodiments, the subject is treated such that an increase in the volume of the at least one tumor cannot be detected for a period of at least 30 days during or after treatment.

In some embodiments, the subject is a mammalian subject.

In some embodiments, the mammalian subject is a human subject.

In some embodiments, the method further comprises administering an antibody to the subject.

In some embodiments, the antibody is an anti-p185her2/neu antibody.

In some embodiments, the antibody is an anti-EGFR antibody.

In some embodiments, the antibody is an anti-PD1 or anti-PD-L1 antibody.

In some embodiments, the erbB inhibitor and the antibody are administered to the subject before IFNγ is administered to the subject.

In some embodiments, the erbB inhibitor and the antibody are administered to the subject at least 0.5, 1, 1.5, 2, 2.5, 3, 3.5, 4. 4.5, or 5 days before IFNγ is administered to the subject.

In some embodiments, IFNγ is administered to the subject concomitantly with the erbB inhibitor and the antibody, or within 24 hours after the erbB inhibitor and the antibody are administered to the subject.

In some embodiments, the antibody is administered to the subject after IFNγ is administered to the subject.

In some embodiments, the antibody is administered to the subject at least 0.5, 1, 1.5, 2, 2.5, 3, 3.5, 4. 4.5, or 5 days after IFNγ is administered to the subject.

In some embodiments, the antibody is a monoclonal antibody.

The present invention provides a method of inhibiting development into cancer cells of breast cells that overexpress p185her2/neu in a subject in need of such inhibition which comprises administering to said subject
i) an erbB inhibitor; and
ii) interferon-gamma (IFNγ),
each in a sufficient amount to down regulate the overexpressed p185her2/neu and inhibit the development of said breast cells that overexpress p185her2/neu into breast cancer cells.

The present invention also provides a method of inhibiting development into cancer cells of breast cells that overexpress EGFR in a subject in need of such inhibition which comprises administering to said subject
i) an erbB inhibitor; and
ii) interferon-gamma (IFNγ),
each in a sufficient amount to down regulate the overexpressed p185 and inhibit the development of said breast cells that overexpress p185 into breast cancer cells.

In some embodiments, the erbB inhibitor is a compound that
a) is in a clinical trial; or
b) is approved for use in human subjects.

In some embodiments, the erbB inhibitor is a p185her2/neu kinase inhibitor.

In some embodiments, the erbB inhibitor is an EGFR kinase inhibitor.

In some embodiments, the erbB inhibitor is an organic compound having a molecular weight less than 1000 Daltons.

In some embodiments, the erbB inhibitor is gefitinib, erlotinib, lapatinib, or vandetanib, or a pharmaceutically acceptable salt or ester thereof.

Gefitinib, is commercially available from AstraZeneca AB (S-151 85 Sodertalje Sweden). The CAS Registry number for gefitinib is 184475-35-2. Gefitinib is also known as Iressa. The structure for gefitinib is:

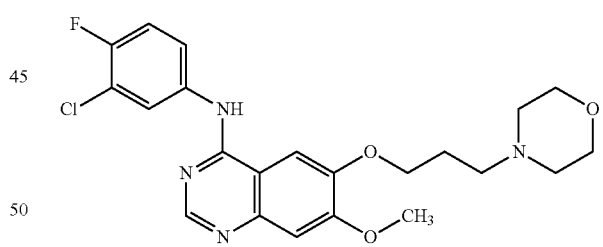

Gefitinib (Iressa)

Gefitinib is described in Lynch, et al., "Activating mutations in the epidermal growth factor receptor underlying responsiveness of non-small-cell lung cancer to gefitinib," N. Engl. J. Med., 350: 2129-39 (2004); Paez, et al., "EGFR mutations in lung cancer: correlation with clinical response to gefitinib therapy," Science, 304: 1497-1500 (2004); and U.S. Pat. No. 8,350,029, issued Jan. 8, 2013, the entire contents of each of which are hereby incorporated herein in their entireties.

Erlotinib, is commercially available from OSI Pharmaceuticals, LLC (Northbrook, Ill., 60062, USA). Erlotinib is also known as Tarceva. The structure for erlotinib is:

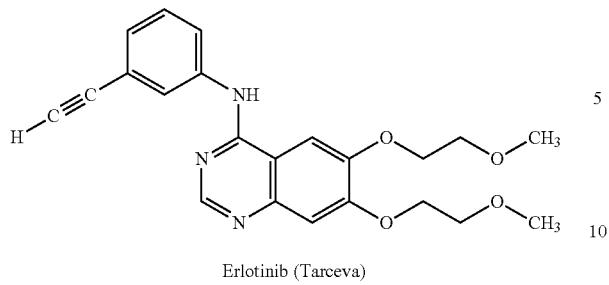

Erlotinib (Tarceva)

Erlotinib is described in U.S. Pat. No. 8,642,758, issued Feb. 4, 2014 the entire content of which is hereby incorporated herein in its entirety.

Lapatinib, is commercially available from GlaxoSmithKline (Research Triangle Park, N.C. 27709, USA). Lapatinib is also known as Tykerb. The structure for lapatinib is:

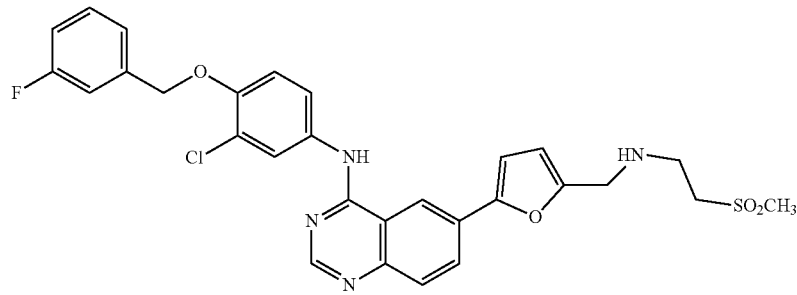

Lapatinib

Lapatinib is described in Burris HA (2004). "Dual kinase inhibition in the treatment of breast cancer: initial experience with the EGFR/ErbB-2 inhibitor lapatinib". Oncologist. 9 Suppl 3: 10-5; and U.S. Pat. No. 8,664,389, issued Mar. 4, 2014 the entire contents of each of which are hereby incorporated herein in their entireties.

Vandetanib is commercially available from AstraZeneca Pharmaceuticals LP (Wilmington, Del. 19850, USA). The structure of vandetanib is:

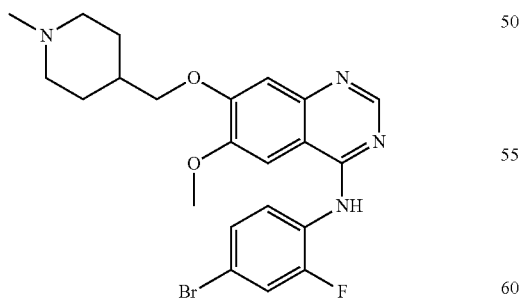

Vandetanib is also known as Caprelsa. Vandetanib is described in Martin, P.; Oliver, S.; Kennedy, S. J.; Partridge, E.; Hutchison, M.; Clarke, D.; Giles, P. (2012). "Pharmacokinetics of Vandetanib: Three Phase I Studies in Healthy Subjects". Clinical Therapeutics 34 (1): 221-237; and U.S. Pat. No. 8,609,673, issued Dec. 17, 2013 the entire contents of each of which are hereby incorporated herein in their entireties.

In some embodiments, the erbB inhibitor has the structure:

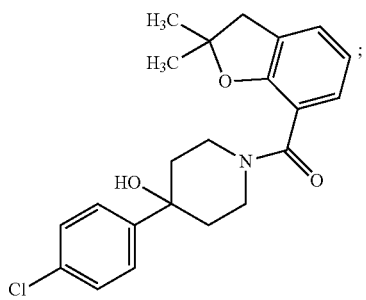

-continued

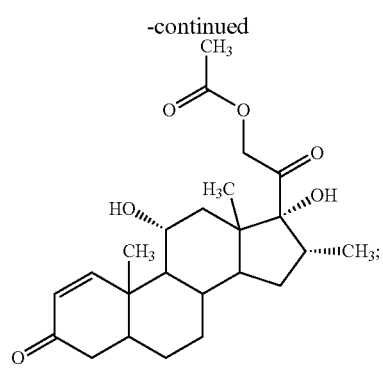

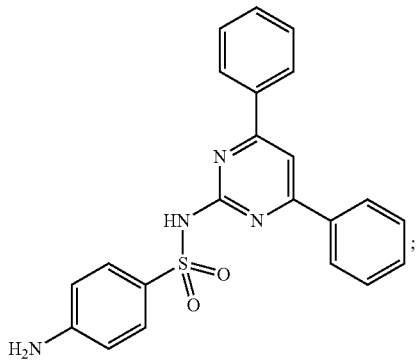

-continued

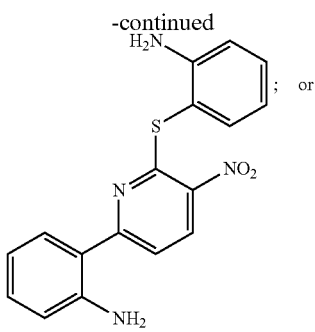
; or

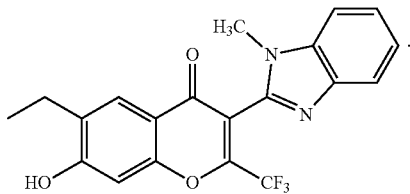

Compounds of these structures are described in U.S. Patent Application Publication No. US 2014-0135298, published May 15, 2014, the entire content of which is incorporated herein by reference.

In some embodiments, the erbB inhibitor has the structure:

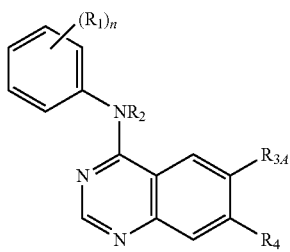

wherein $R_1$ is independently H, optionally substituted amino, optionally substituted $C_{1-6}$ alkyl, optionally substituted $C_{1-6}$ alkoxy, optionally substituted $C_{2-6}$ alkenyl, optionally substituted $C_{2-6}$ alkynyl, optionally substituted benzyloxy, cyano, halo, hydroxy, nitro, optionally substituted phenoxy, or mono-, di-, or trifluoromethyl;

n is 1, 2, or 3;

$R_2$ is independently H or $C_{1-3}$-alkyl;

$R_{3A}$ is —$OR_{5A}$, —$NR_2R_{5A}$, —$SR_{5A}$, —C(O) $R_{5A}$, —C(O) $OR_{5A}$, —C(O) N($R_2$)($R_{5A}$), —OC(O) $R_{5A}$, —OC(O) $OR_{5A}$, —OC(O) $NR_2R_{5A}$, —$NR_2C(O)$ $R_{5A}$, —$NR_2C(O)$ $OR_{5A}$;

$R_4$ is H, —N($R_2$)$_2$, optionally substituted $C_{1-3}$-alkyl, optionally substituted $C_{1-3}$-alkoxy, cyano, halo, hydroxy, nitro, or mono-, di-, or trifluoromethyl;

$R_{5A}$ is —($C_{1-4}$-alkyl)-X—$R_6$—$R_7$;

X is independently O, S, or N($R_2$)

$R_6$ is a bond or $C_{5-6}$ aryl or $C_{5-6}$ heteroaryl;

$R_7$ is either a $C_{1-4}$-alkyl substituted by at least one —OH or —C(O)$OR_2$ or —C(O)N($R_2$)$_2$, or a $C_5$ heteroaryl containing 1-3 heteroatoms and substituted by $R_2$ and either a halo-substituted benzyloxy or —X—$R_8$; and $R_8$ is $C_{1-3}$ alkyl substituted by at least one —OH, —COOH, —C(O)O—$C_{1-4}$ alkyl, —C(O)N($R_2$)$_2$, or $C_{1-5}$ cycloalkyl;

or a pharmaceutically acceptable salt form thereof. Compounds of this structure, as well as processes of synthesizing compounds of this structure are described in U.S. Patent Application Publication No. US 2014-0309246, published Oct. 16, 2014, the entire content of which is incorporated herein by reference.

In some embodiments, the erbB inhibitor has the structure:

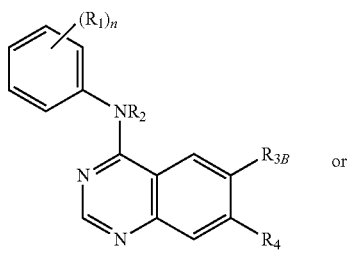 or

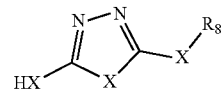

wherein $R_1$ is independently H, optionally substituted amino, optionally substituted $C_{1-6}$ alkyl, optionally substituted $C_{1-6}$ alkoxy, optionally substituted $C_{1-6}$ alkenyl, optionally substituted $C_{1-6}$ alkynyl, optionally substituted benzyloxy, cyano, halo, hydroxy, nitro, optionally substituted phenoxy, or mono-, di-, or trifluoromethyl;

n is 1, 2, or 3;

$R_2$ is independently H or C1_3-alkyl;

$R_{3B}$ is —$OR_{5B}$, —$NR_2R_{5B}$, —$SR_{5B}$, —C(O) $R_{5B}$, —C(O) $OR_{5B}$, —C(O)N($R_2$)($R_{5B}$), —OC(O) $R_{5B}$, —OC(O) $OR_{5B}$, —OC(O) $NR_2R_{5B}$, —$NR_2C(O)$ $R_{5B}$, or —$NR_2C(O)$ $OR_{5B}$;

R4 is H, —N($R_2$)$_2$, optionally substituted $C_{1-3}$-alkyl, optionally substituted $C_{1-3}$-alkoxy, cyano, halo, hydroxy, nitro, or mono-, di-, or trifluoromethyl;

$R_{5B}$ is —($C_{0-4}$-alkyl)-L, wherein L is a leaving group;

X is independently O, S, or N($R_2$); and $R_8$ is $C_{1-3}$ alkyl substituted by at least one —OH, —COOH, —C(O)O—$C_{1-4}$ alkyl, C(O)N($R_2$)$_2$, or $C_{3-5}$ cycloalkyl;

or a pharmaceutically acceptable salt form thereof.

Compounds of this structure, as well as processes of synthesizing compounds of this structure are described in U.S. Patent Application Publication No. US 2014-0309246, published Oct. 16, 2014, the entire content of which is incorporated herein by reference.

In some embodiments, the erbB inhibitor has the structure:
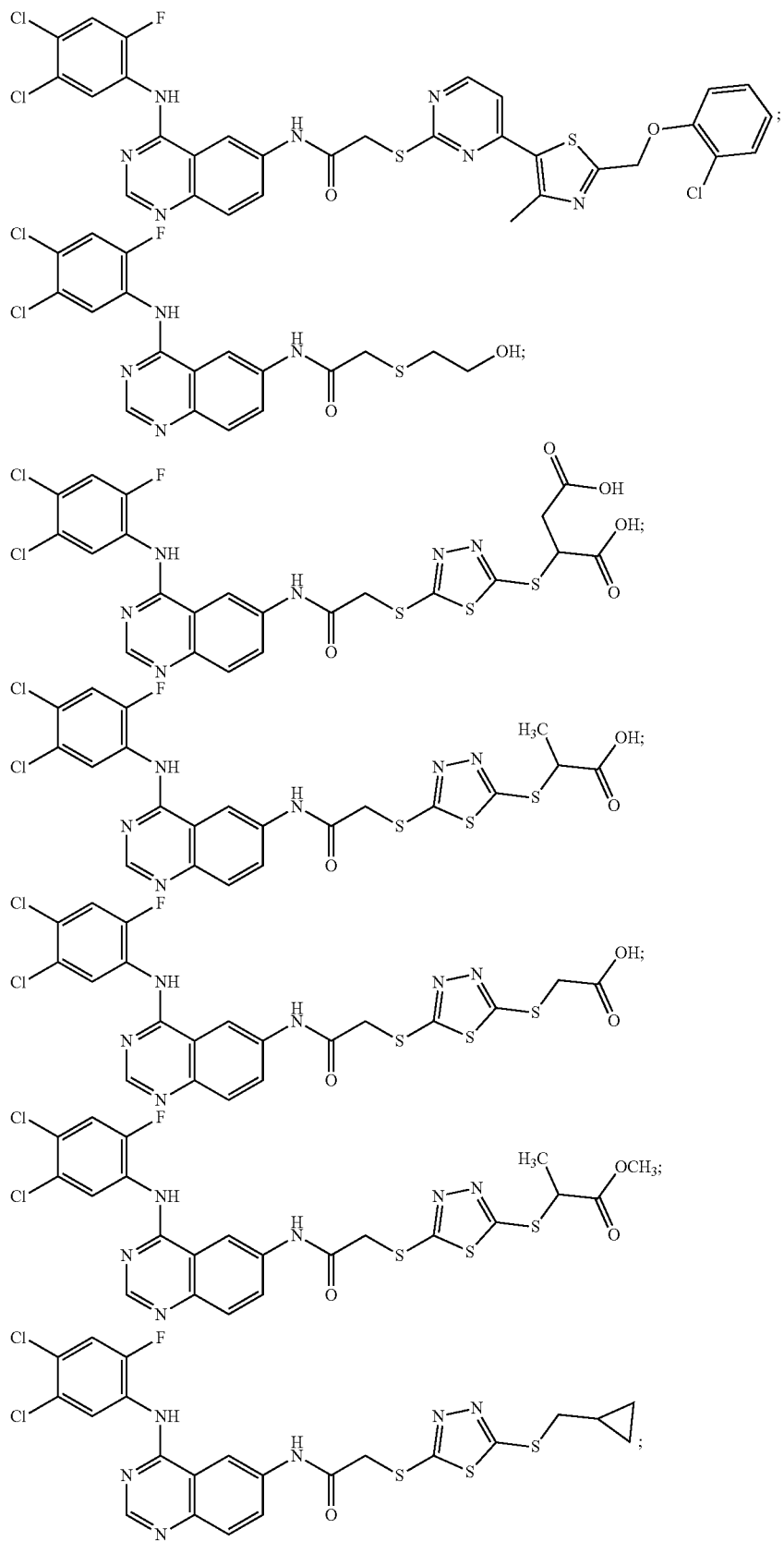

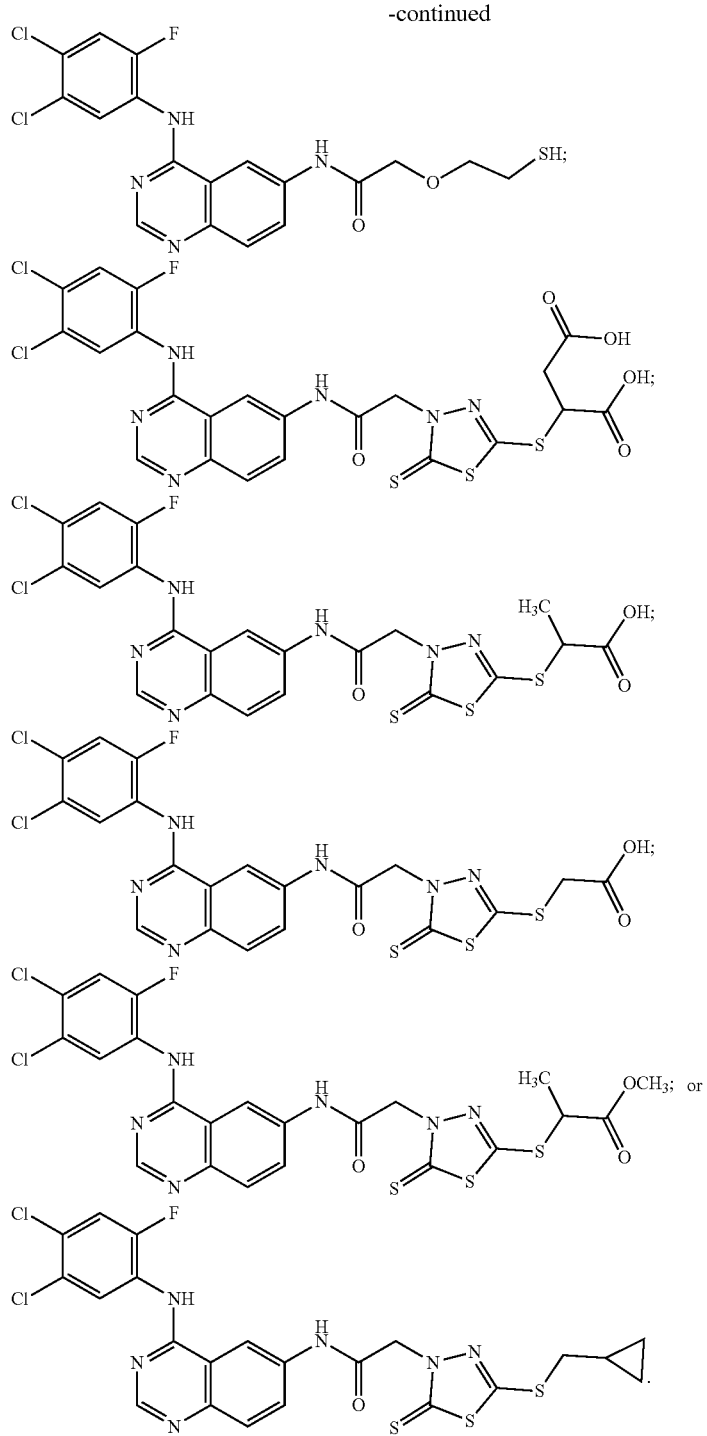

Compounds of these structures, as well as processes of synthesizing compounds of these structures are described in U.S. Patent Application Publication No. US 2014-0309246, published Oct. 16, 2014, the entire content of which is incorporated herein by reference.

Aspects of the present invention relate to a composition for the treatment of a subject afflicted with cancer, comprising i) an erbB inhibitor; and ii) interferon-gamma (IFNγ), and a pharmaceutically acceptable carrier.

Aspects of the present invention also relate to a composition for sensitizing cancer to radiation or a chemotherapeutic agent, comprising i) an erbB inhibitor; and ii) interferon-gamma (IFNγ), and a pharmaceutically acceptable carrier.

Aspects of the present invention relate to a composition for preventing the development of a tumor in a subject at risk of developing the tumor, comprising i) an erbB inhibitor; and ii) interferon-gamma (IFNγ), and a pharmaceutically acceptable carrier.

Aspects of the present invention also relate to a composition for sensitizing a tumor to radiation or a chemotherapeutic agent, comprising i) an erbB inhibitor; and ii) interferon-gamma (IFNγ), and a pharmaceutically acceptable carrier.

Aspects of the present invention relate to a combination for the treatment of a subject afflicted with cancer or preventing the development of a tumor in a subject at risk of developing the tumor, comprising i) an erbB inhibitor; and ii) interferon-gamma (IFNγ), and a pharmaceutically acceptable carrier.

Each embodiment disclosed herein is contemplated as being applicable to each of the other disclosed embodiments. Thus, all combinations of the various elements described herein are within the scope of the invention.

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means±10% of the numerical value or range recited or claimed, unless the context requires a more limited range.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

As used herein, the terms "erbB-associated cancer" and "erbB-associated tumors" are meant to refer to cancer cells and neoplasms which express a member of the erbB gene family, the expression of which results in erbB-mediated transformation.

As used herein "p185" and "p185her2/neu" refer to the erbB2 protein of 185,000 molecular weight. "Neu" or "Her2" or "erbB2" or "erbB2/Her2/neu" refer to the gene that encodes the p185her2/neu protein.

P185her2/neu-associated tumors and EGFR-associated tumors are examples of erbB-associated tumors. As used herein, the terms "erbB2/Her2/neu-associated cancer" "erbB2/Her2/neu associated tumors" and "p185her2/neu-associated cancer" are meant to refer to cancer cells and neoplasms which express p185her2/neu. ErbB2/Her2/neu-associated cancer is an erbB associated cancer in which the cellular transformation is mediated by tyrosine kinase activity related to p185her2/neu.

As used herein, the terms "EGFR-associated cancer" and "EGFR-associated tumors" are meant to refer to cancer cells and neoplasms which express EGFR. EGFR-associated cancer is an erbB-associated cancer in which the cellular transformation is mediated by tyrosine kinase activity related to EGFR.

p185her2/neu is also described in U.S. Pat. No. 7,625,558, issued Dec. 1, 2009, and U.S. Patent Application Publication No. 2012/0164066, published Jun. 28, 2012, the entire content of each of which is incorporated herein by reference.

As used herein, an "anti-p185her2/neu polypeptide" is a polypeptide that is capable of specifically binding to p185her2/neu. In some embodiments, the anti-p185her2/neu polypeptide specifically binds to p185her2/neu, but is incapable of binding to an erbB family protein other than p185her2/neu under cell culture or physiological conditions. In some embodiments, an anti-p185her2/neu polypeptide is capable of binding to p185her2/neu such that it significantly inhibits (either partially or completely) a biological activity of p185her2/neu. In some embodiments, the biological activity of p185her2/neu is dimerization with another p185her2/neu protein, or another erbB family protein. In some embodiments, the biological activity of p185her2/neu is tyrosine kinase activity. In some embodiments, an anti-p185her2/neu polypeptide is capable of binding to p185her2/neu, without significantly inhibiting a biological activity of p185her2/neu.

As used herein, an "anti-EGFR polypeptide" is a polypeptide that is capable of specifically binding to EGFR. In some embodiments, the anti-EGFR polypeptide specifically binds to EGFR, but is incapable of binding to an erbB family protein other than EGFR under cell culture or physiological conditions. In some embodiments, an anti-EGFR polypeptide is capable of binding to EGFR such that it significantly inhibits (either partially or completely) a biological activity of EGFR. In some embodiments, the biological activity of EGFR is dimerization with another EGFR protein, or another erbB family protein. In some embodiments, the biological activity of EGFR is tyrosine kinase activity. In some embodiments, an anti-EGFR polypeptide is capable of binding to EGFR, without significantly inhibiting a biological activity of EGFR.

In some embodiments, peptides which mimic antibodies are provided to inhibit multimeric ensemble formation and the elevated kinase activity associated which such formation. For example, peptides are designed which have sequences corresponding to CDR regions from antibodies. Methods of making such peptides are also described in Ser. No. 08/257,783 filed Jun. 10, 1994 and PCT Application No. PCT/US95/07157 filed Jun. 6, 1995 which is incorporated herein by reference. Peptidomimetics of antibodies against p185her2/neu are described in U.S. Pat. No. 5,663,144 issued Sep. 2, 1997, which is incorporated herein by reference.

As used herein, the term "cytotoxic" agent refers to an agent that inhibits the biological processes of a cell, or reduces the viability or proliferative potential of a cell. As used herein, the term or "cytostatic" agent refers to an agent that inhibits the proliferative potential of a cell. In some embodiments, cytostatic agent inhibits the proliferation of a cancer cell or a cell other than a cancer cell. Cytotoxic or cytostatic agents can function in a variety of ways, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Chemotherapeutic agents include, but are not limited to, synthetic compounds, natural and recombinant bacterial toxins, natural and recombinant fungal toxins, natural and recombinant plant toxins, fissionable nuclides, and radionuclides. Specific examples of chemotherapeutic agents include, but are not limited to, pokeweed antiviral protein, abrin, ricin and each of their A chains, momordin, saporin, bryodin 1, bouganin, gelonin, Diphtheria toxin, Pseudomonas exotoxin, Shiga toxin, calicheamicin, maytansinoid, lead-212, bismuth-212, astatine-211, iodine-131, scandium-47, rhenium-186, rhenium-188, yttrium-90, iodine-123, iodine-124, iodine-125, bromine-77, indium-111, boron-10, actinide, altretamine, actinomycin D, plicamycin, puromycin, gramicidin D, doxorubicin, colchicine, cytochalasin B, cyclophosphamide, emetine, maytansine, amsacrine, platinum-based chemotherapeutic agents including but not limited to cisplastin and carboplatin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxanes including but not limited to paclitaxel, docetaxel and cabazitaxel, tarceva, avastin, mitomycin, 5-fluorouracil, cyclophosphamide and certain cytokines such as TNF-alpha and TNF-beta.

In some embodiments, radiation therapy may commence any time after a sufficient amount of time has elapsed for an active agent or agents to act on cancer or other cells in a subject. Generally, the subject is exposed to radiation in some cases 1-10 minutes after, in some cases 1-10 hours after, and in some cases up to 24-72 hours after administration of the active agent(s). In some cases, the radiation is provided in a single dose while in some embodiments, multiple doses are administered over several hours, days and/or weeks. The active agent renders the radiation resistant tumor cells radiation sensitive. Thus, once the active agent inhibits the kinase activity, exposure to radiation may follow suit. Gamma radiation is delivered according to standard radiotherapeutic protocols using standard dosages and regimens. The administration of the active agent(s) renders the radiation more effective in eradicating tumor cells. Active agents of the present invention include fusion proteins of the present invention, anti-p185her2/neu antibodies, anti-EGFR antibodies, and interferon-gamma.

As in the case of radiation therapy, in some embodiments chemotherapy may commence any time after a sufficient amount of time has elapsed for an active agent or agents to act on cancer or other cells in a subject. Generally, the subject is administered the chemotherapeutic in some cases 1-10 minutes after, in some cases 1-hours after, and in some cases up to 24-72 hours after administration of the 45 kinase inhibiting active agent(s). In some cases, the chemotherapeutic is provided in a single dose while in some embodiments, multiple doses are administered over several hours, days and/or weeks. The active agent(s) renders the tumor cells more sensitive to cytotoxic agents. Thus, once the active agent inhibits, e.g., the kinase activity, administration of chemotherapeutics may follow suit. Chemotherapeutics are delivered according to standard radiotherapeutic protocols using standard agents, dosages and regimens. In some embodiments, chemotherapy and radiation treatments are both employed following the administration of the active agent(s). Active agents of the present invention include fusion proteins of the present invention, anti-p185her2/neu antibodies, anti-EGFR antibodies, and interferon-gamma.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably herein, and refer to an amount of a fusion protein, an antibody, antigen-binding fragment, antibody composition, interferon-gamma, or a combination thereof as described herein, effective to achieve a particular biological or therapeutic result such as, but not limited to, biological or therapeutic results disclosed, described, or exemplified herein. A therapeutically effective amount of the fusion protein, the antibody or antigen-binding fragment thereof may vary according to factors such as the disease state, age, sex, and weight of the subject, and the ability of the antibody or antigen-binding fragment thereof to elicit a desired response in the subject. In embodiments of the invention, such results may include, but are not limited to, the treatment of cancer, as determined by any means suitable in the art.

The fusion proteins, anti-p185her2/neu antibodies, anti-EGFR antibodies, and interferon-gamma may be administered to a subject in a pharmaceutically acceptable carrier or carriers. "Pharmaceutically acceptable" refers to those properties and/or substances which are acceptable to the subject from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

Antibodies

The term "antibody" is used in the broadest sense and specifically covers monoclonal antibodies (including full length monoclonal antibodies), polyclonal antibodies, multispecific antibodies (e.g., bispecific antibodies), monovalent antibodies, and multivalent antibodies. Additionally, the term "antibody" refers to all isotypes of immunoglobulins (IgG, IgA, IgE, IgM, IgD, and IgY) including various monomeric and polymeric forms of each isotype, unless otherwise specified.

"Antibody fragments" comprise a portion of a full length antibody, generally the antigen binding or variable region thereof. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Various techniques have been developed for the production of antibody fragments, including proteolytic digestion of antibodies and recombinant production in host cells; however, other techniques for the production of antibody fragments will be apparent to the skilled practitioner. In some embodiments, the antibody fragment of choice is a single chain Fv fragment (scFv). "Single-chain Fv" or "scFv" antibody fragments comprise the V H and V L domains of antibody, wherein these domains are present in a single polypeptide chain. Generally, the Fv polypeptide further comprises a polypeptide linker between the V H and V L domains which enables the scFv to form the desired structure for antigen binding. For a review of scFv and other antibody fragments, see James D. Marks, Antibody Engineering, Chapter 2, Oxford University Press (1995) (Carl K. Borrebaeck, Ed.).

The term "epitope" refers to a portion of a molecule (the antigen) that is capable of being bound by a binding agent, e.g., an antibody, at one or more of the binding agent's antigen binding regions. Epitopes usually consist of specific three-dimensional structural characteristics, as well as specific charge characteristics.

As used herein, "monoclonal antibody" means an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495-97 (1975), or may be made by recombinant DNA methods (see, e.g., U.S. Pat. No. 4,816,567). The monoclonal antibodies may also be isolated from phage display libraries using the techniques described, for example, in Clackson et al., Nature 352:624-28 (1991) and Marks et al., J. Mol. Biol. 222 (3):581-97 (1991).

The term "hybridoma" or "hybridoma cell line" refers to a cell line derived by cell fusion, or somatic cell hybridization, between a normal lymphocyte and an immortalized lymphocyte tumor line. In particular, B cell hybridomas are created by fusion of normal B cells of defined antigen specificity with a myeloma cell line, to yield immortal cell lines that produce monoclonal antibodies. In general, techniques for producing human B cell hybridomas, are well known in the art (Kozbor et al., Immunol. Today 4:72 (1983); Cole et al., in Monoclonal Antibodies and Cancer Therapy, Alan R. Liss, Inc. 77-96 (1985)).

The term "chimeric" antibody refers to an antibody in which a portion of the heavy and/or light chain is derived from a particular source or species, while the remainder of the heavy and/or light chain is derived from a different source or species.

As used herein, "fully human antibody" is an antibody that is completely human. A human antibody is one which possesses an amino acid sequence which corresponds to that of an antibody produced by a human or a human cell or derived from a non-human source that utilizes human antibody repertoires or other human antibody-encoding sequences. In some embodiments, a human antibody specifically excludes a humanized antibody comprising non-human antigen-binding residues. Fully human antibodies may be generated by, e.g., phage display, or in animals (such as mice) which have been genetically engineered to produce human antibodies. Exemplary methods of producing fully human antibodies are described in U.S. Pat. Nos. 7,414,170; 7,803,981; in U.S. Patent Application No. 2008/0248531, and in McCafferty et al., "Phage antibodies: filamentous phage displaying antibody variable domains" Nature (1990) 348 (6301): 552-554; Osbourn J K, "Proximity-guided (ProxiMol) antibody selection" Methods Mol. Biol. (2002) 178: 201-5; and Lonberg et al., "Human antibodies from transgenic mice" Int. Rev. Immunol. (1995) 13(1):65-93, the contents of each of which are hereby incorporated by reference in their entireties.

"Humanized antibodies" means antibodies that contain minimal sequence derived from non-human immunoglobulin sequences. For the most part, humanized antibodies are human immunoglobulins (recipient antibody) in which residues from a hyper variable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., Nature 332:323-27 (1988); and Presta, Curro Opin. Struct. Biol. 2:593-96 (1992), each of which is incorporated herein by reference.

Antibodies of the invention also include antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered nonfunctional and substituted with the analogous human immunoglobulin loci. These transgenic animals produce human antibodies in the substantial absence of light or heavy host immunoglobulin subunits. See, for example, U.S. Pat. No. 5,939,598, the entire contents of which are incorporated herein by reference.

Those skilled in the art will be aware of how to produce antibody molecules of the present invention. For example, polyclonal antisera or monoclonal antibodies can be made using standard methods. A mammal, (e.g., a mouse, hamster, or rabbit) can be immunized with an immunogenic form of the protein which elicits an antibody response in the mammal. For instance, a mammal can be immunized with irradiated cells that were transfected with a nucleic acid encoding the protein such that high levels of the protein were expressed on the cell surface. The progress of immunization can be monitored by detection of antibody titers in plasma or serum. Standard ELISA or other immunoassay can be used with the immunogen as antigen to assess the levels of antibodies. Following immunization, antisera can be obtained, and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies which are specifically reactive with the oligopeptide, and monoclonal antibodies isolated.

Stretches of Consecutive Amino Acid Sequences

Described herein are fusion proteins comprising stretches of consecutive amino acid sequences that can not only bind to a particular antigen, but can also bind to antibodies and comprise a biologically active portion of interferon-gamma. In some embodiments, the fusion protein binds p185her2/neu. In some embodiments, the fusion protein binds EGFR. Such fusion proteins can have at least one protein segment that is capable of binding to the Fc region of an antibody. In some embodiments, the Fc-binding segment can be contiguous with an antigen-specific peptide. Such an antigen-binding protein can be produced by the combination of a protein derived from a portion of Protein A, a *Staphylococcus aureus* cell wall component that has the ability to bind to certain antibody isotypes, with an antigen-specific peptide. In one embodiment, this type of antigen-binding fusion protein comprises a ZZ polypeptide (SEQ ID NO. 4), derived from a portion of Protein A, linked to AHNP. The fusion protein may also include another stretch of consecutive amino acids that has the sequence of at least a portion of interferon-gamma. A ZZ polypeptide can be linked to an antibody fragment to function as an Fc-binding domain. For example, a ZZ polypeptide could be linked to an antibody-derived fragment single chain Fv (scFv) to allow the scFv to interact with the Fc portion of an antibody. Similarly, ZZ polypeptide could be linked to an interferon-gamma to allow the interferon-gamma to interact with the Fc portion of an antibody. In some embodiments, the ability of the fusion protein to interact with antibodies may allow for indirect interaction with Fc receptors via the constant region of the antibody.

Indirect linkage can be mediated by an "oligopeptide linker" such as poly-glycine or a glycine-serine oligopeptide, for example, GGGGS (SEQ ID NO: 6) or GGGGGS (SEQ ID NO: 7). Other such linkers are known in the art and should be considered to be encompassed by this term. (Robinson and Sauer, 95 PNAS 5929-34 (1998), Tang et al., 271(26) J. Bio. Chem. 15682-86 (1996). In addition, the various components of the fusion proteins described herein can be directly linked to one another by splicing together their respective gene segments via genetic engineering techniques well known in the art. In general, an oligopeptide linker of the invention will range from 5 to 50, from 5 to 30, from 10-30, or from 12-25 amino acids in length.

In addition to the stretches of consecutive amino acid sequences described herein, it is contemplated that variants thereof can be prepared by introducing appropriate nucleotide changes into the encoding DNA, and/or by synthesis of the desired consecutive amino acid sequences. Those skilled in the art will appreciate that amino acid changes may alter post-translational processes of the stretches of consecutive amino acids described herein when expression is the chosen method of synthesis (rather than chemical synthesis for example), such as changing the number or position of glycosylation sites or altering the membrane anchoring characteristics.

Variations in the sequences described herein, can be made, for example, using any of the techniques and guidelines for conservative and non-conservative mutations set forth, for instance, in U.S. Pat. No. 5,364,934. Variations may be a substitution, deletion or insertion of one or more codons encoding the consecutive amino acid sequence of interest that results in a change in the amino acid sequence as compared with the native sequence. Optionally the variation is by substitution of at least one amino acid with any other amino acid in one or more of the domains. Guidance in determining which amino acid residue may be inserted, substituted or deleted without adversely affecting the desired activity may be found by comparing the sequence with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence. It is understood that any terminal variations are made within the context of the invention disclosed herein.

Amino acid sequence variants of the a protein, such as a fusion protein, are prepared with various objectives in mind, including increasing the affinity of the fusion for p185her2/neu or EGFR, facilitating the stability, purification and preparation of the fusion protein, modifying its plasma half life, improving therapeutic efficacy, and lessening the severity or occurrence of side effects during therapeutic use of the fusion protein.

Amino acid sequence variants of these sequences are also contemplated herein including insertional, substitutional, or deletional variants. Such variants ordinarily can prepared by site-specific mutagenesis of nucleotides in the DNA encoding the target-binding monomer, by which DNA encoding the variant is obtained, and thereafter expressing the DNA in recombinant cell culture. Fragments having up to about 100-150 amino acid residues can also be prepared conveniently by in vitro synthesis. Such amino acid sequence variants are predetermined variants and are not found in nature. The variants exhibit the qualitative biological activity (including target-binding) of the nonvariant form, though not necessarily of the same quantative value. While the site for introducing an amino acid sequence variation is predetermined, the mutation per se need not be predetermined. For example, in order to optimize the performance of a mutation at a given site, random or saturation mutagenesis (where all 20 possible residues are inserted) is conducted at the target codon and the expressed variant is screened for the optimal combination of desired activities. Such screening is within the ordinary skill in the art.

Amino acid insertions usually will be on the order of about from 1 to 10 amino acid residues; substitutions are typically introduced for single residues; and deletions will range about from 1 to 30 residues. Deletions or insertions preferably are made in adjacent pairs, i.e. a deletion of 2 residues or insertion of 2 residues. It will be amply apparent from the following discussion that substitutions, deletions, insertions or any combination thereof are introduced or combined to arrive at a final construct.

In an aspect, the invention concerns a compound comprising a stretch of consecutive amino acids having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity to an amino acid sequence disclosed in the specification, a figure, or a SEQ ID NO. of the present application.

The % amino acid sequence identity values can be readily obtained using, for example, the WU-BLAST-2 computer program (Altschul et al., Methods in Enzymology 266:460-480 (1996)).

Fragments of native sequences are provided herein. Such fragments may be truncated at the N-terminus or C-terminus, or may lack internal residues, for example, when compared with a full length native protein. Again, it is understood that any terminal variations are made within the context of the invention disclosed herein. Certain fragments lack amino acid residues that are not essential for a desired biological activity of the sequence of interest.

Any of a number of conventional techniques may be used. Desired peptide fragments or fragments of stretches of consecutive amino acids may be chemically synthesized. An alternative approach involves generating fragments by enzymatic digestion, e.g. by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide/sequence fragment, by polymerase chain reaction (PCR). Oligonucleotides that define the desired termini of the DNA fragment are employed at the 5' and 3' primers in the PCR.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original | Exemplary | Preferred |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the sequence are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro;
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-1085 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Polynucleotides and Expression

The fusion proteins described herein can be made by recombinant processes and, therefore, may include amino acid sequences derived from more than one species (i.e. chimeric constructs) or may be engineered to have a human, or human-like, amino acid composition (i.e., a humanized construct). Accordingly, provided herein are vectors comprising polynucleotides capable of encoding the described fusion proteins. The vectors can be expression vectors. Recombinant expression vectors containing a sequence encoding a polypeptide of interest are thus provided. The expression vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus.

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

The vectors described herein can be used to transform various cells with the genes encoding the disclosed fusion proteins. For example, the vectors may be used to generate scaffold or antigen-binding protein-producing cells or cell lines. Thus, another aspect features host cells transformed with vectors comprising a nucleic acid sequence encoding a fusion protein. The host cells disclosed herein can be prokaryotic or eukaryotic cells, For example the host cell can be a bacteria. In a preferred embodiment, the bacterial host cell is E. coli. Of course, the host cell can also be a mammalian cell, such as a Chinese hamster ovary (CHO) cell line. Numerous other such host cells, prokaryotic and eukaryotic, are known in the art and are considered to be within the scope of this disclosure. Numerous techniques are known in the art for the introduction of foreign genes into cells and may be used to construct the recombinant cells for purposes of carrying out the inventive methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

It is fully contemplated that the vectors such as those described herein can be used to transform prokaryotic and/or eukaryotic cells to facilitate expression of the described fusion proteins. In some embodiments the described vectors are used to facilitate fusion protein expression in bacteria, such as E. coli. While any E. coli strain can be used to express the proteins described herein, some preferred strains include: BL21 (DE3), BL21-CodonPlus® (DE3)-RP, BL21-Codon Plus® (DE3)-RIL, BL21-(DE3)-pLysS (Stratagene). Eukaryotic cells can also be used with vectors to facilitate protein expression. While those of skill in the art will recognize that a wide variety of eukaryotic cells will be suitable for this purpose, some preferred embodiments include mammalian cells and insect cells. For example, in one embodiment Chinese hamster ovary (CHO) cells can be used with the vectors to facilitate expression of the fusion protein constructs provided herein. In alternative embodiments, insect cells, such as Sf9 cells or S2 cells, can be used to with the described vectors to facilitate expression of the protein constructs provided herein. Furthermore, those of skill in the art will understand that vectors, not expressly disclosed herein, can be used for the same purpose of expressing, or replicating nucleic acids encoding, the described antigen binding proteins.

The described fusion proteins can be encoded by a variety of polynucleotides capable of encoding the amino acid sequences provided herein. These polynucleotides can also be incorporated into vectors useful for the maintenance, replication, and/or expression of the polynucleotides encoding the described antigen-binding proteins or the described portions thereof. The vectors described above can be used to engineer cells to express the antigen-binding proteins or the described portions thereof encoded by the polynucleotides disclosed herein.

Compositions

Also described herein are compositions containing a fusion protein or fusion proteins of the invention and a pharmaceutically acceptable carrier. Such compositions can be used to administer the described fusion proteins to a subject or store or to maintain the described fusion proteins. Any of the described fusion proteins can be used to produce such compositions, which may include more than one of the disclosed proteins. In addition, such compositions can include other agents, such as therapeutic agents, preservatives, antimicrobial agents, and the like.

Described herein are compositions comprising at least one disclosed protein and a pharmaceutically acceptable carrier. The compositions can be formulated as any of various preparations that are known and suitable in the art, including those described and exemplified herein. In some embodiments, the compositions are aqueous formulations. Aqueous solutions can be prepared by admixing the antigen-binding proteins in water or suitable physiologic buffer, and optionally adding suitable colorants, flavors, preservatives, stabilizing and thickening agents and the like as desired. Aqueous suspensions can also be made by dispersing the antigen-binding proteins in Water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogennated edible fats or oils); emulsifying agents (e. g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution With a suitable vehicle such as sterile water, physiological buffer, saline solution, or alcohol, before use.

The compositions can be formulated for injection into a subject. For injection, the compositions described can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The proteins described herein may be administered orally in any acceptable dosage form such as capsules, tablets, aqueous suspensions, solutions or the like. The proteins may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the proteins will be intravenously or intraperitoneally, for example, by injection.

The subject can be any animal, and preferably is a mammal such as a mouse, rat, hamster, guinea pig, rabbit, cat, dog, monkey, donkey, cow, horse, pig, and the like. In some embodiments, the mammal is a human.

All publications and other references mentioned herein are incorporated by reference in their entirety, as if each individual publication or reference were specifically and individually indicated to be incorporated by reference. Publications and references cited herein are not admitted to be prior art.

The present invention is not intended to be limited by any theory. This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1

Enhanced Activity of 7.16.4 and IFN-γ on Tumors Transformed by Oncogenic neu.

p185her2/neu is a member of the ERBB family of receptor tyrosine kinases and has been validated as a clinical target for breast and stomach cancers. Monoclonal antibodies to the oncoprotein of the rat origin were developed to establish the foundation for targeted therapies to solid tumors (Drebin et al., 1986; Drebin et al., 1984). One of the monoclonal antibodies, mAb7.16.4, has a shared epitope with trastuzumab, a FDA approved therapeutic agent in clinical use (Zhang et al., 1999). 7.16.4 is active on Erbb2/neu transformed rodent and human tumors in a variety of assays (Cai et al., 2013; Zhang et al., 1999). 7.16.4 has been used in many labs around the world in transgenic animal models of tumors induced by the neu oncogene (Katsumata et al., 1995; Park et al., 2010; Stagg et al., 2011).

Recent studies defined a role for CD8$^+$ IFN-γ secreting cells and NK ADCC mediating cells as contributory elements in 7.16.4 therapy of implanted tumor model of neu transformed cells (Park et al., 2010; Stagg et al., 2011). It is expected that both active innate and adaptive immune cells that translocate and reside in the tumors contribute to the anti-cancer activity of 7.16.4 and trastuzumab.

Figure 1:
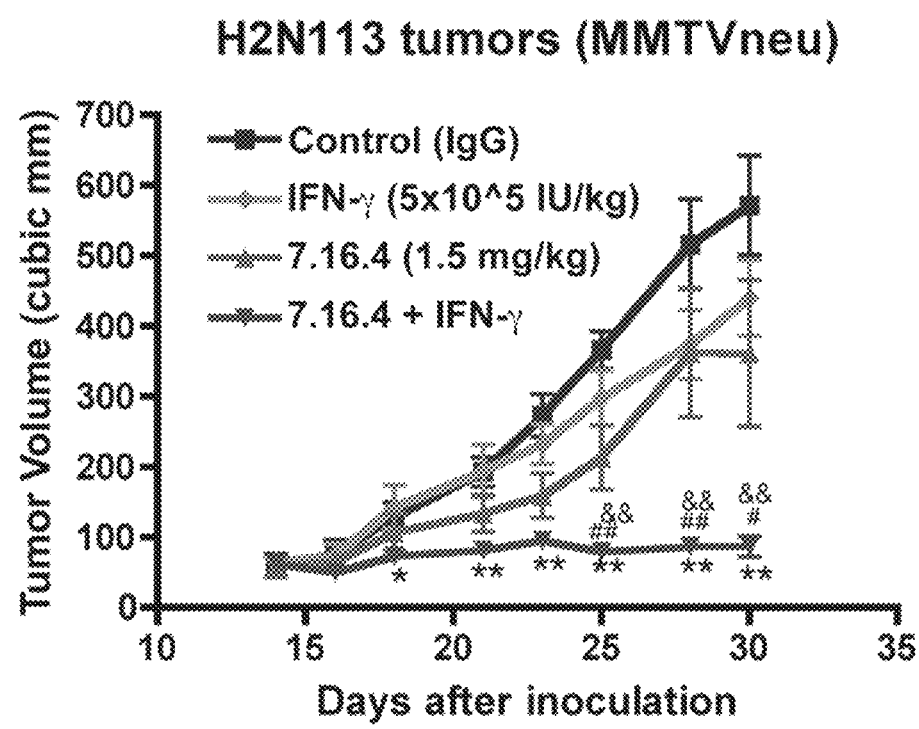
FIG. 1. Enhanced in vivo activity of anti-Her2/neu antibody and IFNγ. H2N113 tumor cells ($1 \times 10^6$) were injected subcutaneously into both side of the back of 6-10 weeks old MMTV-neu mice. Once tumors reached an average size of 30-40 mm³ (10-12 days after tumor inoculation), mice were treated with control IgG, IFN-γ ($5 \times 10^5$ IU/kg, three times per week), 7.16.4 (1.5 mg/kg, twice per week), or the combination of IFN-γ and 7.16.4. Data represent mean+ SEM. t test was performed to compare the difference in the tumor size of different treatment groups. *P<0.05, **P<0.01, compared with control; #P<0.05, ##P<0.01, compared with the 7.16.4 group; &P<0.05, &&P<0.01, compared with the IFN-γ group.
Figure 2A:
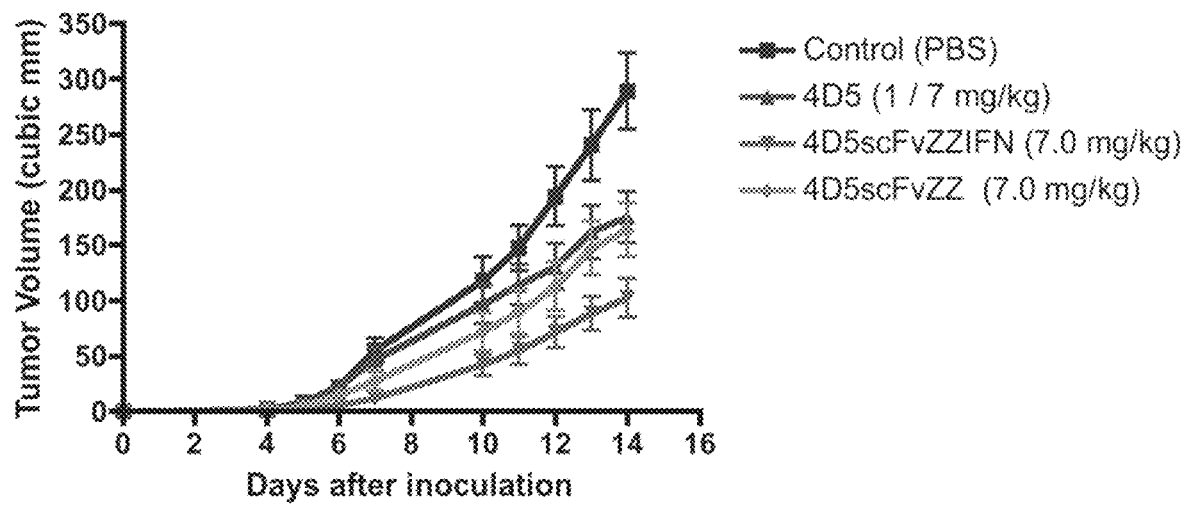
FIG. 2A-FIG. 2B. In vivo activity of 4D5scFvZZ-IFNγ.
Figure 2B:
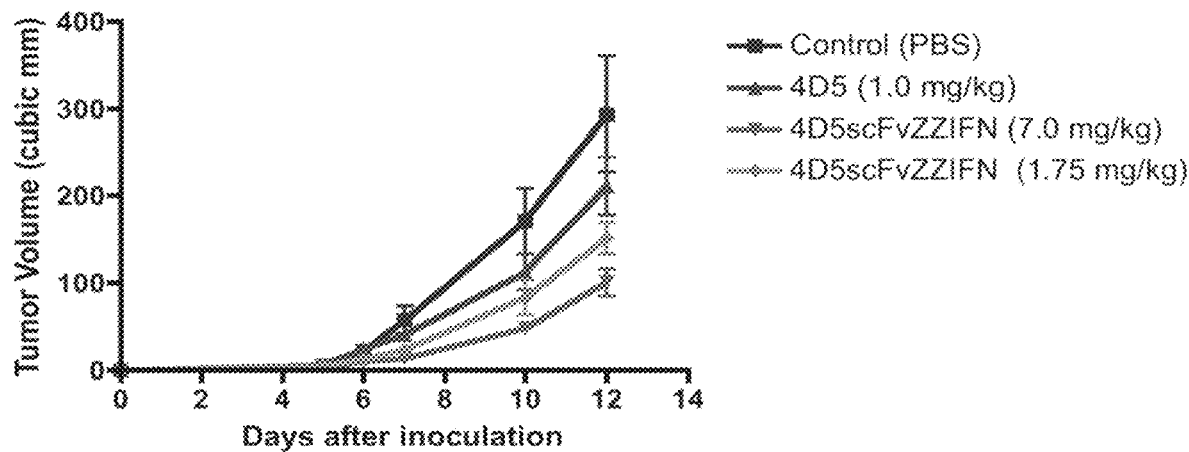

Experiments were conducted to examine whether IFN-γ could directly enhance 7.16.4 anti-tumor activity. The target tumor cell line H2N113 was established from the tumor of MMTV-neu transgenic mice (Stagg et al., 2011). In vitro proliferation assay demonstrated that 7.16.4 could inhibit H2N113 in a dose-dependent manner (Du et al 2013). H2N113 tumor cells were implanted into BALB/c-MMTV-neu mice as reported previously (Stagg et al., 2011). Treatment began when tumors were apparent (10 days after tumor inoculation). Mice were treated with a control antibody, IFN-γ alone, sub-optimal amount of 7.16.4 (5 mg/kg), or the combination of 7.16.4 and IFN-γ. As shown in FIG. 1, the combination group (7.16.4+IFN) showed dramatically suppressed tumor growth. The data herein indicate that IFN-γ enhances the effectiveness of anti-p185her2/neu antibody targeted therapy.

Example 2

Activity of 4D5scFv-IFNγ Fusion Protein on Tumors Transformed by ErbB2

Previously a novel "Grababody" approach to empower a scFv construct with immune cell functions was reported (Cai, 2013) (disclosed in UPN-5599). This approach utilizes the IgG binding Z domain placed on the C-terminus to the scFv to capture endogenous circulating IgG. Using the scFv to p185her2/neu as an example, it was shown that the Grababody 4D5scFvZZ (SEQ ID NO: 1) binds to the target receptor on the tumor cells and demonstrates CDC and ADCC activity towards antigen-positive tumor cells. Most importantly, in the in vivo xenograft mice model, the Grababody significantly reduces the growth of the malignant tumors transformed by ErbB2/Her2/neu (Cai, 2013).

To show that IFN-γ can improve the activity of anti-tumor activity of scFv based Grababody 4D5scFvZZ (SEQ ID NO: 1), a single chain fusion molecule 4D5scFvZZ-IFNγ was constructed (SEQ ID NO: 2). The anti-tumor activity of 4D5scFvZZ (SEQ ID NO: 1) and 4D5scFvZZ-IFNγ (SEQ ID NO: 2) was compared using the T6-17 in vivo model in nude mice. Athymic nude mice were inoculated with $5 \times 10^5$ T6-17 cells. Mice carrying tumor received 4D5scFvZZ (SEQ ID NO: 1), 4D5scFvZZ-IFNγ (SEQ ID NO: 2) or control buffer at the dose of 7 mg/kg, three times per week via i.p. injection. As shown in FIG. 2A-FIG. 2B, 4D5scFvZZ-IFNγ (SEQ ID NO: 2) has better activity than 4D5scFvZZ (SEQ ID NO: 1) to limit the growth of T6-17 tumors.

Binding of 4D5scFv-ZZ-IFNγ and 4D5scFv-IFNγ to p185her2/neu Expressing Cells.

Figure 3:
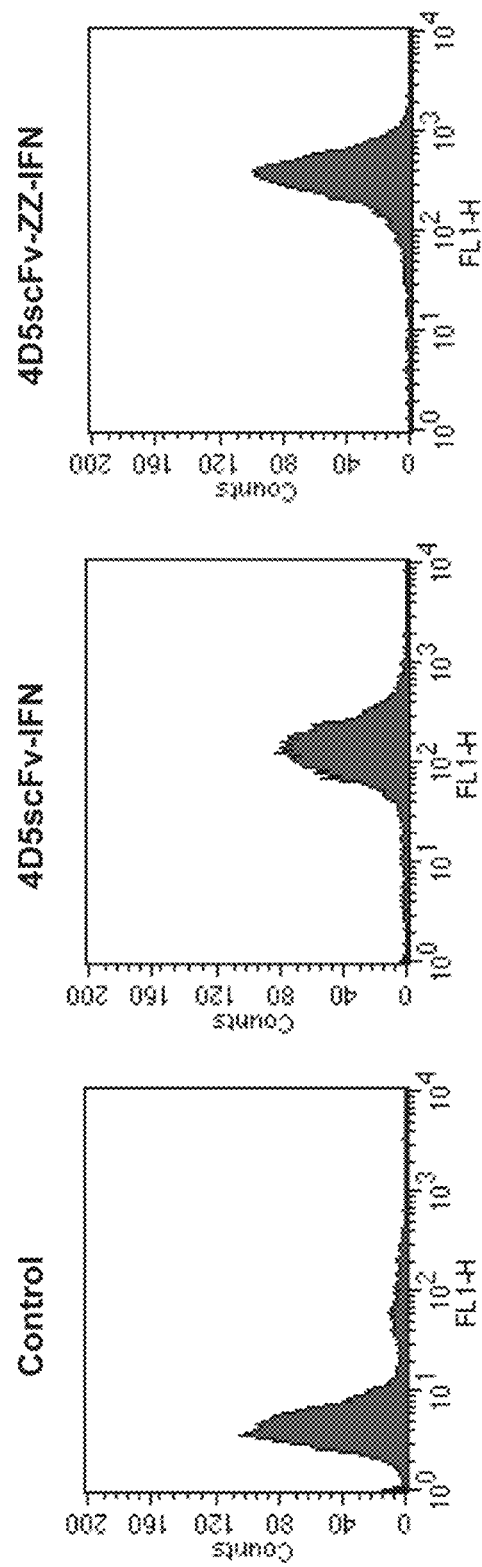
FIG. 3. 4D5scFv-ZZ-IFNγ and 4D5scFv-IFNγ bind to cell surface p185her2/neu. T6-17 cells with the expression of p185her2/neu were prepared for Fluorescence-activated cell sorting (FACS). Histograms represent staining with 0.5 μg of 4D5scFv-IFNγ or 4D5scFv-ZZ-IFNγ, as indicated in the figure, followed by His-Probe antibody and Alexa488-conjugated goat anti-rabbit antibodies. The control staining was obtained with only the His-Probe antibody and the secondary antibody.

It was previously shown that the 4D5scFv in the Grababody 4D5scFv-ZZ was active to bind p185her2/neu that was either immobilized on the chip or expressed on the cell surface (Cai, 2013). To confirm that the 4D5scFv-ZZ-IFNγ and 4D5scFv-IFNγ are also corrected folded and contain active 4D5scFv unit, FACS binding assays on p185her2/neu-expressing T6-17 cells were performed. As shown in FIG. 3, both constructs were able to bind T6-17.

Verification of the Fusion Proteins for IFNγ Activity

Figure 4:
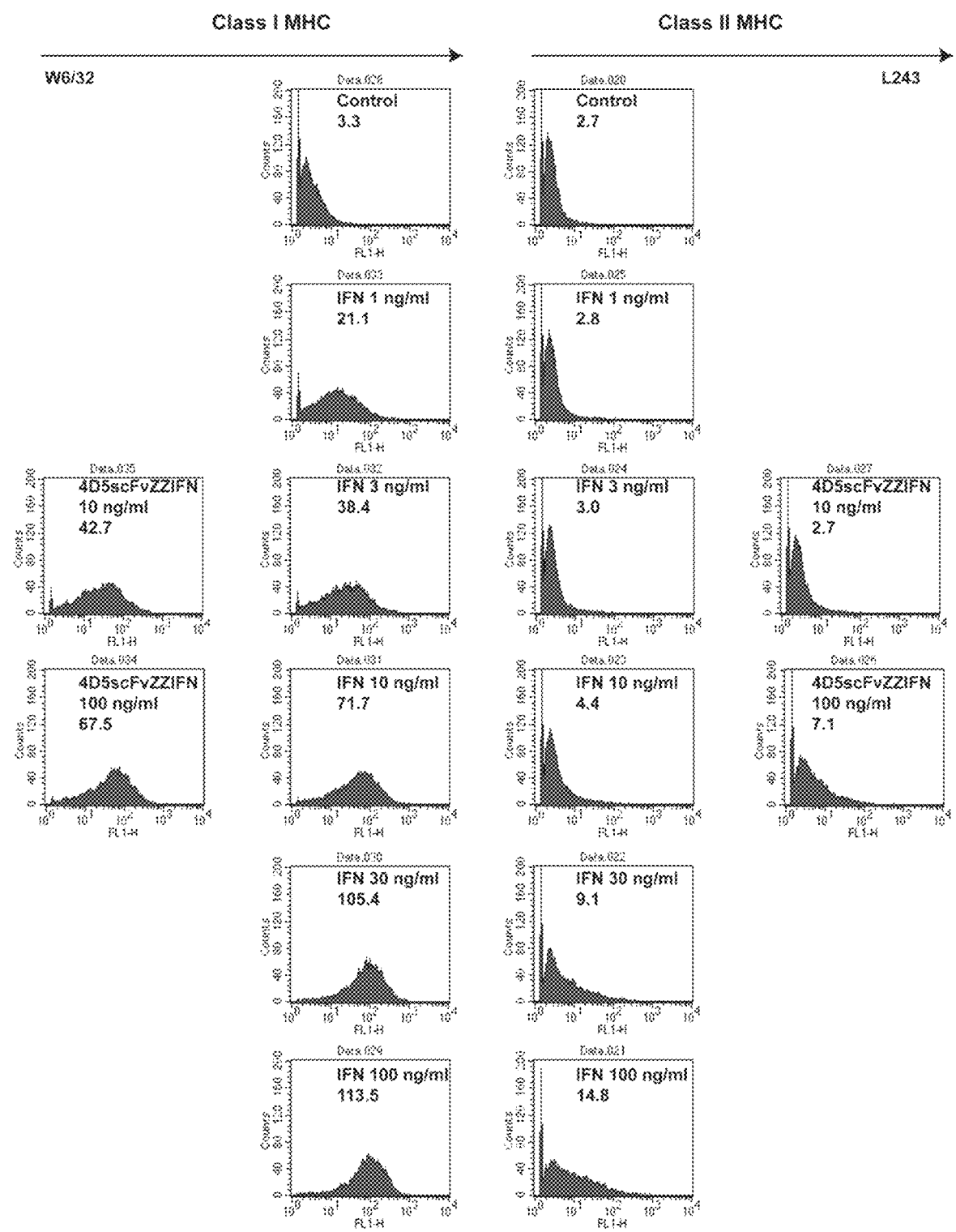
FIG. 4. Effect of 4D5scFv-ZZ-IFNγ on MHC expression. SKBR3 cells were incubated with IFNγ or 4D5scFv-ZZ-IFNγ at different dose. Expression of class I and class II MHC antigens were analyzed by FACS using monoclonal antibodies W6/33 and L243, respectively.

IFNγ is known to be able to induce class I MHC antigen expression in tumor cells. Activity on MHC expression in SKBR3 cells was examined to verify that the IFNγ unit in the fusion protein is active. As shown in FIG. 4, the recombinant protein 4D5scFv-ZZ-IFNγ demonstrated class I MHC-stimulating activity comparable to a free IFNγ molecule. Both IFNγ and 4D5scFv-ZZ-IFNγ had no effect on class II MHC antigen.

Comparison of In Vivo Activity of 4D5scFv-ZZ-IFNγ and 4D5scFv-IFNγ.

Figure 5:
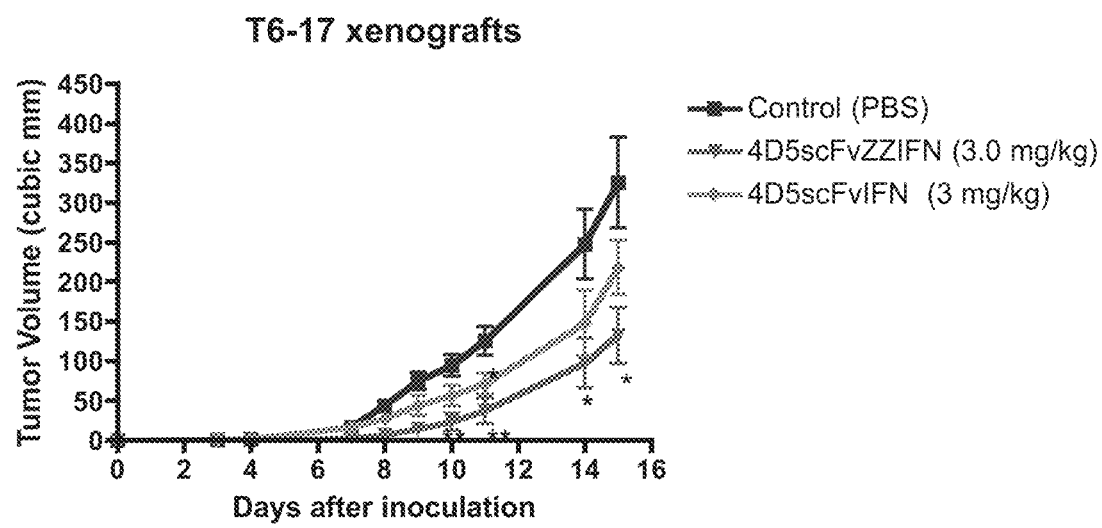
FIG. 5. Comparison of in vivo activity of 4D5scFv-ZZ-IFNγ and 4D5scFv-IFNγ. $5 \times 10^5$ T6-17 cells were injected s.c. into nude mice to induce tumor growth. i.p. treatments with 4D5scFv (SEQ ID NO: 3) or 4D5scFvZZ (SEQ ID NO.

Experiments using T6-17 in vivo model demonstrated that 4D5scFv-ZZ-IFNγ had better activity than 4D5scFv-IFNγ (FIG. 5).

IFNα Appears not to have the Same Activity as IFNγ to Facilitate Anti-p185her2/Neu Antibody.

IFNα appears to have anti-tumor activity on its own in the in vivo tumor model but it could not enhance mAb 7.16.4 activity to suppress the growth of xenografted tumors (FIG. 7).

Effect of Co-Treatment on MDSC

Myeloid-derived suppressor cells (MDSC) are defined as CD45+ cells that are also Cd11b+ and GR-1+. MDSC were isolated from tumors at the end of treatments. As shown in FIG. 8, the co-treatment with 7.16.4 and IFNγ led to the most reduction of MDSC populations in tumor tissues of xenografted mice. This study indicates that the co-treatment may prevent the infiltration of certain immune suppressor cells into the tumor microenvironment (FIG. 8).

An in vitro cell migration experiment was also performed. H2N113 cells were treated with control, 7.16.4, IFNγ, or 7.16.4 plus IFNγ for 3 days. The same treatments were also incubated in blank wells without any H2N113 cells as controls. The conditioned medium from each wells were collected and placed into the bottom chamber of a cell migration device. MDSC isolated from mice were placed into the upper chamber. Cells migrated from the upper chamber to the lower one were counted. As shown in FIG. 9, H2N113 conditioned medium clearly attracted MDSC cells to migrate into the lower chamber. 7.16.4 slightly reduced the migration, but the co-treatment of 7.16.4 and IFNγ completely blocked MDSC migration induced by H2N113. This study suggests that the co-treatment affect the tumor cells and prevent tumor cells from attracting immune suppressor cells.

Example 3

Disabling the erbB2 Kinase Reverses Features of the Malignant Phenotype to Permit Interferon-γ to Act on Human Breast Cancer Cells.

This study provides additional biochemical studies defining the effects of ordered therapy of disabling erbB kinases with either monoclonal antibody or small molecules followed or concomitant with interferon gamma. The data is remarkably clear the there are two steps to phenotypic reversion—one is diminution of malignant properties that accompany disabling of either erbB2/neu or erbB1 kinases. The combination action of antierbB2 and interferon gamma leads to degradation of Snail, which is dependent on GSK3β and can be abolished by a pharmacological inhibitor. Secondly the phenotypically reverted cell can only then be acted on by interferon gamma (and not any other interferon). This is new and profound observation that explains optimal use of these reagents to alter malignant properties and tumor survival.

Summary erbB2 confers transforming properties and is amplified in approximately 30% of breast cancers. One therapeutic approach to dampen erbB2 signaling is monoclonal antibody (mAb) targeting. Although direct action of targeting antibodies results in erbB2 down-modulation and phenotype reversal, use in vivo suggested a contribution of immune cells and cytokines. Unfortunately, mAb-based therapy often is not curative and tumors reoccur, which may be the consequence of cells that self-renew and resist therapy. The data herein show anti-erbB2 mAb concurrent with IFN-γ reverses the malignant phenotype beyond either treatment alone. Exposure of breast cancer cells to anti-erbB2 mAb and IFN-γ reduces the transcriptional repressor snail through accentuated GSK3-β activity. These data identify a mechanism for co-treatment and support an approach for developing therapeutics.

Reversion of the malignant phenotype of erbB2-transformed cells can be driven by anti-erbB2/neu monoclonal antibodies (mAb) which disrupt the receptor's kinase activity. The biologic effects of IFN-γ with anti-erbB2/neu mAb was examined on erbB2-positive cells. IFN-γ had no effect on its own. In contrast, treatment of the tumors with anti-erbB2/neu mAb followed by IFN-γ led to dramatic inhibition of tumor growth in vitro and in vivo with minimal mAb dosing and enhanced the effects of chemotherapy. IFN-γ with mAb treatment of IFNγR knock down tumors did not show combination eradication effects, indicating INF-γ acts dominantly on the tumor itself. mAb and IFN-γ decreased Snail expression in tumor cells, reflecting loss of stem cell-like properties through enhanced activity of GSK3-β and KLF4.

Significance

Monoclonal antibody-based targeted therapy of erbB driven tumors benefits patient outcome in multiple cancers; however, some patients do not respond, and virtually all responders eventually relapse. The experiments described herein found that interferon-gamma (IFN-γ) is essential to modifying intrinsic properties of transformed cells that have undergone phenotypic reversion with p185 kinase disabling anti-erbB2 mAb. These experiments establish that IFN-γ concurrent with or following anti-erbB2 mAb inhibits a vital intrinsic tumor-signaling pathway limiting stem cell-like properties and has a combination effect that provides optimal therapeutic effects on erbB2-transformed human breast cancer cells. Without wishing to be bound by any scientific theory, the data herein suggest that co-administration or sequential ordering of anti-erbB2 mAb with IFN-γ establishes a set of changes of intrinsic cellular phenotype. The present invention provides this combination treatment for therapies as disclosed herein.

Co-administration or sequential ordering of anti-erbB2 mAb with IFN-γ may greatly reduce the need for the mAb components and genotoxic chemotherapeutics necessary for treatment of humans with erbB2-driven cancers.

Highlights

- IFN-γ and 4D5 act directly on HER2-positive breast cancer cells
- Disabling HER2 signaling preferentially inactivates the PI-3K/Akt pathway
- IFN-γ, but not IFN-β, cooperates with 4D5 directly on HER2+ breast cancer cells
- IFN-γ and 4D5 alters KLF4 levels and degrades Snail by GSK3-β/proteasome pathway
- Treatment with IFN-γ and 4D5 degrades snail through the GSK3-β/proteasome pathway
- Combination treatment could reduce the amount of targeted mAb needed in vivo.

Introduction

The erbB or HER family of receptor tyrosine kinases consists of erbB1 (the epidermal growth factor receptor (EGFR)/HER1), erbB2 (p185/neu/HER2), erbB3 (HER3), and erbB4 (HER4), which can form homomeric and heteromeric assemblies (Kokai et al., 1989; Qian et al., 1994). ErbB receptor tyrosine kinases participate in a variety of signal transduction cascades, including the Ras/Raf/MEK/ERK and PI-3K/Akt pathways. ErbB2 is amplified in ~30% of breast cancer patients, and amplification is associated with poor prognosis and decreased survival (Riemsma et al., 2012). In various cancers, amplified or mutated forms of these kinases drive increased proliferation, migration, survival, evasion of apoptosis, metastasis, and resistance to chemotherapeutics and ionizing radiation.

Recognition that mAbs could disable the p185erbB2/HER2/neu tyrosine kinase receptor complex and also lead to reversal of the malignant phenotype challenged the dogma that transformed cells could only progressively become more abnormal (Drebin et al., 1985; Schechter et al., 1984). Reversal of the malignant phenotype by anti-erbB2 mAb occurs within 24 hours of mAb binding (Drebin et al., 1986; Lee et al., 2012; O'Rourke et al., 1997; Qian et al., 1994a) and begins with down regulation of p185erbB2/neu receptor tyrosine kinase proteins causing diminished enzymatic activity (Drebin et al., 1988; Drebin et al., 1986; Furuuchi et al., 2007; Sliwkowski and Mellman, 2013; Wada et al., 1990; Zhang et al., 2007). All of these clinically-relevant features are improved by anti-ErbB2 mAb therapy (Baselga et al., 2001; Hudis, 2007; Kiessling et al., 2002; Meric-Bernstam and Hung, 2006; Romond et al., 2005; Seidman et al., 2001) and more dramatically with the inclusion of a second antibody, which more completely disables erbB2/neu.

The laboratory of Dr. Mark Greene demonstrated that disabling the kinase complex with monoclonal antibodies (mAb) specific for the ectodomain could reverse aspects of the malignant phenotype in vitro and in vivo (Drebin et al., 1988a; Drebin et al., 1985; Drebin et al., 1986). These approaches were advanced to the clinic and single and dual antibody therapies are now applied to human diseases such as erbB2-positive breast cancer (Baselga et al., 2010; Cortes et al., 2012; Portera et al., 2008). The mechanism through which anti-erbB2 mAb acts on tumors in vivo is complicated, but may include elements of both the adaptive and innate immune system for optimal activity (Park et al., 2010). Furthermore, using an implant model, Stagg and colleagues demonstrated a requirement for Type I and II interferons (IFNs) in mediating anti-erbB2 mAb functions in vivo, through endowing CD8 T cell cytotoxic activities (Stagg et al., 2011). The earliest studies by the Hynes laboratory indicated that IFN-γ could limit p185erbB2/neu expression at the mRNA level (Marth et al., 1990) in some tumors. IFN-γ was found to increase erbB1 (EGFR) levels (Hamburger and Pinnamaneni, 1991) and TGF-α secretion through increased EGFR activity (Uribe et al., 2002) as well as to promote tumor evasion of the immune system in models of colon carcinoma (Beatty and Paterson, 2000). IFN-γ was also one of the first recombinant cytokines tested as a single agent in trials of multiple human cancers, but it led to few if any beneficial outcomes. Thus, clinical efforts using IFN-γ alone as a therapeutic for most malignancies have not been pursued (Krigel et al., 1985).

Malignant evolution of tumors that resist targeted therapy involves the emergence of complex transcriptional functions resembling those of stem cells. Co-expression of erbB2 and constitutively active phosphatidylinositol-3 kinase (PI-3K-CA) produces tumors with enriched transcripts similar to those of stem-like cells or cells that have passaged through an epithelial to mesenchymal transition. In addition, mammary tumors in erbB2+/PI-3K-CA transgenic mice are prone to lung metastases. Transformed cells isolated from such tumors more readily form mammospheres in cell culture (Hanker et al., 2013). Analysis of mouse fetal mammary stem cells (fMaSC) revealed that these cells retain stem properties in vitro such as sphere formation and serial propagation as well as express multiple lineage markers. Comparison of fMaSC gene signatures to those of breast tumor arrays identified overlap with basal-like and erbB2+ tumors (Spike et al., 2012). Finally, a recent archival analysis of breast and lung cancers with p53 mutations revealed stem-like transcriptional signatures (Mizuno et al., 2010), implying that loss of p53 functionality allows for some features of phenotypic conversion.

The advanced tumor includes transformed, differentiated, and highly proliferative cells that constitute the majority of the tumor, and a small fraction composed of transformed, stem-like cells with slower proliferation rates that are refractory to therapy and capable of self-renewal (Wicha et al., 2006). Some of these cell types may undergo change; and Chaffer noted that mammary epithelial cells are able to spontaneously convert from differentiated to dedifferentiated stem-like cells, a property that could be further enhanced by oncogenic transformation (Chaffer et al., 2011). Oncogenes such as erbB2 and Ras drive normal cells, including mammary epithelial cells, neurons, and astrocytes, toward a stem cell phenotype in vitro and in vivo leading to phenotypes which resemble the human pathologies that they model (Cicalese et al., 2009; Friedmann-Morvinski et al., 2012; Korkaya et al., 2008).

Certain proteins relevant to these phenotypic changes have been identified. The transcriptional repressor snail is essential for gastrulation and mesoderm formation during mammalian development (Carver et al., 2001). Snail levels increase in erbB2/neu-driven mammary tumors and this promotes tumor recurrence in vivo. Further, elevated levels of snail are a predictor of decreased relapse-free survival in breast cancer patients (Moody et al., 2005). Slug and SOX9 transcriptional proteins may similarly function together to induce a stem-like phenotype in mammary cells in addition to maintaining tumor and metastatic properties (Guo et al., 2012). However, snail, but not slug, is spontaneously increased during recurrent tumor formation (Moody et al., 2005). Glycogen synthase kinase 3-beta (GSK3-β), while inactivated by Akt1, regulates snail through site-specific phosphorylation. These regulatory post-translational modifications alter snail's subcellular localization and stability. Specifically, GSK3-β phosphorylates snail on six serine residues (serines 97, 101, 108, 112, 116, and 120) encompassing two motifs that promote translocation from the nucleus to the cytoplasm and β-TRCP-mediated ubiquitination and degradation (Zhou et al., 2004). There has not been any description of erbB targeted immune processes that govern Snail protein functions.

Products of activated immune cells such as IFN-γ have been shown to enhance the expression of the KLF4 transcription factor which itself can repress Snail transcription (Feinberg et al., 2005; Yori et al., 2011). KLFs are members of the zinc finger family of transcription factors and typically regulate critical aspects of cellular development and differentiation as well as aspects of cellular phenotype. KLF4 can be induced in response to IFN-γ and can be decreased by TGF-β1 exposure. KLF4 over expression induces macrophage activation markers while KLF4 knockdown markedly modulates the ability of IFN-γ to render those effects. Yori et al (Yori et al., 2011) showed that transfection of KLF4 attenuated primary tumor growth as well as affecting development of metastatic lesions due to decreased proliferation and increased apoptosis of the transfected transformed cells.

This study describes a previously undefined mechanism by which limiting erbB2 kinase activity promotes degradation of snail protein, a process dependent on inhibiting PI3-K/Akt signaling and GSK3-β/proteasome-dependent elimination activities. Unexpectedly IFN-γ was found to contribute to phenotypic reversion and cell viability by activating GSK3-β. However this mechanism is operative only if the malignant cells had been phenotypically modified by the actions of the anti-erbB2 mAb. The effect of mAb disabling of erbB2 is to accomplish a first step in malignant phenotypic reversion, which sensitizes the reverted cells to be further modified by IFN-γ, but not IFN-β. Without wishing to be bound by any scientific theory, these findings provide an explanation as to why anti-erbB2 mAb-mediated tumor elimination requires IFN-γ and how this may lead to better human therapeutics.

The results described herein provide new insight into these processes and indicate that combinations of erbB2-targeted mAb and IFN-γ, but not IFN-α or β, modify Snail expression and contribute to phenotypic reversion and cell viability by altering GSK3-β activity and enhancing KLF4 expression in breast tumors.

These efforts have also been extended in vivo in therapeutic and prevention models.

Results

Sequential and Concurrent Anti-erbB2 mAb and Interferon-γ Act Directly on erbB2+ Breast Cancer Cells The laboratory of Dr. Mark Greene found that treatment of erbB2/neu transformed cells with anti-erbB2 mAb leads to rapid down modulation of the p185/erbB2/neu protein from the cell surface beginning within a few hours of their interaction (Drebin et al., 1985; Drebin et al., 1986; Drebin et al., 1984). Disabling the p185/erbB2/neu kinase complex is accompanied by formation of hypophosphorylated, tetrameric species that are associated with growth inhibition and phenotypic reversion (Furuuchi et al., 2007). Further, studies from the laboratory of Dr. Mark Greene and others (Lee et al., 2012; O'Rourke et al., 1998) indicate that disabling erbB receptors prior to addition of a secondary treatment sensitizes the cells to genotoxic signals, a process that occurs within 24 hours of diminishing kinase functions.

In order to establish optimal treatment conditions, treatment dosages as well as ordered pairings with IFN-γ were tested over an eight-day time frame. SK-BR-3 breast cancer cells, which are erbB2-positive, transformed human cells, were treated with three doses of IFN-γ, a single dose of anti-erbB2 mAb (4D5), or control IgG (cIgG) to compare with cells that were first exposed to IFN-γ for four days followed by IFN-γ and 4D5 for an additional four days or treated with 4D5 for four days followed by treatment with 4D5 and IFN-γ for an additional four days. Cells simultaneously exposed to both 4D5 and IFN-γ for eight days were included as well. Pre-treatment with 4D5 for 4 days followed by the addition of IFN-γ at 5, 10, or 20 ng/mL produced a greater reduction in cell viability (viabilities of 50.8±2.3, 47.3±3.7, and 40.9±4.3%, respectively) than pre-treatment with IFN-γ at 5, 10, or 20 ng/mL followed by addition of 4D5 (viabilities of 71.8±5.1, 67.7±5.5, and 55.3±6.2% respectively). Prolonged co-treatment with 4D5 and IFN-γ at 5, 10, or 20 ng/mL resulted in still greater reduction in cell viabilities (40.4±3.7, 39.4±3.2, and 29.9±3.8%, respectively) (FIG. 19A). These studies established that first disabling the erbB2 kinase with mAb followed by IFN-γ or prolonged co-treatment with mAb and IFN-γ treatment produced the most significant viability effect on breast tumor cells.

Figure 19B:
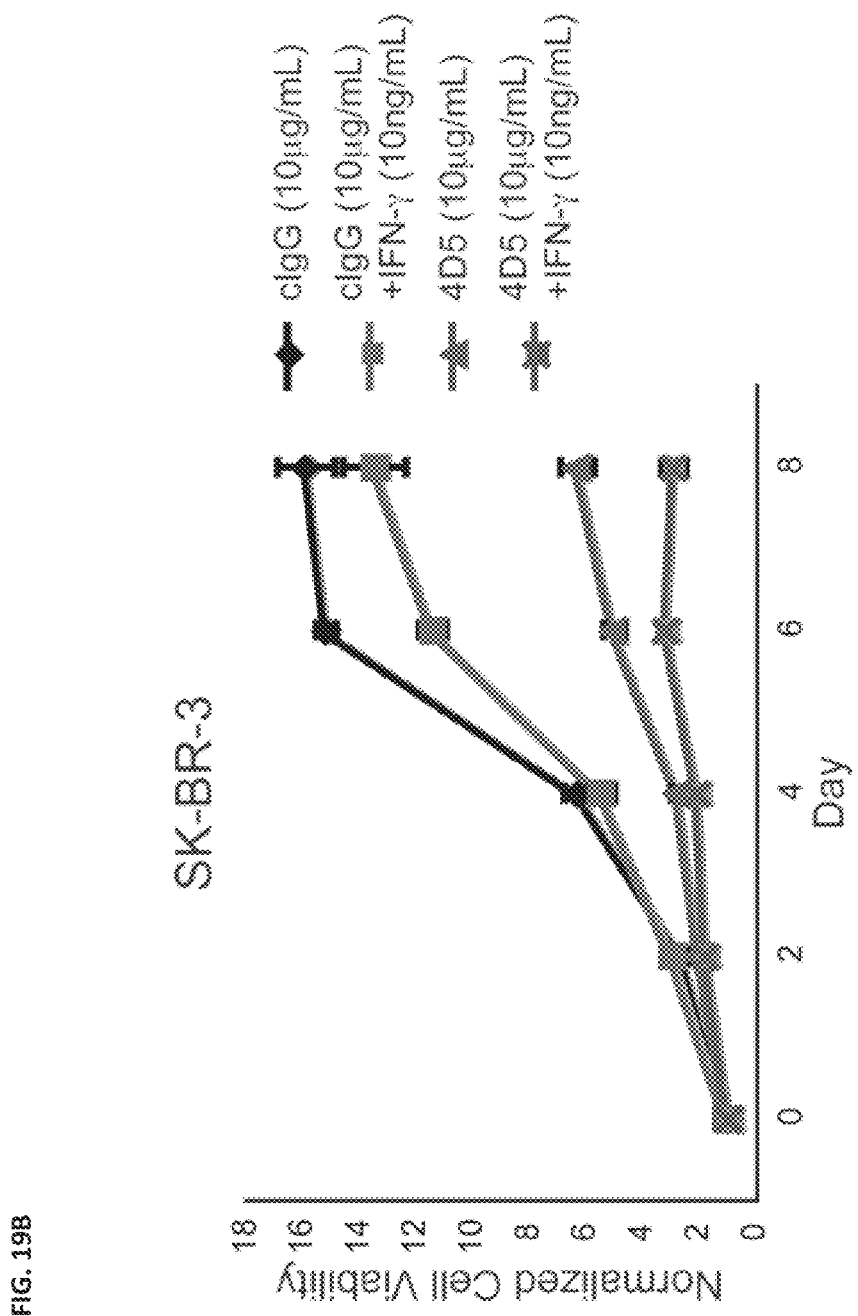

Next, the detailed kinetics of the sensitizing effect using an intermediate dose of IFN-γ (10 ng/mL) was examined. Dramatic reduction in cell viability was noted over an eight-day time course in the presence of 4D5, which could be augmented with the inclusion of IFN-γ (FIG. 19B). These studies, as well as the remaining cell-based studies described herein, were performed with a single treatment of IFN-γ, 4D5, or IFN-γ+4D5 administered the day following cell seeding (i.e. Day 0 on the graph). Immortalized, but untransformed MCF10A cells were not affected either by 4D5 alone or in combination with IFN-γ (FIG. 25). These latter data indicate that the combined ordered effects are manifested only on cells that express the target oncogene and have acquired malignant properties.

Figure 19C:
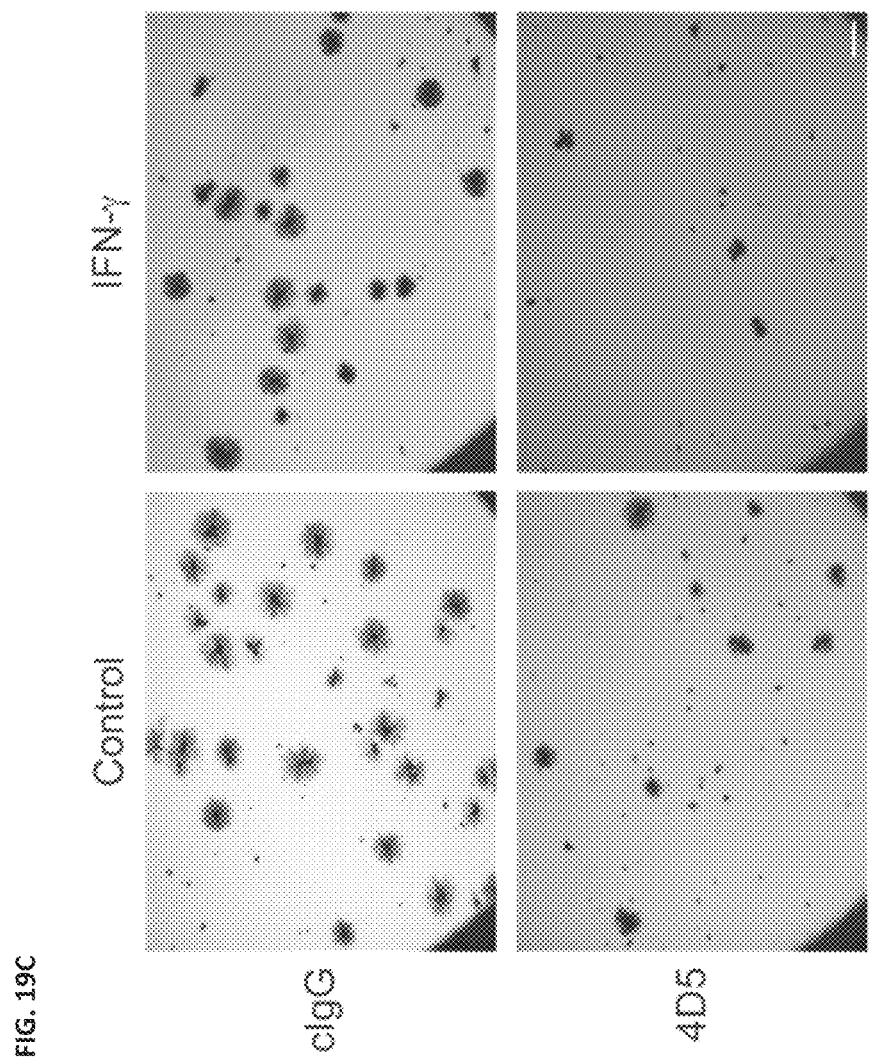
Figure 19D:
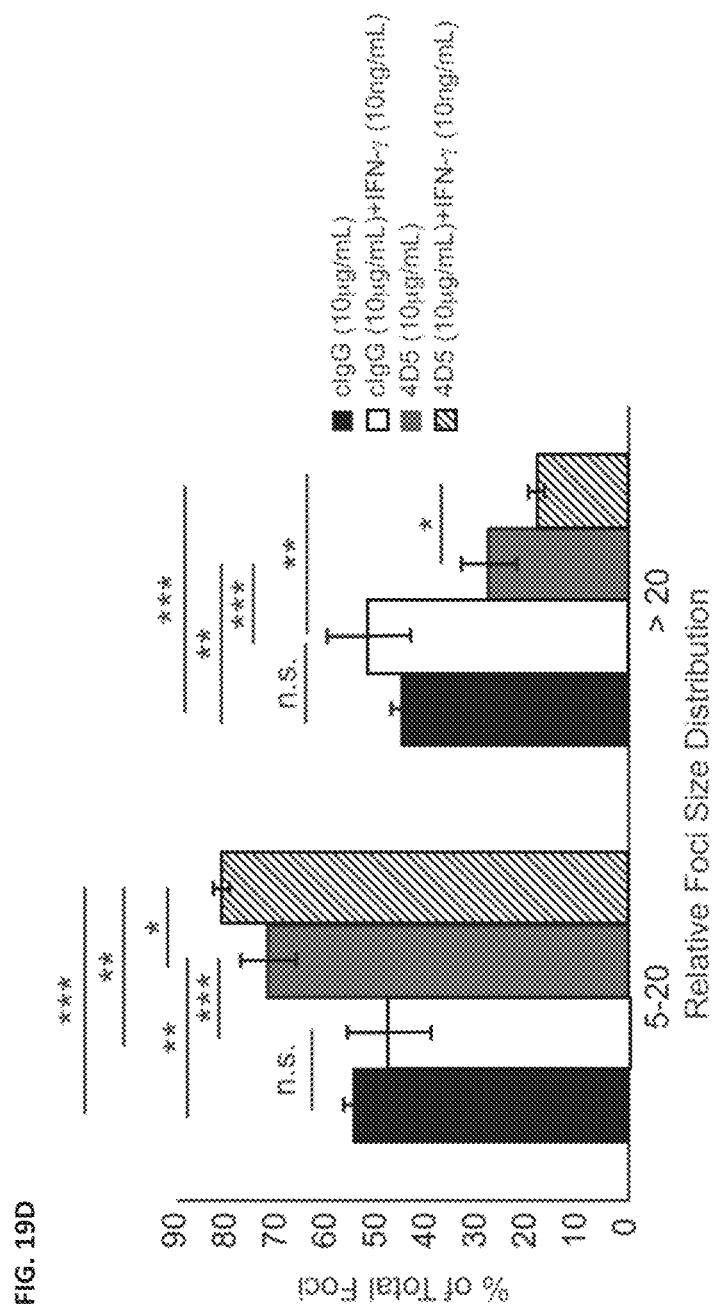

Changes in the malignant phenotype are most conclusively defined in vitro by anchorage independent foci formation in soft agar assays (Montesano et al., 1977). We analyzed the formation of foci based on size using ImageJ software (NIH). In the settings used, foci were apparent when they approached 20 pixels and foci larger than 20 pixels represent cells that exhibit transformed properties. Treatment with 4D5 produced a dramatic reduction in the formation of foci in soft agar compared to cIgG and IFN-γ alone as demonstrated by a greater percentage of foci less than 20 pixels (72±5% vs. 54±2% and 48±8%, respectively) as well as fewer foci greater than 20 pixels (27±6% vs. 45±2% and 52±8%). Inclusion of IFN-γ with 4D5 produced a greater percentage of foci under 20 pixels than 4D5 alone (81±2% vs. 72±5%) and a lesser percentage of foci greater than 20 pixels compared to 4D5 alone (18±2% vs. 27±5%) (FIG. 19C and FIG. 19D). Anchorage independent malignant features are thus most influenced by treatment with anti-erbB2 mAb with the addition of IFN-γ which then act on cells with certain reversed malignant features.

Studies were initiated to examine if IFN-γ could complement anti-erbB2 mAb in tumor growth experiments in rodents. To accomplish this, H2N113 tumor cell lines were used (Stagg et al., 2008), which were derived from MMTV-neu (BALB/c) transgenic mice. The 7.16.4 anti-erbB2 mAb recognizes the rat and human p185/neu and with optimal doses (5 mg/kg) significantly inhibits p185neu driven tumor growth in rodents (Drebin et al., 1988b; Drebin et al., 1985). Importantly, in the experiments reported here, lower doses (1.5 mg/kg) of anti-erbB2 mAb were employed to demonstrate surprisingly increased interactions. These experiments illustrate a demonstrable effect of IFN-γ as well as 7.16.4 on breast tumor growth. However, combinatorial therapy significantly reduces tumor volumes when compared to either alone (FIG. 26). Without wishing to be bound by any scientific theory, it is concluded that the phenotypic reversion activity of anti-erbB2 mAb can be improved by employing IFN-γ as a modality to further alter malignant properties of transformed cells.

Phenotypic Effects of mAb and Interferon-γ on Other Cell Types

Figure 43A:
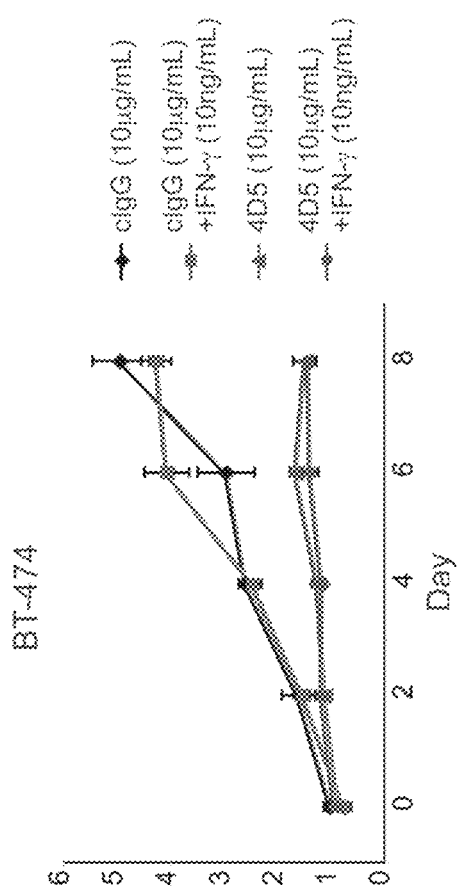
Figure 43B:
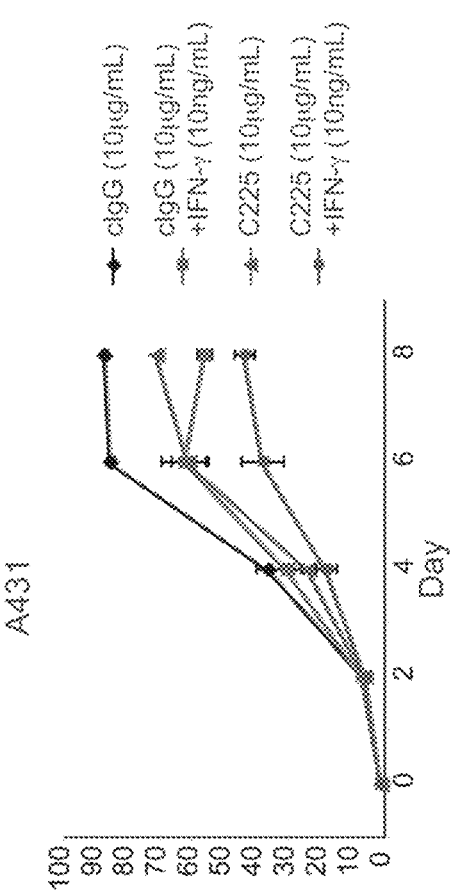
Figure 43C:
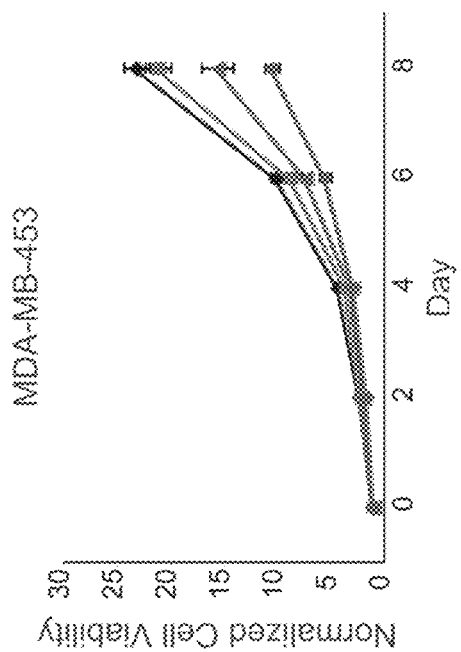
Figure 43D:
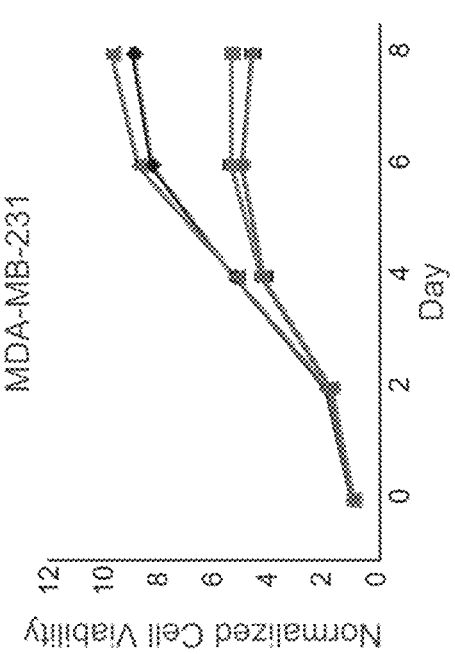

It was speculated that some erbB heteromeric tumors might be similarly sensitized for IFN-γ effects while other erbB1 homomeric tumors might not because of the action of IFN-γ on EGF/TGF expression (Uribe et al 2002). First homomeric EGFR driven cell lines were utilized to determine whether IFN-γ doses were compatible when disabling EGFR. EGFR driven cell lines were utilized to determine whether these are general effects on other cell types. Experiments (FIG. 19A) implied that combined treatments were the most efficacious; therefore, experiments were performed to determine if IFN-γ doses were compatible when disabling EGFR. Dose-response assays were performed using two cell lines expressing EGFR—the epidermoid carcinoma cell line A431 and the glioblastoma cell line U87. The U87 cell line displays a much lower expression level of EGFR than A431 and it is unclear if EGFR solely determines the transformed phenotype. The U87 cell line is driven by EGFR VIII, which lacks portions of the extracellular domain of EGFR. A431 cells, which are transformed by the activity of high levels of EGFR, responded to dose-dependent increases of IFN-γ in the presence of the anti-EGFR mAb C225 (FIG. 27A and FIG. 43D). U87 failed to respond to any dose of IFN-γ and C225. (FIG. 27B and FIG. 49).

Other tumor lines were analyzed, including tumor cell lines which lack or have normal levels of EGFR or erbB2/neu and little effects of the targeting mAb was found with or without IFN-γ (not shown). Without wishing to be bound by any scientific theory, it is concluded that cell lines which are transformed by erbB kinases are generally amenable to combination therapies, while cell lines transformed by undefined genetic changes without a dominant contribution of erbB kinases are not.

The erbB2+ breast cancer cell lines MDA-MB-453 and BT-474 display distinct phenotypes from the SK-BR-3 cells. MDA-MB-453 and BT-474 viabilities were inhibited by 4D5 mAb and MDA-MB-453 cell viability was further impeded by the inclusion of IFN-γ (FIG. 43). BT-474 cells did not respond to this ordered approach (FIG. 43). A possible explanation might be that BT-474 cells express estrogen receptors (ER). Treatment with the ER antagonist 4-OH tamoxifen reduced viability in the cIgG-treated cells and, in agreement with previous reports (Argiris et al., 2004), complemented 4D5 treatment, but did not further sensitize the cells to IFN-γ in combination with 4D5 (FIG. 48). The triple negative breast cancer cell MDA-MB-231 failed to respond to mAb but did respond to IFN-γ alone (FIG. 43).

erbB2 and erbB1 (EGFR) Heteromeric Kinase Activity Primarily Signals Phenotypic Change Through the PI3-KAkt/GSK3-β Pathway and can be Modified by mAb and IFN-γ or Kinase Inhibitors Such as Lapatinib.

Figure 20A:
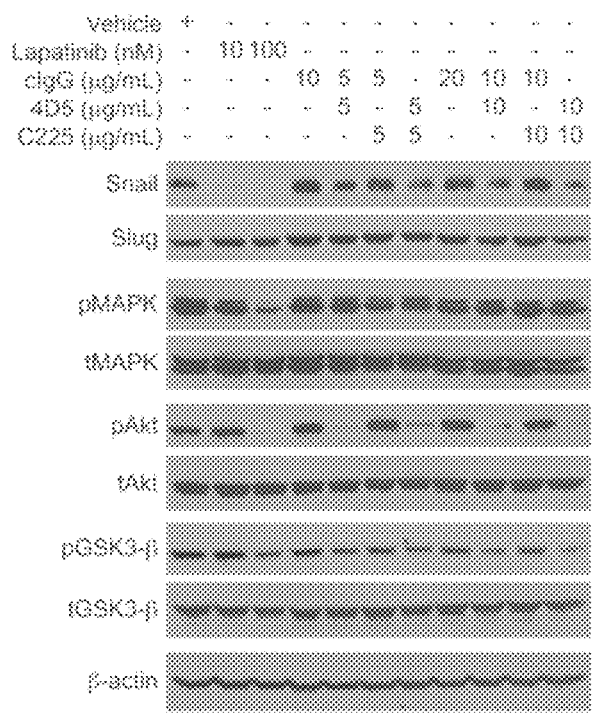

Effects on signal transduction pathways that are activated by erbB receptors were studied. SK-BR-3 cells were treated with the dual EGFR/erbB2 small molecule tyrosine kinase inhibitor lapatinib as well as 4D5 and C225 alone and in combination to determine which signaling pathways were affected. Lapatinib treatment inactivated both the Akt and MAPK pathways as anticipated (FIG. 20A, compare lanes 5 with 6 and lanes 9 with 10). Inhibiting SK-BR-3 cells with 4D5, but not C225, dominantly inactivated Akt while not affecting MAPK activities (FIG. 20A). Combination of two distinct, receptor-specific mAbs (4D5 with C225) inactivated Akt in SK-BR-3 cells.

Disabling erbB2 in these cells was found to activate glycogen synthase kinase 3-beta (GSK3-β, which is negatively regulated by Akt-mediated phosphorylation (Cross et al., 1995) (Lanes 5, 7, 9, and 11). Expression patterns of transcriptional repressors snail and slug were evaluated because of the GSK3-β activation. Snail and slug proteins are determinants of breast cancer progression and metastases and are negatively regulated by GSK3-β (Wu et al., 2012; Zhou et al., 2004). These experiments found that treatment with 4D5, but not C225, selectively reduced snail levels (FIG. 20A, compare lanes 5 with 6 and lanes 9 with 10 and FIG. 50).

Figure 20B:
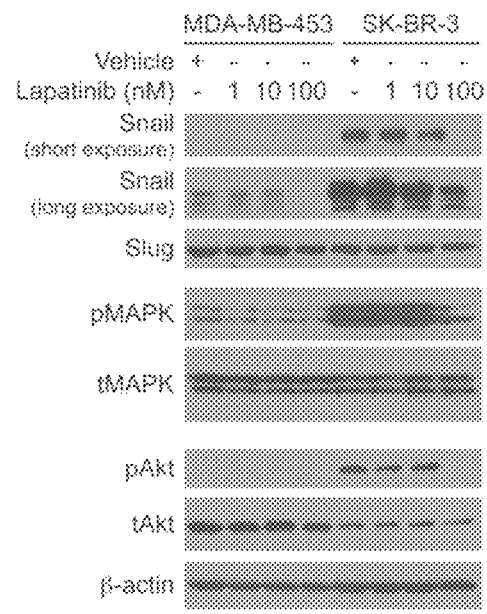

Next, the response was compared to lapatinib in SK-BR-3 and MDAMB-453 cells. Lapatinib treatment diminished Akt activity in both cell lines and, to a lesser extent, MAPK signaling (FIG. 20B). In addition, lapatinib induced a dose-dependent reduction in snail, but not slug. Snail levels in MDA-MB-453 cells are lower than that seen in SK-BR-3 cells; nevertheless, snail is reduced upon lapatinib treatment (FIG. 20B).

Figure 20C:
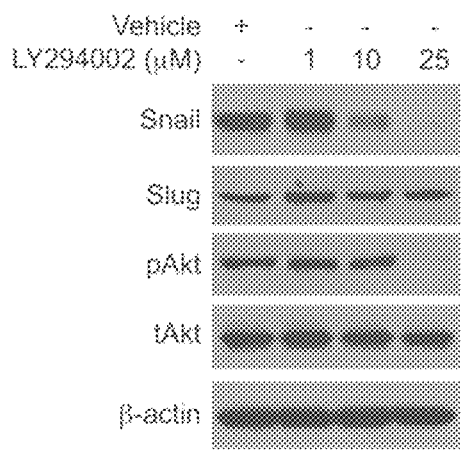
Figure 20D:
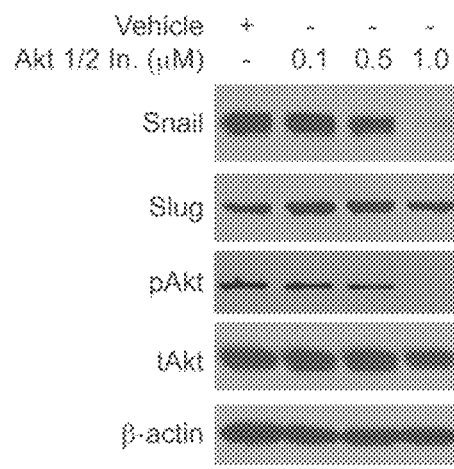

The PI-3K/Akt pathway was studied in greater depth using pharmacological inhibition. Antagonism of PI-3 kinase in SK-BR-3 cells revealed a reduction in snail, but not slug (FIG. 20C). Similarly, SK-BR-3 cells were treated with Akt1/2 inhibitor and displayed a dose-dependent decrease in snail content (FIG. 20D). Therefore, without wishing to be bound by any scientific theory, it is concluded that erbB2 signaling in SKBR-3 operates primarily through the Akt pathway to stabilize snail and inhibition of this pathway leads to a reduction in snail protein levels.

mAb 4D5 and Interferon-γ Cooperatively Reduce Snail Protein Levels

Figure 21A:
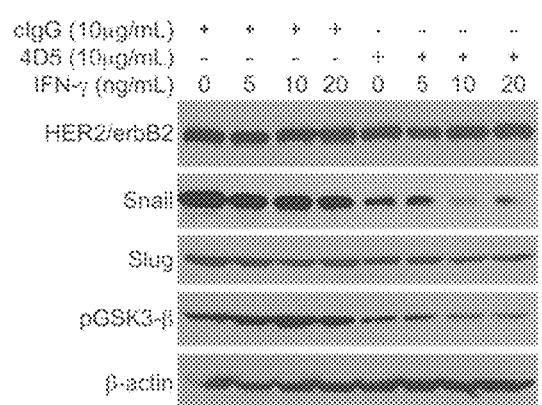
Figure 21B:
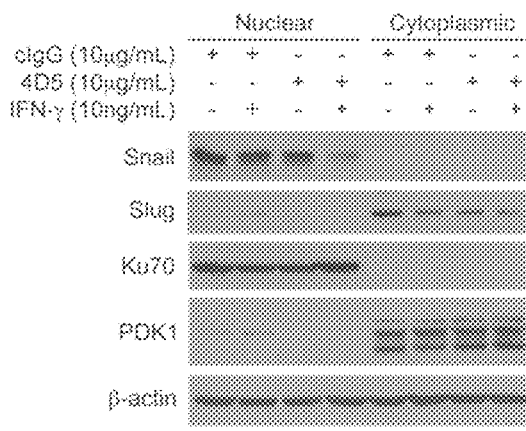

Next, whether the combination of IFN-γ and anti-erbB2 mAb could cooperatively reduce snail protein levels was determined. SK-BR-3 cells were treated with cIgG or 4D5 and increasing doses of IFN-γ. IFN-γ dose-dependent reduction of snail occurred only if cells were treated with 4D5 (FIG. 21A, compare lanes 1-5 with 6-10). IFN-γ is known to activate GSK3-β (Beurel and Jope, 2009; Tsai et al., 2009); however, when cells are transformed by activated erbB2 signaling, IFN-γ is unable to do so. GSK3-β activation was observed to be recovered and enhanced by IFN-γ when cells were treated with mAb-erbB2. Fractionation of SK-BR-3 cells revealed that snail is exclusively present in the nucleus and its degradation is apparent. Surprisingly, slug was found to be mostly present in the cytoplasm and enrichment studies reveal that slug is, in fact, sensitive to these treatments (FIG.

21B). Slug content was unaffected initially (FIG. 21A); however, by three days treatment led to reduction of Slug levels (FIG. 50).

Figure 21C:
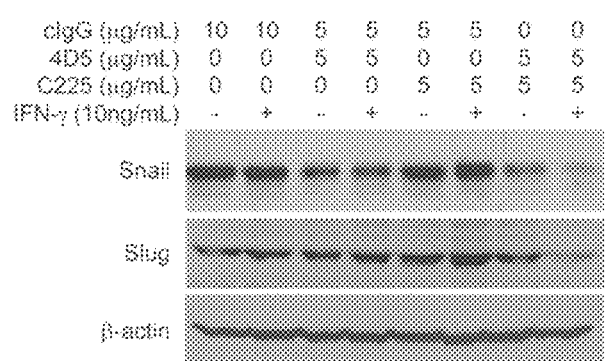
Figure 21D:
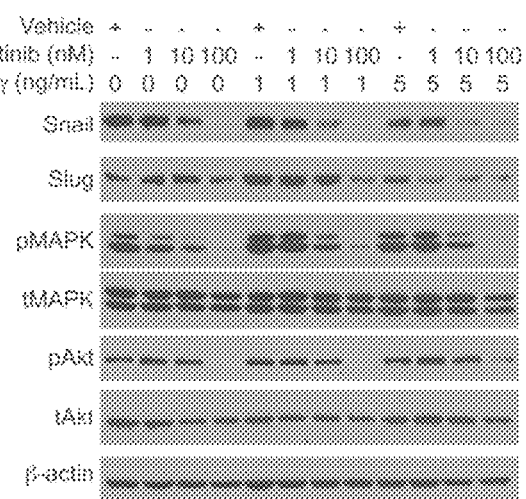

In FIG. 20A, it is noted that combination of antibodies reactive with erbB2 and EGFR produced a significant reduction in snail. Therefore, combining IFN-γ with this approach was explored. Combination of 4D5 and C225 in the presence of IFN-γ produced the most dramatic reduction in snail and also reduced slug content (FIG. 21C). These results indicate that simultaneous inhibition of heteromic kinases can also be improved by co-treatment with IFN-γ. Therefore, whether lapatinib treatment could be modified by IFN-γ was examined. SK-BR-3 cells treated with increasing doses of lapatinib and IFN-γ displayed reduced snail and slug (FIG. 21D).

SK-BR-3 cells were treated with cIgG or 4D5 and increasing doses of IFN-γ. An IFN-γ dose-dependent reduction of Snail was found only in the presence of 4D5 (FIG. 21A, compare lanes 1-5 with 6-10). GSK3-β activation was found to be enhanced by IFN-γ in the presence of 4D5 compared to IFN-γ treated samples in the presence of control IgG. Slug content was unaffected initially (FIG. 21A); however, by three days treatment led to reduction of Slug levels (FIG. 50). Combination of 4D5 and C225 in the presence of IFN-γ produced the most dramatic reduction in Snail and also reduced Slug content (FIG. 21C). Thus, these data demonstrate that erbB receptors erbB2 and EGFR, functioning as heteromeric kinases stabilize snail and slug, and combinatorial receptor disabling in the presence of IFN-γ provides optimal signal disruption and degradation of these proteins.

A recent study demonstrated that inclusion of IFN-β with an EGFR antibody produced a more potent anti-tumor effect than EGFR antibody alone (Yang et al., 2014). Experiments were conducted to examine whether IFN-β functions similarly to IFN-γ in the presence and absence of 4D5. Unexpectedly IFN-β was found to dramatically reduce snail, but not slug, even in the absence of 4D5 treatment (FIG. 22A). Experiments were also conducted to explore whether IFN-β effects cell viability. Surprisingly, IFN-β was found to be cytotoxic to tumor cells even at small doses in the absence of 4D5 (FIG. 22B). Furthermore, while IFN-γ treatment of MCF10A cells caused minimal changes to their viability, even low doses of IFN-β were cytotoxic to these cells (FIG. 22C). In vivo studies also demonstrated no effects of IFN-α and anti-erbB2 mAb (Nagai et al., Manuscript in Preparation). Therefore, without wishing to be bound by any scientific theory, it is believed that under these conditions only IFN-γ acts to complete phenotypic reversion engendered by anti-erbB2 mAb therapy.

Snail Protein Degradation Occurs Through the GSK3-β/Proteasomal Pathway

Snail is a labile protein that is predominantly degraded through the proteasome and, to a lesser extent, the lysosome. Proteasome degradation of snail is controlled largely by GSK3-β through phosphorylation of six serine residues (Zhou et al., 2004). Experiments were conducted to initially test whether treatment with IFN-γ, 4D5, or both mediated snail degradation through the proteasome. Treatment of cells with the proteasome inhibitor MG-132 inhibited the co-treatment-mediated reduction of snail in a dose-dependent manner, with no change in slug content (FIG. 23A). Conversely, inhibition of lysosomal function with chloroquine increased snail content but was unable to rescue the 4D5 and IFN-γ-mediated degradation of snail (FIG. 28). Without wishing to be bound by any scientific theory, it is concluded that while snail can be degraded through the lysosome, 4D5 and IFN-γ-mediated snail degradation occurs primarily through the proteasome. Because co-treatment favored snail proteasomal degradation, the role of GSK3-β was examined using the small molecule inhibitor CHIR99021 that is routinely used to study GSK3-β function (Blaschke et al., 2013; Lian et al., 2012; Lian et al., 2013). Inhibition of GSK3-β in the presence of the co-treatment regimen resulted in a dose-dependent rescue of snail but led to no change in slug content (FIG. 23B).

Since treatment with 4D5 and IFN-γ activated GSK3-β and active GSK3-β caused snail degradation, expression of a version of snail with the GSK3-β phosphorylation sites mutated to alanines would be predicted to prevent such degradation. To this end, empty vector (EV), HA-tagged snail wild type (WT) (Kajita et al., 2004), and HA-tagged snail with serines 97, 101, 108, 112, 116, and 120 mutated to alanine (6SA) (Zhou et al., 2004) were transiently expressed in SK-BR-3 cells. The following day, transfected cells were treated with cIgG or 4D5 in the presence or absence of IFN-γ. After a further 24 hours, we harvested cells and separated cytoplasmic and nuclear fractions. Both nuclear and cytoplasmic expression of exogenous WT snail was observed; however, 6SA snail was largely present in the nucleus with only trace amounts in the cytoplasm (FIG. 23C), consistent with previous reports (Zhou et al., 2004). Further, it was found that in the nuclear fraction, exogenous WT snail was degraded whereas 6SA snail was resistant to 4D5 and IFN-γ-induced proteasomal degradation (FIG. 23C, right panel). Analysis of total snail revealed its presence in the cytoplasmic and nuclear fractions in all samples. In cells transfected with the EV control, snail was observed in the cytoplasm only when the cells were treated with both 4D5 and IFN-γ (FIG. 23C, left panel) implying that both treatments are required for snail translocation to the cytoplasm. Collectively, these experiments identify snail as a target of cooperative anti-erbB2 mAb plus IFN-γ treatment. This ordered therapy leads to GSK3-β-mediated proteasomal pathway degradation of the snail transcriptional repressor. Of note, Snail knock down in SK-BR-3 increased the effect of 4D5 on their proliferation (FIG. 51), indicating Snail decrease is important for this targeted therapy.

Kruppel Like Factor 4 (KLF4) Levels and Phenotypic Reversion Caused by mAb and IFN-γ

Disabling the erbB complex occurred through modifying the activity of the SHP2-PI3' kinase and Akt pathway. Interestingly, Moral and colleagues (Moral et al., 2009) found that KLF4 expression patterns were increased in tumor samples from mice with hyper-activated Akt. Enhanced expression of KLF4 was confirmed in both dysplasias and tumors that arose in Akt overexpressing tissues. Further analysis of human tumor samples confirmed association between active Akt and increased KLF4 expression.

The effects of ordered and combined antibody with IFN-γ were examined on KLF4 levels and Snail expression in SK-BR-3 cells stably transfected with GSK3-β shRNA. The ability to alter Snail functions was directly linked to KLF4 levels and GSK3-β (FIG. 44). While KLF4 levels were also dependent on GSK3-β, other signaling pathways contribute to induce changes in KLF4 (Villarreal et al., 2010).

Effects of mAb and IFN-γ in vivo-combinations reduce the need for large amounts of targeting mAb mAb 7.16.4 is biologically active in vivo and in vitro. In vitro mAb 7.16.4 is active against cells transformed with the rat or human erbB2/neu oncogene and disables the p185erbB2/neu kinase leading to diminished downstream p185erbB2/neu signaling (Drebin et al., 1986; Zhang et al., 1999). In several other studies, the laboratory of Dr. Mark Greene as well as others examined various optimized doses of anti-erbB2/neu mAb therapy. 5 mg/kg of 7.16.4 mAb have been used intravenously (Drebin et al., 1986) and/or on every other day intraperitoneally in therapeutic studies of tumor growth (Du et al., 2013; Stagg et al., 2011).

Based on the studies above, experiments were conducted to examine whether reduced amounts of mAb could be used if IFN-γ were provided after therapy was initiated. As shown in FIG. 1, when entirely syngeneic MMTV-neu transgenic mice were treated with a sub-optimal dose of 7.16.4 (1.5 mg/kg), the mAb was unable to inhibit the growth of H2N113 tumors. IFN-γ treatment alone also failed to significantly inhibit tumor growth. However, the combination of suboptimal amounts of 7.16.4 and IFN-γ completely arrested the growth of H2N113 tumors. Importantly, the pattern of the data in FIG. 1 was reminiscent of the in vitro tumor cell proliferation kinetics in FIG. 19B. Finally, histologic examination of the tumor tissues after treatment revealed significant necrosis only in mice treated with both 7.16.4 and IFN-γ (FIG. 40).

To examine if IFN-γ was targeted to tumor cells directly or to host elements in the vicinity of the tumor, the expression of the IFN-γ receptor was limited on these tumor cells. Using shRNA, an IFN-γ receptor knockdown species of the H2N113 cell line was created: H2N113 (IFNγR KD). The reduced expression level of IFN-γ receptor was confirmed in several distinct ways including 1) flow cytometric analysis (FIG. 32A), 2) IFN-γ induced MHC expression patterns were also diminished in these cells and finally 3) IFNγRKD tumor cells were resistant to IFN-γ mediated growth suppression (FIGS. 32B and C).

Figure 33:
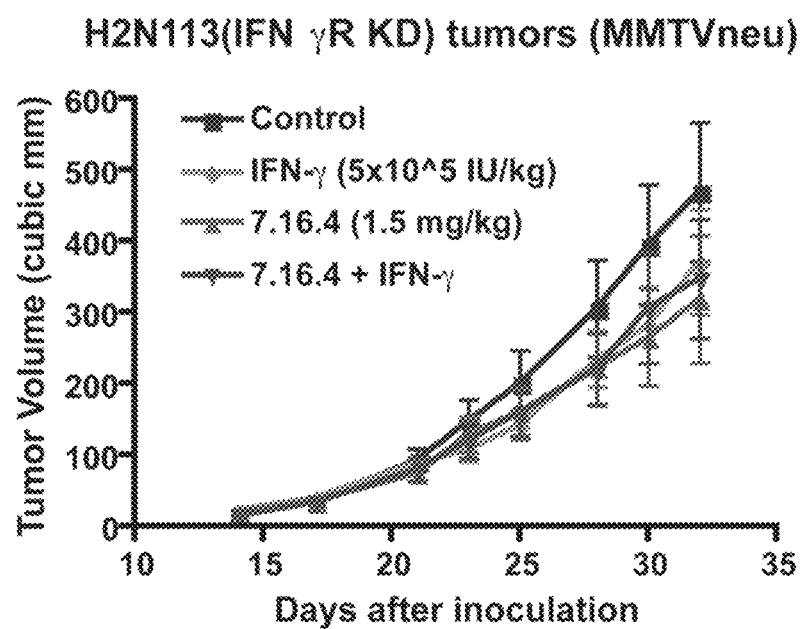

IFNγRKD tumor cells were found to form progressively growing tumors, but treatment with suboptimal mAb doses generated a modest growth reduction comparable to that seen in the studies depicted in FIG. 1. IFN-γ had no effect on its own against tumors with diminished IFN-γ receptor levels. As shown in FIG. 33, the combination effect of mAb and IFN-γ was also abrogated by the absence of IFN-γ receptor in the tumor cells. Without wishing to be bound by any scientific theory, these data indicate that IFN-γ is required to interact directly with tumor cells to enhance the anti-tumor activity driven by the anti-p185erbB2/neu antibody and implies that IFN-γ enhanced host responses may not be sufficiently potent on their own to limit tumor growth. However local effects from cells in the vicinity of the tumor that might contribute to tumor invasion were considered.

Myeloid Derived Suppressor Cells and Foxp3+ Treg Cells

Next endogenous regulatory host processes that might be mitigated by IFN-γ were examined. Myeloid-derived suppressor cells (MDSC) are defined as CD45+ cells that are also CD11b+ and GR-1+. Co-treatment with sub optimal 7.16.4 and IFN-γ led to reduction of MDSC populations invading tumor tissues (FIG. 45A). It was noted that there were limited but comparable numbers of Foxp3 cells in control and treated animals. It is possible that despite similar numbers the control Foxp3+ T cells were more active than those that were noted in tissues of mAb and IFN-γ treated hosts. Foxp3 dependent regulatory activities has not yet been defined since numbers of Treg cells are limited in number. However, as observed in other studies, degradation of FOXP3 following activity of small molecules that disable multiple acetyltransferases (Tip60 and p300), can alter tumor growth (Du et al., 2013). Hence both FOXP3 Treg cells and MDSC both may contribute to limitations of immune mediated cytotoxic elimination of erbB tumors.

To illustrate the chemo-attractant effects of molecules elaborated by tumor cells on MDSC that might be affected by the combined treatment. MDSC isolated from the spleen of tumor-bearing mice were placed into the apical chamber of a transwell system. Conditioned medium from H2N113 cells treated directly with mAb, IFN-γ or their combinations were tested for their ability to attract MDSC cells to migrate into the basolateral chamber. As shown in FIG. 8D, 7.16.4 alone slightly reduced the tumor-promoted migration, but the co-treating the tumor cells themselves with 7.16.4 and IFN-γ blocked MDSC migration. IFN-γ alone had no appreciable effects. Based on these data we suggest that immune regulation is affected in addition to the dominant effect of mAb and IFN-γ on the tumor itself. Ordered therapy reduces regulatory cell activity in tumor tissues.

Enhanced Role for IFN Type II Signals in erbB Cytolytic Immune Responses.

Studies have suggested a role for IFN-γ+ CD8+ T cells (Park et al., 2010; Stagg et al., 2012; Stagg et al., 2011). Suboptimal mAb and IFN-γ were used in syngeneic systems and effector CD8+ T cells were collected from each treatment group to investigate their activity against H2N113 cells. The combination therapy group showed modest but definite effector T cells activity against p185erbB2/neu positive tumors. IFN-γ alone had negligible effects (FIG. 52).

Two types of functional macrophages have been proposed to infiltrate the tumor microenvironment and such invasion is promoted by molecules elaborated directly or indirectly by tumor cells. Tumors were examined for invading anti-inflammatory, pro-tumor M2 and pro-inflammatory, cytolytic anti-tumor M1 types. mAb 7.16.4 and IFN-γ increased M1 accumulation within adjacent areas of the tumor, and animals treated with this combination therapy had the highest M1 frequency. (FIG. 41A-FIG. 41B).

In Vivo Evidence for a Role of Stem Cell Like Phenotypic Contributions.

Molecular analyses in vitro revealed that the ordered treatment of breast tumor cells with anti-erbB2/neu mAb and IFN-γ diminished expression of Snail proteins, which mediates stem cell like properties. ALDH1 expression patterns also define cancer stem cell phenotypes, and its expression correlates with breast cancer prognostic features (Douville et al., 2009; Ginestier et al., 2007). Tumors were compared at the end of treatment for ALDH1 levels. Co-treatment with 7.16.4 and IFN-γ treatment reduced the expression of ALDH1 in p185erbB2/neu tumors. (FIG. 39).

Tumor cells were also examined for expression patterns of Snail. A reduced level of Snail protein was noted in tumors undergoing eradication as a consequence of mAb and IFN-γ therapy in vivo (FIG. 39). These studies directly correlate with in vitro findings described in FIG. 19A-FIG. 19D, FIG. 21A-FIG. 21D, FIG. 22A-FIG. 22C, FIG. 23A-FIG. 23C, and FIG. 43A-FIG. 43D examining anchorage dependent and independent effects of combinations of anti erbB mAb and IFN-γ.

Ordered mAb and IFN-γ Therapy can Prevent Breast Cancer Tumorigenesis and has a Combination Effect in Inhibiting Tumor Growth with Chemotherapy.

To determine if these therapeutic effects were relevant to prevention of tumor development (adjuvant use of this combination) a model previously described, using small tumor inocula, was chosen for examination. The effects of treatment of MMTV-neu female mice were examined with combinations of 7.16.4 and 7.9.5 mAb with or without IFN-γ, in animals implanted with small tumor inocula to mimic incipient tumors. A dramatic reduction was noted when IFN-γ was incorporated in the treatment protocol. As can be seen in FIG. 31, this approach was able to limit tumor growth in this prevention model with minimal amounts of dual targeting mAb. These studies indicate that animals treated with ordered therapy of mAb and IFN-γ can mount potent intrinsic cytotoxic elimination of small numbers of incipient tumor cells. These data support previous studies showing a delayed emergence of tumors when mAb specific for erbB2/neu was used as an adjuvant therapy in mouse prevention studies (Finkle et al., 2004; Katsumata et al., 1995).

To extend these genotoxic observations docetaxel was added in subtherapeutic quantities to evaluate if potent tumor inhibition with small amounts of phenotype reversing mAb would also limit genotoxic amounts of currently employed chemotherapy (FIG. 46). Treatment with 7.16.4 followed by IFN-γ and docetaxel led to inhibition of tumor growth compared with other groups despite using suboptimal doses of both anti erbB antibody and chemotherapy. Without wishing to be bound by any scientific theory, optimizing phenotype reversion represents a critical element the evolution of precision drug therapy of breast carcinoma.

Discussion

This study demonstrates that anti-erbB2 mAb-mediated reversal of breast cancer cell malignant features permits IFN-γ mediated phenotypic effects. These studies provide compelling evidence that mAb specific for p185erbB2/neu kinases and IFN-γ directly target erbB2+ human breast cancer cells and indicate that erbB kinase receptor complexes must be disabled either first or simultaneously with mAb. Phenotypic reversal acts as a permissive state for the action of IFN-γ and explains many of the failures to properly use this cytokine in humans. IFN-γ by itself, in the absence of prior phenotypic reversal, was found to be not as effective as a direct regulator. These studies identify ordered co-treatment as the modality that optimally affects both cell viability and transformation. Signaling downstream of erbB2 occurs primarily through the Akt pathway; and, consequently, 4D5, the precursor mAb to clinically active Herceptin, acts most profoundly on this pathway. Cells such as MCF-10A, which are immortalized but have not acquired malignant properties needed to permit sustained growth in vivo, fail to be influenced by IFN-γ. Evidence is presented that after IFN-γ interacts with phenotype-reversed cells, it complements 4D5-mediated activation of GSK3-β resulting in changes in snail expression.

Interferons have been reported to affect transcription in immune type cells (Qiao et al., 2013; Ucla et al., 1990); however, we find IFN-γ clearly produces broad effects within the transformed breast cancer cell, and this involvement in transcriptional processes relevant to phenotypic behavior may thus play a role in regulating genotoxic sensitivities. For example, IFN-γ negatively regulates skin changes associated with UV damage by controlling the expression of several pigmentation genes (Natarajan et al., 2014). Thus, without wishing to be bound by any scientific theory, IFN-γ may be responsible for dictating the response to signals that affect genomic integrity, including genotoxic signals caused by UV and ionizing radiation.

Prior studies implicated roles for Natural Killer cell functions in mAb therapy (Drebin et al., 1988b) as well as other immune cell types in erbB2 tumor related processes (Park et al., 2010; Stagg et al., 2011). Although a role for host immune system contributions to anti-erbB2 mAb mediated tumor regression has been proposed, a molecular investigation of how IFN-γ elaborated by cells in the tumor microenvironment might cooperate with kinase disabling mAbs is lacking. The studies described herein begin to address this idea in terms of phenotype reversal and limitation of tumorigenesis at the molecular level.

Snail is strongly implicated in the progression of breast cancer and has been attributed to tumor metastasis and recurrence. Unexpectedly, when cell lines that model the various types of breast cancer were analyzed, snail expression was found to vary between different subtypes, while slug expression was relatively constant (FIG. 29). In regards to erbB2/HER2+ breast cancers, this may be attributed to the known dominant activation patterns involving Akt rather than MAPK. The data herein underscore the importance of ordered signals reaching the tumor and show how failure to do so could lessen tumor eradication. The laboratory of Dr. Mark Greene demonstrated that anti-erbB2 mAb could reverse malignant phenotypes of a transformed cell (Drebin et al., 1985; Drebin et al., 1986), and now provides evidence of how IFN-γ provides a secondary reversion of phenotype. Hence, without wishing to be bound by any scientific theory, it is proposed that targeted therapy exists at minimum in a two-transition state, which is only accessible in a defined, linear manner; and therapeutics must be delivered in the proper order to achieve optimal results (summarized in FIG. 24).

Snail is perhaps best known for its role in initiating the epithelial to mesenchymal transition (EMT). While EMT is a theory currently favored by some, it is clear from initial studies that the more differentiated tumors respond more favorably to genotoxic injury induced by chemo- and radiation-based therapies. Therefore, complete reversion of phenotype may be essential to achieving sensitization to more broad based therapeutic strategies. Designing rationalized therapies is complex and clearly requires a thorough understanding of the molecular underpinnings of the specific subtype of cancer. The results provided here would suggest that activation of GSK3-β would be an appropriate approach to complement mAb-erbB2 based on the findings that GSK3-β inhibition opposes efforts to degrade snail (FIG. 23A).

The findings herein represent a rational advance in the understanding of how to treat breast cancer from the earliest time points. Breast cancer begins as low-grade dysplasia and ductal carcinoma in situ (DCIS), which is defined by hyperplastic events, before progressing to palpable tumor formation. erbB2/HER2 kinase activity was detected even at the earliest stages of DCIS (Lodato et al., 1990). Anti-erbB2 mAb can be used as an adjuvant therapeutic to prevent the emergence of tumors in mice (Katsumata et al., 1995), and our data using soft agar assays (FIG. 19C and FIG. 19D) suggests that IFN-γ would add further preventative benefit. While clinical trials that have explored the possibility of IFN-γ alone as a therapeutic have consistently failed, the studies herein explain why this repeated clinical failure was seen. IFN-γ administration must be used in an ordered manner to treat already phenotype reversed tumor cells in order to predictably observe enhanced tumor eradication.

Therapeutics that target p185erbB2/HER2/neu are effective for restraining human malignant disease but are rarely curative. Disabling of the p185erbB2/neu kinase complex leads to phenotypic reversal of malignant properties. This phenotypic state is more sensitive to genotoxic damage by chemotherapeutic and radiation effects, or immune mediated lytic processes. These studies identified a second transition process that occurs after mAb-mediated down-regulation of p185erbB2/neu proteins from the cell surface, which can be induced by IFN-γ. The second transition step renders cells even more sensitive to lytic processes that occur in vivo by certain immune elements and to chemotherapeutics commonly used to treat breast cancer. Dramatic tumor inhibitory effects can be accomplished with minimal amounts of targeting mAb and IFN followed by chemotherapeutics (docetaxel) in vivo. These studies identify a benefit of this rational approach to precision medicine that will be accompanied by lessened toxicity during tumor treatment.

A dramatic and almost complete arrest of tumor growth is described, even with suboptimal doses of anti-ErbB2/neu mAb when IFN-γ is included. The combination effect requires that the tumor cell itself express IFN-γ receptors. Because IFN-γ enhances antibody effects at very low doses in vivo, this approach may improve targeted therapy effectiveness in tissues where only low levels of antibody might penetrate.

The effect of mAb and IFN-γ are a consequence of phenotypic change on the tumor itself. The combination effects of mAb and IFN-γ were lost when tumor cells with reduced IFN-γ receptor levels were targeted. Secondly, we noticed a reduction of regulatory MDSC cells that limit immune reactions by suppressing functions of immune cells. Tumor elaborated chemo-attractants which recruit regulatory cells were diminished upon ordered treatment of tumor cells with mAb and then IFN-γ. Studies not shown have been unable to document any comparable activity when IFN-α or IFN-β were used (in vivo or in vitro respectively) rather than IFN-γ. There was an increase in CD8+ T cells able to lyse erbB2 targets (FIG. 52).

Foxp3+ Treg cells were detected in small numbers in the vicinity of the tumor tissues which supports previous studies that established a role for FOXP3 Treg in erbB tumors. In addition contributions of regulatory MDSC cells in the local tumor environment may be important in limiting immune elimination of breast tumors and their activity is diminished with ordered mAb and IFN therapy. Enhanced accumulation of M1 type macrophages in the local tumor environment in situations using combined mAb and IFN-γ therapy were observed. Modest enhancement of cytolytic T cells active against erbB2 tumors was also noted. Together these data support an observable contributory role for the immune system in targeted therapy and a role for IFN-γ in enhancing immune eradication of erbB tumors that have undergone phenotype reversal.

mAb induced phenotypic reversion is incomplete, or at the very least, is subject to further modification, and can itself (Drebin et al., 1986; Lee et al., 2012; O'Rourke et al., 1997; Wada et al., 1990) then be acted on by IFN-γ to create a second transition state. The second transition involves a role of transcription factors such as Snail thought relevant to cancer stem cell features. IFN-γ alone, without the first reversion step is ineffective in being able to induce a malignant phenotype reversion or change in Snail levels.

In summary, this study provides a mechanistic explanation into how targeted therapy operates at the cellular level. It shows that IFN-γ provides an extraordinary benefit to countering otherwise oncogenic-activated signaling cascades, but only when transformed cells are previously induced into a more normal phenotype. These findings are relevant therapeutically because IFN-γ and the anti-erbB2 mAb (Herceptin) are FDA-approved treatments; therefore this combination represents a potential benefit to patients. The studies herein indicate that targeted therapy must be molecularly ordered to deal with distinct phenotypic states.

Experimental Procedures

Cell Culture—SK-BR-3; MDA-MB-453, MDA-MB-468, MDA-MB-231; MCF7; MCF10A; BT-474; A431; and U87 cells were obtained from the American Type Culture Collection (ATCC; Manassas, Va.). These cells were grown in Dulbecco's Modified Eagle Medium (DMEM) supplemented with 10% FBS, L-glutamine (2 mM), HEPES (15 mM), and antibiotics.

Chemical Compounds—Recombinant human Interferon-gamma and -beta were purchased from BD Pharmingen and Pestka Biomedical Laboratories, respectively. Lapatinib and CHIR99021 (LC Laboratories) were resuspended in DMSO to final concentrations of 10 mM and 50 mM, respectively. Akt inhibitor VIII (DMSO) and MG-132 (95% ethanol) (Calbiochem) were resuspended to final concentrations of 10 mM and 20 mM, respectively. LY294002 (Cell Signaling) was resuspended in DMSO to a final concentration of 50 mM. Chloroquine (ddH20) and 4-OH-tamoxifen (95% ethanol) (Sigma) were resuspended to final concentrations of 50 mM and 10 mM. 4D5 was kindly provided by Dr. Jeffrey Drebin. C225 was purchased from Imclone (Bristol-Myers Squibb). Docetaxel was purchased from LC laboratories.

Plasmid Construction—Wild type (pcDNA3) and 6SA (pCMV-Tag 2B) snail plasmids were purchased from AddGene. The snail 6SA insert was amplified by PCR using primers (forward: 5f-AAAGAAGCTTATGCCGCGCTCTTTCCTC-3' (SEQ ID NO: 8) and reverse: 5'-AAAGTCTAGATCAGCGGGGACATCCTGAGCAG-3' (SEQ ID NO: 9)), which added restriction sites (HindIII and XbaI) for sub-cloning into the pcDNA3 vector. Both plasmids were sequence verified.

Lysate Preparation and Western blotting—Cells were lysed in a RIPA-based buffer consisting of 20 mM Tris-HCl (pH 7.4), 150 mM NaCl, 1 mM EDTA, 1 mM EGTA, 1% Nonidet P-40, 1% sodium deoxycholate, 10 mM NaF, 1 mM sodium orthovanadate, and Complete Mini Protease Inhibitors (Roche Diagnostics) on ice for 15 minutes and lysates were clarified by centrifugation (16,000×g) for 10 minutes. Supernatant was removed for analysis by Western blot. Lysates were fractionated by SDS-PAGE using a 10% resolving gel. Gels were subsequently transferred to nitrocellulose membranes. Membranes were blocked using 5% nonfat dried milk in 1×PBST. Membranes were washed 3 times using 1×PBST and incubated with antibodies overnight. Protein signal was detected using Immobilon chemiluminescent substrate (Millipore). Blots were exposed to x-ray films.

Antibodies for western blotting—The snail, slug, pGSK3-β (S9), and tGSK3-β, pAkt (S473), tAkt, P-p44/42 pMAPK (Erk1/2) (T202/Y204), tMAPK and KLF4 antibodies were purchased from Cell Signaling and used at the manufacturer's suggested dilution. Anti-ALDH1 was purchased from Abcam. The β-actin HRP-conjugated (Sigma), HA HRP-conjugated (Roche), and Ku70 (Abcam) antibodies were also used at the manufacturer's suggested dilution. Secondary antibodies used include peroxidase-conjugated donkey anti-rabbit and sheep anti-mouse IgG (GE Healthcare).

Lysate Preparation and Western blotting—Cells were lysed in a RIPA-based buffer with protease inhibitors (Roche Diagnostics) and used for Western blot.

MTT assays—Cells were seeded in a 96-well (flat bottom) plate at 1,000/well and treated the following day (Day 0). Treated cells were grown in a 5% $CO_2$ incubator at 37° C. for the indicated times; and on the day of the assay, media was exchanged for fresh media. After four hours, MTT (3-[4,5-dimethylthiazol-2-yl]-2,5 diphenyl tetrazolium bromide) reagent was added to a final concentration of 1 mg/ml. Two hours later, lysis buffer (50% N, N-dimethyl formamide, 20% SDS, pH 4.7) was added and incubated overnight. The following day, values were determined by absorbance at 570 nm on a plate reader (Tecan).

Soft agar growth assays—Plates were coated with agarose mixed with DMEM (final agarose concentration of 0.8%). Cells were overlaid on the bottom layer in an agarose (final agarose concentration of 0.2%) DMEM mixture supplemented with the indicated therapeutic treatment. The assay was performed using 6-well plates and 5,000 cells per well were used. After two weeks, viable foci were visualized following overnight incubation with MTT reagent. Each well was imaged using an Alpha Imager, and foci size was determined using NIH-endorsed ImageJ software. It was determined that visible foci constituted 20 pixels using this approach; therefore, this size was used as a baseline for foci size distribution.

Transfection—Transfections were performed using Lipofectamine 2000 (Invitrogen) according to the manufacturer's instructions.

Cellular Fractionation—Cells were collected in a buffer consisting of 10 mM HEPES (pH 7.6), 10 mM KCl, 1.5 mM $MgCl_2$, 0.34M sucrose, 10% glycerol, 1 mM dithiothreitol, 0.1% Nonidet P-40, 10 mM NaF, 1 mM sodium orthovanadate, and Complete Mini Protease Inhibitors followed by a 30-minute incubation on ice. Nuclei were separated by low speed centrifugation (855×g) for 5 minutes. Supernatant containing cytoplasmic extract was removed and further centrifuged (16,000×g) for 10 minutes to remove membranes. Nuclei were resuspended in RIPA buffer (see above) and incubated on ice for 10 minutes followed by centrifugation (16,000×g) for 10 minutes.

Mouse Experiments—In these experiments, 6-10 week old female BALB/cAnNCR mice were used. mAb 7.16.4 and 7.9.5 were purified from hybridoma that was generated in our lab (Drebin et al., 1985; Drebin et al., 1984). An isotype matched, anti-mammalian reovirus-3 hemagglutinin specific antibody (9BG5, mouse IgG2b) was described previously by our laboratory (Sharpe et al., 1984) and was used for control IgG. INF-γ and INF-α were purchased from Sigma-Aldrich and R&D systems, respectively. Mice were maintained on a standard chow diet in a barrier facility and treated with approval from the University of Pennsylvania IACUC in accordance with NIH guidelines. For xenograft experiments, H2N113 cells ($1 \times 10_6$) were injected subcutaneously into both sides of the back of the mice. When tumors reached a size of 30-40=$^3$ (approximately 10-12 days after inoculation), mice were treated intraperitoneally with control (PBS), IFN-γ (three times per week), 7.16.4 (twice per week), or IFN-γ+7.16.4. Tumor sizes were monitored over the course of 7 weeks. Tumor size was measured with a digital caliper and calculated using a simple algorithm (3.14×length×wide×height÷6). For in vivo treatment model, a rodent erbB2/neu transformed Balb/c breast tumor cell line, H2N113 ($1 \times 10^6$) was injected subcutaneously into both sides of the back of mice. Mice were divided into four groups randomly and were treated with control IgG2a, 7.16.4, IFN-γ, 7.16.4+IFN-γ. mAbs were injected 1.5 mg/kg twice a week and IFN-γ was injected $5 \times 10^5$ IU/kg 3 times a week after 14 days from tumor injection. For INFα, $2.5 \times 10^4$ IU/mouse was injected instead of IFN-γ. Tumor size was measured with a digital caliper and calculated using a simple algorithm (3.14×length×wide×height÷6).

Flow cytometry—At 1 day after final treatment, spleens and tumors were collected for single cell suspensions. Cell surface antigens were stained with the antibodies: anti-CD4, CD8, CD45, CD11b, CD11c, MHC Class II and Gr-1 (Biolegend). For intracellular staining of Foxp3 and IFN-γ, Foxp3 staining buffer set (eBioscience) was used according to manufacturer's instruction. Cells were analyzed with FACS LSR (BD Biosciences) and FACS data were analyzed with FlowJo software (Tree Star, Ashland, Oreg.).

MDSC migration assay—To prepare conditioned medium, H2N113 cells were seeded and cultured until sub-confluent in culture media (RPMI supplemented with 10% FBS, 2 mM L-glutamine, 1 mM sodium pyruvate and 1×NEAA (Invitrogen)). Cells were then treated with 7.16.4 and/or IFN-γ at indicated concentrations for 3 days then the supernatants were collected for the migration assay. Migration of MDSC was measured by the Transwell system (pore size: 4 μm, Corning). MDSCs, which were isolated from spleens of tumor-bearing mice using MACS MDSC isolation kit (Miltenyi Biotech), were placed in the upper layers. Condition media was then placed in the bottom layers. After 3 hr incubations in 37° C., the cells which migrated to bottom layers were collected and subjected to flow cytometry.

shRNA—GIPZ Lentivirus vecotors for GSK3β, Snail and control non-silencing shRNA control were obtained from GE Dharmacon. The vectors were transfected in SK-BR-3 with Fugene 6 and selected with puromycin (1 μg/ml) for stable cell line as manufactuarar's instructions. The silencing of target gene was confirmed by western blotting as described above. For IFγR1 knock down to H2N113 cells, five TRC mouse lentiviral shRNA clones targeting IFγR1 and the control pLKO.1 were obtained from The Open Biosystems Expression Arrest™TRC Library (Thermo Scientific). Lentiviruses were produced by VairaSafe™ Lentivirus expression system (Cell Biolabs inc., San Diego, Calif.) as manufacturer's instructions. H2N113 cells were transfected with those lentivituses and selected with 1 μg/ml puromycin and FACS analysis with anti-IFγR1 antibody (Biolegend). IFγR1 knockdown was further confirmed by stimulation with IFN-γ, then analyzing their expression of MHC class I using anti-I-A/I-E (Biolegend) by FACS and proliferation.

Statistical Consideration—When applicable, statistical analysis was performed by Student's t-test using Microsoft Excel. At a minimum, data with a p-value <0.05 were deemed significant. In all cases, experiments shown are representatives that were repeated at least twice.

Histology—Tumor tissues were fixed with 10% neutral buffered formalin and embedded in paraffin. Sections were de-paraffinized and stained with H & E by the Cell Imaging Core of the Abramson Cancer Research Institute.

Flow cytometry—At 1 day after final treatment, spleens and tumors were collected for single cell suspensions. Tumors tissue was cut and digested with Collagenase P for 1 hr, then dispase (Stem Cell) and DNase (1 μg/ml, Roche) were added and incubated for 5 minutes. Then cells are filtrated by cell strainer (Falcon). Single suspension of tumor tissue cells were stained with CD45, F4/80, CD11b, and CD206 antibodies (Biolegend). Cells were analyzed with FACS LSR (BD Biosciences) and FACS data were analyzed with FlowJo software (Tree Star, Ashland, Oreg.).

In vitro proliferation assays—$10^4$ H2N113 transfected with empty vector and IF☐R1 shRNA vector were cultured in 96-well plates for 5 days with indicated concentration of IFN-γ. Relative cell numbers were measured by LDH activities of total cell lysates by CytoTox 96® cytotoxicity assay kit (Promega). The means of each data set were analyzed using Student's t-test with a two tailed distribution.

Cytotoxicity assay—CD8+ T cells (effector cells) were collected from spleen cells and sorted as CD8+CD3+ cells by FACS Aria II (BD Biioscience). H2N113 cells (target cells) were seeded in the 96-well plate at 10,000/well and incubated with CD8+ T cells at the ratio of 1:20. After overnight incubation, the plate was centrifuged and 50 μl of supernatants were measured for LDH release using the CytoTox 96® cytotoxicity assay kit (Promega). LDH release (%) was calculated as [A]sample−[A]minimum/[A]max−[A]minimum×100%, where [A]max is the absorbance value of a positive control (Triton X-100) in which complete target cell lysis occurred and [A] minimum is negative control (without effector cells).

Example 4

IFN-γ Enhances Activity of Dual Antibody

Previous results, with two anti-p185erbB2/neu antibodies 7.16.4 and 7.9.5 mAbs, showed that dual antibody therapy targeting distinct epitopes of the p185 ectodomain (Drebin et al., 1988) is far more effective therapeutically in treating established tumors and this approach has been now clinically adopted with the use of trastuzumab plus pertuzumab for breast cancers. Using H2N113 mammary tumors implanted in MMTVneu mice (Stagg et al., 2011; Du et al., 2013), experiments were performed to evaluate whether IFN-γ could improve the effects of dual anti-p185 mAbs. 1 million H2N113 cells were injected into MMTVneu mice subcutaneously. Once tumors reached 30-50 mm$^3$, mice were divided into four groups for different treatments. After two weeks of treatments (7.16.4 30 μg/mouse, 7.9.5 100 μg/mouse, twice per week; IFN-γ, 10$^4$ IU/mouse). Spleen cells were isolated and studied. As shown in FIG. 30A-FIG. 30B, IFN-γ improved therapeutic activity of two-antibody as determined by the CD8+ dendritic cell (DC) populations in spleen and cytotoxicity CD8+ T cells from spleen against tumor cells.

This regimen was then extended in a "preventative" model, in which treatment started within one day of inoculation of small tumor inocula (0.25 million H2N113 cells) to mimic a preventative therapeutic situation in which very small tumor nests remain after therapeutic surgery (Greenberg and Greene, 1976). Treatments started one day after inoculation of tumor cells. As shown in FIG. 31, more than half of inocula became palpable in the control group on day 16. Treatment with 2 antibodies prevented tumor appearance in half of injections until day 25. At the end of the experiment (day 32), half of inocula in 2 antibodies treated group were still free of palpable tumors. Addition of IFN-γ to the 2 antibodies further prevent the appearance of palpable tumors and near 69.8% of inocula remain free of palpable tumors at the end of the experiment.

Combination Activity of IFN-γ is Dependent on the IFN-γ Receptor Expressed on Tumor Cells.

To examine if IFN-γ was targeted to tumor cells directly the expression of the IFN-γ receptor was limited on these tumor cells. Using shRNA, an IFN-γ receptor knockdown species of the H2N113 cell line was created: H2N113 (IFNγR KD). The same suboptimal mAb approach was employed to maximize the demonstration of the combined role of these two reagents. The reduced expression level of IFN-γ receptor was confirmed by flow cytometric analysis (FIG. 32A-FIG. 32C). IFN-γ induced MHC expression was diminished in these cells and tumor cells were resistant to IFN-γ mediated growth suppression (FIG. 32B and FIG. 32C).

IFN-γ receptor low expressing tumor cells form progressively growing tumors. Treatment with suboptimal mAb 7.16.4 doses generated a modest growth reduction. IFN-γ had no effect on its own against tumors with diminished IFN-γ receptor levels. As shown in FIG. 1 and FIG. 33, the combination effect of mAb and IFN-γ was also abrogated by the absence of IFN-γ receptor in the tumor cells. Without wishing to be bound by any scientific theory, these data indicate that IFN-γ is required to interact directly with tumor cells to enhance the anti-tumor activity driven by the anti-p185erbB2/neu antibody and implies that IFN-γ enhanced host responses may not be sufficiently potent on their own to limit tumor growth.

IFN-γ Enhances the Activity of Anti-p185 Antibody in the Presence of Chemotherapeutic Agents.

In current clinical treatment for HER2 positive tumors, anti-HER2 antibody trastuzumab is administrated together with chemotherapeutic agents, such as docetaxel. To examine if IFN-γ further enhances the activity of antibody in the presence of chemotherapies, H2N113 cells were implanted into MMTVneu mice and subjected mice to control treatment, 7.16.4+docetaxel, or 7.16.4+docetaxel+IFN-γ after tumors became palpable (20-50 mm$^3$). As shown in FIG. 34, 7.16.4 and docetaxel reduced the tumor growth. When IFN-γ was added to the treatment, tumor growth was further reduced and the average tumor size in the triple treatment group even showed trend of shrinking of tumors.

Benefit of Anti-PD1 Antibody to IFN-γ Included Treatments

Previous reports (Stagg et al., 2011) as well as unpublished study in our lab indicated that IFN-γ treatment could induce the expression of PD-L1 on the tumor cells. The implanted tumors (H2N113) in the syngeneic MMTVneu mice model, were used to test whether anti-PD1 antibody could provide benefit by blocking PD-L1 and PD1 interaction and boosting host immunity against tumors. As shown in FIG. 35, treatment of anti-PD1 antibody together with anti-p185 mAb 7.16.4 and IFN-γ showed better activity than treatment with only 7.16.4 and IFN-γ.

New Data on the IFN Fusion Protein

A Mouse Version of the Fusion Protein 4D5scFvZZ-mIFN-γ

The present invention provides a fusion construct 4D5scFvZZ-IFN-γ (SEQ ID NO: 2), which contains the human IFN-γ sequence. While the construct was designed for use in humans, a similar construct 4D5scFvZZ-mIFN-γ was constructed to contain the mouse IFN-γ sequence to have a better assessment for the in vivo activity in the mouse model currently being tested. Athymic nude mice were inoculated with 5×10$^5$ T6-17 cells. Mice carrying tumor were treated with 4D5scFvZZ-mIFN-γ or the clinically used trastuzumab (4D5) at a very low dose of 0.125 mg/kg, five times per week via i.p. injection. As shown in FIG. 36, 4D5scFvZZ-mIFN-γ has much better activity than the anti-HER2 antibody 4D5 to limit the growth of T6-17 tumors.

The Activity of 4D5scFvZZ-mIFN-γ is Also Dependent on the IFN-γ Receptor in the Tumor Cells To examine if IFN-γ receptor is required for the activity of the recombinant fusion protein, a shRNA knock-down of the IFN-γ receptor in T6-17 was performed. T6-17 cells were transfected with either the vector or the IFN-γ receptor shRNA to establish T6-17(Vector) and T6-17(IFN-γR KD) cell lines respectively. An in vivo experiment was performed as in FIG. 36. As shown in FIG. 37A-FIG. 37B, while the activity of 4D5scFvZZ-mIFN-γ is clear on the control cell line T6-17(Vector), its activity against the T6-17(IFN-γR KD) was diminished.

Example 5

Ordered Combination of erbB Targeted Antibody and Immune Therapy of Breast Cancer Summary:

Reversion of the malignant phenotype of erbB2-transformed cells can be driven by monoclonal antibodies (mAb) that bind the p185erbB2/neu ectodomain (anti-erbB2/neu mAb) and disrupt the transforming kinase activity. Cells treated with disabling mAb have limited anchorage-independent and -dependent growth capacity in vitro, and diminished tumor growth in vivo. This study examined the effects of interferon-γ alone on erbB2-positive cells and those that were also treated with anti-erbB2/neu mAb. Interferon-γ was without effect on its own, indicating that immune therapies mediated by this cytokine alone are unlikely to be beneficial. However, it was discovered that treatment of the tumors with anti-erbB2/neu mAb initially for at least 24 hours prior to IFN-γ or concomitant with IFN-γ led to dramatic inhibition of tumor growth in vivo. The tumor growth inhibition could be accomplished with "minimal amounts of mAb" and reflect a combination effect of the two modalities. The use of IFN-γ in conjunction with mAb revealed that the IFN-γ effect was mediated on the tumor itself since dual treatment of IFN-γR null tumors did not show combination effects. IFN-γ had moderate effects on host cell constituents. An increase of M1 macrophage accumulation was noted in the tissues as well as diminished myeloid derived suppressor cells. The tumor cells treated with mAb and IFN-γ underwent changes in phenotypic markers reflecting loss of stem cell-like properties, while mAb treatment alone did not accomplish this phenotypic change.

Recognition that mAb could disable the p185erbB2/HER2/neu tyrosine kinase receptor complex and also lead to reversal of the malignant phenotype challenged the dogma that transformed cells could only progressively become more abnormal (Schechter et al. (1984); Drebin et al. (1985). Reversal of the malignant phenotype by anti-erbB2 mAb occurs rapidly beginning within 24 hours (Drebin et al. (1986); Lee et al. (2012); O'Rourke et al. (1997); (Qian et al. (1994)) beginning with down regulation of p185erbB2/neu receptor tyrosine kinase proteins and diminished enzymatic activity (Drebin et al. (1986); Furuuchi et al. (2007); Sliwkowski et al. (2013); Zhang et al. (2007); Drebin et al. (1988); Wada et al. (1990)). erbB2/HER2/neu genes are amplified and the protein overexpressed in ~30% of breast cancer patients and this oncogenic alteration is associated with aggressive disease, increased recurrence rate, and reduced patient survival. All of these clinical features are improved by anti-ErbB2 mAb therapy (Kiessling et al. (2002); Seidman et al. (2001); Romond et al. (2005); Baselga et al. (2001); Hudis et al. (2007); Meric-Bernstam et al. (2006)).

Both a contributory role of Natural Killer (NK)-like cells in antierbB2/HER2/neu mAb in vivo therapy (Clynes et al. (2000); Park et al. (2010); Junttila et al. (2010); Hurvitz et al. (2012); Drebin et al. (1988)) as well as effects from adaptive immunity in certain stages of tumors subjected to anti-erbB2/neu mAb therapy have been identified. Adaptive responses include CD8+ T cells 19 as well as CD4+ cells (Mortenson et al. (2013)). Stagg et al. suggested that mAb therapy requires type 1 and 2 interferons (IFN), and found IFN-γ induced CD8+ T cells were determinants for effective tumor inhibition (Stagg et al. (2011)). IFN-γ, a cytokine that plays diverse roles in innate and adaptive immune response, was one of the first recombinant proteins examined in human cancer therapy (Platanais et al. (2013); Bekisz et al. (2013); Balachandran et al. (2013); Ernstoff et al. 1987). Recombinant IFN-γ exhibits antiproliferative and apoptotic effects (Zaidi et al. (2011)); however, despite these characteristics, the clinical use of IFN-γ alone for cancer therapy in humans is ineffective (Zaidi et al. (2011); Miller et al. (2009)) and has been all but abandoned for that use.

mAb 7.16.4 is biologically active against cells transformed with the rat or human erbB2/neu oncogene and disables the p185erbB2/neu kinase leading to diminished downstream p185erbB2/neu signaling (Drebin et al. (1985); Zhang et al. (1999)). Previous studies examined various optimized doses of anti-erbB2/neu mAb therapy. 5 mg/kg of 7.16.4 mAb have been used intravenously (Drebin et al. (1985)) and/or on every other day intraperitoneally in therapeutic studies of tumor growth (Stagg et al. (2011); Du et al. (2013)). This study examined if reduced amounts of mAb could be used if IFN-γ were provided after therapy was initiated. As shown in FIG. 1, 7.16.4, anti-p185erbB2/neu mAb, when given at a sub-optimal dose (1.5 mg/kg), was unable to inhibit the growth of H2N113 tumor in entirely syngeneic MMTV-neu transgenic mice. IFN-γ treatment alone also failed to cause significant inhibition of the growth of the tumor. However, the combination of suboptimal amounts of 7.16.4 and IFN-γ "completely arrested" the growth of H2N113 tumors. Histological examination of the tumor tissues after treatment revealed significant necrosis only in mice treated with both 7.16.4 and IFN-γ (FIG. 40).

To examine if IFN-γ was targeted to tumor cells directly limited the expression of the IFN-γ receptor was limited on these tumor cells. Using shRNA, an IFN-γ receptor knockdown species of the H2N113 cell line was created: H2N113 (IFN-γR KD). The same suboptimal mAb approach was employed to maximize the demonstration of the combined role of these two reagents. The reduced expression level of IFN-γ receptor was confirmed by 1) flow cytometric analysis (FIG. 32A), 2) IFN-γ induced MHC expression was diminished in these cells and 3) tumor cells were resistant to IFN-γ mediated growth suppression (FIG. 32B and FIG. 32C).

IFN-γ receptor low expressing tumor cells form progressively growing tumors. Treatment with suboptimal mAb doses generated a modest growth reduction comparable to that seen in the studies depicted in FIG. 1. IFN-γ had no effect on its own against tumors with diminished IFN-γ receptor levels. As shown in FIG. 33, the combination effect of mAb and IFN-γ was also abrogated by the absence of IFN-γ receptor in the tumor cells. These data indicate that IFN-γ is required to interact directly with tumor cells to enhance the anti-tumor activity driven by the anti-p185erbB2/neu antibody and implies that IFN-γ enhanced host responses may not be sufficiently potent on their own to limit tumor growth.

There is a growing momentum for immune therapy of tumors. Even though significant effects of IFN-γ by itself has not been seen, endogenous regulatory host processes that might be mitigated by IFN-γ were examined. Myeloid-derived suppressor cells (MDSC) are defined as CD45+ cells that are also CD11b+ and GR-1+. Cells with the MDSC phenotype from tumors of treated or control BALB/c mice were identified. Co-treatment with sub optimal 7.16.4 and IFN-γ led to reduction of MDSC populations invading tumor tissues (FIG. 38A).

In vitro cell migration studies were performed to illustrate the chemo-attractant effects of molecules elaborated by tumor cells that might be affected by the combined treatment. MDSC isolated from mice spleens were placed into the upper chamber. As shown in FIG. 38B, conditioned medium from H2N113 cells treated directly with mAb, IFN-γ or their combinations attracted MDSC cells to migrate into the lower chamber. 7.16.4 alone slightly reduced the tumor-promoted migration, but the co-treatment of 7.16.4 and IFN-γ of the tumor cells themselves blocked MDSC migration, while IFN alone had no appreciable effects.

Two types of functional macrophages have been proposed to infiltrate the tumor microenvironment also promoted by molecules elaborated directly or indirectly by tumor cells.

Tumors were examined for invading anti-inflammatory, pro-tumor M2 and pro-inflammatory, anti-tumor M1 types. MAb7.16.4 and IFN-γ increased M1 accumulation within adjacent areas of the tumor, and animals treated with this combination therapy had the highest M1 frequency. (FIG. 41A-FIG. 41C).

Studies have suggested a role for IFN-γ induced CD8+ T cells in certain phases of the anti-erbB2/neu mAb treatment in some tumor model systems (Stagg et al. (2011); Stagg et al. (2012)). Sub-optimal mAb and IFN-γ were used in syngeneic systems and effector T cells were collected from each treatment group to investigate their activity against H2N113 cells. The combination therapy group showed only modest effector T cells activity against p185erbB2/neu positive tumors. IFN-γ alone had minimal effects (not shown).

Molecular analyses revealed that in vitro the ordered treatment of breast tumor cells with anti-erbB2/neu mAb followed by IFN-γ, but not with IFN-γ followed by anti-erbB2/neu mAb, diminishes expression of snail proteins, which mediates stem cell like properties (Runkle et al 2014 submitted). ALDH1 expression patterns also define cancer stem cell phenotypes, and its expression correlates with breast cancer prognostic features (Douville et al. (2009); Ginestier et al. (2007)). Tumors were compared at the end of treatment for ALDH1 levels. Co-treatment with 7.16.4 and IFN-γ treatment reduced the expression of ALDH1 in p185erbB2/neu tumors (FIG. 39).

Discussion:

Therapeutics that target p185erbB2/HER2/neu are effective for restraining human malignant disease but are rarely curative. Disabling of the p185erbB2/neu kinase complex leads to phenotypic reversal of malignant properties. This phenotypic state is more sensitive to genotoxic damage by chemotherapeutic and radiation effects, or immune mediated lytic processes. The studies herein identified a second transition process that occurs after mAb-mediated down-regulation of p185erbB2/neu proteins from the cell surface, which can be induced by IFN-γ. The second transition step renders cells even more sensitive to lytic processes that occur in vivo by certain immune elements.

This study describes a dramatic and complete arrest of tumor growth even with suboptimal doses of anti-ErbB2/neu mAb when IFN-γ is included. Moreover, the combined effect requires that the tumor cell itself express IFN-γ receptors. Because IFN-γ enhances antibody effects at very low doses in vivo, it would improve targeted therapy effectiveness in tissues where only low levels of antibody might penetrate.

The effect of mAb and IFN-γ appears to be a consequence of phenotypic change on the tumor itself. The combination effects of mAB and IFN-γ were lost when tumor cells with reduced IFN-γ receptor levels were targeted. Secondly, a reduction of regulatory MDSC cells that limit immune reactions by suppressing functions of immune cells was noticed. Tumor elaborated chemo-attractants which recruit regulatory cells were diminished upon ordered treatment of tumor cells with mAb and then IFN-γ. Studies not shown in this Example were unable to document any comparable activity when IFN-α or IFN-β were used (in vivo or in vitro respectively) rather than IFN-γ. (not shown).

An accumulation of M1 type macrophages in the local tumor environment in situations using combined mAb and IFN-γ therapy was also observed. Together these data support a role for the immune system in targeted therapy and a role for IFN-γ in enhancing immune eradication of erbB tumors that have undergone phenotype reversal. However immune modifications induced by IFN-γ alone are ineffective on their own.

mAb induced phenotypic reversion is incomplete, or at the very least, is subject to further modification, and can itself (Drebin et al. (1986); Lee et al. (2012); O'Rourke et al. (1997); Wada et al. (1990)) then be acted on by IFN-γ to create a second transition state. The second transition involves a role of transcription factors thought relevant to cancer stem cell features (Example 3). IFN-γ alone, without the first reversion step is ineffective in being able to induce a malignant phenotype reversion.

ALDH1 is diminished in tumor cells treated in vivo with combined mAb and IFN therapy. Elevation of ALDH1 enzyme levels correspond to erlotinib resistance in erbB1 (EGFR) mutated human tumors (Corominas-Faja et al. (2013)). Thus metabolic changes occur within tumor cells with stem cell like properties, that are amenable to manipulation by phenotypic reversion best promoted by anti-p185erbB2/neu mAb and by IFN-γ. Consequently, tumor tissues should be examined diagnostically for expression of IFN-γ receptor and aldolase in situations in which targeted therapy might be administered.

Combining targeted therapy with immune therapy in an ordered way may lead to a greatly reduced need for the mAb components and possibly the genotoxic molecules needed to treat humans.

Supplemental Materials and Methods

Histology

Tumor tissues were fixed with 10% neutral buffered formalin and embedded in paraffin. Sections were de-paraffinized and stained with H & E by the Cell Imaging Core of the Abramson Cancer Research Institute.

Flow Cytometry

At 1 day after final treatment, spleens and tumors were collected for single cell suspensions. Tumors tissue was cut and digested with Collagenase P for 1 hr, then dispase (Stem Cell) and DNase (1 μg/ml, Roche) were added and incubated for 5 minutes. Then cells are filtrated by cell strainer (Falcon). Single suspension of tumor tissue cells were stained with CD45, F4/80, CD11b, and CD206 antibodies (Biolegend). Cells were analyzed with FACS LSR (BD Biosciences) and FACS data were analyzed with FlowJo software (Tree Star, Ashland, Oreg.).

In Vitro Proliferation Assays $10^4$ H2N113 transfected with empty vector and IFγR1 shRNA vector were cultured in 96-well plates for 5 days with indicated concentration of IFNγ. Relative cell numbers were measured by LDH activities of total cell lysates by CytoTox 96® cytotoxicity assay kit (Promega). The means of each data set were analyzed using Student's t-test with a two tailed distribution.

Example 6

Summary

Efforts of Dr. Mark Greene's laboratory have focused on improving rationally designed and developed targeted adjuvant therapy for human breast cancer to prevent reoccurrence and limit metastatic spread. The new therapeutics appear to be useful for treating advanced erbB resistant breast cancers.

Evolution of the therapeutic approach described herein has been the result of success in developing completely novel erbB targeting compounds coupled with enhanced molecular understanding of how to disable erbB transformation of breast cancer in vivo. A new therapeutic for use in human breast cancer has been developed, and is expected enter the clinic in the near future.

The therapeutic was developed to combine features of targeted therapy and immune therapy. These two therapeutic approaches can work together in an unexpected way. Two forms of this second therapeutic species have been developed. One approach simply uses two approved molecules used in a specific sequence. The second form is a new single molecule built through genetic engineering that combines the two proteins together. Studies of the two molecules used in a defined sequence have found that a Herceptin-like antibody protein already used to treat cancer in humans becomes far more efficacious when followed sequentially by an immune recombinant protein, interferon-gamma. Interferon-gamma is also approved for human use but not for breast cancer. This sequential use of targeted and immune therapies is expected to be able to enter the clinic in the near future. Only ⅓ the amount of the Herceptin like antibody was found to be required to achieve even more complete tumor eradication when sequential treatment with interferon-gamma was added to the regimen. In addition, new antibody forms were created that combine the Herceptin-like antibody properties with the Interferon in a single new recombinant protein to treat human breast cancer.

Progress

Studies relating to new recombinant proteins that disable the malignant phenotype of breast cancer cells are pursued. The accomplishments as they relate to individual goals are summarized below.

Aim: In this aim disabling the p185erbB2/HER2/neu receptor with monoclonal antibodies followed by recombinant interferon proteins is studied. There is also a focus on studies of the humanized pan erbB recombinant species and scFv forms of Herceptin antibodies linked to IFN-γ as a recombinant structure.

The pan erbB mAb-like S22-23-Fc loop body species, modeled from the ectodomain of erbB2 and capable of limiting erbB2 and erbB3 activity in human breast cancer, has been created. Recombinant technology is also used to embed the IFN-γ sequence to the carboxy termini of a new mAb (Herceptin) scFv species. These erbB receptor disabling molecules coupled with IFN-γ can dramatically limit growth of erbB2 transformed human breast cancer tumors in vivo in animal models.

Several studies were conducted that indicate paired disabling of erbB receptors by mAb along with IFN-γ signals can optimally reverse the malignant cell phenotype in vitro and in vivo. Studies have also identified certain of the molecular mechanisms by which targeted therapy can be augmented by recombinant IFN-γ. The mechanisms of combining oncoprotein targeting effects and the tumor effects of IFN-γ are also being studied. These studies will be important as it has been discovered that combining targeted therapy and IFN-γ reduces tumor growth more completely, reduces the need for targeted antibodies by 66% and reduces amounts of genotoxic molecules (paclitaxel, docetaxel) needed to cause tumor death by 50%.

Specific progress to date.

Combination Effect of Targeted and Immune Therapy Using Recombinant Proteins.

Features of the ordered combination of targeting mAb followed sequentially with recombinant IFN-γ. In addition, significant progress has been made with the recombinant scFv 4D5-human Fc linked to IFN-γ and the pan erbB recombinant S22-human Fc form coupled with IFN-γ on human breast tumor cell growth in vitro and in vivo. Certain of these constructs are designed to express recombinant 4D5 and release IFN-γ upon binding because of a labile cleavage site embedded in the construct.

The data are striking, and the creation of an engineered scFv-species linked with IFN-γ at the carboxy terminus shown in FIG. 36 is more effective than 4D5 (the Herceptin) at limiting erbB2 amplified transformed cell growth. 4D5scFvZZ-mIFN-γ has better activity than 4D5 in the in vivo study. One day after injection of T6-17 cells s.c. into athymic mice, mice were randomly grouped and treated with control, 4D5 or 4D5scFvZZ-mIFN-γ at the dosage of 0.125 mg/kg, 5 days per week, via i.p. injection. Mice treated with 4D5scFvZZ-mIFN-γ had very significantly smaller tumors.

Experiments that were conducted also examined the activity of the S22-Fc pan erbB inhibitory molecule alone and in combination with IFN-γ. These studies have revealed that even this unique pan erbB inhibitor can be made functionally more effective by ordered therapy with IFN-γ (Not shown).

Targeted Therapy with Anti-erbB2 mAb and Sequential IFN-γ Reduces the Amount of Antibody Needed for Phenotypic Reversal.

The possibility of reducing the amount of targeting mAb administered when its effect was enhanced with sequential IFN-γ was examined. Optimized doses of anti-erbB2/neu mAb therapy have been determined and typically 5 mg/kg of 7.16.4 mAb has been used intraperitoneally 2-3 times/week in therapeutic studies of tumor growth. Experiments were conducted to examine if reduced amounts of mAb could be used if IFN-γ were provided after therapy was initiated. As shown in FIG. 1, 7.16.4 anti-p185erbB2/neu mAb, when given at a sub-optimal dose of 1.5 mg/kg (⅓ of the normal dose) was unable to inhibit the growth of H2N113 tumor significantly in entirely syngeneic MMTV-neu transgenic mice. IFN-γ treatment alone also failed to cause significant inhibition of the growth of the tumor. However, the combination of low dose 7.16.4 and IFN-γ "completely arrested" the growth of H2N113 tumors. Histological examination of the tumor tissues after treatment revealed significant necrosis only in mice treated with both 7.16.4 and IFN-γ (not shown).

The Locus of Action of IFN-γ Appears to be Dominantly the Tumor Itself.

To examine if the role of IFN-γ was targeted to tumor cells directly, the expression of the IFN-γ receptor was limited on these tumor cells. Using shRNA, an IFN-γ receptor knockdown version of the H2N113 cell line was created: H2N113 (IFNγR KD) (FIG. 33). The same suboptimal mAb approach was employed to maximize the demonstration of the combined role of these two reagents. The reduced expression level of IFN-γ receptor was confirmed by 1) flow cytometric analysis, 2) that IFN-γ induced MHC expression was diminished in these cells.

As shown in FIG. 33 IFN-γ receptor low expressing tumor cells led to progressively growing tumors. Treatment with suboptimal mAb doses generated a modest growth reduction comparable to that seen in the studies depicted in FIG. 1. IFN-γ had no effect on its own against tumors with diminished IFN-γ receptor levels. As shown in FIG. 33, the combination effect of mAb and IFN-γ was also abrogated by the absence of IFN-γ receptor in the tumor cells. These data indicate that IFN-γ is required to interact directly with tumor cells to enhance the anti-tumor activity driven by the anti-p185erbB2/neu antibody and indicate that IFN-γ alone enhanced host response is not sufficiently potent to limit tumor growth.

Implications of Reduced Amounts of Targeting Antibody and Cytotoxic Reagents.

Therapeutics that target p185erbB2/HER2/neu are effective for restraining human malignant disease but are rarely curative. Down-modulation of the receptor from the cell surface, leads to phenotypic reversal of malignancy. This phenotypic state is more sensitive to genotoxic damage by chemotherapeutic and radiation effects, or immune mediated lytic processes. Studies described herein identified a second transition that can be induced by IFN-γ. The second transition step renders cells more sensitive to lytic processes that occur in vivo by immune elements or cytotoxic chemotherapeutics as shown in FIG. 42.

These studies indicate a dramatic and complete arrest of tumor growth even with suboptimal doses of anti-erbB2/neu mAb when IFN-γ is included. Moreover, the combined effect requires that the tumor cell itself express IFN-γ receptors. These studies indicate the importance of the combination because IFN-γ enhances antibody effects at very low doses in vivo thereby improving targeted therapy effectiveness in tissues where only low levels of antibody might penetrate. In studies not shown in this example been unable to document any comparable activity when IFN-α or IFN-β were used (in vivo or in vitro respectively) rather than IFN-γ.

Additionally, an accumulation of M1 type macrophages was observed in the local tumor environment in situations using combined mAb and IFN-γ therapy. Together, these data support a modest role for the immune system in targeted therapy and a role for IFN-γ in enhancing immune eradication of erbB tumors that have undergone phenotype reversal. Importantly, it was discovered that immune modifications induced by IFN-γ alone are ineffective, indicating a more fundamental process of phenotypic transitions is responsible for the synergistic activities.

Lay Abstract

A new therapeutic approach was studied to treat and eradicate advanced breast cancer and also to preempt tumor re-emergence after breast cancer surgery.

A family of antibody-like proteins have been produced using recombinant engineering. These proteins are pan erbB inhibitors that bind and disable erbB2 active receptors and erbB2-erbB3 receptor forms. Some of these recombinant proteins have been engineered to carry Interferon-gamma, an immune activating molecule. One family of the recombinant proteins has shown promise in limiting growth of human breast tumors that accumulate more than one kind of mutation in their genes and become resistant to current therapy. The recombinant proteins, which combine erbB inhibition with an immune activator such as interferon-gamma, are particularly effective at reversing growth properties of doubly transformed tumor lines, that is breast tumors which have more than one mutated gene, in preclinical studies.

Another major set of studies is using both the synthetic molecules and engineered antibody molecules to prevent tumor formation and tumor reoccurrence. Initial studies have been made in a preclinical setting to show that one anti-HER2 antibody when concomitantly used with Interferon-gamma can actually limit the development of breast tumors in a small animal model. Those studies are extended to see if it is possible more completely arrest tumor development using the synthetic molecules or two antibodies that bind to erbB receptors alone and in combination with immune activators like Interferon-gamma. A unique small animal model is be used to determine if these therapeutics can actually prevent the hyperplasia that occurs very early in breast cancer development and then prevent tumor formation completely. Both of the new therapeutics are expected to reach the clinic in the near future.

Additional Studies: The studies include biochemical and mechanistic studies. These are be extended to in vivo studies using a unique transgenic breast cancer model (MMTV NeuT-tdTomato) that allows cancer cells to be followed because a tomato red chromophore is incorporated in the oncogenic neu construct.

Prevention of Hyperplasia and Tumorigenesis by Combination Effects of mAb and IFN-γ in Transgenic Models.

A). Prevention of tumor occurrence is studied. MMTV-neu BALB/c transgenic mice have been developed by the laboratory of Dr. Mark Greene to study the development of incipient erbB2/HER2/neu mammary tumors in female mice. In the MMTV-neu model, rat oncogenic neu is expressed under the control of the MMTV promotor and tumors arise ~30 weeks stochastically in mice that have delivered and nursed a litter. All control females develop tumors by ~60 weeks of age. In vivo administration of mAb directed at the ectodomain of p185erbB2/neu in MMTV-neu transgenics prior to mammary tumor development significantly inhibits the pre-neoplastic state associated with the initial events of tumorigenesis and delays tumor onset and final extent of metastases.

B). Dual antibody therapy targeting distinct epitopes of the p185 ectodomain is far more effective therapeutically in treating established tumors. Experiments are conducted to evaluate if the effects of dual mAbs can be further improved in prevention models of breast tumors. The experiments examine whether IFN-γ could augment the preventative potency of dual mAb in a simple model of prevention of breast tumor.

Two anti-p185erbB2/neu antibodies, mAbs 7.16.4 and 7.9.5, bind to distinct epitopes on the p185 ectodomain. A "preventative" preliminary study has been completed. In this model inoculation of small tumor masses is used to mimic a preventative therapeutic situation in which very small tumor nests remain after therapeutic surgery. In this preliminary study, 9 out of 10 tumors became palpable in the control group by day 10. Treatment with 2 antibodies prevented tumor appearance in 3 out of 10 mice during the first two weeks. When the two-antibody regimen was combined with IFN-γ most (8 out of 10) in this group failed to develop tumors. Although some tumors became palpable later in the course of the experiment, 60% of the 2 antibodies plus IFN-γ group remained tumor free. This extraordinary observation is extended.

C). Prevention studies are extended to a transgenic model recently developed using MMTV NeuT-tdTomato red constructs. Tumors develop stochastically in females and this genetic construct permits visualization of the earliest lesions (hyperplasia) and the spread of neoplastic tumors. Thus, this novel transgenic allows the visualization of the tumor as it arises stochastically in the breast and metastasizes. Tumors arise at 23-30 weeks and all female mice have tumors by 50 weeks.

These studies examine an effect of mAb antibodies and IFN-γ on the earliest lesions of breast cancer tumor development, when administered prior to tumorigenesis. Experiments are conducted to examine if these animals which develop sequential changes in the breast including hyperplasia and then neoplasia is prevented from developing either of these lesions. The power of the model is that effects of early spread of tumor from the breast can be examined. In these experiments two antibodies plus IFN-γ is administered twice weekly beginning at week 12 after birth. Another group of female mice will receive two antibodies alone or IFN-γ alone and breast tumors and metastases spread monitored. These studies indicate that the combination effects of mAb and IFN-γ limit tumor occurrence and metastatic spread as preliminary studies indicate.
  D). Studies also extend to the use of 2 targeted antibodies, concurrent or sequential administration of IFN-γ, followed by small doses of docetaxel in pre-clinical models of prevention.

Example 7

Sequential Disabling of the erbB Pathway Followed by IFN-γ Modifies Phenotype and Enhances Genotoxic Eradication of Breast Tumors
Summary
  Reversion of the malignant phenotype of erbB2-transformed cells can be driven by anti-erbB2/neu monoclonal antibodies (mAb), which disrupt the receptor's kinase activity. We examined the biologic effects of INF-γ alone or after antierbB2/neu mAb treatment of erbB2-positive cells. IFN-γ had no effect on its own. Treatment of the tumors with anti-erbB2/neu mAb followed by IFN-γ led to dramatic inhibition of tumor growth in vitro and in vivo with minimal mAb dosing. Sequential therapy enhanced the effects of chemotherapy. Moreover, IFN-γ with mAb treatment of mice with IFNγR knock down tumors did not demonstrate marked synergistic eradication effects, indicating an unexpected role of INF-γ on the tumor itself. Additionally, mAb and IFN-γ treatment also induced immune host responses that enhanced tumor eradication. Biochemical analyses identified loss of Snail expression in tumor cells, reflecting diminution of tumor stem cell-like properties as a consequence of altered activity of GSK3-β and KLF molecules.
Significance
  Targeting erbB2-driven tumors with mAb-based targeted therapy benefits patient outcome in breast cancer; however, some patients do not respond, and virtually all responders eventually relapse. We have now found that IFN-γ can modify intrinsic properties of transformed cells that have undergone phenotypic reversion with anti-erbB2 mAb or lapatinib. We establish that IFN-γ concurrent and following anti-erbB2 mAb inhibits certain intrinsic tumor-signaling pathways limiting stem cell-like properties. Sequential therapy synergistically provides optimal immune therapeutic effects on erbB2-transformed human breast cancer cells and mouse erbB2-driven breast tumor models. Co-administration or sequential ordering of anti-erbB2 mAb with IFN-γ greatly reduces the amount of mAb and genotoxic chemotherapeutics necessary for treatment of humans with erbB2-driven cancers.
Highlights
  IFN-γ and 4D5 act directly on erbB2-positive breast cancer cells
  IFN-γ, but not IFN-α or β, cooperates with 4D5 directly on erbB2+breast cancer cells
  IFN-γ and 4D5 alters KLF4 levels and degrades Snail by the GSK3-β/proteasome pathway
  Sequential combination treatment with mAb and IFN-γ sensitizes for tumor eradication
Introduction
  The erbB or HER family of receptor tyrosine kinases consists of erbB1 (the epidermal growth factor receptor (EGFR)/HER1), erbB2 (p185/neu/HER2), erbB3 (HER3), and erbB4 (HER4), all of which can form homomeric and heteromeric assemblies (Kokai et al., 1989; Qian et al., 1994b). These receptor tyrosine kinases participate in a variety of signal transduction cascades, including the Ras/Raf/MEK/ERK and PI-3K/Akt pathways. erbB2 is amplified in approximately 30% of breast cancer patients, and amplification is associated with poor prognosis and decreased survival (Riemsma et al., 2012). In various cancers, amplified or mutated forms of these kinases drive increased proliferation, migration, survival, evasion of apoptosis, metastasis, and resistance to chemotherapeutics and ionizing radiation.
  Recognition that mAbs could disable the p185 erbB2/HER2/neu tyrosine kinase receptor complex and also lead to reversal of the malignant phenotype challenged dogma that transformed cells could only progressively become more abnormal (Drebin et al., 1985; Schechter et al., 1984). Reversal of the malignant phenotype by anti-erbB2 mAb begins rapidly within 24 hours of mAb binding (Drebin et al., 1986; Lee et al., 2012; O'Rourke et al., 1997; Qian et al., 1994a) and occurs with down regulation of p185erbB2/neu receptor tyrosine kinase proteins causing diminished enzymatic activity (Drebin et al., 1988a; Drebin et al., 1986; Furuuchi et al., 2007; Sliwkowski and Mellman, 2013; Wada et al., 1990; Zhang et al., 2007). These mechanistic events altering phenotype occur more dramatically with the inclusion of a second antibody, which more completely disables erbB2/neu kinase function (Drebin et al., 1988b; Furuuchi et al., 2007).
  Tumor eradication that occurs in some partially syngeneic erbB2/neu models also displayed a role for CD8+ T cells, macrophages and Natural Killer cells (Park et al., 2010; Stagg et al., 2011). Cytokines derived from CD8+ T cells and other cell types also contribute in certain tumor models (Park et al., 2010; Stagg et al., 2011). IFN-γ, a cytokine that plays diverse roles in innate and adaptive immune response, has been implicated in tumor immune responses. Stagg and colleagues demonstrated activity of both type 1 and 11 IFNs in mediating anti-erbB2 mAb functions in vivo (Stagg et al., 2011) in non syngeneic tumor host systems.
  Early biochemical studies indicated that IFN-γ could limit p185erbB2/neu expression at the mRNA level (Marth et al., 1990) in some tumor lines. Conversely, IFN-γ alone was thought to increase erbB1 (EGFR) levels (Hamburger and Pinnamaneni, 1991) and TGFα secretion through increased EGFR activity (Uribe et al., 2002) as well as to promote malignant growth of certain murine tumors (Beatty and Paterson, 2000). IFN-γ may also contribute to local environmental angiogenic effects (Coughlin et al., 1998). Historically, IFN-γ was one of the first recombinant cytokines tested as a single agent in trials of multiple human cancers, but led to few if any beneficial outcomes. Thus, clinical efforts using IFN-γ as a primary single therapeutic for most malignancies have not been pursued (Krigel et al., 1985).
  Certain proteins relevant to phenotypic developmental changes in stem cells and transformed cells have been described (Zheng and Kang, 2014). The transcriptional repressor Snail is essential for gastrulation and mesoderm formation during mammalian development (Carver et al., 2001). Snail levels increase in transformed cells. Elevated levels of Snail contribute to tumor recurrence in vivo in erbB2/neu murine models and levels of Snail may be relevant to relapse-free survival patterns in breast cancer patients (Moody et al., 2005). Slug transcriptional proteins may similarly function together to induce a stem-like phenotype in mammary cells in addition to maintaining tumor and metastatic properties (Guo et al., 2012).
  Glycogen synthase kinase 3-beta (GSK3-β), while negatively modified by Akt1, post-translationally regulates Snail through site-specific phosphorylation. Regulatory post-translational phosphorylation modifications alter Snail's subcellular localization and stability.

Specifically, GSK3-β phosphorylates Snail on six serine residues (serines 97, 101, 108, 112, 116, and 120) encompassing two motifs that promote translocation from the nucleus to the cytoplasm and β-TRCP-mediated ubiquitination and degradation (Feinberg et al., 2005; Zhou et al., 2004). Zheng and Kang (Zheng and Kang, 2014) suggested Snail effects phenotypic changes in cancer cells and described epithelial to mesenchymal changes in both neu and ras transformed cells.

Products of activated immune cells such as IFN-γ have been shown to enhance the expression of the KLF4 transcription factor which itself can repress Snail transcription (Feinberg et al., 2005; Yori et al., 2011). KLF4 overexpression induces macrophage activation markers while KLF4 knockdown markedly modulates the ability of IFN-γ to render those effects. Transfection of KLF4 attenuated primary tumor growth as well as affecting development of metastatic lesions. erbB targeted immune therapy processes that govern Snail protein functions have not been described. Here we revealed that combinations of erbB2-targeted mAb and IFN-γ, but not IFN-α or β, can modify Snail expression and contribute to phenotypic reversion and cell viability by altering GSK3-β activity and KLF4 expression in breast tumors. We have also extended these efforts in vivo in therapeutic and prevention models. Our findings provide a better and less toxic human breast cancer therapeutic strategies.

Results

Sequential and Concurrent mAb 4D5 and IFN-γ Activities on erbB2+Breast Cancer Cells erbB2 transformed human SK-BR-3 breast cancer cells were treated with IFN-γ and anti-erbB2 mAb (4D5) or control IgG (cIgG) at different times. Cells simultaneously exposed to both 4D5 and IFN-γ for eight days were included. Pretreatment with 4D5 for 4 days followed by the addition of IFN-γ caused a greater reduction in cell viability than pre-treatment with IFN-γ followed by addition of 4D5. Prolonged co-treatment with 4D5 and IFN-γ resulted in greater reduction in cell viabilities (FIG. 54A).

Kinetics of the sensitizing effect were examined using an intermediate dose of IFN-γ (10 ng/mL). Dramatic reduction in cell viability was noted over an eight-day time course in the presence of 4D5, which could be augmented with the inclusion of IFN-γ (FIG. 54B). These in vitro studies, were performed with a single treatment of IFN-γ, 4D5, or IFN-γ+4D5 administered the day following cell seeding (i.e. Day 0). Immortalized, but untransformed MCF10A cells were refractory to 4D5 alone or in combination with IFN-γ. These latter data indicate that the combined ordered effects are manifest only on cells that have acquired malignant properties.

The effects of this treatment regimen were examined in prevention of foci formation in soft agar assays. Treatment with 4D5 produced a dramatic reduction in the formation of foci in soft agar compared to cIgG and IFN-γ alone as demonstrated by a greater percentage of foci less than 20 pixels as well as fewer foci greater than 20. Addition of IFN-γ produced a greater percentage of foci under 20 pixels than 4D5 alone and a reduced percentage of foci greater than 20 pixels compared to 4D5 alone (FIG. 54C and FIG. 54D).

Collectively, these studies established that disabling the p185erbB2 kinase with mAb followed by IFN-γ produced the most significant phenotypic and viability effects on breast tumor cells.

Phenotypic Effects of mAb and INF-γ on Other Cell Types

We speculated that some erbB1 tumors might not be influenced by ectodomain binding monoclonals, because of the action of IFN-γ on EGF/TGF expression (Uribe et al 2002) or by mutations which limit the effects of targeting mAbs. U87 cells which are driven by EGFR VIII that lacks portions of the extracellular domain of the EGFR, failed to respond to the anti-EGFR mAb C225. However, A431 cells, which lack erbB2, but express EGFR holoreceptor homomeric dimers similarly responded to dose-dependent increases of IFN-γ in the presence of C225 (FIG. 55A) in a similar manner to erbB2/neu transformed cells.

Figure 55A:
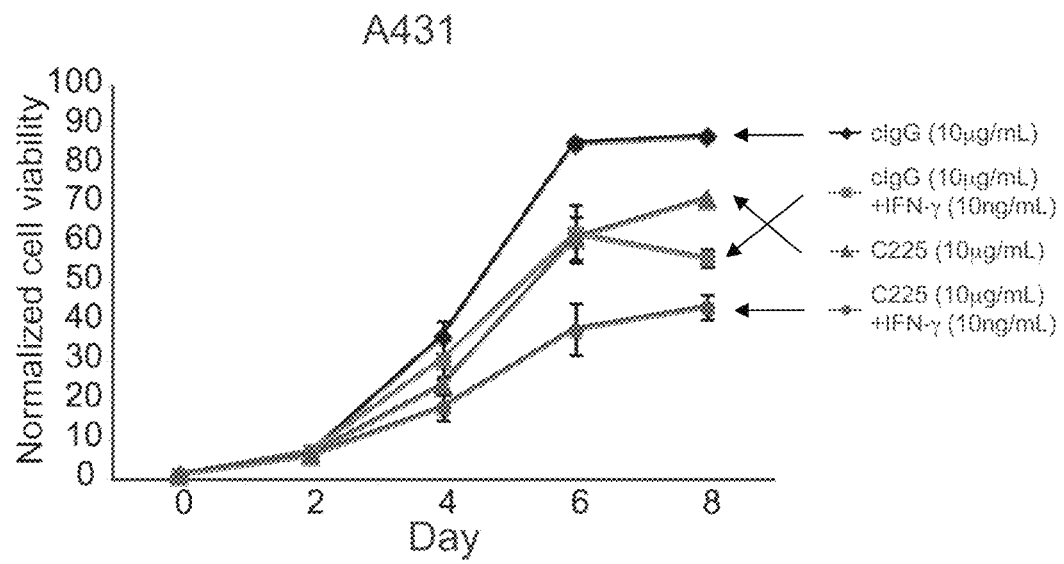
Figure 55B:
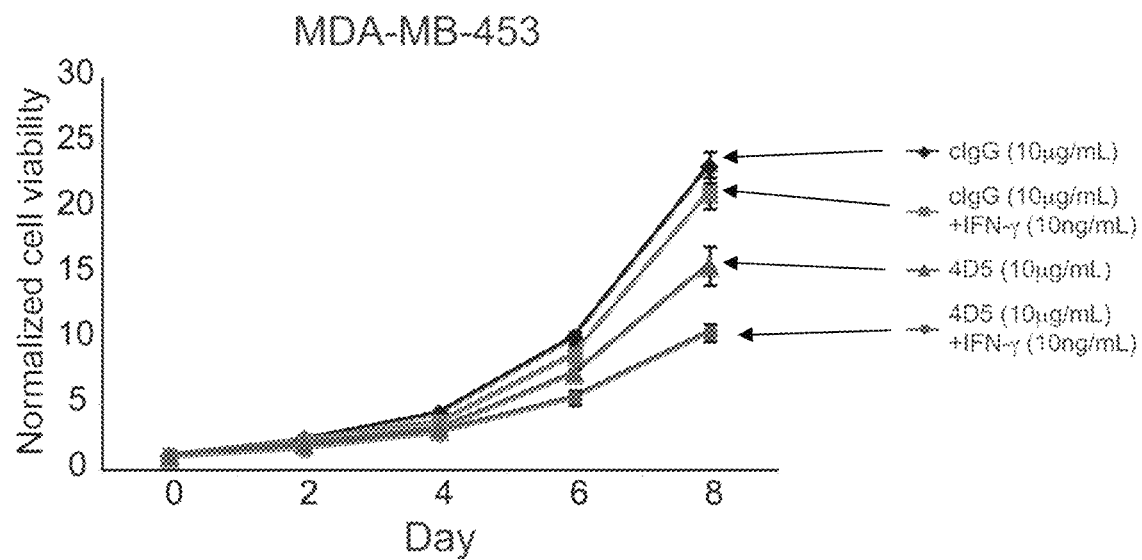
Figure 55C:
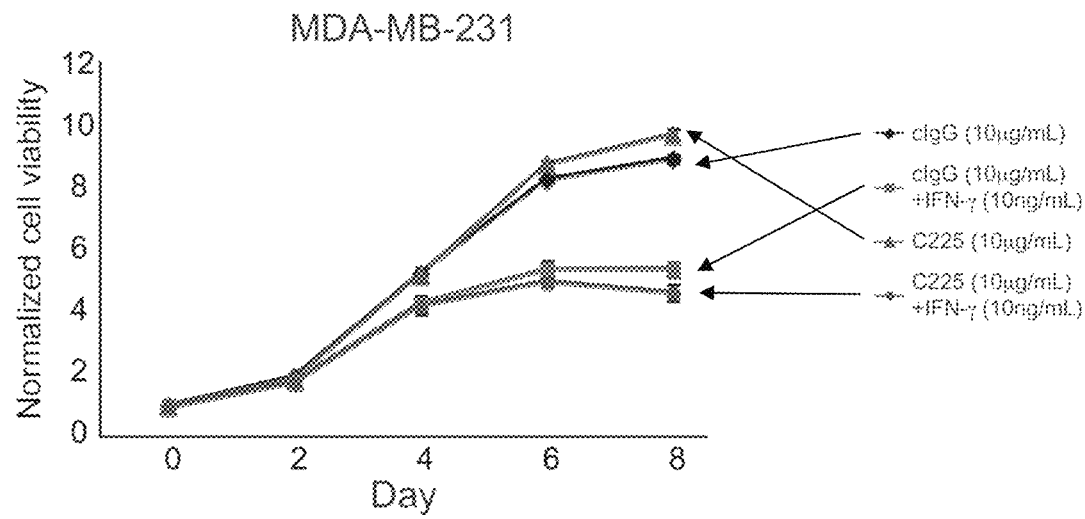
Figure 55D:
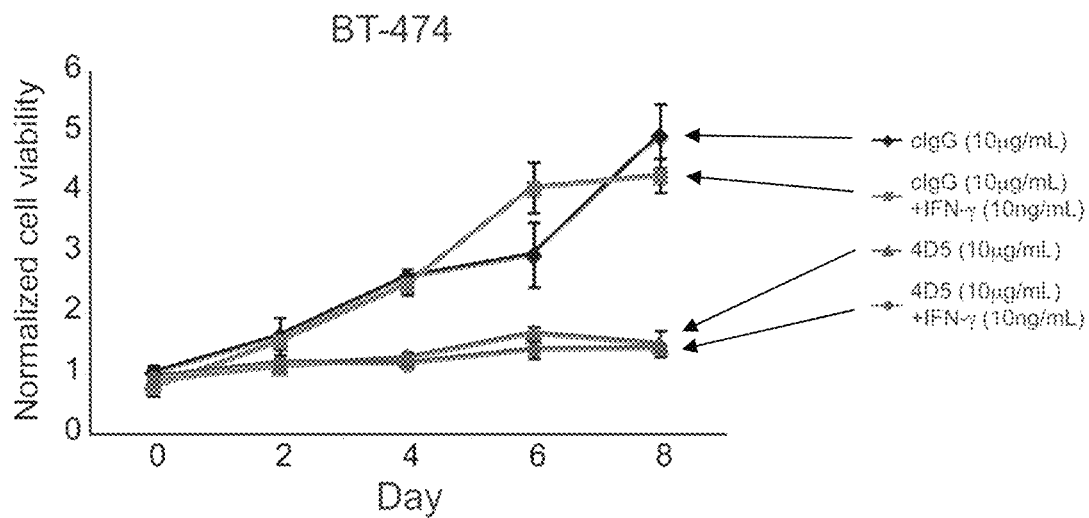

The erbB2+ breast cancer cell lines MDA-MB-453 and BT-474 display distinct phenotypes from the SK-BR-3 cells. MDA-MB-453 and BT-474 were inhibited by 4D5 mAb and MDA-MB-453 cell viability was further affected by the inclusion of IFN-γ (FIG. 55B). Triple negative breast cancer cells, MDA-MB-231, responded minimally to C225 mAb but also responded to IFN-γ alone (FIG. 55C). IFN-γ and a single mAb treatment did not have additive effects on BT-474 cell growth (FIG. 55D)

The PI3-K/Akt/GSK3-0 Snail Pathway can be Modified by mAb and IFN-γ or Kinase Inhibitors Such as Lapatinib.

SK-BR-3 cells were treated with the dual EGFR/HER2 small molecule tyrosine kinase inhibitor lapatinib or 4D5 and C225 alone and in combination to determine which signaling pathways were affected by disabling erbB family members. Lapatinib treatment inactivated both the Akt and MAPK pathways as anticipated. 4D5, but not C225, dominantly inactivated Akt while not affecting MAPK activities. Combinations of 4D5 and C225 to disable heteromeric kinase complexes, also inactivated Akt in SK-BR-3 cells. Disabling erbB2 in these cells activated phosphorylated GSK3-β. We also found that treatment with 4D5, (but unexpectedly not with C225 alone), reduced Snail levels selectively.

We next compared the lapatinib response in SK-BR-3 and MDA-MB-453 cells. Lapatinib treatment diminished Akt activity in both cell lines and, to a lesser extent, MAPK signaling. Lapatinib induced a dose-dependent reduction in Snail. Antagonism of PI3-kinase and AKT1/2 inhibitor in SK-BR-3 cells revealed a reduction in Snail, but not Slug.

We next determined if the combination of IFN-γ and anti-erbB2 mAb could further reduce Snail protein levels. SK-BR-3 cells were treated with cIgG or 4D5 and increasing doses of IFN-γ. We found an IFN-γ dose-dependent reduction of Snail only in the presence of 4D5 (FIG. 56A). We found that GSK3-β activation is enhanced by IFN-γ in the presence of 4D5 compared to IFN-γ treated samples in the presence of control IgG. Slug content was initially unaffected (FIG. 56A); however, by three days treatment led to reduction of Slug levels. Combination of 4D5 and C225 in the presence of IFN-γ produced the most dramatic reduction in Snail and also reduced Slug content (FIG. 56B).

The notion that simultaneous mAb inhibition of HER2 and EGFR could reduce Snail and Slug prompted us to examine whether small molecule kinase inhibitors such as lapatinib treatment could be modified by IFN-γ. SK-BR-3 cells treated with increasing doses of lapatinib and IFN-γ showed reduced Snail and Slug levels (FIG. 56C). Thus, erbB receptors erbB2 and erbB1 (EGFR), functioning as heteromeric kinases stabilize Snail and Slug, and combinatorial receptor disabling events in the presence of IFN-γ provides optimal signal disruption and degradation of these proteins.

IFN α and IFN-β do not induce the phenotypic changes seen with IFN-γ.

A recent study demonstrated that inclusion of IFN-β with an EGFR antibody produced a more potent anti-tumor effect than EGFR antibody alone (Yang et al., 2014). Therefore, we compared IFN-β with IFN-γ in the presence and absence of 4D5. Unexpectedly we found that IFN-β dramatically reduced Snail, even in the absence of 4D5 treatment (FIG. 57A). Surprisingly, we found that IFN-β was cytotoxic to tumor cells even at small doses in the absence of 4D5 (FIG. 57C). IFN-γ treatment of MCF10A cells caused minimal changes to cell viability, whereas even low doses of IFN-β were cytotoxic to these cells (FIG. 57B). In vivo studies also failed to determine effects of IFN-α and anti-erbB2 mAb (data not shown). Therefore, we believe that under these conditions only IFN-γ acts to complete phenotypic reversion engendered by anti-erbB2 mAb therapy.

Reduction of Snail Protein is Triggered by Elevated GSK3-β and Occurs Primarily Through Altered Proteasome-Mediated Degradation Snail is predominantly degraded through the proteasome and, to a lesser extent, the lysosome. We initially tested the role of GSK3-β using the small molecule inhibitor. Inhibition of GSK3-β in the presence of the co-treatment regimen resulted in a dose-dependent rescue of Snail but produced no change in Slug content (FIG. 58A). Proteasome inhibitor MG-132 inhibited the co-treatment mediated reduction of Snail in a dose-dependent manner, also with no change in Slug content (FIG. 58B). Conversely, inhibition of lysosomal function with chloroquine was not able to rescue the 4D5 and IFN-γ-mediated degradation of Snail. Therefore, we conclude that 4D5 and IFN-γ-mediated Snail degradation is mediated primarily through the proteasome.

Next we examined direct effect of snail decrease by this ordered treatment in GSK3-β knockdown cells. Although GSK3-β was knockdowned in SK-BR3 cells by shRNA vectors, snail expression was still significantly decreased.

We consider other pathways are also affected by snail functions. Moral and colleagues (Moral et al., 2009) reported that KLF4 expression patterns were increased in tumor samples from mice with hyper-activated Akt. We examined the effects of ordered and combined targeting antibody and IFN-γ on KLF4 levels in SK-BR-3 cells stably transfected with GSK3-β shRNA. The ability to alter Snail functions was directly linked to KLF4 levels and GSK3-β.

Since treatment with 4D5 and IFN-γ activated GSK3-β and active GSK3-β promotes Snail degradation, expression of a version of Snail with the GSK3-β phosphorylation sites mutated to alanines should prevent this degradation. We transiently expressed empty vector (EV), HA-tagged Snail wild type (WT) (Kajita et al., 2004), and HA-tagged Snail with serines 97, 101, 108, 112, 116, and 120 mutated to alanine (6SA) (Zhou et al., 2004) in SK-BR-3 cells. Exogenous WT Snail was degraded whereas 6SA Snail was largely resistant to 4D5 and IFN-γ-induced proteasomal degradation in the nuclear fraction (FIG. 58C). In cells transfected with the EV control, we observed Snail in the cytoplasm only when the cells were treated with both 4D5 and IFN-γ (FIG. 58C) indicating that both treatments are required for Snail translocation to the cytoplasm. In addition, Snail knock down in SK-BR-3 cells increases the effects of 4D5 targeted therapy on anchorage dependent cell growth patterns. These results indicate that snail degradation that are promoted by 4D5 plus IFN-γ ordered treatment occurs through the GSK3-β/proteasome pathway, and decreasing Snail levels are important for targeted therapy.

Effects of mAb and IFN-γ In Vivo: Ordered Combinations Reduce the Need for Large Amounts of Targeting mAb mAb 7.16.4 is biologically active in vivo and in vitro. In vitro mAb 7.16.4 is active against cells transformed with the rat or human erbB2/neu oncogene and disables the p185erbB2/neu kinase leading to diminished downstream p185erbB2/neu signaling (Drebin et al., 1986; Zhang et al., 1999). We as well as others examined various optimized doses of anti-erbB2/neu mAb therapy. Five mg/kg of 7.16.4 mAb have been used intravenously (Drebin et al., 1986) and/or on every other day intraperitoneally in therapeutic studies of tumor growth (Du et al., 2013; Stagg et al., 2011).

We examined if reduced amounts of mAb could be used if IFN-γ was provided after therapy was initiated. As shown in FIG. 59A, when entirely syngeneic MMTV-neu transgenic mice were treated with a sub-optimal dose of 7.16.4 (1.5 mg/kg), the mAb was unable to substantially inhibit the growth of H2N113 tumors. IFN-γ treatment alone also failed to significantly inhibit tumor growth. However, the combination of suboptimal amounts of 7.16.4 and IFN-γ completely arrested the growth of H2N113 tumors. Importantly, the pattern of the data in FIG. 59A was reminiscent of the in vitro tumor cell proliferation kinetics in FIG. 59B. Finally, histologic examination of the tumor tissues after treatment revealed significant necrosis only in mice treated with both 7.16.4 and IFN-γ.

To examine if IFN-γ was targeted to tumor cells directly or to host elements in the vicinity of the tumor, we limited the expression of the IFN-γ receptor on these tumor cells. Using shRNA, we created an IFN-γ receptor knockdown species of the H2N113 cell line: H2N113 (IFNγR KD) (FIG. 59B). The reduced expression level of IFN-γ receptor was confirmed in several distinct ways. IFNγRKD tumor cells form progressively growing tumors. Nevertheless treatment with suboptimal mAb doses generated only a modest growth reduction of IFNγRKD tumor growth (FIG. 59B). IFN-γ had no effect on its own against tumors that had diminished IFN-γ receptor levels.

Ordered Therapy Also Affects Myeloid Derived Suppressor Cells

Myeloid-derived suppressor cells (MDSC) are phenotypically CD45+, CD11b+ and GR-1+. Co-treatment with sub optimal 7.16.4 and IFN-γ led to reduction of MDSC populations invading tumor tissues (FIG. 59C). We noted that there were limited but comparable numbers of Foxp3 cells in control and treated animals.

Since we have determined that both mAb and IFN-γ must interfere with tumor cells directly, we evaluated chemo-attractant effects of molecules elaborated by tumor cells on MDSC that might be affected by the combined treatment. MDSC isolated from the spleen of tumor-bearing mice were placed into the apical chamber of a transwell system. Conditioned medium from H2N113 cells treated directly with mAb, IFN-γ or their combinations were tested for their ability to attract MDSC cells to migrate into the basolateral chamber. As shown in FIG. 59D, 7.16.4 alone slightly reduced the tumor-promoted migration, but cotreatment of the tumor cells with 7.16.4 and IFN-γ blocked MDSC migration. IFN-γ alone had no appreciable effects.

Enhanced Role for IFN Type II Signals in erbB Cytolytic Immune Responses.

Several researches suggested a role for T cells (Park et al., 2010; Stagg et al., 2012; Stagg et al., 2011) in some component of the host response to 7.16.4 monoclonal antibody. We used suboptimal mAb and IFN-γ in syngeneic systems and collected effector CD8+ T cells from each treatment group to investigate their activity against H2N113 cells. The combination therapy group showed modest but definite effector T cells activity against p185erbB2/neu positive tumors. IFN-γ alone had negligible effects. These data support the notion that minor antigens become more relevant when we use mAb and IFN-γ ordered therapy.

Macrophages may contribute to the effector response. Two types of functional macrophages have been proposed to infiltrate the tumor microenvironment and such invasion is promoted by molecules elaborated directly or indirectly by tumor cells. We examined tumors for invading antiinflammatory, pro-tumor M2 and pro-inflammatory, cytolytic anti-tumor M1 types. mAb 7.16.4 and IFN-γ increased M1 cell accumulation within adjacent areas of the tumor, and animals treated with this combination therapy had the highest M1 frequency.

Based on these data we suggest that immune regulation is affected indirectly by the dominant effect of mAb and IFN-γ on the tumor itself. Ordered therapy reduces tissue and immune regulatory cell activity in the microenvironment and this reduction is permissive for effector T cells to act on phenotype reversed tumor cells.

In Vivo Evidence of Modification of Stem Cell Characteristics by mAb and IFN-γ.

Molecular analyses in vitro revealed that the ordered treatment of breast tumor cells with anti-erbB2/neu mAb and IFN-γ diminished expression of Snail proteins, which mediates stem cell like properties. ALDH1 expression patterns also define cancer stem cell phenotypes, and its expression correlates with breast cancer prognostic features (Douville et al., 2009; Ginestier et al., 2007). We compared tumors at the end of treatment for ALDH1 levels. Co-treatment with 7.16.4 and IFN-γ treatment reduced the expression of ALDH1 in p185erbB2/neu tumors (FIG. 59E).

Growing tumor cells were also studied for expression patterns of Snail. We noted a reduced level of Snail protein in tumors undergoing eradication as a consequence of mAb and IFN-γ therapy in vivo (FIG. 59E). These studies directly correlate with in vitro findings described in FIG. 54A-FIG. 54D examining anchorage dependent and independent effects of combinations of anti erbB mAb and IFN-γ.

Ordered mAb and IFN-γ Therapy can Prevent Breast Cancer Tumorigenesis and Synergistically Inhibits Tumor Growth with Chemotherapy.

To determine if these therapeutic effects were relevant to prevention of tumor development (adjuvant use of this combination) we chose to examine a model we have previously described, using small tumor inocula. We examined the effects of treatment of MMTV-neu female mice with combinations of 7.16.4 and 7.9.5 mAb, with or without IFN-γ, in animals implanted with small tumor inocula to mimic incipient tumors. We noted a dramatic reduction when IFN-γ was incorporated in the treatment protocol. As can be seen in FIG. 59F, we were able to limit tumor growth in this prevention model with minimal amounts of dual targeting mAb. These studies indicate that animals treated with ordered therapy of mAb and IFN-γ can mount potent intrinsic cytotoxic elimination of small numbers of incipient tumor cells. These data support previous studies showing a delayed emergence of tumors when mAb specific for erbB2/neu was used as an adjuvant therapy in mouse prevention studies (Finkle et al., 2004; Katsumata et al., 1995)

To extend these studies to a clinical context, we added docetaxel in subtherapeutic quantities to evaluate if potent tumor inhibition with small amounts of phenotype reversing mAb would also limit the required genotoxic amounts of currently employed chemotherapy (FIG. 59G). Treatment with 7.16.4 followed by IFN-γ and docetaxel led to inhibition of tumor growth compared with other groups despite using suboptimal doses of both anti erbB antibody and chemotherapy. Our conclusion is that optimizing phenotype reversion represents a critical element the evolution of precision drug therapy of breast carcinoma.

IFN-γ Dramatically Promotes Tumor PD-L1 Expression and which Represents a Target for Tumor Therapy.

We observed aggressive tumor growth with IFN-γ alone treated mice. This is also consistent with why IFN-γ alone is not useful for cancer therapy (Zaidi and Merlino, 2011). Stagg and colleagues showed treatment with IFN-γ induces PDL1 expression (Stagg et al., 2011). It is possible that PD-L1 acts as a negative immune regulator induced by IFN-γ treatment alone. As shown in FIG. 60A, IFN-γ dramatically induced PD-L1 expression in IFN-γ treated tumor tissues. FACS analysis showed this up-regulation also occurs in tumor cells themselves (FIG. 60B). To determine if PD-L1 can be further targeted for this ordered therapy, we used anti-PD-L1 antibody along with 7.16.4 and IFN-γ. As expected, administration of anti-PD-L1 antibody with 7.16.4 and IFN-γ caused the most significant tumor regression in those groups (FIG. 60C). These results indicate that PD-L1 represents an additional target when used with mAb and IFN-γ ordered therapy.

Discussion

Therapeutics that target p185erbB2/HER2/neu are effective for restraining human malignant disease but are rarely curative. Disabling of the p185erbB2/neu kinase complex leads to phenotypic reversal of malignant properties, but is incomplete and subject to further modification (Drebin et al., 1986; Lee et al., 2012; O'Rourke et al., 1997; Wada et al., 1990). This phenotypic state is more sensitive to genotoxic damage by chemotherapeutic and radiation effects, or immune mediated lytic processes. Our studies identified a second transition process that occurs after mAb-mediated down-regulation of p185erbB2/neu proteins from the cell surface, which can be induced by IFN-γ. This transition involves a role of transcription factors such as Snail known to be relevant to cancer stem cell features. IFN-γ alone, without the first reversion step is ineffective in being able to induce a malignant phenotype reversion or change in Snail levels.

We describe a dramatic and almost complete arrest of tumor growth even with suboptimal doses of anti-erbB2/neu mAb when IFN-γ is included and in vivo. Because IFN-γ enhances antibody effects at very low doses, this approach may improve targeted therapy effectiveness in tissues where only low levels of antibody might penetrate. Dramatic tumor inhibitory effects can be also accomplished with minimal amounts of targeting mAb and IFN-γ followed by chemotherapeutics (docetaxel). These studies identify a benefit of this rational approach to precision medicine that will be accompanied by lessened toxicity during tumor treatment.

The effect of mAb and IFN-γ are a consequence of phenotypic reversal changes on the tumor itself as well as effects of IFN-γ on host elements. The synergistic effects of mAb and IFN-γ were lost when tumor cells with reduced IFN-γ receptor levels were targeted. At the microenvironment level, we noticed a reduction of regulatory cells that limit immune reactions by suppressing functions of immune cells. Tumor elaborated chemo-attractants which recruit regulatory cells were diminished upon ordered treatment of tumor cells with mAb and then IFN-γ. We have been unable to document any comparable phenotypic activity in the well established models we use, when IFN-α or IFN-β were used (in vivo or in vitro respectively) rather than IFN-γ.

Contributions of regulatory MDSC cells in the local tumor environment may be important in limiting immune elimination of breast tumors and their activity is diminished with ordered mAb and IFN-γ therapy. Enhanced accumulation of M1 type macrophages in the local tumor environment in situations using combined mAb and IFN-γ therapy were observed. Modest enhancement of cytolytic T cells active against erbB2 tumors was also noted. Together these data support an observable contributory role for the immune system in targeted therapy and a role for IFN-γ in enhancing immune eradication of erbB tumors that have undergone phenotype reversal. ALDH1 is diminished in tumor cells treated in vivo with combined mAb and IFN-γ therapy. Elevation of ALDH1 enzyme levels correspond to erlotinib resistance in erbB1 (EGFR) mutated human tumors (Corominas-Faja et al., 2013). Thus metabolic changes occur within tumor cells with stem cell like properties, that are amenable to manipulation by phenotypic reversion best promoted by anti-p185erbB2/neu mAb and by IFN-γ. Consequently, tumor tissues should be examined diagnostically for expression of IFN-γ receptor and aldolase in situations in which targeted therapy might be administered.

IFN-γ is a cytokine which is considered to activate anti-tumor immunity with its cytostatic/cytotoxic activities. However, there are few IFN-γ defined beneficial outcomes clinically when used alone. Thus, clinical efforts using IFN-γ as a primary single therapeutic for most malignancies have not been pursued (Krigel et al., 1985). We found, as has been reported by others that IFN-γ treatment increases PD-L1 expression in the tumor tissues and cells. The PD-1/PD-L1 pathways along with CTLA-4 represent elements of a checkpoint pathway and contribute to regulating tumor immunity (Ott et al., 2013). Interestingly the fact that PD-L1 expression is increased by IFN-γ in tumor site/cells may be relevant to the success of ordered therapy. Combining targeted therapy with immune therapy in an ordered way can lead to a greatly reduced need for the mAb components and the genotoxic chemotherapeutics needed to treat humans with erbB caused cancers.

Experimental Procedures

Lysate Preparation and Western Blotting

Cells were lysed in a RIPA-based buffer with protease inhibitors (Roche Diagnostics) and used for Western blot.

MTT Assays

Cells were seeded and treated the following day (Day 0). Treated cells were grown for the indicated times; and on the day of the assay MTT (3-[4,5-dimethylthiazol-2-yl]-2,5 diphenyl tetrazolium bromide) reagent was added and values were determined by absorbance at 570 nm on a plate reader (Tecan).

Soft Agar Growth Assays

Plates were coated with agarose mixed with DMEM. Cells were overlaid on the bottom layer in an agarose (final agarose concentration of 0.2%) DMEM mixture supplemented with the indicated therapeutic treatment. After two weeks, viable foci were visualized with MTT reagent. Each well was imaged using an Alpha Imager, and foci size was determined using NIH-endorsed ImageJ software.

Mouse In Vivo Experiments 6-10 weeks old female MMTV-neu mice were used for this set of experiments. For the in vivo treatment model, a rodent erbB2/neu transformed Balb/c breast tumor cell line, H2N113 (1×106), was injected subcutaneously into both sides of the back of mice. Tumor size was measured with a digital caliper and calculated using a simple algorithm (3.14×length×wide×height÷6.)

Flow Cytometry

At 1 day after final treatment, spleens and tumors were collected and single cell suspensions made. Cell surface antigens were stained with the antibodies indicated. Cells were analyzed with FACS LSR (BD Biosciences) and FACS data were analyzed with FlowJo software (Tree Star, Ashland, Oreg.).

MDSC Migration Assay

To prepare conditioned medium, H2N113 cells were seeded and cultured until sub-confluent in culture. Cells were then treated with 7.16.4 and/or IFN-γ at indicated concentrations for 3 days. Then the supernatants were collected for the migration assay. Migration of MDSC was measured by the Transwell system (pore size: 4 μm, Corning). After 3 hr incubations at 37° C., the cells that migrated to bottom layers were collected and subjected to flow cytometry.

Statistical Consideration

When applicable, statistical analysis was performed by Student's t-test using Microsoft Excel. At a minimum, data with a p-value <0.05 were deemed significant. In all cases, experiments shown are representatives that were performed at least twice.

Discussion

Unlike non-transformed replicating cells which can be killed by exposure to therapeutic radiation or chemotherapy, tumor cells are resistant to induction of cell death by radiation and chemotherapy. It has been discovered that by disrupting the multimeric ensembles which produce elevated kinase activity associated with the transformed phenotype of a cancer cell, such a cancer cell, which is ordinarily resistant to radiation or chemotherapy induced cell death, becomes sensitive to radiation. Accordingly, one aspect of the present invention provides methods of making radiation or chemotherapy-resistant cancer cells radiation or chemotherapy-sensitive. The present invention relates to methods of treating an individual who has cancer cells that have multimeric receptor ensembles comprising p185her2/neu or EGFR which provide kinase activity associated with a transformed phenotype. The method comprises the step of first administering to the subject a composition that disrupts the kinase activity associated with the multimeric receptor ensemble. The composition may also inhibit the attraction of immune suppressor cells by cancer cells. The subject is then treated with radiation or a chemotherapeutic agent.

There are several known receptor ensembles which, in cancer cells, display elevated kinase activity that is associated with the transformed phenotype. Members of the erbB family of receptors are known to form multimeric ensembles which result in elevated tyrosine kinase activity in tumor cells. Multimeric ensembles involving erbB family members include erbB homodimers as well as erbB heterodimers comprising monomeric components from different erbB family members. Multimeric receptor ensembles of platelet derived growth factor receptors (PDGFR) also display elevated kinase activity that is associated with the transformed phenotype.

The present invention is useful to therapeutically treat an individual identified as suffering from erbB-associated tumors, such as neu-associated tumors, in order to reverse the transformed phenotype of the tumor cells. The present invention is useful to prophylactically treat an individual who is predisposed to develop erbB-associated tumors or who has had erbB-associated tumors and is therefore susceptible to a relapse or recurrence.

According to one aspect of the present invention, dimer formation of erbB proteins in erbB mediated cancer cells is disrupted to render such cells more susceptible to cell destruction using radiation or chemotherapy. The ability of the cancer cells to attract immune suppressor cells may also be disrupted to render such cells more susceptible to cell destruction using radiation or chemotherapy. Accordingly, combination therapies are provided that comprise first administering to an individual a composition which comprises an active agent that results in interference of erbB dimerization, and interferon-gamma, followed by exposing the subject to therapeutic amounts of radiation or administering to the patient a therapeutic amount of a chemotherapeutic agent. According to these aspects of the invention, methods for treating individuals who have an erbB protein mediated tumor are provided.

In some tumor cells, the p185her2/neu translation product of c-erbB2 gene is overexpressed and forms homodimers and heterodimers with other erbB family members. Such dimerization of overexpressed p185her2/neu leads to elevated tyrosine kinase activities which is associated with the transformed phenotype. Disruption of tyrosine kinase activity, such as by inhibiting dimer formation between monomeric components, results in a cytostatic effect on the tumor cells. The disruption also renders the previously resistant cancer cells radiation-sensitive and chemoptherapy-sensitive.

Similarly, in some tumor cells, a mutant form of EGFR (AEGFR) is expressed which is ligand-independent. AEGFR forms homodimers and heterodimers with wild-type EGFR and other erbB family members. Such dimerization of AEGFR leads to elevated tyrosine kinase activities which is associated with the transformed phenotype. Disruption of tyrosine kinase activity, such as by inhibiting dimer formation between monomeric components, results in a cytostatic effect on the tumor cells. This disruption also renders the previously resistant cancer cells radiation-sensitive and chemoptherapy-sensitive.

In some embodiments, the erbB-protein mediated tumor is a brain cancer tumor. In some preferred embodiments, the erbB-protein mediated tumor is a glial tumor. In some preferred embodiments, the erbB-protein mediated tumor is a glioblastoma. In some embodiments, the erbB-protein mediated tumor is a breast cancer tumor. In some embodiments, the erbB-protein mediated tumor is an ovarian cancer tumor. In some embodiments, the erB-protein mediated tumor is a pancreatic cancer tumor.

As described and exemplified herein, IFN-gamma (IFNγ) in combination with an antibody against p185her2/neu leads to a much more effective treatment for erbB2/Her2/neu cancers than IFN-gamma or the antibody when administered singly. The present invention provides clinical applications using currently available IFN-gamma together with anti-ErbB antibodies (e.g, Herceptin, Pertuximab, or Erbitux, etc).

The activity of IFNγ in combination with an anti-p185her2/neu or an anti-EGFR antibody is profoundly enhanced. The significant effect described herein is surprising.

When administered singly, IFNγ has no significant activity. The examples herein show that it has little or no effect on the proliferation of cancer cells. As a monotherapy, IFNγ is not effective for treating subjects afflicted with cancer. Surprisingly, the combination of IFNγ with an anti-ErbB antibody has enhanced activity on cancer cells. Additionally, the combination of IFNγ with an anti-p185her2/neu antibody or an anti-EGFR antibody increases the sensitivity of cancer cells to radiation therapy and chemotherapy.

In Example 2, IFNα appears to have anti-tumor activity when administered as a monotherapy in an in vivo tumor model, but the combination of IFNα and an anti-p185her2/neu antibody does not have significantly enhanced activity. Without wishing to be bound by any scientific theory, it appears that IFNα behaves differently from IFNγ when administered as a monotherapy or in combination with an anti-p185her2/neu antibody.

Aspects of the present invention relate to the surprising discovery that the combination of IFNγ with an anti-p185her2/neu or an anti-EGFR antibody has profoundly enhanced activity, and has enhanced efficacy for treating cancer. In some embodiments the combination of IFNγ with an anti-p185her2/neu or an anti-EGFR antibody increases sensitivity of cancer cells to a chemotherapeutic agent or radiation.

The action of the 4d5 construct on tumor cells in vitro, as shown in the Examples, suggests that a dominant phenotype is induced with altered growth and reduced snail expression. In some embodiments, there is an intrinsic stem cell like phenotype that is inhibited by the actions of IFNγ after the malignant phenotype is reversed by disabling the receptor kinase. Without wishing to be bound by any scientific theory, an ordered disabling needed; first with the anti-p185her2/neu or an anti-EGFR antibody or with a kinase inhibitor of p185her2/neu or EGFR, resulting in a phenotype which is more normalized, i.e. less malignant. The resultant phenotype which is more normalized can then be acted on by the IFNγ. The IFNγ disables the stem cell like features of this more normalized transformed cell. Accordingly, aspects of the invention are useful both for the prevention of tumor development, and for cancer treatment.

Without wishing to be bound by any scientific theory, in some embodiments the intent of treatment is to sensitize cells by conversion of phenotype. In the first event the anti-p185her2/neu or an anti-EGFR antibody disables the p185her2/neu or EGFR kinase making the cells amenable to further phenotypic change by IFNγ which renders them more able to be damaged by genotoxic signals.

Snail and Slug Data Shown in FIG. 11-FIG. 13

Epithelial to mesenchymal transition (EMT) is believed to be a critical determinant of breast cancer progression. Cells that have undergone EMT share features of cancer stem cells (Mani et al., 2008) such as resistance to therapy (Korkaya et al., 2012) and evasion of the host immune system (Akalay et al., 2013). EMT is mediated by a group of transcription factors including Snail, Slug, Twist, and ZEB1, which are collectively known as the master regulators of EMT. Snail is a well-established critical determinant of breast cancer EMT and metastasis and its regulation at the post-translational level is believed to be critical to breast cancer progression. Therefore, treatment strategies that accelerate and/or maintain the degradation of Snail or Slug (or both) would be adventitious because they would reverse the phenotype of a dedifferentiated or stem-like cell to a more differentiated cell. The biological significance of this is these cells would then be more sensitive to genotoxic insults.

Aspects of the present invention relates to the discovery that co-administration of IFNγ and an anti-ErbB antibody accelerates and/or maintains the degradation of Snail or Slug (or both) in cells that are not malignant. Some embodiments of the present invention relate to first treating a subject with IFNγ and an anti-ErbB antibody or a fusion protein of the invention to increase the sensitivity of cancer cells, and of cells that have undergone EMT, to chemotherapy or radiation, and then administering chemotherapy or radiation to the subject.

REFERENCES

Argiris, A., Wang, C. X., Whalen, S. G., and DiGiovanna, M. P. (2004). Synergistic interactions between tamoxifen and trastuzumab (Herceptin). Clin Cancer Res 10, 1409-1420.

Balachandran, S. & Adams, G. P. Interferon-gamma-induced necrosis: an antitumor biotherapeutic perspective. Journal of interferon & cytokine research: the official journal of the International Society for Interferon and Cytokine 33, 171-180 (2013).

Baselga, J., Albanell, J., Molina, M. A. & Arribas, J. Mechanism of action of trastuzumab and scientific update. Semin Oncol 28, 4-11 (2001).

Beatty, G. L., and Paterson, Y. (2000). IFN-gamma can promote tumor evasion of the immune system in vivo by down-regulating cellular levels of an endogenous tumor antigen. Journal of immunology 165, 5502-5508.

Bekisz, J., et al. Immunomodulatory effects of interferons in malignancies. Journal of interferon & cytokine research: the official journal of the International Society for Interferon and Cytokine 33, 154-161 (2013).

Beurel, E., and Jope, R. S. (2009). Glycogen synthase kinase-3 promotes the synergistic action of interferon-gamma on lipopolysaccharide induced IL-6 production in RAW264.7 cells. Cell Signal 21, 978-985.

Blaschke, K., Ebata, K. T., Karimi, M. M., Zepeda-Martinez, J. A., Goyal, P., Mahapatra, S., Tam, A., Laird, D. J., Hirst, M., Rao, A., et al. (2013). Vitamin C induces Tet-dependent DNA demethylation and a blastocyst-like state in ES cells. Nature 500, 222-226.

Cai Z, Fu T, Nagai Y, Lam L, Yee M, Zhu Z, Zhang H. scFv-Based "Grababody" as a General Strategy to Improve Recruitment of Immune Effector Cells to Antibody-Targeted Tumors. Cancer Res. 2013; 73(8):2619-2627. PMCID: 3630244.

Carver, E. A., Jiang, R., Lan, Y., Oram, K. F., and Gridley, T. (2001). The mouse snail gene encodes a key regulator of the epithelial-mesenchymal transition. Mol Cell Biol 21, 8184-8188.

Chaffer, C. L., Brueckmann, I., Scheel, C., Kaestli, A. J., Wiggins, P. A., Rodrigues, L. O., Brooks, M., Reinhardt, F., Su, Y., Polyak, K., et al. (2011). Normal and neoplastic nonstem cells can spontaneously convert to a stem-like state. Proc Natl Acad Sci USA 108, 7950-7955.

Cicalese, A., Bonizzi, G., Pasi, C. E., Faretta, M., Ronzoni, S., Giulini, B., Brisken, C., Minucci, S., Di Fiore, P. P., and Pelicci, P. G. (2009). The tumor suppressor p53 regulates polarity of self-renewing divisions in mammary stem cells. Cell 138, 1083-1095.

Clynes, R. A., Towers, T. L., Presta, L. G. & Ravetch, J. V. Inhibitory Fc receptors modulate in vivo cytotoxicity against tumor targets. Nature medicine 6, 443-446 (2000).

Corominas-Faja, B., et al. Stem cell-like ALDH(bright) cellular states in EGFR-mutant non-small cell lung cancer: a novel mechanism of acquired resistance to erlotinib targetable with the natural polyphenol silibinin. Cell Cycle 12, 3390-3404 (2013).

Cortes, J., Fumoleau, P., Bianchi, G. V., Petrella, T. M., Gelmon, K., Pivot, X., Verma, S., Albanell, J., Conte, P., Lluch, A., et al. (2012). Pertuzumab monotherapy after trastuzumab-based treatment and subsequent reintroduction of trastuzumab: activity and tolerability in patients with advanced human epidermal growth factor receptor 2-positive breast cancer. J Clin Oncol 30, 1594-1600.

Coughlin, C. M., Salhany, K. E., Gee, M. S., LaTemple, D. C., Kotenko, S., Ma, X., Gri, G., Wysocka, M., Kim, J. E., Liu, L., et al. (1998). Tumor cell responses to IFNgamma affect tumorigenicity and response to IL-12 therapy and antiangiogenesis. Immunity 9, 25-34.

Cross, D. A., Alessi, D. R., Cohen, P., Andjelkovich, M., and Hemmings, B. A. (1995). Inhibition of glycogen synthase kinase-3 by insulin mediated by protein kinase B. Nature 378, 785-789.

Douville, J., Beaulieu, R. & Balicki, D. ALDH1 as a functional marker of cancer stem and progenitor cells. Stem cells and development 18, 17-25 (2009).

Drebin J A, Link V C, Weinberg R A, Greene M I. Inhibition of tumor growth by a monoclonal antibody reactive with an oncogene-encoded tumor antigen. Proc Natl Acad Sci USA. 1986; 83(23):9129-9133.

Drebin J A, Stern D F, Link V C, Weinberg R A, Greene M I. Monoclonal antibodies identify a cell-surface antigen associated with an activated cellular oncogene. Nature. 1984; 312(5994):545-548.

Drebin, J. A., Link, V. C., and Greene, M. I. (1988a). Monoclonal antibodies reactive with distinct domains of the neu oncogene-encoded p185 molecule exert synergistic anti-tumor effects in vivo. Oncogene 2, 273-277.

Drebin, J. A., Link, V. C., and Greene, M. I. (1988b). Monoclonal antibodies specific for the neu oncogene product directly mediate anti-tumor effects in vivo. Oncogene 2, 387-394.

Drebin, J. A., Link, V. C., Stern, D. F., Weinberg, R. A., and Greene, M. I. (1985). Down-modulation of an oncogene protein product and reversion of the transformed phenotype by monoclonal antibodies. Cell 41, 697-706.

Du T, Nagai Y, Xiao Y, Greene M I, Zhang H. Lysosome-dependent p300/FOXP3 degradation and limits T cell functions and enhances targeted therapy against cancers. Exp Mol Pathol. 2013; 95(1):38-45.

Ernstoff, M. S., et al. A randomized phase I/II study of continuous versus intermittent intravenous interferon gamma in patients with metastatic melanoma. Journal of clinical oncology: official journal of the American Society of Clinical Oncology 5, 1804-1810 (1987).

Feinberg, M. W., Cao, Z., Wara, A. K., Lebedeva, M. A., Senbanerjee, S., and Jain, M. K. (2005). Kruppel-like factor 4 is a mediator of proinflammatory signaling in macrophages. The Journal of biological chemistry 280, 38247-38258.

Finkle, D., Quan, Z. R., Asghari, V., Kloss, J., Ghaboosi, N., Mai, E., Wong, W. L., Hollingshead, P., Schwall, R., Koeppen, H., and Erickson, S. (2004). HER2-targeted therapy reduces incidence and progression of midlife mammary tumors in female murine mammary tumor virus huHER2-transgenic mice. Clinical cancer research: an official journal of the American Association for Cancer Research 10, 2499-2511.

Furuuchi, K., Berezov, A., Kumagai, T., and Greene, M. I. (2007). Targeted antireceptor therapy with monoclonal antibodies leads to the formation of inactivated tetrameric forms of ErbB receptors. J Immunol 178, 1021-1029.

Ginestier, C., et al. ALDH1 is a marker of normal and malignant human mammary stem cells and a predictor of poor clinical outcome. Cell Stem Cell 1, 555-567 (2007).

Greenberg A H, Greene M. Non-adaptive rejection of small tumour inocula as a model of immune surveillance. Nature. 1976; 264(5584):356-359.

Guo, W., Keckesova, Z., Donaher, J. L., Shibue, T., Tischler, V., Reinhardt, F., Itzkovitz, S., Noske, A., Zurrer-Hardi, U., Bell, G., et al. (2012). Slug and Sox9 cooperatively determine the mammary stem cell state. Cell 148, 1015-1028.

Hamburger, A. W., and Pinnamaneni, G. D. (1991). Increased epidermal growth factor receptor gene expression by gamma-interferon in a human breast carcinoma cell line. British journal of cancer 64, 64-68.

Hanker, A. B., Pfefferle, A. D., Balko, J. M., Kuba, M. G., Young, C. D., Sanchez, V., Sutton, C. R., Cheng, H., Perou, C. M., Zhao, J. J., et al. (2013). Mutant PIK3CA accelerates HER2-driven transgenic mammary tumors and induces resistance to combinations of anti-HER2 therapies. Proc Natl Acad Sci USA 110, 14372-14377.

Hudis, C. A. Trastuzumab—mechanism of action and use in clinical practice. The New England journal of medicine 357, 39-51 (2007).

Hurvitz, S. A., et al. Analysis of Fcgamma Receptor IIIa and IIa Polymorphisms: Lack of Correlation with Outcome in Trastuzumab-Treated Breast Cancer Patients. Clinical cancer research: an official journal of the American Association for Cancer Research 18, 3478-3486 (2012).

Junttila, T. T., et al. Superior in vivo efficacy of afucosylated trastuzumab in the treatment of HER2-amplified breast cancer. Cancer research 70, 4481-4489 (2010).

Kajita, M., McClinic, K. N., and Wade, P. A. (2004). Aberrant expression of the transcription factors snail and slug alters the response to genotoxic stress. Mol Cell Biol 24, 7559-7566.

Katsumata M, Okudaira T, Samanta A, Clark D P, Drebin J A, Jolicoeur P, Greene M I. Prevention of breast tumour development in vivo by downregulation of the p185neu receptor. Nature medicine. 1995; 1(7):644-648.

Kiessling, R., et al. Cellular immunity to the Her-2/neu protooncogene. Advances in cancer research 85, 101-144 (2002).

Kokai, Y., Myers, J. N., Wada, T., Brown, V. I., LeVea, C. M., Davis, J. G., Dobashi, K., and Greene, M. I. (1989). Synergistic interaction of p185cneu and the EGF receptor leads to transformation of rodent fibroblasts. Cell 58, 287-292.

Korkaya, H., Paulson, A., Iovino, F., and Wicha, M. S. (2008). HER2 regulates the mammary stem/progenitor cell population driving tumorigenesis and invasion. Oncogene 27, 6120-6130.

Krigel, R. L., Odajnyk, C. M., Laubenstein, L. J., Ostreicher, R., Wernz, J., Vilcek, J., Rubinstein, P., and Friedman-Kien, A. E. (1985). Therapeutic trial of interferon-gamma in patients with epidemic Kaposi's sarcoma. J Biol Response Mod 4, 358-364.

Lam L, Czerniecki B, Fitzpatrick E, Xu S, Schuchter L, Xu X, Zhang H. Interference-Free HER2 ECD as a Serum Biomarker in Breast Cancer. J Mol Biomark Diagn. 2013; 4(151):2. NIHMS #583957.

Lee, M. J., Ye, A. S., Gardino, A. K., Heijink, A. M., Sorger, P. K., MacBeath, G., and Yaffe, M. B. (2012). Sequential application of anticancer drugs enhances cell death by rewiring apoptotic signaling networks. Cell 149, 780-794.

Lian, X., Hsiao, C., Wilson, G., Zhu, K., Hazeltine, L. B., Azarin, S. M., Raval, K. K., Zhang, J., Kamp, T. J., and Palecek, S. P. (2012). Robust cardiomyocyte differentiation from human pluripotent stem cells via temporal modulation of canonical Wnt signaling. Proc Natl Acad Sci USA 109, E1848-1857.

Lian, X., Zhang, J., Azarin, S. M., Zhu, K., Hazeltine, L. B., Bao, X., Hsiao, C., Kamp, T. J., and Palecek, S. P. (2013). Directed cardiomyocyte differentiation from human pluripotent stem cells by modulating Wnt/beta-catenin signaling under fully defined conditions. Nat Protoc 8, 162-175.

Lodato, R. F., Maguire, H. C., Jr., Greene, M. I., Weiner, D. B., and LiVolsi, V. A. (1990). Immunohistochemical evaluation of c-erbB-2 oncogene expression in ductal carcinoma in situ and atypical ductal hyperplasia of the breast. Mod Pathol 3, 449-454.

Marth, C., Muller-Holzner, E., Greiter, E., Cronauer, M. V., Zeimet, A. G., Doppler, W., Eibl, B., Hynes, N. E., and Daxenbichler, G. (1990). Gamma-interferon reduces expression of the protooncogene c-erbB-2 in human ovarian carcinoma cells. Cancer Res 50, 7037-7041.

Meric-Bernstam, F. & Hung, M. C. Advances in targeting human epidermal growth factor receptor-2 signaling for cancer therapy. Clinical cancer research: an official journal of the American Association for Cancer Research 12, 6326-6330 (2006).

Miller, C. H., Maher, S. G. & Young, H. A. Clinical Use of Interferon-gamma. Annals of the New York Academy of Sciences 1182, 69-79 (2009).

Mizuno, H., Spike, B. T., Wahl, G. M., and Levine, A. J. (2010). Inactivation of p53 in breast cancers correlates with stem cell transcriptional signatures. Proc Natl Acad Sci USA 107, 22745-22750.

Montesano, R., Drevon, C., Kuroki, T., Saint Vincent, L., Handleman, S., Sanford, K. K., DeFeo, D., and Weinstein, I. B. (1977). Test for malignant transformation of rat liver cells in culture: cytology, growth in soft agar, and production of plasminogen activator. Journal of the National Cancer Institute 59, 1651-1658.

Moody, S. E., Perez, D., Pan, T. C., Sarkisian, C. J., Portocarrero, C. P., Sterner, C. J., Notorfrancesco, K. L., Cardiff, R. D., and Chodosh, L. A. (2005). The transcriptional repressor Snail promotes mammary tumor recurrence. Cancer Cell 8, 197-209.

Moral, M., Segrelles, C., Martinez-Cruz, A. B., Lorz, C., Santos, M., Garcia-Escudero, R., Lu, J., Buitrago, A., Costa, C., Saiz, C., et al. (2009). Transgenic mice expressing constitutively active Akt in oral epithelium validate KLFA as a potential biomarker of head and neck squamous cell carcinoma. In vivo 23, 653-660.

Mortenson, E. D., Park, S., Jiang, Z., Wang, S. & Fu, Y. X. Effective anti-neuinitiated antitumor responses require the complex role of CD4+ T cells. Clinical cancer research: an official journal of the American Association for Cancer Research 19, 1476-1486 (2013).

Natarajan, V. T., Ganju, P., Singh, A., Vijayan, V., Kirty, K., Yadav, S., Puntambekar, S., Bajaj, S., Dani, P. P., Kar, H. K., et al. (2014). IFNgamma signaling maintains skin pigmentation homeostasis through regulation of melanosome maturation. Proc Natl Acad Sci USA 111, 2301-2306.

O'Rourke, D. M., Kao, G. D., Singh, N., Park, B. W., Muschel, R. J., Wu, C. J., and Greene, M. I. (1998). Conversion of a radioresistant phenotype to a more sensitive one by disabling erbB receptor signaling in human cancer cells. Proc Natl Acad Sci USA 95, 10842-10847.

O'Rourke, D. M., et al. Trans receptor inhibition of human glioblastoma cells by erbB family ectodomains. Proc Natl Acad Sci USA 94, 3250-3255 (1997).

Otto, A. P., Hodi, F. S., and Robert, C. (2013). CTLA-4 and PD-1/PD-L1 blockade: New Immunotherapeutic modalities with durable clinical benefit in melanoma patients. Clin Cancer Res 19, 5309-5309.

Park S, Jiang Z, Mortenson E D, Deng L, Radkevich-Brown O, Yang X, Sattar H, Wang Y, Brown N K, Greene M, Liu Y, Tang J, Wang S, Fu Y X. The therapeutic effect of anti-HER2/neu antibody depends on both innate and adaptive immunity. Cancer cell. 2010; 18(2):160-170. PMCID: 2923645.

Platanias, L. C. Interferons and their antitumor properties. Journal of interferon & cytokine research: the official journal of the International Society for Interferon and Cytokine 33, 143-144 (2013).

Portera, C. C., Walshe, J. M., Rosing, D. R., Denduluri, N., Berman, A. W., Vatas, U., Velarde, M., Chow, C. K., Steinberg, S. M., Nguyen, D., et al. (2008). Cardiac toxicity and efficacy of trastuzumab combined with pertuzumab in patients with [corrected] human epidermal growth factor receptor 2-positive metastatic breast cancer. Clin Cancer Res 14, 2710-2716.

Qian, X., Dougall, W. C., Hellman, M. E. & Greene, M. I. Kinase-deficient neu proteins suppress epidermal growth factor receptor function and abolish cell transformation. Oncogene 9, 1507-1514 (1994).

Qian, X., LeVea, C. M., Freeman, J. K., Dougall, W. C., and Greene, M. I. (1994). Heterodimerization of epidermal growth factor receptor and wildtype or kinase-deficient Neu: a mechanism of interreceptor kinase activation and transphosphorylation. Proc Natl Acad Sci USA 91, 1500-1504.

Qiao, Y., Giannopoulou, E. G., Chan, C. H., Park, S. H., Gong, S., Chen, J., Hu, X., Elemento, O., and Ivashkiv, L. B. (2013). Synergistic activation of inflammatory cytokine genes by interferon-gamma-induced chromatin remodeling and toll-like receptor signaling. Immunity 39, 454-469.

Riemsma, R., Forbes, C. A., Amonkar, M. M., Lykopoulos, K., Diaz, J. R., Kleijnen, J., and Rea, D. W. (2012). Systematic review of lapatinib in combination with letrozole compared with other first line treatments for hormone receptor positive (HR+) and HER2+ advanced or metastatic breast cancer (MBC). Curr Med Res Opin.

Romond, E. H., et al. Trastuzumab plus adjuvant chemotherapy for operable HER2-positive breast cancer. The New England journal of medicine 353, 1673-1684 (2005).

Runkle E A, Young P, Nagai Y, Tsuchiya H, Zhang H, and Greene M I. Disabling the erbB2 Kinase Reverses Features of the Malignant Phenotype to Permit Interferon-γ to Act on Human Breast Cancer Cells. (In preparation).

Schechter, A. L., et al. The neu oncogene: an erb-B-related gene encoding a 185,000-Mr tumour antigen. Nature 312, 513-516 (1984).

Seidman, A. D., et al. Weekly trastuzumab and paclitaxel therapy for metastatic breast cancer with analysis of efficacy by HER2 immunophenotype and gene amplification. Journal of clinical oncology: official journal of the American Society of Clinical Oncology 19, 2587-2595 (2001).

Sliwkowski, M. X. & Mellman, I. Antibody therapeutics in cancer. Science 341, 1192-1198 (2013).

Spike, B. T., Engle, D. D., Lin, J. C., Cheung, S. K., La, J., and Wahl, G. M. (2012). A mammary stem cell population identified and characterized in late embryogenesis reveals similarities to human breast cancer. Cell Stem Cell 10, 183-197.

Stagg J, Loi S, Divisekera U, Ngiow S F, Duret H, Yagita H, Teng M W, Smyth M J. Anti-ErbB-2 mAb therapy requires type I and II interferons and synergizes with anti-PD-1 or anti-CD137 mAb therapy. Proceedings of the National Academy of Sciences of the United States of America. 2011; 108(17):7142-7147. PMCID: 3084100.

Stagg, J., Andre, F. & Loi, S. Immunomodulation via Chemotherapy and Targeted Therapy: A New Paradigm in Breast Cancer Therapy? Breast Care (Basel) 7, 267-272 (2012).

Stagg, J., Sharkey, J., Pommey, S., Young, R., Takeda, K., Yagita, H., Johnstone, R. W., and Smyth, M. J. (2008). Antibodies targeted to TRAIL receptor-2 and ErbB-2 synergize in vivo and induce an antitumor immune response. Proc Natl Acad Sci USA 105, 16254-16259.

Tsai, C. C., Kai, J. I., Huang, W. C., Wang, C. Y., Wang, Y., Chen, C. L., Fang, Y. T., Lin, Y. S., Anderson, R., Chen, S. H., et al. (2009). Glycogen synthase kinase-3beta facilitates IFN-gamma-induced STAT1 activation by regulating Src homology-2 domain-containing phosphatase 2. J Immunol 183, 856-864.

Tsuchiya H, Nagai Y, Ji M Q, Drebin J A, Norton L, Runkle E A, Zhang H, and Greene M I. Ordered combination of erbB targeted antibody and immune therapy of breast cancer. (In preparation)

Ucla, C., Roux-Lombard, P., Fey, S., Dayer, J. M., and Mach, B. (1990). Interferon gamma drastically modifies the regulation of interleukin 1 genes by endotoxin in U937 cells. J Clin Invest 85, 185-191.

Uribe, J. M., McCole, D. F., and Barrett, K. E. (2002). Interferon-gamma activates EGF receptor and increases TGF-alpha in T84 cells: implications for chloride secretion. Am J Physiol Gastrointest Liver Physiol 283, G923-931.

Villarreal, G., Jr., Zhang, Y., Larman, H. B., Gracia-Sancho, J., Koo, A., and Garcia-Cardena, G. (2010). Defining the regulation of KLF4 expression and its downstream transcriptional targets in vascular endothelial cells. Biochemical and biophysical research communications 391, 984-989.

Wada, T., et al. Anti-receptor antibodies reverse the phenotype of cells transformed by two interacting proto-oncogene encoded receptor proteins. Oncogene 5, 489-495 (1990).

Wicha, M. S., Liu, S., and Dontu, G. (2006). Cancer stem cells: an old idea—a paradigm shift. Cancer Res 66, 1883-1890; discussion 1895-1886.

Wu, Z. Q., Li, X. Y., Hu, C. Y., Ford, M., Kleer, C. G., and Weiss, S. J. (2012). Canonical Wnt signaling regulates Slug activity and links epithelial-mesenchymal transition with epigenetic Breast Cancer 1, Early Onset (BRCA1) repression. Proc Natl Acad Sci USA 109, 16654-16659.

Yang, X., Zhang, X., Fu, M. L., Weichselbaum, R. R., Gajewski, T. F., Guo, Y., and Fu, Y. X. (2014). Targeting the tumor microenvironment with interferon-beta bridges innate and adaptive immune responses. Cancer Cell 25, 37-48.

Yori, J. L., Seachrist, D. D., Johnson, E., Lozada, K. L., Abdul-Karim, F. W., Chodosh, L. A., Schiemann, W. P., and Keri, R. A. (2011). Kruppel-like factor 4 inhibits tumorigenic progression and metastasis in a mouse model of breast cancer. Neoplasia 13, 601-610.

Zaidi, M. R. & Merlino, G. The two faces of interferon-gamma in cancer. Clinical cancer research: an official journal of the American Association for Cancer Research 17, 6118-6124 (2011).

Zhang H, Wang Q, Montone K T, Peavey J E, Drebin J A, Greene M I, Murali R. Shared antigenic epitopes and pathobiological functions of anti-p185(her2/neu) monoclonal antibodies. Exp Mol Pathol. 1999; 67(1):15-25.

Zhang H. Empowering scFv with effector cell functions for improved anticancer therapeutics. Oncoimmunology. 2013; 2(6):e24439. PMCID: PMC3716736.

Zhang, H., et al. ErbB receptors: from oncogenes to targeted cancer therapies. J Clin Invest 117, 2051-2058 (2007).

Zheng, H., and Kang, Y. (2014). Multilayer control of the EMT master regulators. Oncogene 33, 1755-1763.

Zhou, B. P., Deng, J., Xia, W., Xu, J., Li, Y. M., Gunduz, M., and Hung, M. C. (2004). Dual regulation of Snail by GSK-3beta-mediated phosphorylation in control of epithelial-mesenchymal transition. Nat Cell Biol 6, 931-940.

The invention claimed is:

1. A method of increasing response to radiation therapy in a subject afflicted with a cancer, comprising:
   a) reducing the ability of an immune suppressor cell to migrate to the microenvironment of the cancer; and
   b) exposing the subject to radiation therapy
   wherein step a) comprises administering to the subject a therapeutically effective amount of a first anti-p185her2/neu antibody or an antigen binding portion thereof, a second anti-p185her2/neu antibody or an antigen binding portion thereof, and interferon-gamma (IFNγ).

2. The method of claim 1, wherein the immune suppressor cell is a myeloid-derived suppressor cell (MDSC).

3. The method of claim 1, comprising inducing accelerated degradation of Snail or Slug in a cancer cell of the cancer.

* * * * *